(12) United States Patent
Shen et al.

(10) Patent No.: US 6,927,286 B1
(45) Date of Patent: Aug. 9, 2005

(54) BLEOMYCIN GENE CLUSTER COMPONENTS AND THEIR USES

(75) Inventors: Ben Shen, Davis, CA (US); Liangcheng Du, Davis, CA (US); Cesar Sanchez, Asturias (ES); Mei Chen, Davis, CA (US); Daniel J. Edwards, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/477,962

(22) Filed: Jan. 5, 2000

Related U.S. Application Data

(60) Provisional application No. 60/118,848, filed on Feb. 5, 1999, and provisional application No. 60/115,435, filed on Jan. 6, 1999.

(51) Int. Cl.[7] .............................................. C07H 12/04
(52) U.S. Cl. .................... 536/23.2; 536/23.1; 536/23.7; 435/320.1; 435/252.3; 435/254.11; 435/419; 435/325; 435/252.35
(58) Field of Search .............................. 536/23.1, 23.2, 536/23.7; 435/320.1, 252.3, 254.11, 419, 325, 252.35

(56) References Cited

U.S. PATENT DOCUMENTS 6,121,029 A * 9/2000 Schupp et al.

OTHER PUBLICATIONS

Shen et al. Bleomycin biosynthesis in *Streptomyces verticillus* ATCC15003: the search for a hybrid polyketide and peptide biosynthetic system. Book of Abstracts, 217th ACS National Meeting, Anaheim, CA, Mar. 21–125 (1999). ORGN–153.*
Du et al. Bleomycin biosynthesis in *Streptomyces verticillus* ATTCC15003: A model for hybrid polyketide and peptide biosynthesis. Book of Abstracts, 219th ACS National Meeting, San Francisco, CA, Mar. 26–30 (2000). ORGN–822.*
Du et al. The biosynthetic gene cluster for the antitumor drug bleomycin from *Streptomyces verticillus* ATCC15003 supporting functional interactions between nonribosomal peptide synthetases and a polyketide synthase. Chem Biol Aug. 2000;7(8):623–42.*
Shen et al. The biosynthetic gene cluster for the anticancer drug bleomycin from *Streptomyces verticillus* ATCC15003 as a model for hybrid peptide–polyketide natural product biosynthesis. J Ind Microbiol Biotechnol Dec. 2001;27(6):378–85.*
Redenbach et al. A set or ordered cosmids and a detailed genetic and physical map for the 8 Mb *Streptomyces coelicolor* A3(2) chromosome. Mol Microbiol Jul. 1996;21(1):77–96.*
GenBank Accession No. AL136503 submitted Jan. 17, 2000.*

Dabobov et al. (1996) "The D–Alanyl Carrier Protein in *Lactobacillus casei*: Cloning, Sequencing, and Expression of dltC." J. Bacteriol., 178(13): 3869–3876.
Gaidenko et al. (1992) "Characterization of the New Pleutropic Regulatory Gene from *Bacillus licheniformis*". Biotechnologia, 13–19.
Bao et al. (1998) "Reconstitution of the Iterative Type II Polyketide Synthase for Tetracenomycin F2 Biosynthesis." Biochemistry 37: 8132–8138.
Borchert et al. (1994) "Induction of Surfactin Production of *Bacillus subtilis* by gsp, a Gene Located Upstream of the Gramicidin S. Operon in *Bacillus brevis*." J. Bacteriol. 176:2458–2462.
Calcutt and Schmidt (1994) "Gene organization in the bleomycin–resistance region of the producer organism *Streptomyces verticillus*." Gene, 151: 17–21.
Cane et al. (1998) "Harnessing the Biosynthetic Code: Combinations, Permutations, and Mutations." Science 282: 63–68.
Carreras and Khosla (1998) "Purification and in Vitro Reconstituition of the Essential Protein Components of an Aromatic Polyketide Synthase." Biochemistry 37:2084–2088.
Carreras et al. (1997) "Utilization of Enzymatically Phosphopantetheinylated Acyl Carrier Proteins and Actyl—Acyl Carrier Proteins by the Actinorhodin Polyketide Synthase." Biochemisty 36: 11757–11761.
Coderre et al., (1989) "The *entD* Gene of the *Escherichia coli* K12 Enterobactin Gene Cluster." J. Gen. Microbiology. 135:3043–3055.
Conti et al. (1997) "Structural basis for the activation of phenylalanine in the non–ribosomal biosynthesis of gramicidin S." EMBO J. 16: 4174–4183.
Cosmina et al. (1993) "Sequence and analysis of the genetic locus responsible for surfactin synthesis in *Bacillus subtilis*." Mol. Microbiology. 8:821–831.
Cox et al. (1997) "Post–translation modification of heterologously expressed *Streptomyces* type II Polyketide synthase acyl carrier proteins." FEBS Lett. 405: 267–272.

(Continued)

*Primary Examiner*—Kathleen Kerr
(74) *Attorney, Agent, or Firm*—Quine I.P. Law Group, PC.; Tom Hunter

(57) ABSTRACT

This invention provides detailed sequence analysis and characterization of the gene cluster responsible for the synthesis of bleomycin in *Streptomyces verticillus*. The bleomycin gene cluster provides the first hybrid polyketide synthase/nonribosomal peptide synthetase pathway and elucidation of the various modules and enzymatic domains characterizing the pathway provides convenient synthetic routes for bleomycins, bleomycin analogs, and various other polyketides.

10 Claims, 19 Drawing Sheets

OTHER PUBLICATIONS

Du and Shen (1999) "Identification and characterization of a type II peptide carrier protein from the bleomycin producer *Streptomyces verticillus* ATCC 15003." Chem. Biol. 6: 507–517.

Epple et al. (1998) "Characterization of a Novel Acyl Carrier Protein, RKpf, Encoded by an Operon Involved in Capsular Polysaccharide Biosynthesis in *Sinorhizobium meliloti*." J. Bacteriol. 180: 4950–4954.

Fitzmaurice and Kolattukudy (1997) "Open Reading Frame 3, Which is Adjacent to the Mycocerosic Acid Synthase Gene, Is Expressed as an Acyl Coenzyme A Synthase in *Mycobacterium bovis* BCG." J. Bacteriol. 179: 2608–2615.

Fitzmaurice and Kolattukudy (1998) "An Acyl–CoA Synthase (acoas) Gnen Adjacent to the Mycocersic Acid Synthase (mas) Locus Is Necessary for Mycocerosyl Lipid Synthesis in *Mycobacterium tuberculosis* var. *bovis* BCG." J. Biol. Chem. 273: 8033–8039.

Gehring et al. (1996) "Ability of *Streptomyces* spp. Acyl carrier proteins and coenzyme A analogs to serve as substrates in vitro for *E. coli* holo–ACP synthase." Chem. Biol. 4: 17–24.

Gehring et al. (1998) "The Nonribosomal Peptide Synthetase HMWP2 Forms a Thiazoline Ring During Biogenesis of Yeriniabactin, an Iron–Chelating Virulence Factor of *Yersinia pestis*." Biochemistry 37: 11637–11650.

Gehring et al. (1998) "Reconsitiution and Characterization of the *escherichia coli* Enterobactin Synthetase from EntB, EntE, and EntF." Biochemistry 37: 2648–2659.

Gehring et al. (1998) "Iron acquisition in Plaque: modular logic in enzymatic biogenesis of yeriniabactin by *Yersinia pestis*." Chem. Biol. 5: 573–586.

Gokhale et al. (1999) "Dissecting and Exploiting Intermodular Communication in Polyketide Synthases." Science 284: 482–485.

Guenzi et al. (1998) "Coordinate Transcription and Physical Linkage of Domains in Surfactin Synthetase Are Not Essential for Proper Assembly and Activity of the Multienzyme Complex." J. Biol. Chem. 273: 14403–14410.

Guenzi et al. (1998) "Characterization of the Syringomycin Synthetase Gene Cluster." J. Biol. Chem. 273:32857–32863.

Haese et al. (1994) "Bacterial Expression of Catalytically Active Fragments of the Multifunctional Enzyme Enniatn Synthetase." J. Mol. Bol. 243: 116–122.

Haydock et al. (1995) "Divergent sequence motifs correlated with the substrate specificity of (methyl)malony–CoA:acyl carrier protein transacylase domains in modular polyketide synthases." FEBS Lett. 374:246–248.

Hopwood (1997) "Genetic Contributions to Understanding Polyketide Synthases." Chem Rev. 97: 2465–2497.

Huang et al. (1993) "Nucleotide Sequence and Characterisitics of the Gene, *Ipa–14,* Responsible for Biosynthesis for the Lipopeptide Antibiotics Iturn A and Surfactin from *Bacillus subtillis* RB14." J. Ferment. Bioeng. 76:445–450.

Kennedy et al. (1999) "Modulation of Polyketide Synthase Activity During Lovastatin Biosynthesis." Science 284: 1368–1372.

Kleinkauf and Von Döhren (1996) "A nonribosomal system of peptide biosynthesis." Eur. J. Biochem. 236: 335–351.

Konig et al. (1997) "The pipecolate–incorporating enzyme for the biosynthesis of the immunosuppressant rapamycin." Eur. J. Biochem. 247: 526–534.

Konz et al. (1997) "The bacitracin biosynthesis operon of *Bacillus licheniformis* ATCC 10716: molecular characterization of three multi–modular prptide synthetases." Chem. Biol. 4: 927–937.

Ku et al. (1997) "Expression of a functional non–ribosomal peptide synthetase module in *Escherichia coli* by coexpressiom with a phosphopantetheinyl transferases." Chem. Biol. 4: 203–207.

Lambalot and Walsh (1995) "Coining, Overproduction, and Characterization of the *Escherichia coli* Holo–acyl Carrier Protein Synthase." J. Biol. Chem. 270: 24658–24661.

Lamblot et al. (1996) "A New enzyme superfamily–the phosphopantetheinyl transferases." Chem. Biol. 3: 923–936.

Lee and Lipmann (1975) "Tyrocidine Synthetase System." Method Emzmol. 43: 585–602.

Li et al. (1990) "Nucleotide sequence and transcriptional analysis of the nosiheptide–resistance gene from *Streptomyces actuosus*." Gene 91:9–17.

Li et al. (1996) "From Peptide Precursors to Oxazole and Thiazole–Containing Prptide antibioics: Microcin B17 Synthase." Science 274: 1188–1193.

Marahiel et al. (1997) "Modular Peptide Synthesis Involved in Nonribosomal Peptide Synthesis." Chem. Rev. 97: 2651–2673.

Milne, et al. (1999) "Cofactor Requirements and Reconstitution Of Microcin B17 Synthetase: A Multienzyme Complex that Catalyzes the Formation of Oxazoles and Thiazoles in the Antibiotic Microcin B17." Biochemistry 38: 4768–4781.

Mootz and Marahiel (1997) "The Tyrocidine Biosynthesis Operon of *Bacillus brevis:* Complete Nucleotide Sequence and Biochemical Characterization of Functional Internal Adenylation Domains." J. Bacteriol. 179: 6843–6850.

Mori et al. (1997) "Purification and Cloning of a Proline 3–Hydroxylase, a Novel Enzyme Which Hydroxylates Free L–Proline to cis–3–Hydroxy–L–Proline." J. Bacteriol. 179:5677–5683.

Nakano et al. (1992) "Isolation and Characterization of *sfp*: a gene that functions in the production of the lipoptide biosurfactant, surfactin, in *Bacillus subtilis*." Mol. Gen. Genet., 232: 313–321.

Natrajan and Hecht (1994) "Chapter 5: Bleomycins: Mechanism of Polynucleotide Recoginition and Oxidative Degradation." pp. 197–242 In: Molecular Aspects of Anticancer Drug–DNA Interaction vol. 2, Neidle and Waring Eds., Macmillan, London.

Ojima et al. (1999) "A common pharmacophore to cytotoxic natural products that stabiliza microtubules," Proc. Natl. Acad. Sci. USA 96: 4256–4261.

Paitan et al. (1999) "The First Gene in the Biosynthesis of the Polyketide Antibiotic TA of *Myxococcus xanthus* Codes for a Unique PKS Module Coupled to a Peptide Synthetase." J. Mol. Biol. 286: 465–474.

Pelludat et al. (1998) "The Yersiniabactin Biosynthetic Gene Cluster of The Yersininabactin Biosynthetic Gene Cluster of *Yersinia enterocolitica:* Organization and Siderophore–Dependent Regulation." J. Bacteriol. 180: 538–546.

Perego et al. (1995) "Incorporattion of D–Alanine into Lipoteichoci Acid and Wall Teichoic Acid in *Bacillus subtilis*." J. Biol. Chem. 270: 15598–15606.

Pfeifer et al. (1995) "Characterization of Tyrocidine Synthetase 1 (TY1): Requirement of Posttranslation Modification for Peptide Biosynthesis." Biochemistry 34: 7450–7459.

Quadri et al. (1998) "Identification of a *Mycobacterium tuberculosis* gene cluster encoding the biosynthetic enzymes for assembly of the virulence–conferring siderophore mycobactin." Chem. Biol. 5:631–645.

Quadri et al. (1998) "Characterization of Sfp, a *Bacillus subtilis* Phsophopantetheinyl Transferase for Peptidyl Carrier Protein Domains in Peptide Synthetases." Biochemistry 37: 1585–1595.

Shen and Hutchinson (1993) "Enzymatic Synthesis of a Bacterial Polyketide from Acetyl and Malonyl Coenzyme A." Science 262: 1535–1540.

Shen et al. (1992) "Purification and Characterization of the Acyl Carrier Protein of the *Strepomyces glaucesens* Tetracenomycin C Polyketide Synthase." J. Bacteriol. 174:3818–3821.

Shen et al. (1999) "Bleomycin Biosynthesis in *Streptomyces verticillus* ATCC15003: A Model of Hybrid Peptide and Polyketide Biosynthesis." Bioorganic Chem. 27: 155–171.

Spaink et al. (1991) "A novel highly unsaturated fatty acid moiety of lipo–oligosaccharide signals determins host specificity of *Rhizobium*." Nature 354: 125–130.

Stachelhaus and Marahiel (1995) "Modular structure of genes encoding multifunctional peptide synthetases required for non–ribosomal peptide synthesis." FEMS Microbiol. Lett. 125: 3–14.

Stachelhaus et al. (1996) "Biochemical Characterization of peptidyl carrier protein (PCP), the thiolation domain of multifunctional peptide synthetases." Chem. Biol. 3: 913–921.

Stachelhaus et al. (1998) "Peptide Bond Formation in Nonribosomal Peptide Biosynthesis." J. Biol. Chem., 273: 22773–22781.

Stachelhaus et al. (1999) "The specificity–conferring sode of adenylation domains in nonribosomal peptide synthetases." Chem. Biol. 6: 493–505.

Stachlhaus and Marahiel (1995) "Modular Structure of Peptide Synthetases Revealed by Dissection of the Multifunctional Enzyme GrsA." J. Biol. Chem. 270: 6163–6169.

Stein et al. (1996) "The Multiple Carrier Model of Nonribosomal Peptide Biosynthesis at Modular Multienzymatic Templates." J. Biol. Chem. 271: 15428–15435.

Sugiyama et al. (1994) "Characterisation by molecular cloning of two genes from *Streptomyces verticillus* encoding resistance to bleomycin." Gene 151: 11–16.

Takita and Muroka (199) "Biosynthesis and Chemical Synthesis of Bleomycin." Chapter 11, pp. 289–309 in Biochemistry of Peptide Antibiotics: Recent Advances in the Biotechnology of b–Lactams and Microbial Peptides, Kleinkauf, H. & von Döhren, H. eds., W. de Gruyter, N.Y.

Von Döhren et al. (1997) "Multifunctional Peptide Synthetases." Chem. Rev. 97: 2675–2705.

Walsh et al. (1997) "Post–translation modification of polyketide and nonribosomal peptide synthesis." Curr. Opin. Chem. Biol. 1: 309–315.

Weinreb et al. (1998) "Stoichiometry and Specificity of In Vitro Phosphopantetheinylation and Aminoacylation of the Valine–Activating Module of Surfactin Synthetase." Biochemistry 37: 1575–1584.

Wright et al. (1992) "Codon usage in the G+C–rich Streptomyces genome." Gene 113:55–65.

* cited by examiner

| NRPS module | Substrate | Residues (PheA numbering) (16) | | | | | | | |
|---|---|---|---|---|---|---|---|---|---|
| | | 236 | 239 | 278 | 299 | 301 | 322 | 330 | 331 |
| HMWP2 | Cys | L | Y | N | M | S | M | I | W |
| AngR | Cys | L | Y | N | M | S | M | I | W |
| BacA-2 | Cys | L | Y | N | L | S | L | I | W |
| MbtB | Ser/Thr | M | L | N | A | G | L | V | H |
| Blm NRPS-0 | Cys | L | Y | H | L | G | L | P | W |
| Blm NRPS-1 | Cys | L | Y | N | L | S | L | I | W |
| SyrE-7 | Dhb | F | W | N | V | G | M | V | H |
| AcmB-1 | Thr | F | W | N | V | G | M | V | H |
| SnbC-1 | Thr | F | W | N | I | G | M | V | H |
| FxbC-2 | Thr | F | W | N | V | G | M | V | H |
| Blm NRPS-6 | Thr | F | W | S | V | G | M | I | H |

X = S (cysteine)
X = O (serine)

X = S (cysteine)
X = O (serine)

```
                                                        -18    RBS
                                             CC GGACGG CGGCCCGCTC
ATGAGCGCCCCGCGGGGCGAGCGGACCCGGCGCCGCGCGCTCGAACGCGACATCGCCGCGATCTGGGCCGAGACCCTCGGCAGGGACAGCGTC 93
 M  S  A  P  R  G  E  R  T  R  R  R  A  L  E  R  D  I  A  A  I  W  A  E  T  L  G  R  D  S  V
GGCCCGCACGAGGACTTCGCCGCGCTGGGCGGCAACTCCATCCACGCCATCAAGATCACCAACCGGGTGGAGGAACTCGTCGACGCCGAGCTG 186
 G  P  H  E  D  F A A L G G N S I  H  A  I  K  I  T  N  R  V  E  E  L  V  D  A  E  L
TCCATCCGCGTCCTGCTCGAGACCCGCACCGTGGCCGGCATGACGGACCACGTCCACGCCACGCTCACGGGGGAGCGGGACCGGTGA         273
 S  I  R  V  L  L  E  T  R  T  V  A  G  M  T  D  H  V  H  A  T  L  T  G  E  R  D  R  *
```

Fig. 8C

```
Grs-2      3045-ISIGTEYVAPRTMLEGKLEEIWKDVLGLQRVIEDDFFTIGGHSL-3089
Srfa-3      960-DQLAEEWIGPPNEMEETIAQIWSEVIGRKQIIHDDFFALGGHSL-1004
Vir-S       557-GRSVEGRGVPPTPQQEILASLFAEVIGLSKVIIEDFPDLLGHSL- 601
Saf-B      1661-LDPGQDYLAPRNELEARIAAIWEGLRRERVIVDSFPDLLGNSL-1705
BlmI          1-MSAPRGERTRRRALERDIAAIWAETLGRDSVGPHEDFAALGGNSI-  45
consensus     1-i  g  eyvapR  le   ia iw evLgr  rvGiHddFf  lGGhSl-  45

Grs-2      3090-KMAVISQVHKECQTEVPLRVLFITETIQGLAKYIEETDTEQYMA-3134
Srfa-3     1005-KMTAVPH.QQELGIDLPVKLLFLAEIIAGISAYLKNGGSDGLQD-1048
Vir-S       602-LTRLTSRIRTVLGAEIAVRDLFEAEIVEALAETLEEAREVRPAL- 646
Saf-B      1706-LTRLATRLAATLQVQAGVRTVFEHRIVAAQAAHFTQATKTHQAH-1750
BlmI         46-HIKITNRVEELVDAELSIRVLLETRVAGMTDHVHATLTGERDR-  90
consensus    46-kAmrv srv    l  ev vrvlfE pTvagla   i  g t      -  90
```

Fig. 9

Nonreiterative Type I Modular Protein Template

PKS

NPRS

Iterative Type II Protein Complex

PKS

NPRS

US 6,927,286 B1

BLEOMYCIN GENE CLUSTER COMPONENTS AND THEIR USES

CROSS-REFERENCE TO RELATED APPLICATIONS

This application claims benefit under 35 U.S.C. § 119 of provisional applications U.S. Ser. No. 60/115,435, filed on Jan. 6, 1999, and U.S. Ser. No. 60/118,848, filed on Feb. 5, 1999, both of which are herein incorporated by reference in their entirety for all purposes.

STATEMENT AS TO RIGHTS TO INVENTIONS MADE UNDER FEDERALLY SPONSORED RESEARCH AND DEVELOPMENT

This work was supported in part by an Institutional Research Grant from the American Cancer Society and the School of Medicine, University of California, Davis, National Institutes of Health Grant Number AI40475, and a grant from the Searle Scholars Program of the Chicago Community Trust. The Government of the United States of America may have certain rights in this invention.

FIELD OF THE INVENTION

This invention relates the field of polyketide synthesis and nonribosomal polypeptide synthesis. In particular this invention pertains to the isolation of the bleomycin gene cluster which encodes the first identified hybrid polyketide synthase/nonribosomal peptide synthetase pathway.

BACKGROUND OF THE INVENTION

Polyketides and nonribosomal peptides are two large families of natural products that include many clinically valuable drugs, such as erythromycin and vancomycin (antibacterial), FK506 and cyclosporin (immunosuppresant), and epothilone and bleomycin (BLM) (antitumor). The biosyntheses of polyketides and nonribosomal peptides are catalyzed by polyketide synthases (PKSs) (Hopwood (1997) Chem. Rev. 97: 2465; Katz (1997) Chem. Rev., 97: 2557; C. Khosla, (1997) Chem. Rev., 97: 2577; Ikeda and Omura, (1997) Chem. Rev., 97: 2591; Staunton and Wilkinson (1997) Chem. Rev., 97: 2611; Cane et al. (1998) Science 282: 63) and nonribosomal peptide synthetases (NRPSs) (Cane et al. (1998) Science 282: 63. Marahiel et al. (1997) Chem. Rev. 97: 2651; von Döhren et al. (1997) Chem. Rev. 97: 2675), respectively. Remarkably, PKSs and NRPSs use a very similar strategy for the assembly of these two distinct classes of natural products by sequential condensation of short carboxylic acids and amino acids, respectively, and utilize the same 4'-phosphopantetheine prosthetic group, via a thioester linkage, to channel the growing polyketide or peptide intermediate during the elongation processes.

Both type I PKSs and NRPSs are multifunctional proteins that are organized into modules. (A module is defined as a set of distinctive domains that encode all the enzyme activities necessary for one cycle of polyketide or peptide chain elongation and associated modifications.) The number and order of modules and the type of domains within a module on each PKS or NRPS protein determine the structural variations of the resulting polyketide and peptide products by dictating the number, order, choice of the carboxylic acid or amino acid to be incorporated, and the modifications associated with a particular cycle of elongation. These features of PKS and NRPS inspired us to search for a hybrid PKS and NRPS system. Since the modular architecture of both PKS (Cane et al. (1998) Science 282: 63; Katz and Danadio (1993) Ann. Rev. Microbiol. 47: 875 (1993); Hutchinson and Fujii (1995) Ann. Rev. Microbiol. 49: 201) and NRPS (Cane et al. (1998) Science 282: 63, Stachelhaus et al. (1995) Science 269: 69; Stachelhaus et al. (198) Mol. Gen. Genet. 257: 308; Belshaw et al. (1999) Science 284, 486) has been exploited successfully in combinatorial biosynthesis of diverse "unnatural" natural products, it is imagined that a hybrid PKS and NRPS system, capable of incorporating both carboxylic acids and amino acids into the final products, could surely lead to even greater chemical structural diversity.

The BLMs, differing structurally at the C-terminal amines of the glycopeptides, are a family of antibiotics produced by *Streptomyces verticillus* (*Sv*). BLMs exhibit strong antitumor activity through a metal-dependent oxidative cleavage of DNA or RNA in the presence of molecular oxygen and are incorporated into current chemotherapy of several malignancies under the trade name of Blenoxane® that contains BLM A2 and BLM B2 as the principal constituents (Sikic et al. Eds. (1985) *Bleomycin Chemotherapy*, Academic Press, New York; Natrajan and Hecht (1994) pages 197–242 In: *Molecular Aspects of Anticancer Drug-DNA Interaction Vol. 2*, Neidle and Waring Eds., Macmillan, London). Umezawa, Fujii, Takita, and co-workers extensively studied the biosynthesis of BLM in *Sv* ATCC15003 by feeding isotope-labeled precursors and by isolating various biosynthetic intermediates and shunt metabolites, establishing that the BLMs are in fact natural hybrid metabolites of polyketide and peptide biosynthesis (Takita and Muroka (1990) pages 289–309 In: *Biochemistry of Peptide Antibiotics: Recent Advances in the Biotechnology of β-Lactams and Microbial Peptides*, Kleinkauf and Von Döhren Eds., W. de Gruyter, New York). On the assumption that BLM biosynthesis follows the paradigm for peptide and polyketide biosynthesis, we predict that the Blm megasynthetase, which catalyzes the assembly of the BLM backbone from nine amino acids and one acetate, should bear the characteristics of both NRPS and PKS, providing an excellent model to study the mechanism by which NRPS and PKS could be integrated into a productive biosynthetic system to synthesize a hybrid peptide and polyketide metabolite (FIG. 1A) (Shen et al. (1999) Bioorg. Chem. 27: 155).

SUMMARY OF THE INVENTION

This invention pertains to the isolation and elucidation of the bleomycin gene cluster. Nucleic acid sequences encoding all of the open reading frames (ORFs) that encode polypeptides sufficient to direct the biosynthesis of bleomycin are provided. The nucleic acids can be used in their "native" format or recombined in a wide variety of manners to create novel synthetic pathways.

In one embodiment, this invention provides an isolated nucleic acid comprising a nucleic acid selected from the group consisting of a nucleic acid encoding any one of Blm open reading frames (ORFs) 8 through 41, and/or a nucleic acid encoding a polypeptide encoded by any one of Blm open reading frames (ORFs) 8 through 41, and/or a nucleic acid amplified by polymerase chain reaction (PCR) using any one of the primer pairs identified in Table II and the nucleic acid of a bleomycin-producing organism as a template. The nucleic acid may comprise one or multiple (e.g. two, more preferably 3 or more) bleomycin open reading frames (i.e. BLM ORFs 8 through 41). One preferred nucleic acid comprises a nucleic acid encoding a C domain lacking one or more His residues of the conserved HHxxxDG (SEQ ID NO:4) active site for transpeptidation. In another preferred embodiment the nucleic acid comprises a nucleic acid encoding a protein encoded by a gene selected from the group consisting of blmI, blmII, and blmXI.

In another embodiment this invention provides an isolated nucleic acid encoding a (biosynthetic) module comprising two or more (more preferably three or more, most preferably four or more) catalytic domains of a protein encoded by a nucleic acid of a bleomycin gene cluster wherein said catalytic domains are selected from the group consisting of a condensation (C) domain, an adenylation (A) domain, a peptidyl carrier protein (PCP) domain, a condensation/cyclization domain (Cy), an acyl-carrier protein (ACP)-like domain, an oxidization domain (Ox), a ketoacyl synthase (KS) domain, an acetyl transferase (AT) domain, a ketoreductase (KR) domain, and a methyltransferase (MT) domain. Preferred nucleic acids comprises a nucleic acid encoding one or more proteins comprising a module selected from the group consisting of NRPS-0, NRPS-1, NRPS-2, NRPS-3, NRPS-4, NRPS-5, NRPS-6, NRPS-7, NRPS-7, NRPS-9, and PKS. Particularly preferred nucleic acids comprise an open reading frame from SEQ ID NO: 1, SEQ ID NO: 2, or SEQ ID NO: 3.

In still another embodiment, this invention provides an isolated nucleic acid comprising a nucleic acid encoding a protein encoded by a gene from a BLM gene cluster. Preferred nucleic acids encode a protein encoded by a gene selected from the group consisting of blmI, blmII, and blmXI. In another embodiment, preferred nucleic acids encode a protein encoded by a gene selected from the group consisting of blmIII, blmIV, blmV, blmVI, blmVII, blmIX, and blmX. In still yet another embodiment, the nucleic acid comprises a nucleic acid encoding a protein encoded by blmVIII. Particularly preferred nucleic acids comprise a nucleic acid selected from the group consisting of blmI, blmII, and blmXI. Other particularly preferred nucleic acids comprise a nucleic acid selected from the group consisting of blmIII, blmIV, blmV, blmVI, blmVII, blmIX, and blmX, while still other particularly preferred nucleic acids comprise blmVIII.

In still yet another embodiment, this invention provides an isolated nucleic acid comprising a nucleic acid that encodes a protein comprising at least one catalytic domain selected from the group consisting of a condensation (C) domain, an adenylation (A) domain, a peptidyl carrier protein (PCP) domain, a condensation/cyclization domain (Cy), an acyl-carrier protein (ACP)-like domain, an oxidization domain (Ox), a ketoacyl synthase (KS) domain, an acetyl transferase (AT) domain, a ketoreductase (KR) domain, and a methyltransferase (MT) domain, and that hybridizes to a nucleic acid selected from the group consisting of orf8, orf9, orf10, orf11, orf12, orf13, orf14, orf15, orf15, orf16, orf17, orf18, orf19, orf20, orf21, orf22, orf23, orf24, orf25, orf26, orf27, orf28, orf29, orf33, orf34, orf35, orf36, orf37, orf38, orf39, and orf40 under stringent conditions. In certain embodiments this also includes nucleic acids that would stringently hybridizes indicated above, but for, the degeneracy of the nucleic acid code. In other words, if silent mutations could be made in the subject sequence so that it hybridizes to he indicated sequence(s) under stringent conditions, it would be included in certain embodiments. A preferred isolated nucleic acid comprises a nucleic acid encoding a module. A particularly preferred isolated nucleic acid comprises a nucleic acid encoding a BLM gene.

This invention also provides a nucleic acid comprising a nucleic acid selected from the group consisting of consisting of orf8, orf9, orf10, orf11, orf12, orf13, orf14, orf15, orf15, orf16, orf17, orf18, orf19, orf20, orf21, orf22, orf23, orf24, orf25, orf26, orf27, orf28, orf29, orf30, orf31, orf32, orf33, orf34, orf35, orf36, orf37, orf38, orf39, and orf40, or an allelic variant thereof. Preferred nucleic acids comprise a nucleic acid that is a single nucleotide polymorphism (SNP) of a nucleic acid selected from the group consisting of consisting of orf8, orf9, orf10, orf11, orf12, orf13, orf14, orf15, orf15, orf16, orf17, orf18, orf19, orf20, orf21, orf22, orf23, orf24, orf25, orf26, orf27, orf28, orf29, orf30, orf31, orf32, orf33, orf34, orf35, orf36, orf37, orf38, orf39, and orf40.

This invention also provides an isolated gene cluster comprising open reading frames encoding polypeptides sufficient to direct the assembly of a bleomycin.

In one embodiment this invention provides an isolated multi-functional protein complex comprising both a polyketide synthase (PKS) and a polypeptide synthetase (NRPS) and/or an isolated nucleic acid encoding a multi-functional protein complex comprising both a polyketide synthase (PKS) and a polypeptide synthetase (NRPS).

This invention also provides various blm cluster polypeptides or blm cluster-derived polypeptides. Thus, in one embodiment this invention provides an isolated polypeptide comprising a catalytic domain encoded by a nucleic acid of a bleomycin gene cluster wherein said nucleic acid comprises a nucleic acid selected from the group consisting of a nucleic acid encoding any one of Blm open reading frames (ORFs) 8 through 41; and/or a nucleic acid amplified by polymerase chain reaction (PCR) using any one of the primer pairs identified in Table II. Preferred polypeptides comprise an enzymatic domain selected from the group consisting of a condensation (C) domain, an adenylation (A) domain, a peptidyl carrier protein (PCP) domain, a condensation/cyclization domain (Cy), an acyl-carrier protein (ACP)-like domain, an oxidization domain (Ox), a ketoacyl synthase (KS) domain, an acetyl transferase (AT) domain, a ketoreductase (KR) domain, and a methyltransferase (MT) domain. Particularly preferred polypeptides are encoded by the nucleic acids described above and herein.

This invention also provides expression vectors comprising any of the nucleic acids described herein and/or host cells (e.g. *Streptomyces*) transfected and/or transformed with any of these expression vectors. A preferred host cell is transformed with an exogenous nucleic acid comprising a gene cluster encoding polypeptides sufficient to direct the assembly of a bleomycin or bleomycin analog.

This invention also provides methods of use of the blm and blm-derived nucleic acid(s) and/or polypeptides. One such method is a method of chemically modifying a biological molecule. The method involves contacting a biological molecule that is a substrate for a polypeptide encoded by one or more bleomycin biosynthesis gene cluster open reading frames with the polypeptide encoded by one or more bleomycin biosynthesis gene cluster open reading frames, whereby the polypeptide chemically modifies the biological molecule. In one particularly preferred embodiment, the biological molecule is an amino acid and said polypeptide is a peptide synthetase. In another preferred embodiment, the polypeptide is a methyl transferase. Other substrates and blm encoded polypeptides are illustrated in Table II.

In another embodiment this invention provides a method of coupling a first amino acid to a second amino acid. This method involves contacting the first and second amino acid with a recombinantly expressed bleomycin nonribosomal peptide synthetase (NRPS). A preferred NRPS is selected from the group consisting of NRPS-5, NRPS-4, NRPS-3, NRPS-9, NRPS-8, and NRPS-7. Another preferred NRPS is selected from the group consisting of NRPS-6, NRPS-2, NRPS-1, and NRPS-0. The contacting can be in vivo (e.g. in a host cell) or ex vivo.

In another embodiment this invention provides a methods of coupling a first fatty acid to a second fatty acid, said method comprising contacting the first and second fatty acids with a recombinantly expressed bleomycin polyketide synthase (PKS). Again, the contacting can be in vivo (e.g. in a host cell) or ex vivo.

In still another embodiment, this invention provides a method of producing a bleomycin or bleomycin analog. The method involves providing a cell transformed with an exogenous nucleic acid comprising a bleomycin gene cluster encoding polypeptides sufficient to direct the assembly of said bleomycin or bleomycin analog; culturing the cell under conditions permitting the biosynthesis of bleomycin or bleomycin analog; and isolating said bleomycin or bleomycin analog from said cell.

This invention also provides an isolated nucleic acid comprising a nucleic acid encoding a phosphopantetheinyl transferase said nucleic acid encoding a phosphopantetheinyl transferase being selected from the group consisting of: a nucleic acid encoding the protein encoded by the nucleic acid of SEQ ID NO:3; a nucleic acid amplified by polymerase chain reaction (PCR) using primers that specifically amplify ORF 41 (primers: SEQ ID NO:71 and SEQ ID NO:72) and *Streptomyces* nucleic acid as a template; a nucleic acid encoding a polypeptide having phosphopantetheinyl transferase activity where said nucleic acid specifically hybridizes to the nucleic acid of SEQ ID NO: 3 under stringent conditions. In one embodiment, the nucleic acid comprises the nucleic acid of SEQ ID NO:3.

In another embodiment, this invention provides a polypeptide comprising a phosphopantetheinyl transferase encoded by SEQ ID NO:3 or a polypeptide having phosphopantetheinyl transferase activity and the sequence encoded by the nucleic acid of SEQ ID NO: 3 or conservative substitutions of that polypeptide.

Also provided are vectors comprising a nucleic acid encoding a phosphopantetheinyl transferase (e.g., as described above) and cells transfected with the vector.

This invention also provides a method of converting an apo carrier protein to a holo carrier protein, said method comprising reacting said apo-carrier protein with a recombinant phosphopantetheinyl transferase encoded by SEQ ID NO:3 and coenzyme A thereby producing a holo-carrier protein.

In certain embodiments, this invention specifically excludes one or more of open reading frames 1 through 41. In particularly preferred embodiments, this invention excludes open reading frames 1 through 7 (Orf 1–Orf 7).

Definitions

The "polyketide synthases" (PKSs) refers are multifunctional enzymes, related to fatty acid synthases (FASs). PKSs catalyze the biosynthesis of polyketides through repeated (decarboxylative) Claisen condensations between acylthioesters, usually acetyl, propionyl, malonyl or methylmalonyl. Following each condensation, they typically introduce structural variability into the product by catalyzing all, part, or none of a reductive cycle comprising a ketoreduction, dehydration, and enoylreduction on the β-keto group of the growing polyketide chain. PKSs incorporate enormous structural diversity into their products, in addition to varying the condensation cycle, by controlling the overall chain length, choice of primer and extender units and, particularly in the case of aromatic polyketides, regiospecific cyclizations of the nascent polyketide chain. After the carbon chain has grown to a length characteristic of each specific product, it is typically released from the synthase by thiolysis or acyltransfer. Thus, PKSs consist of families of enzymes which work together to produce a given polyketide. Two general classes of PKSs exist. One class, known as Type I PKSs, is represented by the PKSs for macrolides such as erythromycin. These "complex" or "modular" PKSs include assemblies of several large multifunctional proteins carrying, between them, a set of separate active sites for each step of carbon chain assembly and modification (Cortes et al. (1990) *Nature* 348: 176; Donadio et al. (1991) *Science* 252: 675; MacNeil et al. (1992) *Gene* 115: 119). Structural diversity occurs in this class from variations in the number and type of active sites in the PKSs. This class of PKSs displays a one-to-one correlation between the number and clustering of active sites in the primary sequence of the PKS and the structure of the polyketide backbone. The second class of PKSs, called Type II PKSs, is represented by the synthases for aromatic compounds. Type II PKSs typically have a single set of iteratively used active sites (Bibb et al. (1989) *EMBO J.* 8: 2727; Sherman et al. (1989) *EMBO J.* 8: 2717; Fernandez-Moreno, et al. (1992) *J. Biol. Chem.* 267:19278).

A "nonribosomal peptide synthase" (NRPS) refers to an enzymatic complex of eucaryotic or procaryotic origin, that is responsible for the synthesis of peptides by a nonribosomal mechanism, often known as thiotemplate synthesis (Kleinkauf and von Doehren (1987) *Ann. Rev. Microbiol.*, 41: 259–289). Such peptides, which can be up to 20 or more amino acids in length, can have a linear, cyclic (cyclosporine, tyrocidine, mycobacilline, surfactin and others) or branched cyclic structure (polymyxin, bacitracin and others) and often contain amino acids not present in proteins or modified amino acids through methylation or epimerization.

A "module" refers to a set of distinctive polypeptide domains that encode all the enzyme activities necessary for one cycle of polyketide or peptide chain elongation and associated modifications.

The terms "isolated" "purified" or "biologically pure" refer to material which is substantially or essentially free from components which normally accompany it as found in its native state. With respect to nucleic acids and/or polypeptides the term can refer to nucleic acids or polypeptides that are no longer flanked by the sequences typically flanking them in nature.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Teterahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487;

Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp169–176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

A "coding sequence" or a sequence which "encodes" a particular polypeptide (e.g. a PKS, an NRPS, etc.), is a nucleic acid sequence which is ultimately transcribed and/or translated into that polypeptide in vitro and/or in vivo when placed under the control of appropriate regulatory sequences. In certain embodiments, the boundaries of the coding sequence are determined by a start codon at the 5' (amino) terminus and a translation stop codon at the 3' (carboxy) terminus. A coding sequence can include, but is not limited to, cDNA from procaryotic or eucaryotic mRNA, genomic DNA sequences from procaryotic or eucaryotic DNA, and even synthetic DNA sequences. In preferred embodiments, a transcription termination sequence will usually be located 3' to the coding sequence.

Expression "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Recombination" refers to the reassortment of sections of DNA or RNA sequences between two DNA or RNA molecules. "Homologous recombination" occurs between two DNA molecules which hybridize by virtue of homologous or complementary nucleotide sequences present in each DNA molecule.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes part I chapter 2 Overview of principles of hybridization and the strategy of nucleic acid probe assays*, Elsevier, New York. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) *Molecular Cloning—A Laboratory Manual* (2nd ed.) Vol. 1–3, Cold Spring Harbor Laboratory, Cold Spring Harbor Press, NY, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

A "library" or "combinatorial library" of polyketides and/or polypeptides is intended to mean a collection of polyketides and/or polypeptides (or other molecules) catalytically produced by a PKS and/or NRPS and/or hybrid PKS/NRPS (or other possible combination of synthetic elements) gene cluster. The library can be produced by a gene cluster that contains any combination of native, homolog or mutant genes from aromatic, modular or fungal PKSs and/or NRPSs. The combination of genes can be derived from a single PKS and/or NRPS gene cluster, e.g., act, fren, gra, tcm, whiE, gris, ery, or the like, and may optionally include genes encoding tailoring enzymes which are capable of catalyzing the further modification of a polypeptide, polyketide, or other molecule. Alternatively, the combination of genes can be rationally or stochastically derived from an assortment of NRPS and/or PKS gene clusters. The library of polyketides and/or polypeptides and/or other molecules thus produced can be tested or screened for biological, pharmacological or other activity.

By "random assortment" is intended any combination and/or order of genes, homologs or mutants which encode for the various PKS and/or NRPS enzymes, modules, active sites or portions thereof derived from aromatic, modular or fungal PKS and/or NRPS gene clusters.

By "genetically engineered host cell" is meant a host cell where the native PKS and/or NRPS gene cluster has been altered or deleted using recombinant DNA techniques or a host cell into which a heterologous PKS and/or NRPS and/or hybrid PKS/NRPS gene cluster has been inserted. Thus, the term would not encompass mutational events occurring in nature. A "host cell" is a cell derived from a procaryotic microorganism or a eucaryotic cell line cultured as a unicellular entity, which can be, or has been, used as a recipient for recombinant vectors bearing the PKS, NRPS, and/or hybrid gene clusters of the invention. The term includes the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired PKS, are included in the definition, and are covered by the above terms.

Expression vectors are defined herein as nucleic acid sequences that are direct the transcription of cloned copies of genes/cDNAs and/or the translation of their mRNAs in an appropriate host. Such vectors can be used to express genes or cDNAs in a variety of hosts such as bacteria, bluegreen algae, plant cells, insect cells and animal cells. Expression vectors include, but are not limited to, cloning vectors, modified cloning vectors, specifically designed plasmids or viruses. Specifically designed vectors allow the shuttling of DNA between hosts, such as bacteria-yeast or bacteria-animal cells. An appropriately constructed expression vector preferably contains: an origin of replication for autonomous replication in a host cell, a selectable marker, optionally one or more restriction enzyme sites, optionally one or more constitutive or inducible promoters. In preferred embodiments, an expression vector is a replicable DNA construct in which a DNA sequence encoding a one or more PKS and/or NRPS domains and/or modules is operably linked to suitable control sequences capable of effecting the expression of the products of these synthase and/or synthetases in a suitable host. Control sequences include a transcriptional promoter, an optional operator sequence to control transcription and sequences which control the termination of transcription and translation, and so forth.

A "bleomycin open reading frame", or "bleomycin ORF", or "BLM Orf" refers to a nucleic acid open reading frame that encodes a polypeptide or polypeptide domain that has an enzymatic activity used in the biosynthesis of a bleomycin.

A "PKS/NRPS/PKS" system refers to a synthetic system comprising an NRPS flanked by two PKSs. A "NRPS/PKS/NRPS" system refers to a synthetic system comprising a PKS flanked by two NRPSs. A "hybrid PKS/NRPS system" or a "hybrid NRPS/PKS system" refers to a hybrid synthetic system comprising at least one PKS and one NRPS module. The system can comprise multiple modules and the order can vary.

A "biological molecule that is a substrate for a polypeptide encoded by a bleomycin biosynthesis gene" refers to a molecule that is chemically modified by one or more polypeptides encoded by open reading frame(s) of the blm gene cluster. The "substrate" may be a native molecule that typically participates in the biosynthesis of a bleomycin, or can be any other molecule that can be similarly acted upon by the polypeptide.

A "polymorphism" is a variation in the DNA sequence of some members of a species. A polymorphism is thus said to be "allelic," in that, due to the existence of the polymorphism, some members of a species may have the unmutated sequence (i.e. the original "allele") whereas other members may have a mutated sequence (i.e. the variant or mutant "allele"). In the simplest case, only one mutated sequence may exist, and the polymorphism is said to be diallelic. In the case of diallelic diploid organisms, three genotypes are possible. They can be homozygous for one allele, homozygous for the other allele or heterozygous. In the case of diallelic haploid organisms, they can have one allele or the other, thus only two genotypes are possible. The occurrence of alternative mutations can give rise to trialleleic, etc. polymorphisms. An allele may be referred to by the nucleotide(s) that comprise the mutation.

"Single nucleotide polymorphism" or "SNPs are defined by their characteristic attributes. A central attribute of such a polymorphism is that it contains a polymorphic site, "X," most preferably occupied by a single nucleotide, which is the site of the polymorphism's variation (Goelet and Knapp U.S. patent application Ser. No. 08/145,145). Methods of identifying SNPs are well known to those of skill in the art (see, e.g., U.S. Pat. No. 5,952,174).

The following abbreviations are used herein:: A, adenylation; ACP, acyl carrier protein; AT, acyltransferase; BLM, bleomycin; C, condensation; Cy, condensation/cyclization; KR, ketoreductase; KS, ketoacyl synthase; MT, methyltransferase; NRPS, nonribosomal peptide synthetase; orf, open reading frame; Ox, oxidation; PCP, peptidyl carrier protein; PCR, polymerase chain reaction; PKS, polyketide synthase; *Sv, Streptomyces verticillus*, ArCP, aryl carrier protein, bp, base pair, CoA, co-enzyme A, DTT, dithiothreitol; FAS, fatty acid synthase; kb, kilobase; PPTase, 4'-phosphopantetheinyl transferase; TCA, trichloroacetic acid; and DEBS, 6-deoxyerythronolide B synthase.

BRIEF DESCRIPTION OF THE DRAWINGS

FIG. 1A illustrates a biosynthetic pathway for BLM in *Sv* ATCC15003-intermediates except those in brackets were identified. FIG. 1B shows a linear model for the Blm megasynthetase-templated assembly of the BLM peptide/polyketide/peptide aglycone from nine amino acids and one acetate-shaded circles represent atypical domains carrying out the proposed novel chemistry, and arrows with broken line indicate where biosynthetic intermediates were derailed. Three-letter amino acid designations were used. [HO], hydroxylation; [H], reduction.

FIG. 3A shows a comparison of the A3 to A6 region of A domains to 84 NRPS modules available at GenBank that activate various amino acids. FIG. 3B shows a comparison of amino acid residues that putatively line the substrate binding pockets for A domains (single-letter amino acid designations were used). The number following the protein name indicates the order of a particular A domain in the multimodular NRPS protein. The protein accession numbers are P48663 (HMWP2), P19828 (AngR), AAC06346 (BacA-2), CAB03756 (MbtB), 3510629 (SyrE-7), 3114612 (AcmB-1), CAA67248 (SnbC-1), and 3560507 (FxbC-2). Dhb stands for 2,3-dehydroaminobutyric acid. It is not known if Dhb is the direct substrate for SyrE-7 or resulted from dehydration of an SyrE-7 activated Thr (Guenzi et al. (1998) *J. Biol. Chem.* 273: 32857–32863). FIG. 3C illustrates purified proteins after overexpression in *E. coli* as analyzed by electrophoresis on a 10% SDS-polyacrylamide gel (the calculated molecular weights for NRPS-1A and NRPS-6A are 64,212 and 61,899, respectively). FIG. 3D illustrates substrate specificities as determined by the ATP-PPi exchange reaction with the amino acids of BLM as substrates (100% relative activity corresponds to 103,000 cpm for NRPS-1A and 256,000 cpm for NRPS-6A).

FIG. 6A synthesis using BlmIX, BlmVIII, and BlmVII. FIG. 6B synthesis using NRPS, BlmVIII, and BlmVII. FIG. 6C synthesis using BlmIX, BlmVIII, and BlmVII. FIG. 6D synthesis using BlmIX, BlmVIII, and NRPS (C, $A^N$, PCP). FIG. 6E synthesis using BlmIX, BlmVIII and NRPS (C, $A^C$, PCP). FIG. 6F synthesis using BlmIX, BlmVIII, and NRPS (C, $A^C$, PCP, OX).

FIG. 9 shows an amino acid sequence comparison of BlmI (SEQ ID NO:133) with PCP domains of known type I NRPSs (Grs-2 [P14688] (SEQ ID NO:129), 36% identity, 58% similarity; Srfa-3 [Q08787] (SEQ ID NO:130), 40% identity, 64% similarity; Vir-s [Y11547] (SEQ ID NO:131), 36% identity, 60% similarity; Saf-b [U24657] (SEQ ID NO:132), 40% identity, 54% similarity). Given in brackets are nucleotide sequence accession numbers. The shaded letters indicate similar amino acids. Consensus residues are amino acids that are similar in more than three sequences.

FIG. 11A illustrates a Type I PKS. FIG. 11B illustrates a Type I NRPS. FIG. 11C illustrates a Type II PKS. FIG. 11D illustrates a Type II NRPS.

DETAILED DESCRIPTION

Figure 1A:
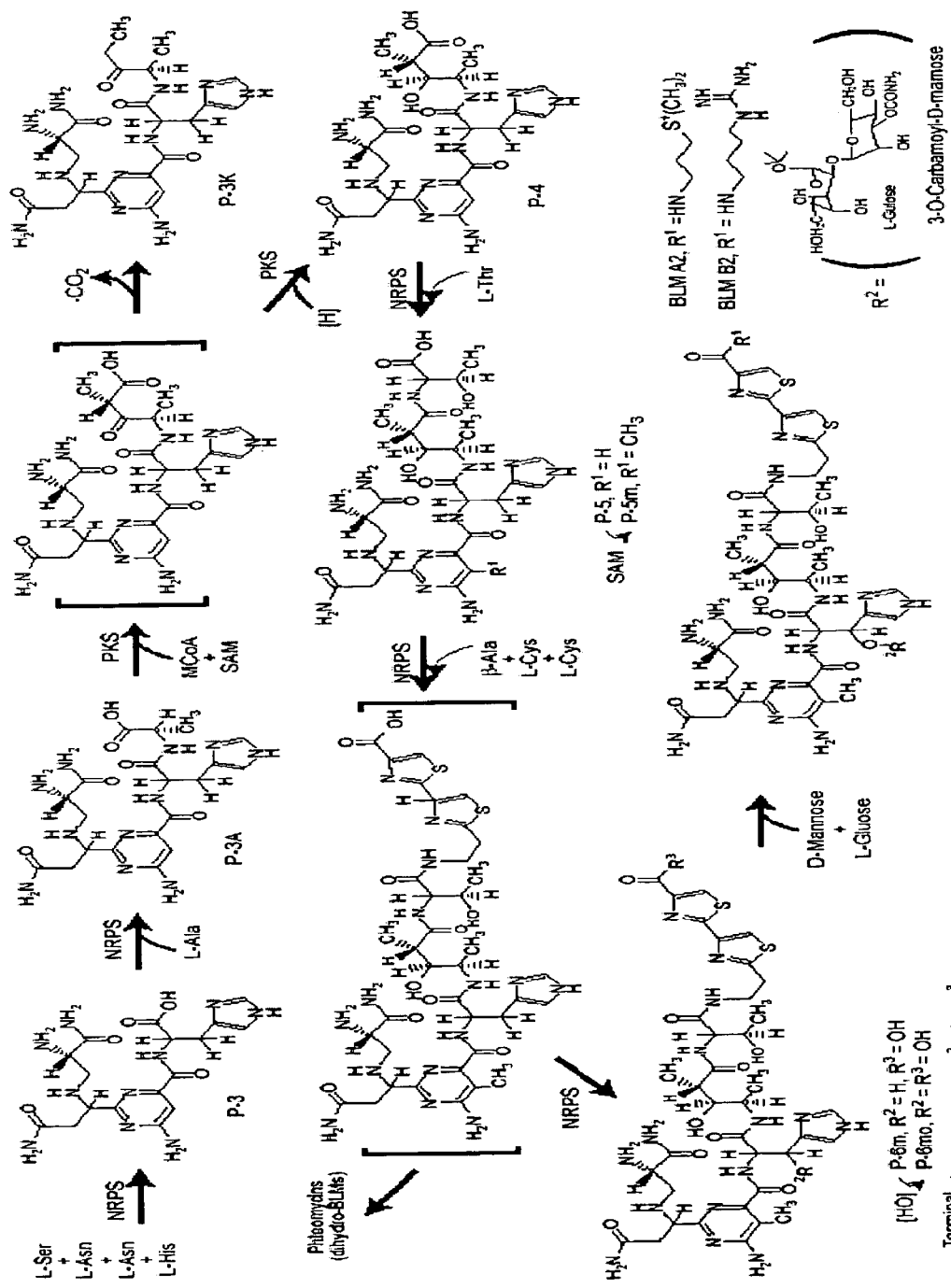
FIGS. 1A and 1B illustrate the biosynthetic pathway for bleomycin in *Sv* (ATCC 15003).

Polyketides and polypeptides can be assembled in a remarkably similar manner by repetitive addition of an extending unit to a growing chain by polyketide synthases (PKS) and nonribosomal peptide synthetase (NRPS) respectively. In the case of polyketides, the extending unit is typically a fatty acid (activated as an acyl CoA thioester) while the extending unit for polypeptides is typically an amino acid (activated as an aminonacyl adenylate). Both the PKS and NRPS systems have evolved a modular organization to define the number, sequence, and specificity of the incorporation of the extending unit and utilized the 4'-phosphopanththeine prosthetic group to channel the growing intermediate during the elongation process.

This invention pertains to the discovery that a PKS-bound growing polyketide intermediate could be further elongated by an NRPS module, or conversely, a NRPS-bound growing polypeptide intermediate can be further elongated by a PKS module. This discovery permits the exploitation of NPRS, PKS, and hybrid NRPS/PKS systems to provide a number of novel hybrid peptide/polyketide metabolites from amino acids and short fatty acids.

It was also a discovery of this invention that this hybrid NRPS/PKS/NRPS system is exemplified by the bleomycin (Blm) biosynthesis pathway in *Streptomyces verticillus* (*Sv.*) (ATCC 15003). The bleomycins are a family of glycopeptide-derived antibiotics originally isolated by Umezawa in 1996 from the fermentation broth of *S. verticillus*. Bleomycins (BLMs) exhibit strong anti-tumor activity are currently used in the treatment of lymphoma, particularly Hodgkin's disease, testicular tumors, squamous cell carcinomas of skin, head, cervix, penis, rectum, and for intracavitary therapy of malignant effusions in ovarian and breast cancer. The commercial product, Blenoxane®, contains BLM A2 and B2 as the principle constituents. Almost uniquely among anticancer drugs, BLM does not cause myelosuppression, promoting its wide application in combination chemotherapy.

In one aspect, this invention provides a cloned and characterized BLM gene cluster consisting of characteristic NRPS and PKS genes from the Blm producer *Streptoveticillum* sp. (ATCC 15003). The cloned and isolated Blm gene cluster provides a method of recombinantly expressing bleomycin and/or bleomycin analogues. Thus, in one embodiment, this invention provides for nucleic acids encoding bleomycin synthetic machinery or subunits thereof, for cells recombinantly modified to express a bleomycin and/or bleomycin analogue, and for a bleomycin or bleomycinh analogue recombinantly expressed in such cells.

Like other polyketide synthase or nonribosomal peptide synthetases, the bleomycin synthetic pathway is organized into modules, each module catalyzing the addition and/or modification of one subunit (e.g. fatty acid or amino acid). Each module is organized into a number of domains each domain having a characteristic activity (e.g. activation, condensation, condensation/cyclization, etc.). The catalytic domains within a module and the modules themselves are often arranged collinearly and the order of biosynthetic modules from $NH_2$- to COOH-terminus on each PKS and NRPS polypeptide and the number and type of catalytic domains within each determine the order of structural and functional elements in the resulting product. The size and complexity of the ultimately formed product are controlled by the number of repeated acyl chain extension steps that are, in turn, a function of the number and placement of carrier protein domains in these multimodular enzymes. The number composition and order of such domains can be altered either to introduce modifications, e.g. into the bleomycin to produce bleomycin analogues, or to produce different or completely new molecules. Such "recombination" is not restricted solely to recombination among the bleomycin catalytic domains and/or modules, but can also involve recombination between beomycin modules and/or subunits and other PKS and/or NRPS modules and/or subunit. Moreover the discovery that synthetic pathways can incorporate both PKS and NRPS modules and/or catalytic domains makes available hybrid PKS/NRPS syntheses.

Thus, in one embodiment this invention contemplates the use of blm gene cluster modules and/or catalytic domains to make various peptide and/or polyketide, and/or hybrid polypeptide/polyketide metabolites (including, but not limited to bleomycin intermediates or shunt metabolites), in combinatorial biosynthesis with other polyketide synthases and/or other nonribosomal peptide synthetases.

The blm gene cluster contains several glycosylases which can be used alone or in context with other PKS and/or NRPS modules or catalytic domains to make various metabolites with sugars associated with bleomycins (bleomycin sugars).

In addition, the blm gene cluster includes a novel methyltransferase domain that can be used to make polyketide metabolites with methyl branch(es).

The blm gene cluster also is characterized by the unusual Cy domains as well as the unprecedented Ox domain (see, e.g. BlmIV and BlmIII NRPSs), providing an efficient biosynthesis for a bithiazole structure. The blm gene cluster, blm modules, or blm catalytic domains can be used either individually or collectively (alone or in combinations with other nonribosomal peptide synthetases or polyketide synthases) to make thiazolidine, thiazoline and thiazole; bi-thiazolidine, bithiazoline, and bithiazole-containing microbioal metabolites.

Other uses include, but are not limited to the usage of the blm gene cluster/modules/catalytic units (either individually or collectively) or the Blm model to make heterocyclic ring-containing microbioal metabolites, such as five member S- and N-containing compounds of the thiazolidine, thiazoline and thiazole family or the O- and N-containing compounds of the oxazolidine, oxazoline, and oxazole family or to make sugars, such L-sugars (with the BlmG epimerase), sugars modified by carbamoyl group (with BlmD), and disaccharides.

This invention also includes the discovery of a novel discrete PCP protein (encoded by the BlmI gene). Apo-BlmI can be efficiently modified into holo-BlmI either in vivo or in vitro by PCP-specific 4'-phosphopantetheine transferases (PPTases) such as Gsp and Sfp. Unlike the PCP domains in type I NRPSs, blmI lacks its cognate A domain and can be aminoacylated by Val-A, an A domain from a completely unrelated type I NRPS. BlmI, therefore, represents the first characterized bype II PCP, providing the genetic and biochemical evidence to support the existence of a bype II NRPS. The latter system is useful, in a manner analogous to the type I NRPS, i.e., modular NRPS, in the combinatorial manipulation of NRPS proteins to generate novel peptides. This invention also includes the discovery and characterization of a novel PPTase (encoded by the pptA gene in FIG. 13). This PPTase can be used in engineered biosynthesis of polyketides, peptides, hybrid peptide and polyketide metabolites, hybrid polyketide and peptide metabolites, or the combination of both types of metabolites. The PPTase can also be used in converting apo-peptidyl carrier proteins (both type I and type II) and acyl carrier proteins (both type I and type II) into the holo-proteins.

The Examples provided herein and the accompanying primers permit one of ordinary skill in the art to isolate the blm gene cluster of this invention, its constituent ORFs, various modules, or enzymatic domains. The isolated nucleic acid components can be used to express one or more polypeptide components for in vivo (e.g. recombinant) synthesis of one or more polypeptides and/or polyketides as indicated above. It will also be appreciated that the blm cluster polypeptides can be used for ex vivo assembly of various macromolecules.

I. BLM Gene Cluster and the PPTase Gene.

A) The BLM Gene Cluster.

The nucleic acids comprising the blm gene cluster are identified in Tables I and II and listed in the sequence listing provided herein (SEQ ID NOS: 1 and 2, GenBank Accession number AF210249 (which replaces sequence AF149091), and SEQ ID NO:3, GenBank Accession number AF210311). In particular, Table I identifies genes and functions of open reading frames (ORFs) responsible for the biosynthesis of the hybrid peptide/polyketide/peptide backbone and sugar moieties of bleomycin, while Table II identifies a number of ORFs comprising the blm gene cluster, identifies the activity of the catalytic domain encoded by the ORF and provides primers for the amplification and isolation of that orf.

As illustrated in Example 1, the blm cluster comprises a PKS module, flanked by several NRPS modules along with several sugar biosynthesis genes and genes encoding other biosynthesis enzymes as well as several resistance and regulatory genes (Table 1).

TABLE I

Determined functions of ORFs in the bleomycin biosynthesis gene cluster

| Gene | Amino acids | Sequence Homolog[1] | Proposed function[2,3] |
| --- | --- | --- | --- |
| orf8 | 424 SEQ ID NO: 115 | YqeR (BAA12461) | Oxidase |
| orf9 (blmC) | 498 SEQ ID NO: 114 | RfaE (AAD07904) | NDP-glucose synthase |
| orf10 (blmI) | 90 SEQ ID NO: 113 | GrsB (P14688) | Type II PCP |
| orf11 (blmD) | 545 SEQ ID NO: 112 | NodU (Q53515) | Carbamoyl transferase |
| orf12 (blmE) | 390 SEQ ID NO: 111 | RfaF (AAD16056) | Glycosyl transferase |
| orf13 | 187 SEQ ID NO: 110 | MbtH (O05821) | Unknown |
| orf14 (blmII) | 462 SEQ ID NO: 109 | Nrp (CAA98937) | NRPS condensation enzyme |
| orf15 | 339 SEQ ID NO: 108 | SyrP (1890776) | Regulation |
| orf16 (blmIII) | 935 SEQ ID NO: 107 | HMWP2 (P48633), McbC (P23185) | A PCP Ox |
| orf17 (blmIV) | 2626 SEQ ID NO: 106 | HMWP2 (P48633) | C A PCP Cy A PCP Cy |
| orf18 | 638 SEQ ID NO: 105 | AsnB (2293165) | Asparagine synthetase |
| orf19 (blmF) | 494 SEQ ID NO: 104 | RfbC (Q50864)/BlmOrf1 (507319) | Glycosyl transferase/β-hydroxylase |
| orf20 (blmG) | 325 SEQ ID NO: 103 | YtcB (2293288) | Sugar epimerase |
| orf21 (blmV) | 645 SEQ ID NO: 102 | McyB (2708278) | PCP C |
| orf22 (blmVI) | 2675 SEQ ID NO: 101 | ACoAS (1658531), PksD (S73014) SnbDE (CAA67249) | A[4] ACP C A PCP C A |
| orf23 (blmVII) | 1218 SEQ ID NO: 100 | SyrE (3510629) | C A PCP |
| orf24 (blmVIII) | 1841 SEQ ID NO: 99 | HMWP1 (CAA73127) | KS AT MT KR ACP |
| orf25 (blmIX) | 1066 SEQ ID NO: 98 | SafB (1171128) | C A PCP |
| orf26 (blmX) | 2162 SEQ ID NO: 97 | TycC (2623773) | C A PCP C A PCP |
| orf27 (blmXI) | 688 SEQ ID NO: 96 | SyrE (3510629) | NRPS condensation enzyme |
| orf28 | 239 SEQ ID NO: 95 | SC9C7 04C (CAA22716) | Unknown |
| orf29 | 582 SEQ ID NO: 94 | YvdB (CAB08068) | Transmembrane transporter |
| orf30 | 113 SEQ ID NO: 93 | SmtB (P30340) | Regulation |
| orf31 | 117 SEQ ID NO: 116 | PhnA (P16680) | Unknown |

[1]Protein accession numbers are given in parentheses.
[2]Underlined domains contain motifs that are clearly different from known NRPS or PKS domains.
[3]This A domain lacks the typical NRPS A1, A2, A4, A8, and A9 motifs and more closely resembles acyl CoA synthases.
ORF1 to ORF7 were reported by Schmidt (1994) Gene 151:17–21, who assigned ORF2 as blmA and ORF4 as blmB.

Noteworthy are the genes encoding the NRPS and PKS enzymes. The blmI, blmII, and blmXI genes encode NRPSs with an unusual architecture. In contrast to all known NRPSs, which are of modular organization with each module consisting minimally of a condensation (C), an adenylation (A), and a peptidyl carrier protein (PCP) domain, BlmI, BlmII, and BlmXI are discrete proteins homologous to individual domains of type I NRPSs. We have characterized BlmI as a type II PCP (Du and Shen (1999) Chem. Biol. 6: 507–517). The BlmII and BlmXI proteins can serve as candidates for type II condensation enzymes.

The blmIII, blmIV, blmV, blmVI, blmVII, blmIX, and blmX genes encode modular NRPSs consisting of domains characteristic for known type I NRPSs, such as the A, PCP, C, and condensation/cyclization (Cy) domains, as well as an unprecedented oxidation (Ox) domain. BlmVI is unique among all the Blm NRPSs identified. Its N-terminal module (NRPS-5) consists of an atypical A domain, which bears a close resemblance to a family of acyl CoA synthases (Fitzmaurice and Kolattukudy (1997) J. Bacteriol. 179: 2608–2615; Fitzmaurice and Kolattukudy (1998) J. Biol. Chem. 273: 8033–8039) and an acyl carrier protein (ACP)-like domain. Its C-terminal module is truncated and presumably interacts with BlmV to constitute the complete NRPS-3 module (FIG. 1B). Also noteworthy are the C domain of NRPS-3 that lacks both His residues of the conserved HHxxxDG (SEQ ID NO: 4) active site for transpeptidation (Stachelhaus et al. (1998) J. Biol. Chem. 273: 22773–22781) and the extra C domain at the C-terminus of BlmV. These unusual features associated with BlmVI and BlmV may play roles in the formation of the β-aminoalaninamide and the pyrimidine moieties of BLM, which are unprecedented in peptide biosynthesis.

The blmVIII gene encodes a PKS module consisting of domains characteristic for known PKSs, such as ketoacyl synthase (KS), acyltransferase (AT), ketoreductase (KR), and ACP, with malonyl CoA acting as an extending unit according to sequence comparison of the AT domain (Haydock et al. (1995) *FEBS Lett*. 374: 246–248) (FIG. 1B).

The identification of an integrated methyltransferase (MT) domain in the middle of BlmVIII is unique, representing the first PKS from actinomycetes that contains an internal MT domain.

TABLE II

Blm gene cluster open reading frames (ORFs) and primers for ORF amplification.

| Orf # | Activity | Method | Primers Forward Reverse | Seq ID No. |
|---|---|---|---|---|
| orf-8 SEQ ID NO:115 | Oxygen-independent coproporphyrinogen III oxidase | Gapped-blast comparison[1] | F: ATGAGCCACGCCATCGGA R: TCAGGCGCGTTCGGGGGC | 5 6 |
| orf-9 SEQ ID NO:114 | ADP-heptose synthase (blmC) | Gapped-blast comparison[1] | F: GTGAACACCGACCTGCCC R: TCATGGGGTGTCTCCCTC | 7 8 |
| orf-10 SEQ ID NO:113 | Peptidyl carrier protein (blmI) | Expression and biochemical characterization.[2] | F: ATGAGCGCCCCGCGGGGC R: TCACCGGTCCCGCTCCCC | 9 10 |
| orf-11 SEQ ID NO:112 | Carbamyltransferase (blmD) | Gapped-blast comparison[1] | F: ATGAGCGCCGACCCGTCC R: TCATGAGCGGGCCGCCGT | 11 12 |
| orf-12 SEQ ID NO:111 | ADP-heptose:LPS heptosyl transferase (blmE) | Gapped-blast comparison[1] | F: ATGACCACCCCCATGACC R: TCATGGGGTACTCCTGAT | 13 14 |
| orf-13 SEQ ID NO:110 | Homolog of mbtH in the synthesis of mycobactin | Gapped-blast comparison[1] | F: ATGACCACGACCCCGCGG R: TCAGGTGCCGGACACGCG | 15 16 |
| orf-14 SEQ ID NO:109 | Peptide synthetase (condensation, blmII) | Gapped-blast comparison[1] | F: GTGACCGCCCCGGCACA R: TCATCGGTGGCTCCTCGT | 17 18 |
| orf-15 SEQ ID NO:108 | Regulatory gene (homolog of syrP) | Gapped-blast comparison[1] | F: GTGAACCGGCACGGCCCC R: TCACGCGCTCACCTCGTC | 19 20 |
| orf-16 SEQ ID NO:107 | Mutated peptide synthetase-oxidase (NRPS-0, blmIII) | Gapped-blast comparison[1] | F: GTGACGAGCGCCCGGCCC R: TCACGGGGCCTCCGTGCG | 21 22 |
| orf-17 SEQ ID NO:106 | Peptide synthetase (NRPS-2-1, blmIV) | Expression and biochemical characterization.[2] | F: ATGCTGCACGGCGCCGCG R: TCACTCCGGTCCACCTCC | 23 24 |
| orf-18 SEQ ID NO:105 | Asparagine synthetase | Gapped-blast comparison[1] | F: GTGAGGCCCGTGTGCGGC R: TCAGCCACCGTTGCCGCC | 25 26 |
| orf-19 SEQ ID NO:104 | Homolog of hydroxylase-dehydrogenase (blmF) | Gapped-blast comparison[1] | F: GTGAAGGACCTCGGCCGG R: TCACTCCCCCGGTGCCGG | 27 28 |
| orf-20 SEQ ID NO:103 | Nucleotide-sugar epimerase (blmG) | Gapped-blast comparison[1] | F: GTGACATGGACCGTGGTG R: TCAGGCATCGGCCCTCCC | 29 30 |
| orf-21 SEQ ID NO:102 | Peptide synthetase (NRPS-3CT, blmV) | Gapped-blast comparison[1] | F: ATGCGCGGGCATGACGAC R: TCACGGTGTCTCTCCCTC | 31 32 |
| orf-22 SEQ ID NO:101 | Peptide synthetase (NRPS-5-4-3, blmVI) | Expression and biochemical characterization.[2] | F: ATGAGCCGGCCGGCCGGC R: TCATGCTCGGTCATCGCC | 33 34 |
| orf-23 SEQ ID NO:100 | Peptide synthetase (NRPS-6, blmVII) | Expression and biochemical characterization.[2] | F: GTGACCACGCCCCGCATC R: TCATTCGGGACGCGGGCA | 35 36 |
| orf-24 SEQ ID NO:99 | Polyketide synthase (blmVIII) | Gapped-blast comparison[1] | F: ATGAGCCATGCCGACGCG R: TCACAGCACCACCTCTTC | 37 38 |
| orf-25 SEQ ID NO:98 | Peptide synthetase (NRPS-7, blmIX) | Gapped-blast comparison[1] | F: ATGACCCCGGCCGCCGAC R: TCATCGTCCGCCGCCTTT | 39 40 |
| orf-26 SEQ ID NO:97 | Peptide synthetase (NRPS-9-8, blmX) | Gapped-blast comparison[1] | F: ATGCCTCGGTGTGCCCGA R: TCATTCGGCGGCACCTCC | 41 42 |
| orf-27 SEQ ID NO:96 | Peptide synthetase (condensation, blmXI) | Gapped-blast comparison[1] | F: GTGGGTTTCCGTCGAGCG R: TTACACCCTCCGTTTCTC | 43 44 |
| orf-28 SEQ ID NO:95 | Phosphatidylserine decarboxylase | Gapped-blast comparison[1] | F: ATGGCACAGGACCTGAAC R: TCAACGCCACCGGATCTT | 45 46 |
| orf-29 SEQ ID NO:94 | Transmembrane transporter | Gapped-blast comparison[1] | F: GTGAGCTCCCTCGCCGTC R: TCATCGTCGGGCACTCGG | 47 48 |
| orf-30 SEQ ID NO:93 | Metal dependent regulatory element | Gapped-blast comparison[1] | F: GTGCCGGTTCCGCTGTAT R: TCACCGGGCACTGACCTC | 49 50 |
| orf-31 SEQ ID NO:116 | PHNA homolog | Gapped-blast comparison[1] | F: GTGACCGAGAACCTTCCG R: TCAGACCTTCTTGACCAC | 51 52 |
| orf-32 SEQ ID NO:117 | Peptide synthetase (NRPS-11-10) | Gapped-blast comparison[1] | F: ATGGCCTCAGACGCTTTG R: TCATTGAGACTCCTCCTC | 53 54 |
| orf-33 SEQ ID NO:118 | Putative transporter | Gapped-blast comparison[1] | F: ATGATGAAGTCAAGCCGC R: TCAGTGGCTTACAAGGAG | 55 56 |
| orf-34 | Homolog of | Gapped-blast | F: ATGACTGACCTGCCGTTG | 57 |

TABLE II-continued

Blm gene cluster open reading frames (ORFs) and primers for ORF amplification.

| Orf # | Activity | Method | Primers Forward Reverse | Seq ID No. |
|---|---|---|---|---|
| SEQ ID NO:119 | clavaminic acid synthase | comparison[1] | R: TCACACCAGCAGCGAGGT | 58 |
| orf-35 | Thioesterase | Gapped-blast | F: ATGGATTTCCCCCTCACC | 59 |
| SEQ ID NO:120 | | comparison[1] | R: TCATGCCCCTACCTCGGC | 60 |
| orf-36 | Putative transporter | Gapped-blast | F: ATGACCGCGCGCGTCGAC | 61 |
| SEQ ID NO:121 | | comparison[1] | R: TCACTCCTCGGCTTCGGC | 62 |
| orf-37 | Unknown | Gapped-blast | F: GTGTCCAAGAACGCGGCG | 63 |
| SEQ ID NO:122 | | comparison[1] | R: TCATCGGCTCGCCTCGTG | 64 |
| orf-38 | Peptide synthetase | Gapped-blast | F: ATGACCCTCACCCTGCGG | 65 |
| SEQ ID NO:123 | (NRPS-12) | comparison[1] | R: TCACTCGGGCACTCCTTC | 66 |
| orf-39 | Regulatory gene | Gapped-blast | F: GTGACCGGTTCCGTAACG | 67 |
| SEQ ID NO:124 | (homolog of SyrP) | comparison[1] | R: TCATGAGTCCGCCGAGGT | 68 |
| orf-40 | Peptide synthetase | Gapped-blast | F: ATGACAGAGGTCCGAGGT | 69 |
| SEQ ID NO:125 | | comparison[1] | R: CCCGGCAACCGCCCTCCC | 70 |
| orf-41 | 4'- | Expression and | F: GTGATCGCCGCCCTCCTG | 71 |
| SEQ ID NO:126 | phosphopantetheinyl transferase (pptA) | biochemical characterization.[2] | R: TTACGGGACGGCGGTCCG | 72 |

Figure 1B:
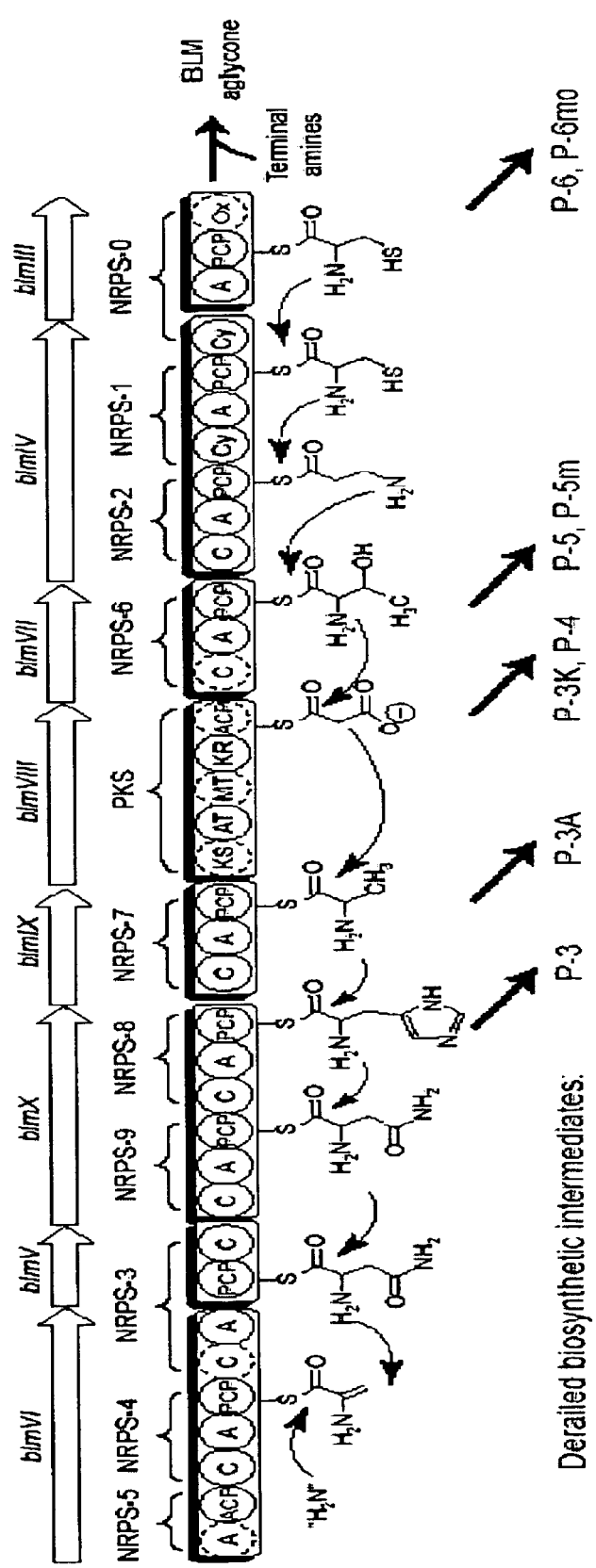

The Blm megasynthetase comprises nine NRPS modules and one PKS module forming a hybrid NRPS/PKS/NRPS metasynthetase (FIG. 1A). Inspection of the blm gene cluster (FIG. 2) showed that the Blm NRPS and PKS modules apparently are not organized according to the "colinearity rule" for BLM biosynthesis (FIG. 1). Detailed functional organization of the megasynthetase and the BLM synthetic pathway is provided in Example I.

B) PPTase

This invention also provides the gene (pptA, FIG. 13) encoding phosphopantetheine transferase (PPTase) (GenBank Accession No: AF210311) (see, SEQ ID NO: 3). PPTase converts carrier proteins for the growing acyl chain from inactive apo-forms to functional holo-forms by the covalent attachment of the 4'-phosphopantetheine moiety of coenzyme A to a conserved serine residue of the carrier-protein substrate (see, e.g., FIG. 1A).

Using the sequence information provided herein (e.g. primer sequences and PPTase sequence) the PPTase nucleic acids can be routinely isolated according to standard methods (e.g. PCR amplification). Detailed protocols for the isolation of the PPTase are provided in Example 3.

Other PPTases can be identified using the probes and primers illustrated in Example 3. Briefly, using a primer to the THC motif (5'-C GGC ATG GTC GGC TCC HTN CAN CAY TG-3' (SEQ ID NO: 73) where H=C+A, N=A+C+T+G, Y=C+T, K=G+T, R=A+G, W=T+A), and a primer designed around the typical C-terminal PPTase motif (e.g., KEA-1: 5'-T GCA GCA GAA CAG GAG GCK NYC CCA NKG-3' (SEQ ID NO: 74) and KEA-2: 5'-TG GGT CAG CGG GTA CCA NRC YTT RWA-3' (SEQ ID NO: 75), and using S. verticillus chromosomal DNA as template, the set of primers THC/KEA-2 a probe can be amplified (about 250 bp), that specifically binds to a PPTase. Libraries of organisms comprising NRPS, PKS, and/or hybrid PKS/NRPS pathways can be probed for the presence of a PPTase sequence. Once hybridizing clones are identified, the PPTase sequence can be isolated according to standard methods well know to those of skill in the art (see, e.g., Example 3).

C) Isolation/Preparation of Nucleic Acids

In one embodiment, this invention provides nucleic acids for the recombinant expression of a bleomycin. Such nucleic acids include isolated gene cluster(s) comprising open reading frames encoding polypeptides sufficient to direct the assembly of a bleomycin.

In other embodiments of this invention, modified bleomycins (e.g. bleomycin analogs), novel polyketides, polypeptides, and combinations thereof (polyketide/polypeptide hybrids) are created by modifying-PKSs and/or NRPSs so as to introduce variations into known polymers synthesized by the enzymes. Such variations may be introduced by design, for example to modify a known molecule in a specific way, e.g. by replacing a single monomeric unit within a polymer with another, thereby creating a derivative molecule of predicted structure. Alternatively, variations can be made randomly, for example by making a library of molecular variants of a known polymer by systematically or haphazardly replacing one or more modules or enzymatic domains in a known PKS or NRPS with a collection of alternative modules or domains. Production of alternative/modified PKSs, NRPSs and hybrid systems is described below.

Using the primer and sequence information provided herein, one of ordinary skill in the art can routinely isolate/clone the PKS and/or NRPS modules and/or enzymatic domains described herein. For example, the PCR primers provided in Table II, above, can be used to amplify any of the orfs identified therein. Moreover, using the sequence information for the blm gene cluster provided herein, the design of other primers suitable of the amplification of individual ORFs, combinations of ORFs, genes, etc. is routine.

Typically such amplifications will utilize the DNA of an organism containing the requisite genes (e.g. Streptomyces verticillus) as a template. Typical amplification conditions include a PCR mixture consisting of 5 ng of S verticillus genomic or plasmid DNA as template, 25 pmoles of each primers, 25 µM dNTP, 5% DMSO, 2 units of Taq polymerase, 1× buffer, with or without 20% glycerol in a final volume of 50 µL. PCR is carried out (e.g. on a Gene Amp PCR System 2400 (Perkin-Elmer/ABI)) with a cycling scheme as follows: initial denaturing at 94° C. for 5 min, 24–36 cycles of 45 sec at 94° C., 1 min at 60° C., 2 min at 72° C., followed by additional 7 min at 72° C. One of skill will appreciate that optimization of such a protocol, e.g. to improve yield, etc. is routine (see, e.g., U.S. Pat. No. 4,683,202; Innis (1990) PCR Protocols A Guide to Methods and Applications Academic Press Inc. San Diego, Calif., etc). In addition, primer may be designed to introduce restriction sites and so facilitate cloning of the amplified sequence into a vector.

Using the information provided herein other approaches to cloning the desired sequences will be apparent to those of skill in the art. For example, the PKS or NRPS modules or enzymatic domains of interest can be obtained from an organism that expresses the same, using recombinant methods, such as by screening cDNA or genomic libraries, derived from cells expressing the gene, or by deriving the gene from a vector known to include the same. The gene can then be isolated and combined with other desired NRPS and/or PKS modules or domains, using standard techniques. If the gene in question is already present in a suitable expression vector, it can be combined in situ, with, e.g., other PKS subunits, as desired. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence can be assembled from overlapping oligonucleotides prepared by standard methods and assembled into a complete coding sequence (see, e.g., Edge (1981) *Nature* 292:756; Nambair et al. (1984) *Science* 223: 1299; Jay et al. (1984) *J. Biol. Chem.* 259:6311). In addition, it is noted that custom gene synthesis is commercially available (see, e.g. Operon Technologies, Alameda, Calif.).

Examples of such techniques and instructions sufficient to direct persons of skill through many cloning exercises are found in Berger and Kimmel (1989) *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY; Ausubel (19 1994) *Current Protocols in Molecular Biology*, Current Protocols, a joint venture between Greene Publishing Associates, Inc. and John Wiley & Sons, Inc., U.S. Pat. No. 5,017,478; and European Patent No. 0,246,864.

II. Expression of blm Gene Clusters Modules, and Enzymatic Domains

As indicated above, in one embodiment this invention provides novel NRPS and PKS genes for the efficient recombinant production of both novel and known polyketides, peptides, and polyketide/polypeptide hybrids by expressing them in vivo. In other embodiments, such syntheses are carried out in vitro. Even in vitro syntheses, however, typically utilize recombinantly expressed PKSs, NRPSs, or enzymatic domains thereof. Thus, it is frequently desirable to express protein components of the PKSs or NRPs described above.

Typically expression of the protein components of the pathway and/or of the products of the NRPS/PKS pathway is accomplished by placing the subject PKS or NRPS nucleic acid(s) in an expression vector, and transfecting a cell with the vector such that the cell expresses the desired product(s).

A) Expression Vectors

The choice of vector depends on the sequence(s) that are to be expressed. Any transducible cloning vector clan be used as a cloning vector for the nucleic acid constructs of this invention. However, where large clusters are to be expressed, it phagemids, cosmids, P1s, YACs, BACs, PACs, HACs or similar cloning vectors be used for cloning the nucleotide sequences into the host cell. Phagemids, cosmids, and BACs, for example, are advantageous vectors due to the ability to insert and stably propagate therein larger fragments of DNA than in M13 phage and lambda phage, respectively. Phagemids which will find use in this method generally include hybrids between plasmids and filamentous phage cloning vehicles. Cosmids which will find use in this method generally include lambda phage-based vectors into which cos sites have been inserted. Recipient pool cloning vectors can be any suitable plasmid. The cloning vectors into which pools of mutants are inserted may be identical or may be constructed to harbor and express different genetic markers (see, e.g., Sambrook et al., supra). The utility of employing such vectors having different marker genes may be exploited to facilitate a determination of successful transduction.

In preferred embodiments of this invention, vectors are used to introduce PKS, NRPS, or NRPS/PKS genes or gene clusters into host (e.g. *Streptomyces*) cells. Numerous vectors for use in particular host cells are well known to those of skill in the art. For example described in Malpartida and Hopwook, (1984) *Nature*, 309:462–464; Kao et al., (1994), *Science*, 265: 509–512; and Hopwood et al., (1987) *Methods Enzymol.*, 153:116–166 all describe vectors for use in various *Streptomyces* hosts.

In a preferred embodiment, *Streptomyces* vectors are used that include sequences that allow their introduction and maintenance in *E. coli*. Such *Streptomyces/E. coli* shuttle vectors have been described (see, for example, Vara et al., (1989) *J. Bacteriol.*, 171:5872–5881; Guilfoile & Hutchinson (1991) *Proc. Natl. Acad. Sci. USA*, 88: 8553–8557.)

The gene sequences, or fragments thereof, which collectively encode a PKS and/or NRPS and/or PKS/NRPS gene cluster, one or more ORFs, one or more modules, or one or more enzymatic domains of this invention, can be inserted into one or more expression vectors, using methods known to those of skill in the art. Expression vectors will include control sequences operably linked to the desired NRPS and/or PKS coding sequence or fragment thereof. Suitable expression systems for use with the present invention include systems that function in eucaryotic and prokaryotic host cells. However, as explained above, prokaryotic systems are preferred, and in particular, systems compatible with *Streptomyces* spp. are of particular interest. Control elements for use in such systems include promoters, optionally containing operator sequences, and ribosome binding sites. Particularly useful promoters include control sequences derived from PKS and/or NRPS gene clusters, such as one or more act promoters. However, other bacterial promoters, such as those derived from sugar metabolizing enzymes, such as galactose, lactose (lac) and maltose, will also find use in the present constructs. Additional examples include promoter sequences derived from biosynthetic enzymes such as tryptophan (trp), the beta-lactamase (bla) promoter system, bacteriophage lambda PL, and T5. In addition, synthetic promoters, such as the tac promoter (U.S. Pat. No. 4,551,433), which do not occur in nature also function in bacterial host cells. In *Streptomyces*, numerous promoters have been described including constitutive promoters, such as ermE and tcmG (Shen and Hutchinson, (1994) *J. Biol. Chem.* 269: 30726–30733), as well as controllable promoters such as actI and actIII (Pleper et al., (1995) *Nature*, 378: 263–266; Pieper et al., (1995) *J. Am. Chem. Soc.*, 117: 11373–11374; and Wiesmann et al., (1995) *Chem. & Biol.* 2: 583–589).

Other regulatory sequences may also be desirable which allow for regulation of expression of the PKS replacement sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid. Alternatively, several polyketides are naturally colored and this characteristic provides a built-in marker for selecting cells successfully transformed by the present constructs.

The various PKS and/or NRPS clusters or subunits of interest can be cloned into one or more recombinant vectors as individual cassettes, with separate control elements, or under the control of, e.g., a single promoter. The PKS and/or NRPS subunits can include flanking restriction sites to allow for the easy deletion and insertion of other PKS subunits so that hybrid PKSs can be generated. The design of such unique restriction sites is known to those of skill in the art and can be accomplished using the techniques described above, such as site-directed mutagenesis and PCR.

Methods of cloning and expressing large nucleic acids such as gene clusters, including PKS- or NRPS-encoding gene clusters, in cells including *Streptomyces* are well known to those of skill in the art (see, e.g., Stutzman-Engwall and Hutchinson (1989) *Proc. Natl. Acad. Sci. USA*, 86: 3135–3139; Motamedi and Hutchinson (1987) *Proc. Natl. Acad. Sci. USA*, 84: 4445–4449; Grim et al. (1994) *Gene*, 151: 1–10; Kao et al. (1994) *Science*, 265: 509–512; and Hopwood et al. (1987) *Meth. Enzymol.*, 153:116–166). In some examples, nucleic acid sequences of well over 100 kb have been introduced into cells, including prokaryotic cells, using vector-based methods (see, for example, Osoegawa et al., (1998) *Genomics*, 52: 1–8; Woon et al., (1998) *Genomics*, 50: 306–316; Huang et al., (1996) *Nucl. Acids Res.*, 24: 4202–4209). In addition, the cloning and overexpression of NRPS-1 and NRPS-6 is illustrated in Example 1.

In certain embodiments this invention may make use of genetically engineered cells that either lack PKS and/or NRPS genes or have their naturally occurring PKS and/or NRPS genes substantially deleted. These host cells can be transformed with recombinant vectors, encoding a variety of PKS and/or NRPS gene clusters, for the production of active polyketides. The invention provides for the production of significant quantities of product, e.g. a bleomycin, at an appropriate stage of the growth cycle. The BLMs or other hybrid polyketide/peptide metabolites so produced can be used as therapeutic agents, to treat a number of disorders, depending on the type of metabolites in question. For example, several of the polyketides and peptides produced by the present method will find use as immunosuppressants, as anti-tumor agents, as well as for the treatment of viral, bacterial and parasitic infections. The ability to recombinantly produce polyketides and peptides also provides a powerful tool for characterizing PKSs and/or NRPSs and the mechanism of their actions.

B) Host Cells

The vectors described above can be used to express various protein components of the polyketide and/or polypeptide synthetic modules for subsequent isolation and/or to provide a biological synthesis of one or more desired biomolecules (e.g. polyketides, peptides, etc.). Where one or more proteins of the blm cluster are expressed (e.g. overexpressed) for subsequent isolation and/or characterization, the proteins are expressed in any prokaryotic or eukaryotic cell suitable for protein expression. In one preferred embodiment, the proteins are expressed in *E. coli*. Overexpression of blmI in *E. coli* is described in Example 2.

Host cells for the recombinant production of the subject polyketides can be derived from any organism with the capability of harboring a recombinant PKS, NRPS or PKS/NRPS gene cluster. Thus, the host cells of the present invention can be derived from either prokaryotic or eucaryotic organisms. However, preferred host cells are those constructed from the actinomycetes, a class of mycelial bacteria which are abundant producers of a number of polyketides and peptides. A particularly preferred genus for use with the present system is *Streptomyces*. Thus, for example, *S. verticillus S. ambofaciens, S. avermitilis, S. azureus, S. cinnamonensis, S. coelicolor, S. curacoi, S. erythraeus, S. fradiae, S. galilaeus, S. glaucescens, S. hygroscopicus, S. lividans, S. parvulus, S. peucetius, S. rimosus, S. roseofulvus, S. thermotolerans, S. violaceoruber*, among others, will provide convenient host cells for the subject invention, with *S. coelicolor* being preferred (see, e.g., Hopwood, D. A. and Sherman, D. H. *Ann. Rev. Genet.* (1990) 24:37–66; O'Hagan, D. *The Polyketide Metabolites* (Ellis Horwood Limited, 1991), for a description of various polyketide-producing organisms and their natural products.)

In a preferred embodiment, the above-described cells are genetically engineered by deleting one or more naturally occurring PKS and/or NRPS genes therefrom, using standard techniques, such as by homologous recombination. (see, e.g., Khosla, et al. (1992) *Molec. Microbiol.* 6: 3237).

In certain embodiments, a eukaryotic host cell is preferred (e.g. where certain glycosylation patterns are desired). Suitable eukaryotic host cells are well known to those of skill in the art. Such eukaryotic cells include, but are not limited to yeast cells, insect cells, plant cells, fungal cells, and various mammalian cells (e.g. COS, CHO HeLa cells lines and various myeloma cell lines).

C) Protein/Polyketide Recovery

Polypeptide and/or polyketide recovery is accomplished according to standard methods well known to those of skill in the art. Thus, for example where blm cluster proteins are to be expressed and isolated, the proteins can be expressed with a convenient tag to facilitate isolation (e.g. a His$_6$) tag. Other standard protein purification techniques are suitable and well known to those of skill in the art (see, e.g., Quadri et al. (1998) *Biochemistry* 37: 1585–1595; Nakano et al. (1992) *Mol. Gen. Genet.* 232: 313–321, etc.).

Similarly where components (e.g. modules and/or enzymatic domains) of the blm cluster are used to express various biomolecules (e.g. polyketides, sugars, polypeptides, etc.) the desired product and/or shunt metabolite(s) are isolated according to standard methods well know to those of skill in the art (see, e.g., Carreras and Khosla (1998) supra.) Purification and in vitro reconstitution of the essential protein components of an aromatic polyketide synthase. *Biochemistry* 37: 2084–2088, Deutscher (1990) *Methods in Enzymology Volume* 182: *Guide to Protein Purification*, M. Deutscher, ed.

III. Synthesis of Recombinant Bleomycins

In one embodiment this invention provides methods of synthesizing bleomycins and recombinantly synthesized bleomycins. As indicated above, this is generally accomplished by providing an organism (e.g. a bacterial cell) containing sufficient components of the blm gene cluster to direct synthesis of a complete bleomycin.

In one embodiment, the entire blm cluster is cloned into a *Streptomyces* strain (e.g., *S. lividans* or *S. coelicolor*). Kao et al. (1994) *Science*, 265: 509–512, have cloned the 30 kb DEBS genes from *Sacc. erythmea* into *S. coelicolor* and produced 6-deoxyerythronolide B in *S. coelicolor* and these methods can be used construct an expression plasmid for heterologous expression of the blm cluster. This method involves the transfer of DNA between a temperature-sensitive plasmid and a shuttle vector by means of a homologous double recombination event in *E. coli* (Id.). In a preferred embodiment, the two ends spanning the blm cluster are cloned into a temperature-sensitive plasmid that is chloramphenicol resistant ($CM^R$) such as pCK6. *S. verticillus* DNA is then rescued from a donor into the temperature-sensitive recipient by co-transforming *E. coli* with the $Cm^R$ recipient plasmid and the apramycin resistant ($Ap^R$) pKC505 donor cosmid that contains the blm gene cluster, followed by chloramphenicol and apramycin selection at 30° C. Colonies harboring both plasmids ($Cm^R$, $Ap^R$) will be shifted to 44° C. on chloramphenicol and apramycin plates and only those cointegrates formed by a single recombination event between the two plasmids are viable. Surviving colonies are then propagated at 30° C. on $Cm^R$ plates to select for recombinant plasmids formed by the resolution of cointegrates through a second recombinant event. The desired blm cluster is cloned into the $Cm^R$ temperature-sensitive plasmid and is ready to be moved into any expression plasmid by a similar means of homologous recombinant event.

For example, if pWHM861 is the choice of shuttle plasmid for the expression of the blm cluster in *S. lividans* (Meurer and Hutchinson (1995) *J. Bacteriol.*, 177: 477–481), the two ends spanning the blm cluster downstream of the ErmE* promoter in the ampicillin resistant ($AM^R$) plasmid pWHM861 are cloned. The resulting plasmid is co-transformed with the temperature-sensitive plasmid containing the blm cluster described above into *E. coli* under the selection of chloramphenicol and ampicillin at 30° C. These $Cm^R$ and $AM^R$ colonies are shifted to 44° C. on chloramphenicol and ampicillin plates to undergo a single recombination event and the surviving colonies are resolved on ampicillin plates at 30° C. by completing the double recombination process. The resulting plasmid is suitable for transformation into *S. lividans* by selection of thiostrepton, in which the expression of the desired blm cluster is under the control of the ErmE* promoter. The *S. lividans* transformants are cultured and any metabolites produced are isolated and characterized.

Once production of BLM in *S. lividans* is established, mutated alleles of the blm synthetase can be introduced into the blm cluster for the production of BLM analogs.

IV. Altered Endogenous Expression of Bleomycins

Using the Blm gene cluster information provided herein, one of skill in the art may regulating the synthesis of endogenous bleomycin. The expression of various ORFs comprising the blm gene cluster may be increased or decreased to alter bleomycin synthesis levels.

Methods of altering the expression of endogenous genes are well known to those of skill in the art. Typically such methods involve altering or replacing all or a portion of the regulatory sequences controlling expression of the particular gene that is to be regulated. In a preferred embodiment, the regulatory sequences (e.g., the native promoter) upstream of one or more of the blm ORFs are altered.

This is typically accomplished by the use of homologous recombination to introduce a heterologous nucleic acid into the native regulatory sequences. To downregulate expression of one or more blm ORFs, simple mutations that either alter the reading frame or disrupt the promoter are suitable.

To upregulate expression of the blm ORF(s) the native promoter(s) can be substituted with heterologous promoter(s) that induce higher than normal levels of transcription.

In a particularly preferred embodiment, nucleic acid sequences comprising the structural gene in question or upstream sequences are utilized for targeting heterologous recombination constructs.

The use of homologous recombination to alter expression of endogenous genes is described in detail in U.S. Pat. No. 5,272,071, WO 91/09955, WO 93/09222, WO 96/29411, WO 95/31560, and WO 91/12650.

V. Synthesis of BLM Analogs.

In one embodiment, this invention provides methods of synthesizing modified bleomycins or bleomycin analogs. In preferred embodiments, the BLM analogs are synthesized either by introducing specific perturbations into individual NRPS and/or PKS enzymatic domains or modules, or by reprogramming the linear order in which the NRPS or PKS enzymatic domains and/or modules appear in the blm synthetase genes. The former will lead to BLM analogs with targeted modifications at the BLM backbone and the latter will allow incorporation of other extension units in variable sequence into the biosynthesis of BLM. In particularly preferred embodiments, the genetically modified blm synthetases are produced in *S. verticilus*, however, it will be recognized that the entire blm gene cluster can be cloned into other hosts, e.g. into *S. lividans* or *S. coelicolor*.

In preferred embodiments modification of the blm gene cluster to yield BLM analogues is accomplished by one of two different approaches. In one approach, the BLM enzymatic domains and/or modules are altered in a directed manner (i.e. they are changed in a preselected way), while in another approach, random/haphazard alterations are introduced into the blm cluster and the resulting products are screened to identify those with desired properties.

A) Synthesis of BLM Analogs by Specific Engineering of the blm Synthetase Genes

The blm synthetase genes can be re-engineered by means of specific mutations or by reprogramming the linear order of the NRPS or PKS enzymatic domains or modules. In this approach, a wild-type blm synthetase allele is replaced with these mutants in and expressed in an appropriate host (e.g., *S. verticillus* or in a heterologous host). Since both NRPSs (Stachelhaus et al. (1995) *Science*, 269: 69–72) and PKSs (Donadio et al. (1993) *Proc. Natl. Acad. Sci. USA*, 90: 7119–7123, Donadio et al. (1995) *J. Am., Chem. Soc.*, 117: 9105–9106, Cortes et al. (1995) *Science*, 268: 1487–1489) have shown considerable tolerance to reprogramming, it is expected that these modifications of the BLM synthetase will result in the production of BLM analogs with predicted structural alterations. For example, targeted modification at the (2S,3S,4R)-4-amino-3-hydroxy-2-methyl/pentanoic acid AHM moiety of BLM can be accomplished by introduction of mutations into the BLMVIII PKS module of the BLM synthetase locus. Inactivation of the MT or KR motif by in-frame deletion or site-directed mutagenesis will result in the production of BLM analogs containing a demethyl-AHM, oxo-AHM, or oxo-demethyl-AHM moiety, etc.

Alternatively, individual functional NRPS domains and/or the PKS module can be deleted or the PKS module can be duplicated in-frame to produce BLM analogs with shorter or longer backbone, respectively. Alternatively, or in addition, the NRPS domains or the PKS module can be rearranged for the production of BLM analogs with a completely different backbone. The NRPS and PKS features can be combined into one integrated system, providing access to a structural variation not available by either the NRPS or PKS system alone.

To create such mutations, plasmids are constructed carrying in-frame deletions of DNA segments encompassing a portion of the blm synthetase activities. Construction of specific deletions is preferably accomplished by one of the following two strategies. The first involves subcloning of a DNA fragment in a gene replacement vector, selection of two restriction sites suitably located at the two ends of the DNA segments, and deletion of this segment from within the plasmid by rejoining the two resulting ends. An in-frame deletion can be obtained by a suitable combination of Klenow filling and S1 treatment of both ends prior to ligation.

The second approach involves polymerase chain reaction (PCR) amplification of two DNA segments that separate the region to be deleted followed by joining of the two fragments in the correct orientation in a gene replacement vector. This can be accomplished by designing PCR primers with suitable restriction sites. The restriction site used to generate the deletion and the sequences to serve as templates for the PCR amplification are chosen so as to generate two segments of blm synthetase DNA of approximately equal length in the construction in order to maximize the chance of gene replacement. The gene replacement vector containing the allelic or deletion mutation is introduced into a *Streptomyces* strain (e.g., *S. verticillus*). Integration of the plasmid into the *S. verticillus* chromosome via a single reciprocal homologous recombination will yield a recombinant that will be isolated by selection for the vector marker. The resulting integrants are then grown under non-selective conditions and further resolution by selection for the loss of the vector marker via the second homologous recombination event will produce the desired deletion mutants.

Southern analysis of the isolated deletion mutants with the target DNA is performed to ensure that the expected double crossover recombination event has taken place. The first approach is convenient if there are suitably spaced restriction sites in the DNA sequence. The second approach enables the deletion of any DNA segment but may be limited by the size of the DNA segments that can be amplified by PCR. These *S. verticillus* recombinants are cultured under typical conditions for BLM production and the fermentation broth is screened for the production of any novel BLM analogs resulted from the specific mutations in the blm synthetase locus.

B) Synthesis of BLM Analogs by "Random" Modification of blm Synthetase Genes

Bleomycin analogs can also be synthesized by randomly/haphazardly altering genes in the BLM cluster expressing the products of the randomly modified megasynthetase and then screening the products for the desired activity. Methods of "randomly" altering blm cluster genes are described below.

VI. Generation of other Synthetic Systems

In addition to the production of bleomycin or modified bleomycins, the blm gene cluster or elements thereof can be used by themselves or in combination with NRPS and/or PKS modules and/or enzymatic domains of other PKS and/or NRPS systems to produce a wide variety of compounds including, but not limited to various polyketides, polypeptides, polyketide/polypeptide hybrids, various oxazoles and thiazoles, various sugars, various methylated polypeptides/polyketides, and the like. As with the production of modified bleomycins described above, such compounds can be produced, in vivo or in vitro, by catalytic biosynthesis using large, modular PKSs, NRPSs, and hybrid PKS/NRPS systems. The megasynthetases directing such syntheses can be rationally designed e.g. by predetermined alteration/modification of polyketide and/or polypeptide and/or hybrid PKS/NRPS pathways. Alternatively, large combinatorial libraries of cells harboring various megasynthetases can be produced by the random modification of particular pathways and then selected for the production of a molecule or molecules of interest. It will be appreciated that, in certain embodiments, such libraries of megasynthetases/modified pathways, can be used to generate large, complex combinatorial libraries of compounds which themselves can be screened for a desired activity.

A) Directed Modification of Biomolecules

Elements (e.g. open reading frames) of the blm biosynthetic gene cluster and/or variants thereof can be used in a wide variety of "directed" biosynthetic processes (i.e. where the process is designed to modify and/or synthesize one or more particular preselected metabolite(s)). Polypeptides encoded by particular open reading frames or combinations of open reading frames can be utilized to perform particular chemical modifications of biological molecules.

Thus, for example, open reading frames encoding a polypeptide synetase can be used to chemically modify an amino acid by coupling it to another amino acid. In another example, the methyl transferase in BlmVIII can be utilized to introduce methyl groups into polyketides, and other, substrates. The glycosyl transferases can be used to glycosylate appropriate substrates, and so forth. These examples, are merely illustrative. One of skill in the art, utilizing the information provided here, can perform literally countless chemical modifications and/or syntheses using either "native" bleomycin biosynthesis metabolites as the substrate molecule, or other molecules capable of acting as substrates for the particular enzymes in question. Other substrates can be identified by routine screening. Methods of screening enzymes for specific activity against particular substrates are well known to those of skill in the art.

The biosyntheses can be performed in vivo, e.g. by providing a host cell comprising the desired blm gene cluster open reading frame(s) and/or in vivo, e.g., by providing the polypeptides encoded by the blm gene cluster ORFs and the appropriate substrates and/or cofactors.

B) Directed Engineering of Novel Synthetic Pathways

In numerous embodiments of this invention, novel polyketides, polypeptides, and combinations thereof are created by modifying known PKSs or NRPSs so as to introduce variations into known polymers synthesized by the enzymes. Such variations may be introduced by design, for example to modify a known molecule in a specific way, e.g. by replacing a single monomeric unit within a polymer with another, thereby creating a derivative molecule of predicted structure. Such variations can also be made by adding one or more modules to a known PKS or NRPS, or by removing one or more module from a known PKS or NRPS. Such novel PKSs or NRPSs can readily be made using a variety of techniques, including recombinant methods and in vitro synthetic methods.

Using any of these methods, it is possible to introduce PKS domains into a NRPS, or vice versa, thereby creating novel molecules including both peptide and polyketide structural domains. For example, a PKS enzyme producing a known polyketide can be modified so as to include an additional module that adds a peptide moiety into the polyketide. Novel molecules synthesized using these methods can be screened, using standard methods, for any activity of interest, such as antibiotic activity, effects on the cell cycle, effects on the cytoskeleton, etc.

Novel polyketides, polypeptides, or combinations thereof can also be made by creating novel PKSs or NRPSs de novo, using recombinant or in vitro synthetic methods. Such novel arrangements of domains can be designed, i.e. to create a specific polymer. In addition to creating novel PKSs or NRPSs by combining modules, the methods of this invention can also be used to make novel modules that can add new monomeric units to a growing polypeptide or polyketide chain. Because the identity of each module, and, consequently, the identity of the monomer added by the module, is determined by the identity and number of the functional domains comprising the module, it is possible to produce novel monomeric units by creating novel combinations of functional domains within a module. Such novel modules can be created by design, for example to make a specific module that will add a specific monomer to a polyketide or polypeptide, or can be created by the random association of domains so as to produce libraries of novel modules. Such novel modules can be made using recombinant or in vitro synthetic means.

Mutations can be made to the native NRPS and/or PKS subunit sequences and such mutants used in place of the native sequence, so long as the mutants are able to function with other PKS and/or PKS subunits to collectively catalyze the synthesis of an identifiable polyketide and/or polypeptide. Such mutations can be made to the native sequences using conventional techniques such as by preparing synthetic oligonucleotides including the mutations and inserting the mutated sequence into the gene encoding a NRPS and/or PKS subunit using restriction endonuclease digestion. (see, e.g., Kunkel, (1985) *Proc. Natl. Acad. Sci. USA* 82: 448; Geisselsoder et al. (1987) *BioTechniques* 5: 786). Alternatively, the mutations can be effected using a mismatched primer (generally 10–20 nucleotides in length) which hybridizes to the native nucleotide sequence, at a temperature below the melting temperature of the mismatched duplex. The primer can be made specific by keeping primer length and base composition within relatively narrow limits and by keeping the mutant base centrally located (Zoller and Smith (1983) *Meth, Enzymol.* 100: 468). Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations (see, e.g., Dalbie-McFarland et al. (1982) *Proc. Natl. Acad. Sci USA* 79:6409). PCR mutagenesis will also find use for effecting the desired mutations.

C) Random Modification of PKS/NRPS Pathways

In another embodiment, variations can be made randomly, for example by making a library of molecular variants of a known polymer by randomly mutating one or more PKS or NRPS modules and/or enzymatic domains or by randomly replacing one or more modules or enzymatic domains in a known PKS or NRPS with a collection of alternative modules and/or enzymatic domains.

The PKS and/or NRPS modules can be combined into a single multi-modular enzyme, thereby dramatically increasing the number of possible combinations obtained using these methods. These combinations can be made using standard recombinant or nucleic acid amplification methods, for example by shuffling nucleic acid sequences encoding various modules or enzymatic domains to create novel arrangements of the sequences, analogous to DNA shuffling methods described in Crameri et al., (1998) Nature 391: 288–291, and in U.S. Pat. Nos. 5,605,793 and in 5,837,458. In addition, novel combinations can be made in vitro, for example by combinatorial synthetic methods. Novel polymers, or polymer libraries, can be screened for any specific activity using standard methods.

Random mutagenesis of the nucleotide sequences obtained as described above can be accomplished by several different techniques known in the art, such as by altering sequences within restriction endonuclease sites, inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-aminopurine, or acridine intercalating agents such as proflavine, acriflavine, quinacrine, and the like. Generally, plasmid DNA or DNA fragments are treated with chemicals, transformed into *E. coli* and propagated as a pool or library of mutant plasmids.

Large populations of random enzyme variants can be constructed in vivo using "recombination-enhanced mutagenesis." This method employs two or more pools of, for example, $10^6$ mutants each of the wild-type encoding nucleotide sequence that are generated using any convenient mutagenesis technique, described more fully above, and then inserted into cloning vectors.

D) Incorporation and/or Modification of Non-blm Cluster Elements

In either the directed or random approaches, nucleic acids encoding novel combinations of modules and/or enzymatic are introduced into a cell. In one embodiment, nucleic acids encoding one or more PKS or NRPS domains are introduced into a cell so as to replace one or more domains of an endogenous PKS or NRPS within a chromosome of the cell. Endogenous gene replacement can be accomplished using standard methods, such as homologous recombination. Nucleic acids encoding an entire PKS, NRPS, or combination thereof can also be introduced into a cell so as to enable the cell to produce the novel enzyme, and, consequently, synthesize the novel polymer. In a preferred embodiment, such nucleic acids are introduced into the cell optionally along with a number of additional genes, together called a 'gene cluster,' that influence the expression of the genes, survival of the expressing cells, etc. In a particularly preferred embodiment, such cells do not have any other PKS- or NRPS-encoding genes or gene clusters, thereby allowing the straightforward isolation of the polymer synthesized by the genes introduced into the cell.

Furthermore, the recombinant vector(s) can include genes from a single PKS and/or NRPS gene cluster, or may comprise hybrid replacement PKS gene clusters with, e.g., a gene for one cluster replaced by the corresponding gene from another gene cluster. For example, it has been found that ACPs are readily interchangeable among different synthases without an effect on product structure. Furthermore, a given KR can recognize and reduce polyketide chains of different chain lengths. Accordingly, these genes are freely interchangeable in the constructs described herein. Thus, the replacement clusters of the present invention can be derived from any combination of PKS and/or NRPS gene sets that ultimately function to produce an identifiable polyketide and/or peptide.

Examples of hybrid replacement clusters include, but are not limited to, clusters with genes derived from two or more of the act gene cluster, the whiE gene cluster, frenolicin (fren), granaticin (gra), tetracenomycin (tcm), 6-methylsalicylic acid (6-msas), oxytetracycline (otc), tetracycline (tet), erythromycin (ery), griseusin (gris), nanaomycin, medermycin, daunorubicin, tylosin, carbomycin, spiramycin, avermectin, monensin, nonactin, curamycin, rifamycin and candicidin synthase gene clusters, among others. (For a discussion of various PKSs, see, e.g., Hopwood and Sherman (1990) *Ann. Rev. Genet.* 24: 37–66; O'Hagan (1991) The Polyketide Metabolites, Ellis Horwood Limited.

A number of hybrid gene clusters have been constructed, having components derived from the act, fren, tcm, gris and gra gene clusters (see, e.g., U.S. Pat. No. 5,712,146). Other hybrid gene clusters, as described above, can easily be produced and screened using the disclosure herein, for the production of identifiable polyketides, polypeptides or polyketide/polypeptide hybrids.

Host cells (e.g. *Streptomyces*) can be transformed with one or more vectors, collectively encoding a functional, PKS/NRPS set (e.g. a bleomycin or bleomycin analog), or a cocktail comprising a random assortment of PKS and/or NRPS genes, modules, active sites, or portions thereof. The vector(s) can include native or hybrid combinations of PKS and/or NRPS subunits or cocktail components, or mutants thereof. As explained above, the gene cluster need not correspond to the complete native gene cluster but need only encode the necessary PKS and/or NRPS components to catalyze the production of the desired product. For example, in *Streptomyces* aromatic PKSs, carbon chain assembly requires the products of three open reading frames (ORFs). ORF1 encodes a ketosynthase (KS) and an acyltransferase (AT) active site (KS/AT); ORF2 encodes a chain length determining factor (CLF), a protein similar to the ORF1 product but lacking the KS and AT motifs; and ORF3 encodes a discrete acyl carrier protein (ACP). Some gene clusters also code for a ketoreductase (KR) and a cyclase, involved in cyclization of the nascent polyketide backbone. However, it has been found that only the KS/AT, CLF, and ACP, need be present in order to produce an identifiable polyketide. Thus, in the case of aromatic PKSs derived from *Streptomyces*, these three genes, without the other components of the native clusters, can be included in one or more recombinant vectors, to constitute a "minimal" replacement PKS gene cluster.

E) Variation of Starter and Extender Units

In addition to varying the PKS and/or NRPS modules and/or domains, variations in the products produced by various PKS/NRPS systems can be obtained by varying the starter units and/or the extender units. Thus, for example, a considerable degree of variability exists for starter units, e.g., acetyl CoA, maloamyl CoA, propionyl CoA, acetate, butyrate, isobutyrate and the like. In addition, naturally occurring PKSs and/or NRPSs have shown some tolerance for varying extender units.

F) Examples of Preferred Modifications

As indicated above, the novel PKS and NRPS modules and enzymatic domains identified herein can be used to perform specific single modifications of particular substrates, or as components of complex synthetic pathways to generate particular products or large combinatorial libraries. As described in the Examples, a number of modules of the blm gene cluster provide novel functionality. By way of example, a few preferred reactions are listed below. These examples are intended to be illustrative and are not exhaustive nor limiting.

1. Use of BlmVIII PKS to Introduce Branched Methyl Group.

Figure 5:
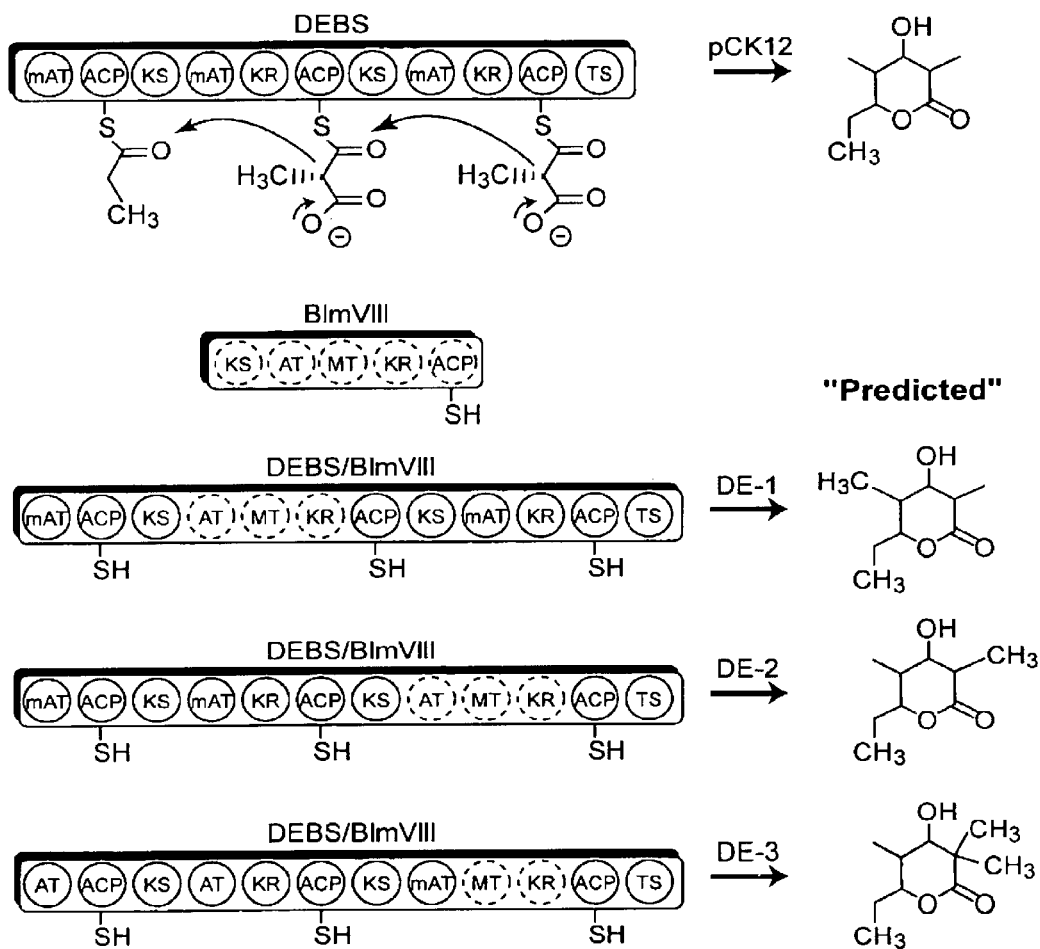
FIG. 5 illustrates the use of blmVIII methyltransferase domain to introduce branched methyl groups in a polyketide synthesis. PCK12 has been described by Kao et al. (1995) *J. Am. Chem. Soc.*, 7: 9105–9106. DE-1, DE-2 and DE-3 rae three representative products demonstrating the strategy and utility of blmVIII in introducing a $CH_3$ group in polyketide biosynthesis.
Figure 6A:
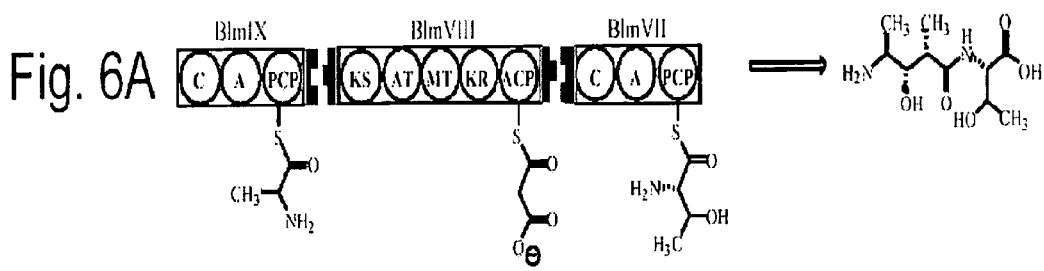
FIGS. 6A–6F illustrate the use of the blm NRPS and PKS enzymes to synthesize a variety of hybrid polyketide/peptide molecules including, but not limited to, a family of oxazolines/oxazoles, and thiazoline/thiazoles.
Figure 6B:
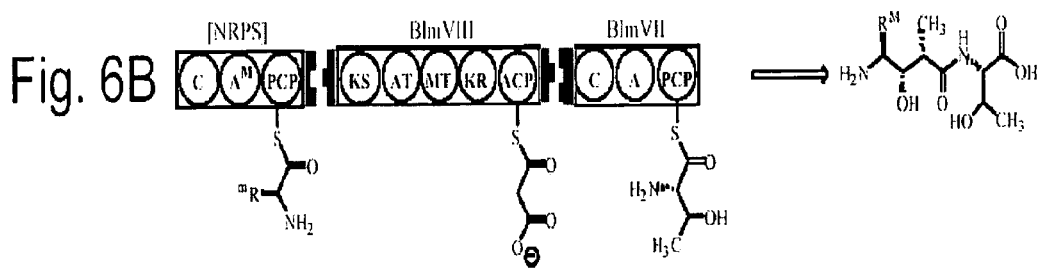
Figure 6C:
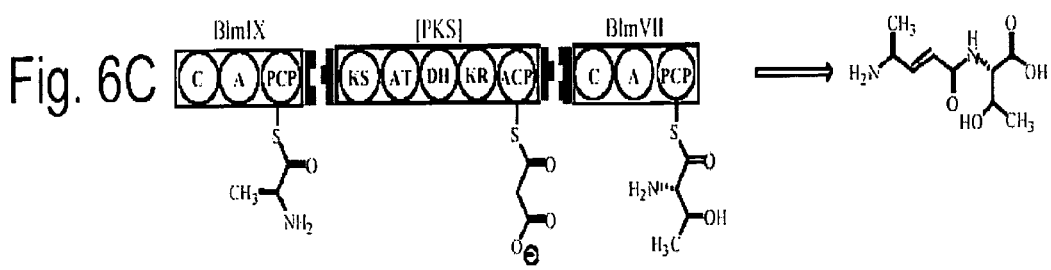
Figure 6D:
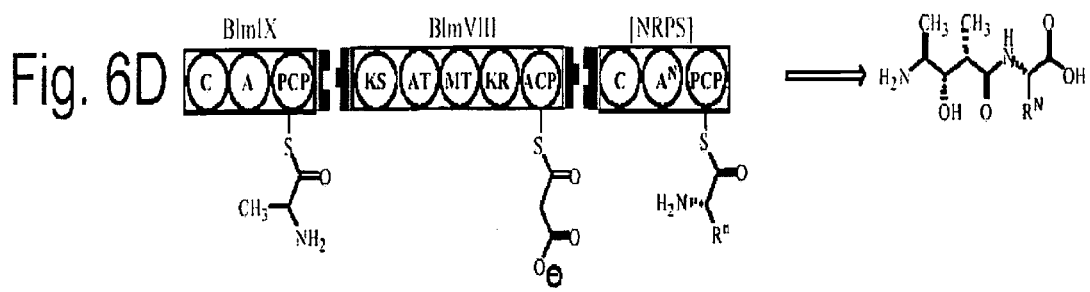
Figure 6E:
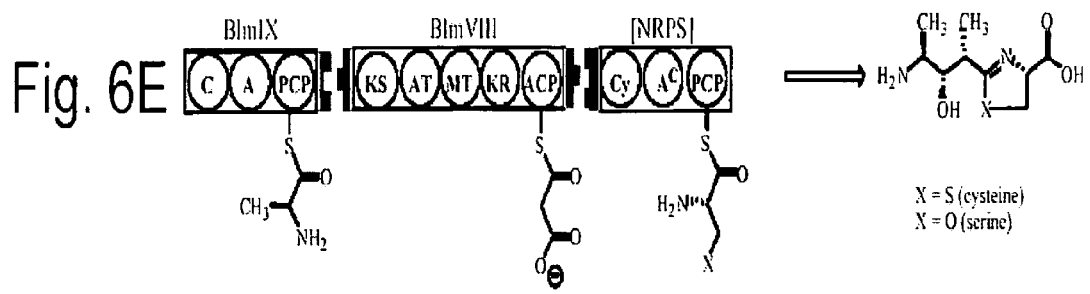
Figure 6F:
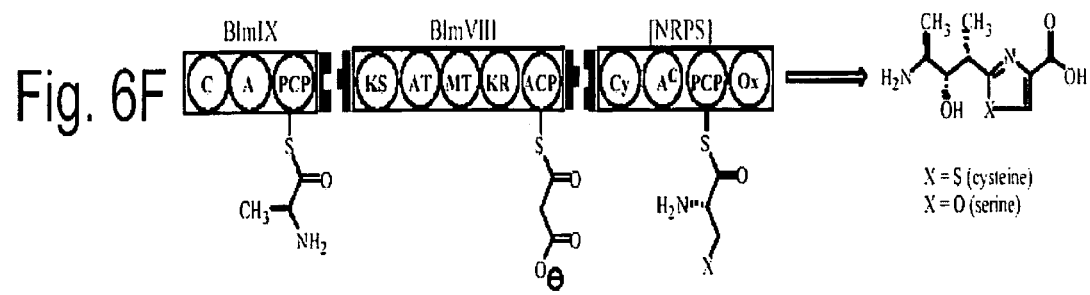

The blmVIII gene identified herein encodes a PKS module consisting of domains characteristic for known PKSs, such as ketoacyl synthase (KS), acyltransferase (AT), ketoreductase (KR), and ACP, with malonyl CoA acting as an extending unit. However, the identification of an integrated methyltransferase (MT) domain in the middle of BlmVIII is unique, representing the first PKS from actinomycetes that contains an internal MT domain. The use of this methyltransferase domain allows the introduction of a branched methyl group during a polyketide and/or polypeptide and/or hybriding polyketide/polypeptide synthesis. FIG. 5 illustrates the use of BlmVIII PKS in engineering a polyketide biosynthesis that introduces a branched methyl group.

The first formula in FIG. 5 illustrates a polyketide synthesis mediated by 6-deoxyerythronolide B synthase (DEBS) which normally catalyzes the biosynthesis of the erythromycin aglycone, 6-deoxyerythronolide B. The remaining formulas show how the use of the blmVIII methyltransferase (MT) group at different points in the synthesis results in the introduction of a methyl group at different locations in the resulting product.

In view of this illustration, one of skill in the art would appreciate that the blmVIII MT domain can be used in a wide variety of biosyntheses to introduce methyl groups.

2. Use of the blm Gene Cluster to Make Thiazolidine, Thiazoline, Thiazole, Bi-thiazolidine, Bithiazoline, and Bithiazole-containing Compounds.

The BlmIV and BlmIII NRPSs are characterized by unusual Cy domains as well an unprecedented Ox domain, providing an efficient biosynthesis for a bithiazole structure. While thiazoline is the direct product of the Cy domain, the thiazoline-to-thiazole conversion generally is performed with an additional oxidation step. We identified at the C-terminus of NRPS-0 an additional domain that shows low, but significant, sequence homology to a family of putative oxidases/dehydrogenases, including the McbC protein of the microcin B17 synthase (Table 1). Microcin B17 synthase catalyzes the synthesis of the oxazole and thiazole-containing peptide antibiotic microcin B17, and McbC has been proposed to play a role in catalyzing the oxazoline/thiazoline-to-oxazole/thiazole conversion. Consequently, we propose that this extra domain at the C-terminus of NRPS-0 provides the oxidase/dehydrogenase activity for the biosynthesis of the bithiazole moiety of BLM, defining a novel Ox domain for NRPSs.

It is noteworthy that a cell-free preparation from *Sv* ATCC15003 has been reported to catalyze the conversion of phleomycins to BLMs in the presence of $NAD^+$, supporting the hypothesis that the bithiazole moiety of BLM results from stepwise oxidations of a bithiazoline precursor (FIG. 1A). (The phleomycin producer could be imagined to result from the loss of its Ox activity for the first thiazoline ring.) Given the wide distribution of thiazole or oxazole rings in natural products exhibiting an impressive array of biological activities, the cloning of the blmIV, III genes and the identification of the Ox domain open many opportunities thiazole biosynthesis and to synthesize novel thiazole containing molecules by engineering peptide biosynthesis.

Representative thiazole syntheses using variants of the blm NRPS are illustrated in FIG. 6. Note that in FIG. 6, $A^M$ and $A^N$ refer to an A domain that activates and amino acid with $R^M$ and $R^N$ groups, respectively. $A^C$ refers to an A domain that activates Cys (x=SH) or Ser (X=OH) that can be cyclized to form the oxiaoline/thiazoline or oxazole/thiazole structures. DH is a dehydratase. In view of these representative examples, one of skill in the art would appreciate that the blm NRPS domain and its variants can be used in a wide variety of chemical syntheses make thiazolidine, thiazoline, thiazole, bi-thiazolidine, bithiazoline, or bithiazole-containing compounds.

3. Use of the blm Gene Cluster to Make Heterocyclic Ring-containing Compounds.

Various blm modules can be used to produce heterocyclic ring-containing compounds. Such heterocycles include, but are not limited to five member S- and N-containing compounds of the thiazolidine, thiazoline and thiazole family or the O- and N-containing compounds of the oxazolidine, oxazoline, and oxazole family. Again, the preparation of such compounds is illustrated in FIG. 6.

4. Use of the blm Gene Cluster to Make Sugars.

Figure 7:
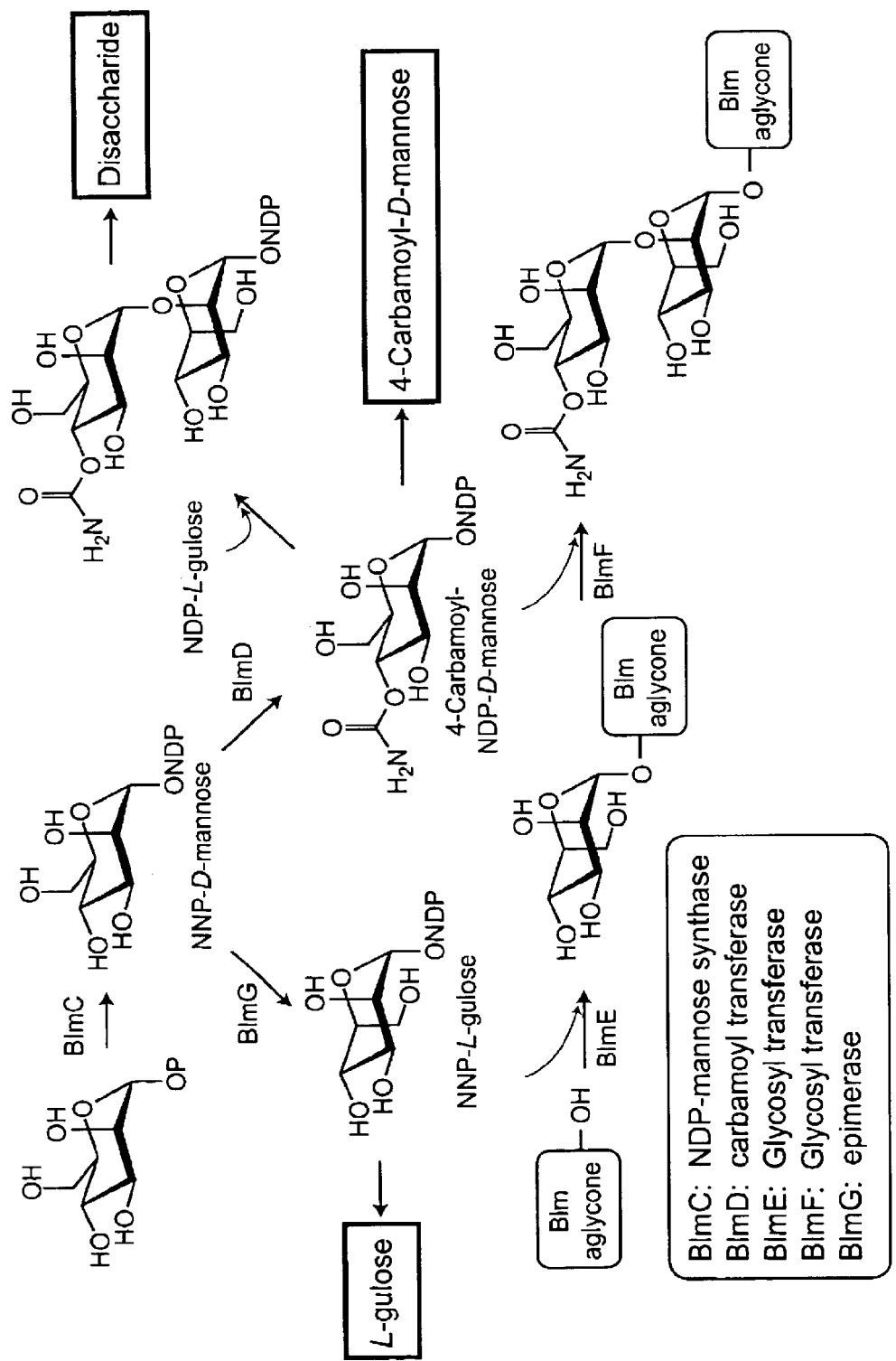
FIG. 7 illustrates the use of elements of the blm gene cluster to synthesize various sugars.

In still another embodiment, the blm gene cluster or elements thereof can be used to make sugars. Such sugars include, but are not limited to L-sugars (with the BlmG epimerase), sugars modified by a carbamoyl group (e.g., using BlmD), and various disaccharides. Representative examples of such syntheses are illustrated in FIG. 7. Such sugar biosynthesis genes can also e used to attach sugars onto other polyketide and/or peptide aglycones.

F) Screening of Products

Particularly where large combinatorial libraries are synthesized, e.g. using one or more modules and/or enzymatic domains of the blm gene cluster it will often be desired to screen the resulting compound(s) for the desired activity. Methods of screening compounds (e.g. polypeptides, polyketides, sugars, thiazoles, etc.) for various activities of interest (e.g. cytotoxicity, antimicrobial activity, particular chemical activities, etc.) are well known to those of skill in the art.

Where large numbers of compounds are produced, it is often desired to rapidly screen such compounds using "high throughput systems" (HTS). High throughput assays systems are well known to those of skill in the art and many such systems are commercially available. (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems typically provide detailed protocols for the various high throughput screens.

VII. In Vitro Syntheses

In additional embodiments of this invention, bleomycins and other polyketides and/or polypeptides are synthesized and/or modified in vitro. Individual enzymatic domains or modules can be used in vitro to modify a unit and/or to add a single monomeric unit to a growing polyketide or polypeptide chain. In one approach a metasynthetase providing all the desired synthetic activities recombinantly expressed and then provided, the appropriate substrates and buffer system e.g. in a bioreactor, to direct the synthesis of the desired product. In another approach, various PKSs and/or NRPSs are provided in different solutions and the growing polymer chains can be sequentially introduced into the plurality of solutions, each containing a single (or several) PKS or NRPS modules. In still another embodiment, the PKS and/or NRPS modules or enzymatic domains are provided attached to a solid support and a fluid containing the growing macromolecule is passed over the surface whereby the PKSs or NRPSs are able to react with the target substrate.

In one preferred embodiment, a combinatorial library of polyketides or polypeptides, or combinations thereof, is created by using automated means to facilitate the sequential introduction of a multitude of polymeric chains, each attached to a solid support, to a collection of solutions, each containing a single PKS or NRPS module. These automated means can be used to systematically vary the sequence by which each polymeric chain is introduced into the various solutions, thereby creating a combinatorial library. Numerous methods are well known in the art to create combinatorial libraries of molecules by the sequential addition of monomeric units, for example as described in WO 97/02358.

VIII. Kits

In still another embodiment, this invention provides kits for practice of the methods described herein. In one preferred embodiment, the kits comprise one or more containers containing nucleic acids encoding one or more of the blm gene cluster ORFs and/or one or more of the BLM PKS or NRPS modules or enzymatic domains. Certain kits may comprise vectors encoding the blm orfs and/or cells containing such vectors. The kits may optionally include any reagents and/or apparatus to facilitate practice of the assays described herein. Such reagents include, but are not limited to buffers, labels, labeled antibodies, bioreactors, cells, etc.

In addition, the kits may include instructional materials containing directions (i.e., protocols) for the practice of the methods of this invention. Preferred instructional materials provide protocols utilizing the kit contents for creating or modifying blm module or ORF and/or for synthesizing or modifying a molecule using one or more blm modules and/or enzymatic domains. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Figure 2:
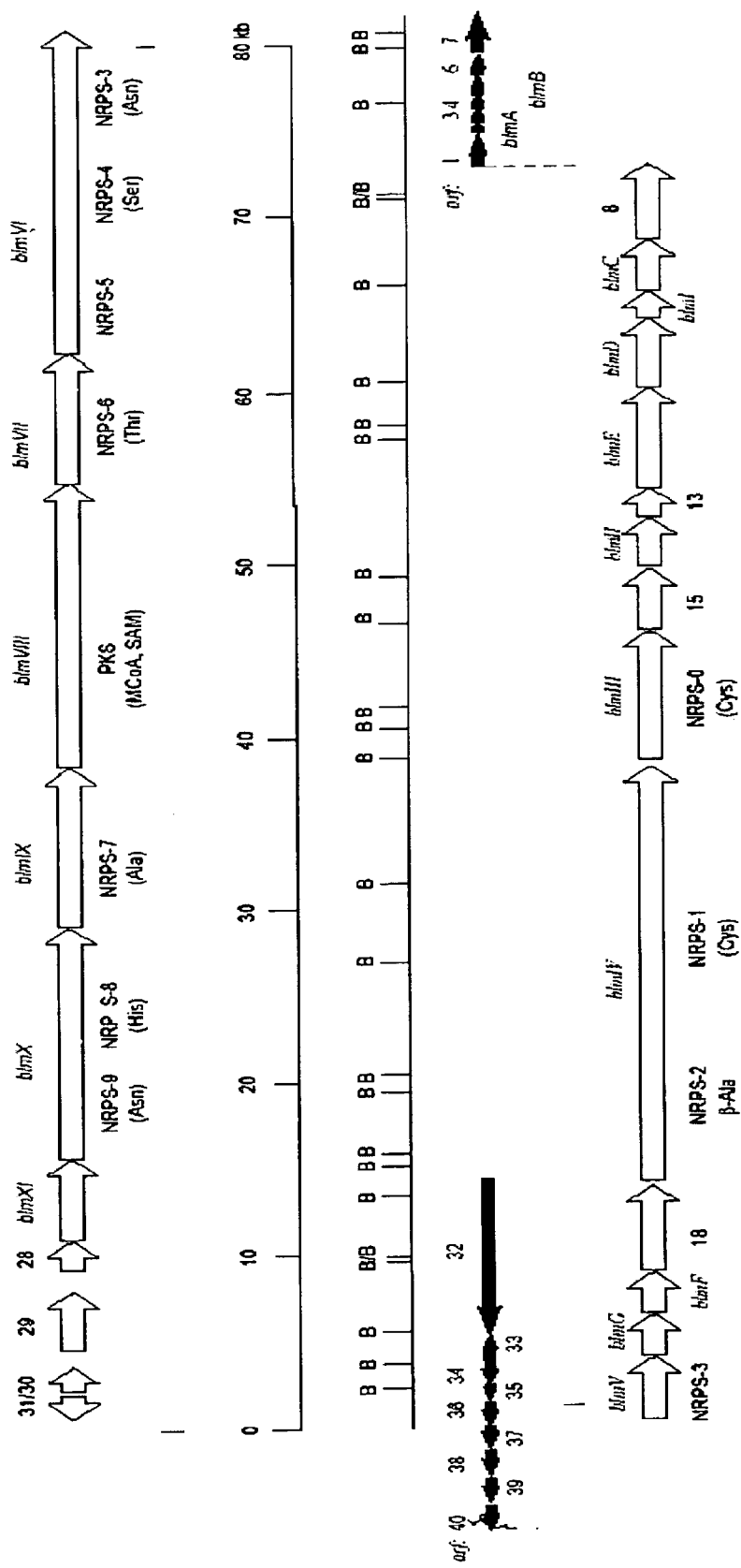
FIG. 2 provides a restriction map and gene organization of the blm gene cluster from Sv ATCC15003 (B, BamHI). Proposed functions for individual open reading frames are summarized in Tables I and II. Modules for individual NRPS and PKS were given along with their proposed substrates in parentheses.

Bleomycin Biosynthesis in *Streptomyces verticillus* ATCC15003, a Model for Hybrid Peptide and Polyketide Biosynthesis Here we report the cloning and characterization of the blm biosynthesis gene cluster from *Sv* ATCC15003 (FIG. 2). Sequence analysis and biochemical characterization of individual modules enabled us to align the nine NRPS and one PKS modules in a linear order to constitute the Blm megasynthetase complex (FIG. 1B). These studies revealed several unprecedented features for peptide and polyketide biosynthesis, setting the stage to investigate the molecular basis for intermodular communication between NRPS and PKS, and supported the wisdom of combining individual NRPS and PKS modules for combinatorial biosynthesis to make novel "unnatural" natural products from amino acids and short carboxylic acids.

Materials and Methods

General Procedures

*Escherichia coli* DH5α (Sambrook et al. (1989) *Molecular Cloning: A Laboratory Manual*, 2nd ed, Cold Spring Harbor Laboratory Press, Cold Spring Harbor, USA), *E. coli* XL 1-Blue MR (Stratagene, La Jolla, Calif.), *E. coli* BL21

(DE-3) (Novagen, Madison, Wis.), and *Sv* ATCC5003. (American Type Culture Collection, Rockville, Md.) were used in this work. pOJ446 (Agricultural Research Service Culture Collection, Peoria, Ill.), pQE60 (Qiagen, Santa Clarita, Calif.), pET28a and pET29a (Novagen), and other plasmids were from commercial sources. *E. coli* (Sambrook, supra.) and *Sv* ATCC15003 strains (Hopwood et al. (1985) *Genetic Manipulation of Streptomyces: A Laboratory Manual*, The John Innes Foundation, Norwich, UK) were cultured under standard conditions.

Plasmid preparation was carried out by using commercial kits (Qiagen). Total *Sv* ATCC15003 DNA was isolated according to literature protocols (Hopwood et al. (1985) *Genetic Manipulation of Streptomyces: A Laboratory Manual*, The John Innes Foundation, Norwich, UK; Nagaraja et al. (1987) *Methods Enzymol.* 153: 166–198). Restriction enzymes and other molecular biology reagents were from commercial sources, and digestions and ligation followed standard methods (Sambrook, supra.). For Southern analysis, digoxigenin labelling of DNA probes, hybridization, and detection were performed according to the protocols provided by the manufacturer (Boehringer Mannheim Biochemicals, Indianapolis, Ind.).

Automated DNA sequencing was carried out on an ABI Prism 377 DNA Sequencer (Perkin-Elmer/ABI, Foster City, Calif.), and this service was provided by either the DBS Automated DNA Sequencing Facility, UC Davis, or Davis Sequencing (Davis, Calif.). Data were analyzed by the ABI Prism Sequencing 2.1.1 software and the Genetics Computer Group (GCG) program (Madison, Wis.).

Cloning and Sequencing of the blm Gene Cluster.

A genomic library of *Sv* ATCC15003 was constructed in pOJ446 according to literature procedures (Nagaraja et al. (1987) *Methods Enzymol.* 153: 166–198) and screened with probes made from both ends of the blmAB locus (Sugiyama et al. (1994) *Gene* 151: 11–16; Calcutt and Schmidt (1994) *Gene* 151: 17–21), leading to the localization of 140-kb contiguous DNA, of which 100-kb is upstream (FIG. 2) and 40-kb is downstream (data not shown) of the blmAB genes. Heterologous NRPS probes were amplified from *Sv* ATCC15003 by polymerase chain reaction (PCR) according to literature procedures (Turgay and Marahiel (1994) *Peptide Res.* 7: 238–241) and used to screen the entire 140-kb DNA by Southern analysis under various hybridization conditions (Shen et al. (1999) *Bioorg. Chem.* 27: 155–171).

Prediction of Substrate Specificity of NRPSs.

The nine Blm NRPS modules were compared with eighty four modules from various bacterial and fungal NRPSs available at the GenBank, including those with known or putative specificity for amino acids present in BLM. A table of overall similarities/identities was generated by PILEUP analysis of the A3 to A6 regions, and the residues lining the substrate binding pocket by comparison with PheA (Conti et al. (1997) *EMBO J.* 16, 4174–4183) were determined by PILEUP/PRETTY analysis. The percentage similarities for each Blm NRPS module were plotted against the rest of the NRPS modules to display the overall sequence homology between the A3 to A6 region. Those modules that showed significantly higher homology were selected to compare the amino acid residues that line the substrate binding pocket.

Overproduction and Biochemical Characterization of the NRPS-1A and NRPS-6A Proteins.

Heterologous expression of the A domain in *E. coli* were performed according to literature procedures (Mootz and Marahiel (1997) *J. Bacteriol.* 179: 6843–6850). NRPS-1A (forward primer 5'-AAC CCA TGG CTG CTT CCC TGA CCC GCC TGG CC-3' (SEQ ID NO:76) and reverse primer 5'-CCT AGA TCT ACG GGC AGG TGG GGC GGT-3' (SEQ ID NO:77) and NRPS-6A (forward primer 5'-GGG AAT TCC ATA TGA TCC TCA CGT CCT TCC AC-3', (SEQ ID NO:78), and reverse primer 5'-GGC AAG CTT GGG TGA GGG TCC GTT CGG T-3', (SEQ ID NO:79) were amplified by PCR from *Sv* ATCC15003 cosmid clones. The resulting 1.6-kb fragment of NRPS-1A was first cloned into the NcoI/BglII sites of pQE60 and then moved as an NcoI/HindIII fragment into the similar sites of pET29a to yield pBS10, and the resulting 1.6-kb fragment of NRPS-6A was directly cloned into the NdeI/HindIII sites of pET28a to yield pBS11. Introduction of pBS10 and pBS11 into *E. coli* BL21(DE-3) under standard expression conditions resulted in production of NRPS-1A (with an N-terminal S-tag and a C-terminal His$_6$-tag) and NRPS-6A (with an N-terminal His$_6$-tag), respectively. The soluble fractions of fusion proteins were subjected sequentially to an affinity chromatography on Ni-NTA resin and an anion exchange chromatography on a Hyper-D column (PerSeptive Biosystem, Framingham, Mass.), resulting in NRPS-1A and NRPS-6A with near homogeneity.

Results and Discussion

Cloning of the blm Gene Cluster from *Sv* ATCC15003.

Davies and co-workers previously cloned two BLM resistance genes (blmA and blmB) from *Sv* ATCC15003 (Sugiyama et al. (1994) *Gene* 151: 11–16), and Calcutt and Schmidt (1994) *Gene*, 151: 17–21, sequenced a 7.2-kb DNA fragment flanking the blmAB genes, revealing seven open reading frames (orfs), none of which were found to encode Blm NRPS or PKS enzymes. Given the precedent that antibiotic production genes commonly occur as a cluster in actinomycetes, we adopted an approach combining chromosomal walking from the blmAB resistance locus and DNA hybridization with heterologous NRPS probes to clone and identify the blm cluster, leading to the localization of 140-kb contiguous *Sv* ATCC15003 DNA. DNA sequencing of approximately 90-kb of the blm gene cluster, including the 7.2-kb blmAB locus, revealed 40 ORFs (FIG. 2). Preliminary functional assignments were made by comparison of the deduced gene products with proteins of known functions in the database. Among the ORFs identified from the blm cluster, we indeed found a PKS module, flanked by several NRPS modules—a fact that supports the hybrid NRPS/PKS/NRPS hypothesis for BLM biosynthesis—along with several sugar biosynthesis genes and genes encoding other biosynthesis enzymes as well as several resistance and regulatory genes (Table 1).

Noteworthy are the genes encoding the putative NRPS and PKS enzymes. The blmI, blmII, and blmXI genes encode NRPSs with an unusual architecture. In contrast to all known NRPSs, which are of modular organization with each module consisting minimally of a condensation (C), an adenylation (A), and a peptidyl carrier protein (PCP) domain (1), BlmI, BlmII, and BlmXI are discrete proteins homologous to individual domains of type I NRPSs. We have characterized BlmI as a type II PCP. The BlmII and BlmXI proteins could serve as candidates for type II condensation enzymes. It is unclear yet what role if any these discrete NRPS enzymes could play in BLM biosynthesis.

The blmIII, blmIV, blmV, blmVI, blmVII, blmIX, and blmX genes encode modular NRPSs consisting of domains characteristic for known type I NRPSs (A special thematic issue on polyketide and nonribosomal polypeptide biosynthesis, (1997) *Chem. Rev.* 97: 2463–2706), such as the A, PCP, C, and condensation/cyclization (Cy) domains (Konz et al. (1997) *Chem. Biol.* 4: 927–937), as well as an unprecedented oxidation (Ox) domain (see discussion below). However, BlmVI is unique among all the Blm NRPSs identified. Its N-terminal module (NRPS-5) consists of an atypical A domain, which bears a close resemblance to a family of acyl CoA synthases (Fitzmaurice and Kolattukudy (1997) *J. Bacteriol.* 179: 2608–2615; Fitzmaurice and Kolattukudy (1998) *J. Biol. Chem.* 273: 8033–8039), and an acyl carrier protein (ACP)-like domain (A special thematic issue on polyketide and nonribosomal polypeptide biosynthesis, (1997) *Chem. Rev.* 97: 2463–2706). Its C-terminal module is truncated and presumably interacts with BlmV to constitute the complete NRPS-3 module (FIG. 1B). Also noteworthy are the C domain of NRPS-3 that lacks both His residues of the conserved HHxxxDG (SEQ ID NO:4) active site for transpeptidation (Stachelhaus et al. (1998) *J. Biol. Chem.*, 273: 22773–22781) and the extra C domain at the C-terminus of BlmV. These unusual features associated with BlmVI and BlmV may play roles in the formation of the β-aminoalaninamide and the pyrimidine moieties of BLM, which are unprecedented in peptide biosynthesis. For example, we propose that the NRPS-4-activated Ser is first dehydrated into dehydroalanine before condensation—an analogous Thr-to-2,3-dehydroaminobutyric acid dehydration has been observed in syringomycin biosynthesis (Guenzi et al. (1998) *J. Biol. Chem.* 273: 32857–32863). Conjugate addition to dehydroalanine by Asn on the NRPS-3 module downstream followed by an aminolysis to cleave the Ser-Asn adduct off the Blm megasynthetase furnishes the β-aminoalaninamide moiety (FIG. 1B). The former reaction could be catalyzed by the C domain of NRPS-3 that apparently is nonfunctional for normal transpeptidation due to the lack of the active sites, and the latter reaction could be catalyzed by the acyl CoA synthase-like domain of NRPS-5 in a process that resembles the acyl CoA synthase-catalyzed synthesis of acyl CoA from carboxylic acid (Stachelhaus et al. (1998) *J. Biol. Chem.* 273: 22773–22781; Guenzi et al. (1998) *J. Biol. Chem.* 273: 32857–32863) but in the reverse direction in the presence of an amino donor (FIG. 1B).

The blmVIII gene encodes a PKS module consisting of domains characteristic for known PKSs, such as ketoacyl synthase (KS), acyltransferase (AT), ketoreductase (KR), and ACP, with malonyl CoA acting as an extending unit according to sequence comparison of the AT domain (Haydock et al. (1995) *FEBS Lett.* 374: 246–248) (FIG. 1B). However, the identification of an integrated methyltransferase (MT) domain (Kagan and Clarke (1994) *Arch. Biochem. Biophys.* 310: 417–427) in the middle of BlmVIII is unique, representing the first PKS from actinomycetes that contains an internal MT domain. The only other example of PKS from bacteria that contains an internal MT domain is HMWP1 of the yersiniabactin gene cluster (Pelludat et al. (1998) *J. Bacteriol.* 180: 538–546). It has been assumed that fungal PKSs in general contain internal MTs for the introduction of methyl branch into the polyketide products, as it has been shown recently in lovastatin biosynthesis (Kennedy et al. (1999) *Science* 284: 1368–1372).

The Blm Megasynthetase-templated Assembly of BLM.

According to the hybrid NRPS/PKS/NRPS model for BLM biosynthesis (FIG. 1A), we predict a linear modular organization of individual NRPS and PKS modules to constitute the Blm megasynthetase. Thus, the first functional domain of the Blm megasynthetase should be a NRPS module that initiates BLM biosynthesis by activating L-Ser as an amino acylthioester to set the stage for transpeptidation. Chain elongation proceeds by sequential incorporation of L-Asn, L-Asn, L-His, and L-Ala, requiring four additional NRPS modules. In the next step, a malonate reacts with the resulting pentapeptide intermediate to form a β-ketothioester intermediate that is subsequently methylated at the α-position and reduced at the β-keto group. A PKS module presumably dictates all these biosynthetic events and interacts With the aligned NRPS module upstream to channel the growing peptide intermediate from an NRPS module to a PKS module. After one cycle of polyketide elongation, peptide elongation is resumed by incorporation of an L-Thr residue. This step is presumably catalyzed by an NRPS module that interacts with the upstream PKS module to channel the growing polyketide intermediate (as far as the active site is concerned) from a PKS module to an NRPS module. At this stage, methylation occurs at the pyrimidine moiety of the growing intermediate, presumably catalyzed by a discrete methyltransferase; chain elongation is continued by three additional NRPS modules that incorporate a β-Ala and two L-Cys molecules sequentially. Finally, the fully assembled BLM peptide/polyketide/peptide backbone is hydroxylated at the β-position of the His residue, presumably by a discrete hydroxylase, and released from the Blm megasynthetase complex via nucleophilic substitution of the RCO-S-PCP species by a terminal amine to form the BLM aglycone. Intermediates after five of the nine proposed elongation steps were in fact isolated as P-3, P-3A, P-3K, P-4, P-5, P-5m, P-6m, and P-6mo (Takita and Muroka (1990) pages 289–309 in *Biochemistry of Peptide Antibiotics: Recent Advances in the Biotechnology of β-Lactams and Microbial Peptides*, Kleinkauf, H. & von Döhren, H. eds., W. de Gruyter, N.Y.), which presumably resulted from premature departure from the Blm megasynthetase complex before the chain reaches its full length (FIG. 1B).

Figures 3A, 3B:
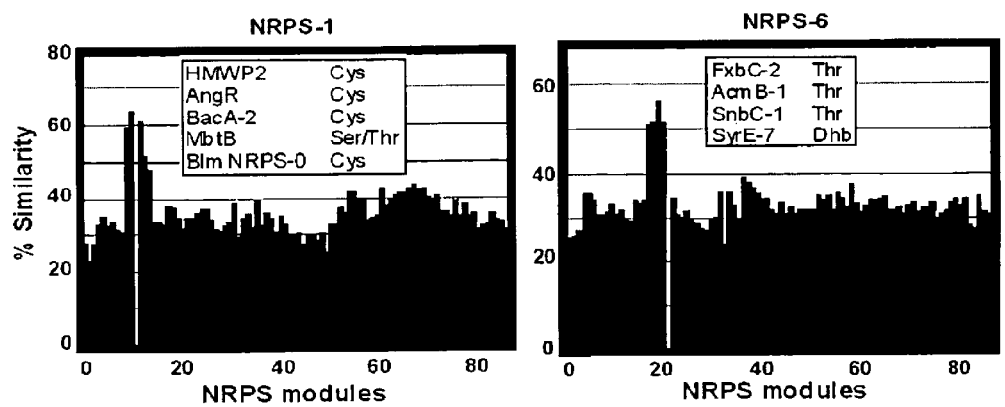
FIGS. 3A, 3B, 3C, and 3D illustrate the determination of substrate specificity for NRPS-1 and NRPS-6.
Figure 3C:
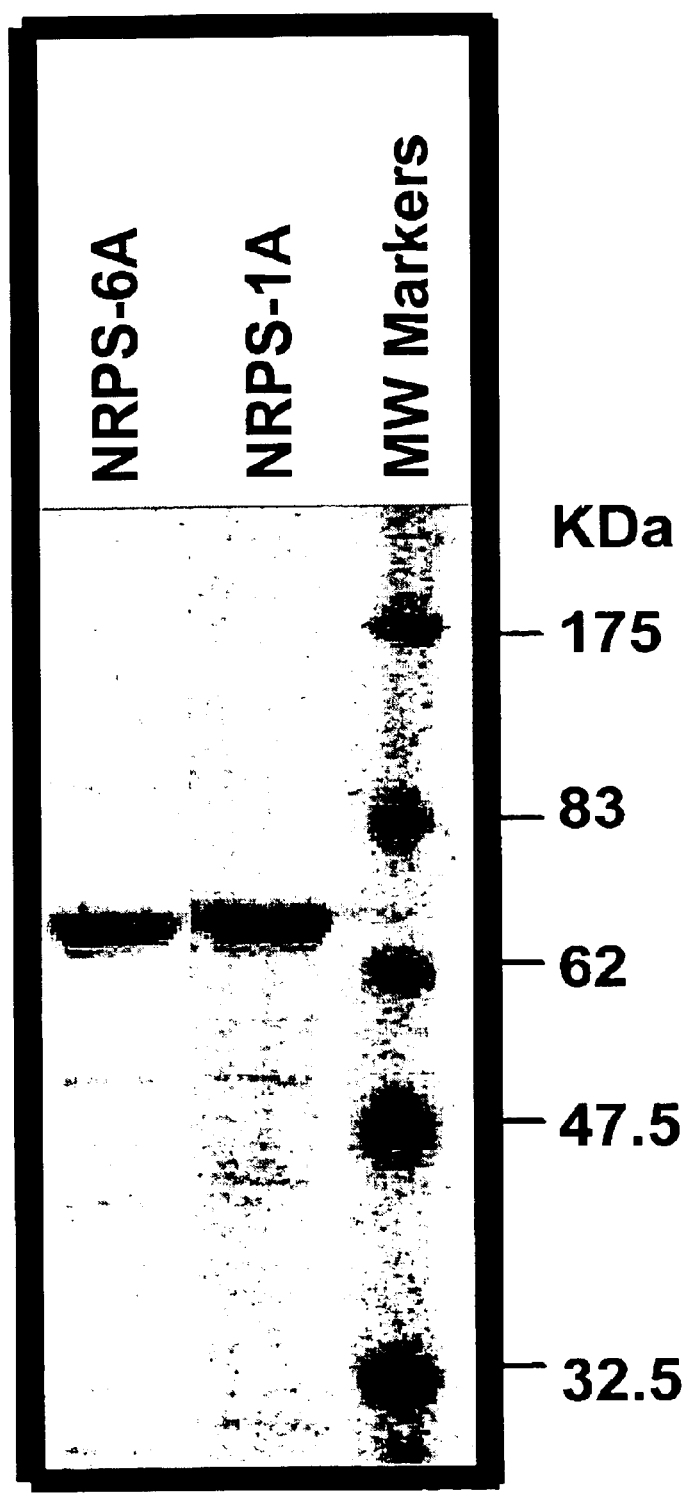
Figure 3D:
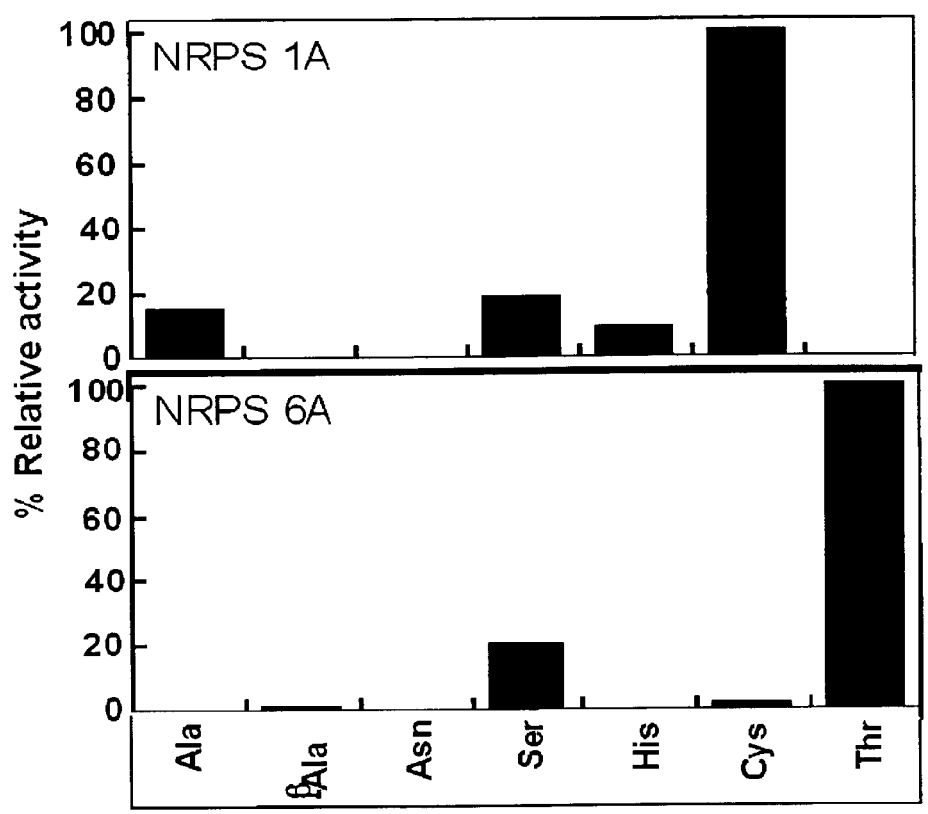

Most of the bacterial NRPS gene clusters characterized to date are organized in operon-type structures, encoding multimodular NRPS proteins with individual modules organized along the chromosome in a linear order that parallels the order of the amino acids in the resultant peptides, i.e., following the "colinearity rule" for the NRPS-templated assembly of peptides from amino acids (A special thematic issue on polyketide and nonribosomal polypeptide biosynthesis, (1997) *Chem. Rev.* 97: 2463–2706; Cane et al. (1998) *Science* 282: 63–68). Inspection of the blm gene cluster (FIG. 2) showed that the Blm NRPS and PKS modules apparently are not organized according to the "colinearity rule" for BLM biosynthesis (FIG. 1). [Exception to the "colinearity rule" was also noted in the syringomycin synthetase gene cluster (Guenzi et al. (1998) *J. Biol. Chem.* 273: 32857–32863), and in fact, Grandi and co-workers have demonstrated recently in *Bacillus subtilis* that neither the operon-type structure nor the physical linkage of individual modules is essential for proper assembly and activity of the surfactin NRPS megasynthetase (Guenzi et al. (1998) *J. Biol. Chem.* 273: 14403–14410).] Realizing that the BLM biosynthesis cannot be rationalized according to the "colinearity rule", we determined the substrate specificity of individual NRPS and PKS modules in an attempt to shed light on the modular organization of the Blm megasynthetase complex. Brick and co-workers postulated, based on the X-ray structural analysis of the A domain of GrsA, PheA, that the region between core sequences A3 to A6 represent the amino acid specificity determinant of an NRPS module (Conti et al. (1997) *EMBO J.* 16: 4174–4183). Since the A domains in all known NRPSs share a significant sequence identity (ensuring that the main chain conformation of the enzymes is likely to be very similar), they further proposed that the differing substrate specificity of individual NRPS modules will be mainly determined by the nature of the amino acids lining the substrate binding pocket (Stachelhaus et al. (1999) *Chem. Biol.* 6: 493–505; Conti et al. (1997) *EMBO J.* 16: 4174–4183). Given this structural information and the vast amount of NRPS sequences available at the GenBank, we developed a novel approach for predicting substrate specificity for NRPS modules by comparing the overall sequence between the A3 to A6 region and the eight amino acid residues that line up the substrate binding pocket. While a constant level of similarities (30%–40%) was evident among all the NRPS modules analyzed, most of the Blm NRPS modules showed striking similarities (50%–60%) to a particular cluster of NRPS modules as exemplified in FIG. 3A for NRPS-1 and NRPS-6. Close examination of these modules clustered with higher similarities revealed that they activate the same or very similar amino acid, based on which the putative substrate for the NRPS in query could be predicted, i.e., NRPS-1 and NRPS-6A activate L-Cys and L-Thr, respectively. These predictions were further supported by comparing the residues lining the substrate binding pocket. For example, the amino acid residues lining the substrate binding pocket for NRPS-1 and NRPS-6 are almost identical to those NRPS modules that are known to activate L-Cys and L-Thr, respectively, as shown in FIG. 3B. To verify the predicted amino acid specificity, we overproduced and purified the NRPS-1A and NRPS-6A proteins (FIG. 3C) and examined their substrate specificity according to the amino acid-dependent ATP-PPi assay (Lee et al. (1970 *Meth. Enzymol.*, 43: 585–602; Ku et al. (1997) *Chem. & Biol.*, 4: 203–207). NRPS-1A and NRPS-6A indeed activate specifically L-Cys and L-Thr, respectively, among the amino acids tested (FIG. 3D). The latter results greatly enhanced our confidence in predicting the substrate specificity of a NRPS module by the above method. We subsequently determined the substrate specificity for all the NRPS modules identified from the blm gene cluster and they in fact accounted for all nine amino acids required for BLM biosynthesis (FIG. 2).

Using the substrate specificity of individual NRPS and PKS modules as a guide, we can align the nine NRPS and one PKS modules to constitute the Blm megasynthetase as shown in FIG. 1B according to our hybrid NRPS/PKS/NRPS model for BLM biosynthesis (FIG. 1A). Among all the PKSs or NRPS systems examined so far, the Blm megasynthetase consists of the largest number of individual proteins. The precise interactions among all the Blm NRPS and Blm PKS proteins to constitute the Blm megasynthetase complex, therefore, reflect a remarkable power of protein-protein recognition (Guenzi et al. (1998) *J. Biol. Chem.* 273: 14403–14410; Gokhale et al. (1999) *Science* 284: 482–485). Although we are yet to provide direct evidence supporting the specific protein-protein interactions between the neighboring proteins, it is striking to note that all the biosynthetic intermediates isolated are derailed from either PKS or NRPS modules at the junctions between the interacting proteins (FIG. 1B). Since it is not difficult to imagine that an intermediate is more likely to fall off the enzyme complex when it is subjected to interpeptide transfer than to intrapeptide transfer, we view the latter observation as strong evidence supporting the current model of the Blm megasynthetase.

BlmIX/BlmVIII/BlmVII as a Hybrid NRPS/PKS/NRPS Model.

Recent biosynthetic studies on rapamycin in *Streptomyces hygroscopicus* (Konig et al. (1997) *Eur. J. Biochem.* 247: 526–534), yersiniabactin in *Yersinia enterocolitica* and *Y. pestis* (Pelludat et al. (1998) *J. Bacteriol.* 180: 538–546; Gehring et al. (1998) *Chem. Biol.* 5: 573–586; Gehring et al. (1998) *Biochemistry* 37: 11637–11650) and TA in *Myxococcus xanthus* (Paitan et al. (1999) *J. Mol. Biol.* 286, 465–474) are starting to shed light on hybrid peptide and polyketide biosynthesis. Two models are emerging for the alignment between a NRPS and a PKS module. The interacting NRPS and PKS modules could be either covalently linked by arranging all domains in a linear order on the same protein (Pelludat et al. (1998) *J. Bacteriol.* 180: 538–546; Gehring et al. (1998) *Chem. Biol.* 5: 573–586; Gehring et al. (1998) *Biochemistry* 37: 11637–11650; Paitan et al. (1999) *J. Mol. Biol.* 286: 465–474) or physically located on two separate proteins, requiring specific protein-protein recognition to ensure the correct pairing between the interacting modules (Pelludat et al. (1998) *J. Bacteriol.* 180: 538–546; Konig et al. (1997) *Eur. J. Biochem.* 247: 526–534; Gehring et al. (1998) *Chem. Biol.* 5: 573–586; Gehring et al. (1998) *Biochemistry* 37: 11637–11650). Common to all these systems, however, are the unusual features associated with the interacting modules, such as the lack of the AT domain of the PKS module in Ta1 (Paitan et al. (1999) *J. Mol. Biol.* 286: 465–474) and the lack of the A domain and the presence of the Cy domain of the NRPS modules in both HMWP1 and HMWP2 (Pelludat et al. (1998) *J. Bacteriol.* 180: 538–5461; Gehring et al. (1998) *Chem. Biol.* 5: 573–586; Gehring et al. (1998) *Biochemistry* 37: 11637–11650). While extremely intriguing, the latter features complicate mechanistic analysis of these systems, making them less ideal candidates for studying how NRPS and PKS integrate into a productive hybrid NRPS/PKS complex.

Figure 4:
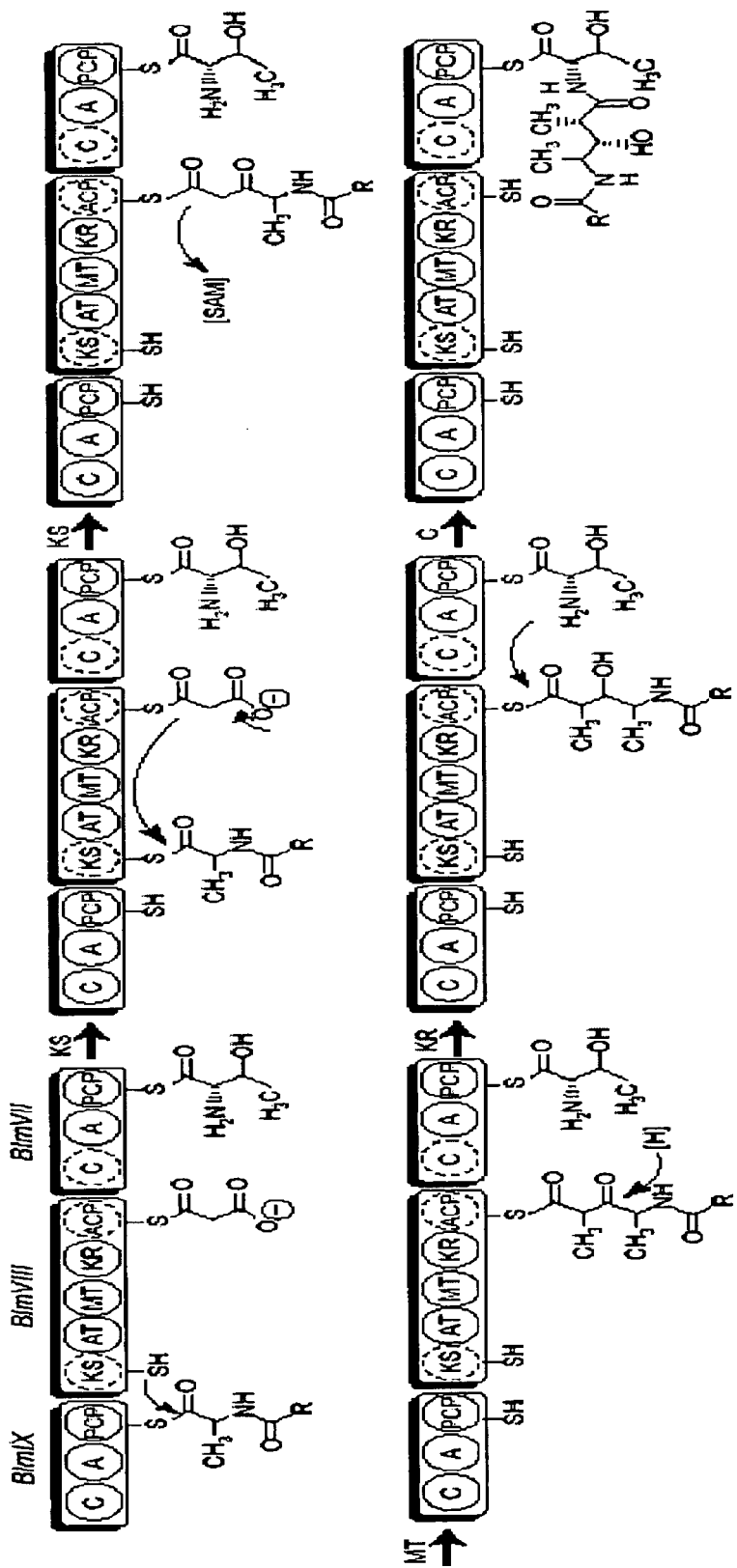
FIG. 4 illustrates a three-module NRPS/PKS/NRPS model for channeling the growing intermediate between NRPS and PKS modules and between PKS and NRPS modules. The KS, ACP, and C domains are shaded to emphasize their unique activities that are responsible for elongating a growing peptide with a short carboxylic acid and a growing polyketide with an amino acid in hybrid peptide/polyketide/peptide biosynthesis.

The BlmIX/BlmVIII/BlmVII system combines the features of both hybrid NRPS/PKS and PKS/NRPS systems, serving as an ideal model for studying hybrid peptide and polyketide biosynthesis. The fact that both the BlmIX and BlmVII NRPS modules and the BlmVIII PKS module themselves are three separate proteins with a typical domain organization for NRPS and PKS enzymes greatly simplifies the mechanistic analysis of the hybrid NRPS/PKS/NRPS complex. We have found that the KS domain of BlmVIII is more similar to the KSs of HMWP1 (Pelludat et al. (1998) *J. Bacteriol.* 180: 538–546) and Ta1 (Paitan et al. (1999) *J. Mol. Biol.* 286: 465–474), both of which catalyze the elongation of a peptidyl intermediate with a malonate, than to KSs of type I PKSs. We attribute these subtle differences to their unique reactivity that catalyzes the transfer of the peptidyl intermediate from the PCP to the KS domain, which presumably takes place prior to chain elongation (FIG. 4). Subsequent condensation catalyzed by the KS domain between the peptidyl intermediate and malonyl-S-ACP results in the elongation of the growing peptide with a carboxylic acid. Equally striking are the discoveries that the ACP domain of BlmVIII is more similar to a PCP than to an ACP and that the C domain of BlmVII has an additional N-terminal segment of about 50 amino acids that is rich in arginine, aspartic acid, and glutamic acid. The latter feature is analogous to the N-terminal interpolypeptide linker for type I PKS, which has recently been demonstrated to play a critical role in intermodular communication (Gokhale et al. (1999) *Science* 284: 482–485). We propose that these unique features of the ACP domain from the BlmVIII PKS module and the C domain from the BlmVII NRPS module provide the molecular basis for the C domain to recognize the acyl-S-ACP as a substrate. Subsequent condensation catalyzed by the C domain between acyl-S-ACP and amino acyl-S-PCP results in the elongation of the growing polyketide (as far as this condensation is concerned) with an amino acid (FIG. 4).

Novel Domains for the Blm NRPS and PKS Modules.

Various NRPS and PKS domains have been characterized, which are the building blocks for the entire field of combinatorial biosynthesis. The success for combinatorial biosynthesis depends critically upon the repertoire of these individual domains. Genetic analysis of the blm gene cluster has uncovered several novel NRPS and PKS domains. Without being bound to a particular theory, it is believed that BlmVI and BlmV are involved in the biosynthesis of the β-aminoalaninamide and pyrimidine moieties of BLM). In addition, the MT domain in BlmVIII, the Cy domains in BlmIV, and the Ox domain in BlmIII are novel domains.

The BlmVIII PKS module apparently furnishes the "propionate" unit into BLM in two steps by evolving a malonyl CoA-specifying AT domain coupled with a novel S-adenosylmethionine-requiring MT domain, representing a new mechanism to introduce methyl branches into polyketides (FIG. 4). This biosynthetic reaction sequence is unprecedented for polyketide biosynthesis since all PKSs from actinomycetes examined to date incorporate the alkyl branches into the resultant polyketides by selecting various alkyl malonates as the extending units that are determined by the AT domains. Yet, feeding experiments have unambiguously established that the polyketide moiety of BLM was derived from an acetate and a methionine (Takita and Muroka (1990) pages 289–309 in *Biochemistry of Peptide Antibiotics: Recent Advances in the Biotechnology of β-Lactams and Microbial Peptides*, Kleinkauf, H. & von Döhren, H. eds., W. de Gruyter, N.Y.), a fact that fits well with the observed unusual domain organization of the blmVIII PKS module (FIG. 4). It is conceivable that the combination of this MT domain with an AT domain specific for a methyl malonate extending unit (Haydock et al. (1995) *FEBS Lett.* 374: 246–248) could result in the synthesis of polyketides with a gem-dimethyl moiety via engineering polyketide biosynthesis. Such a gem-dimethyl group has been found to be a very important pharmacophore for the epothilones, a family of hybrid peptide and polyketide metabolites that exhibits a remarkable antitumor activity similar to taxol (Ojima et alo. (1999) *Proc. Natl. Acad. Sci. USA* 96: 4256–4261).

The BlmIV and BlmIII NRPSs are characterized by the unusual Cy domains as well as the unprecedented Ox domain, providing an efficient biosynthesis for a bithiazole structure. The Cy domain was first defined by Marahiel and co-workers in their study of bacitracin biosynthesis in *B. licheniformis* (Konz et al. (1997) *Chem. Biol.* 4: 927–937), and the Cy activity was demonstrated recently by Walsh and co-workers in their study of the HMWP1 and HMWP2 proteins for yersiniabactin biosynthesis in *Y. pestis* (Gehring et al. (1998) *Chem. Biol.* 5: 573–586; Gehring et al. (1998) *Biochemistry* 37: 11637–11650). While thiazoline is the direct product of the Cy domain, the thiazoline-to-thiazole conversion requires an additional oxidation step. We identified at the C-terminus of NRPS-0 an additional domain that shows low, but significant, sequence homology to a family of putative oxidases/dehydrogenases, including the McbC protein of the microcin B17 synthase (Table 1). Microcin B17 synthase catalyzes the synthesis of the oxazole and thiazole-containing peptide antibiotic microcin B17, and McbC has been proposed to play a role in catalyzing the oxazoline/thiazoline-to-oxazole/thiazole conversion (Li et al. (1996) *Science* 274: 1188–1193; Milne, et al. (1999) *Biochemistry* 38: 4768–4781). Consequently, we propose that this extra domain at the C-terminus of NRPS-0 could provide the oxidase/dehydrogenase activity needed for the biosynthesis of the bithiazole moiety of BLM, defining a novel Ox domain for NRPSs. It is noteworthy that a cell-free preparation from *Sv* ATCC15003 has been reported to catalyze the conversion of phleomycins to BLMs in the presence of $NAD^+$ (Takita and Muroka (1990) pages 289–309 in *Biochemistry of Peptide Antibiotics: Recent Advances in the Biotechnology of β-Lactams and Microbial Peptides*, Kleinkauf, H. & von Döhren, H. eds., W. de Gruyter, N.Y.), supporting the hypothesis that the bithiazole moiety of BLM results from stepwise oxidations of a bithiazoline precursor (FIG. 1A). (The phleomycin producer could be imagined to result from the loss of its Ox activity for the first thiazoline ring.) Given the wide distribution of thiazole or oxazole rings in natural products (Ojima et alo. (1999) *Proc. Natl. Acad. Sci. USA* 96: 4256–4261; Li et al. (1996) *Science* 274: 1188–1193) exhibiting an impressive array of biological activities, the cloning of the blmIV,III genes and the identification of the Ox domain open many opportunities to define the mechanism for thiazole biosynthesis and to potentially synthesize novel thiazole containing molecules by engineering peptide biosynthesis.

Example 2

Identification and Characterization of a Type II Peptidyl Carrier Protein from the Bleomycin Producer *Streptomyces verticillus* ATCC15003

Results

Cloning and Sequence Analysis of the blmI Gene

Figure 8A:
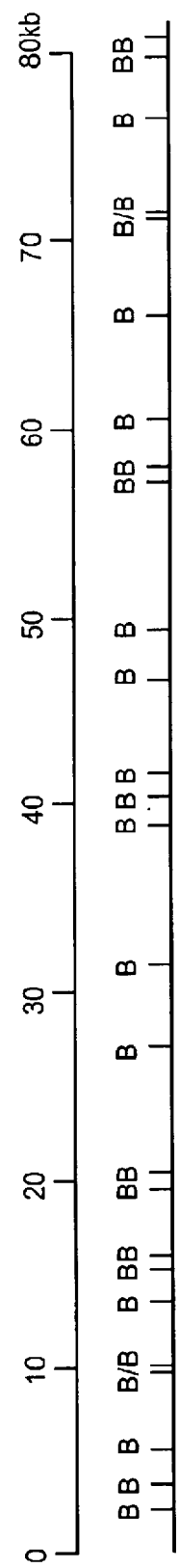
FIG. 8A shows a restriction map of the blm gene cluster from Sv ATCC15003 (B, BamHI). 8B shows the relative position of the blmI, blmII, and blmXI genes to the two blmAB resistance genes (blm$^R$, Blm resistance). Individual open reading frames are represented by open arrows.
Figure 8B:
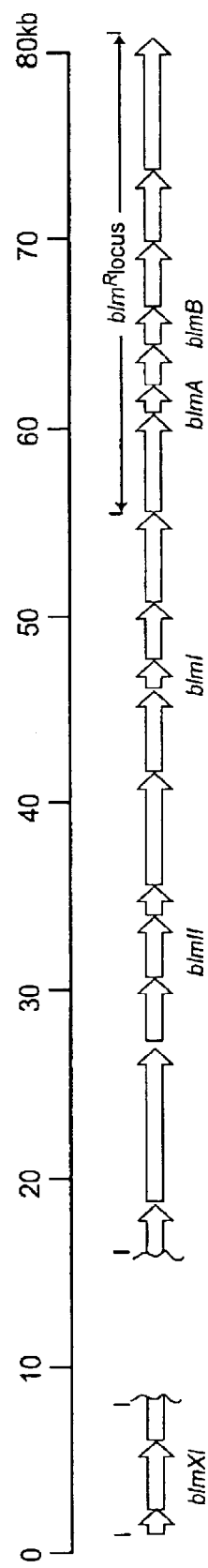
FIG. 8C (SEQ ID NO:127 nucleotide sequence and SEQ ID NO:128 amino acid sequence) shows the nucleotide sequence of the blmI gene. The potential ribosome-binding site (RBS) and the conserved motif for 4'-phosphopantetheinylation are underlined. The sequence has been deposited into GenBank under accession no. AF210249.

In our effort to clone the gene cluster responsible for BLM biosynthesis, we have determined 80 kb DNA sequence from *Sv* ATCC15003 (FIG. 8). Among the orfs identified within the blm gene cluster is the small orf of 273 base pairs (bp), blmI, which is located approximately 4 kb upstream of the previously characterized blmAB resistance locus (Sugiyama et al. (1994) *Gene* 151: 11–16; Calcutt and Schmidt (1994) *Gene* 151: 17–21) (FIG. 8B). The blmI gene encodes a protein of 90 amino acids with a molecular weight of 9957 and a pI of 6.52 (FIG. 8C). Computer-assisted analysis (Altschul et al. (1997) *Nucleic Acids Res.* 25: 3389–3402) of the deduced amino acid sequence indicates that BlmI is very similar to various PCP domains of NRPSs (ranging around 40% identity and 60% similarity, as shown in FIG. 9). Like known PCP domains of NRPS, BlmI has the highly conserved signature motif of LGGXS, within which the serine residue is the site for 4'-phosphopantetheinylation (Stachelhaus and Marahiel (1995) *FEMS Microbiol. Lett.* 125: 3–14; Marahiel et al. (1997) *Chem. Rev.* 97: 2651–2673). The latter posttranslational modification is generally necessary for peptide biosynthesis; converting the apo-PCP into the functional holo-PCP (Marahiel et al. (1997) *Chem. Rev.* 97: 2651–2673; Walsh et al. (1997) *Curr. Opin. Chem. Biol.* 1: 309–315). Based on sequence comparison, BlmI is most related to PCPs and not to other kinds of carrier proteins that also share the same LGGXS (SEQ ID NO:80) motif and undergo the same posttranslational 4'-phosphopantetheinylation [31], such as the *E. coli* acyl carrier protein (ACP) (Lambalot and Walsh (1995) *J. Biol. Chem.* 270: 24658–24661), the ACP domain of type I PKS and the type II PKS ACP (Cox and Simpson (1997) *FEBS Lett.* 405: 267–272; Carreras et al. (1997) *Biochemistry* 36: 11757–11761), the ArCP domain (Gehring et al. (1998) *Biochemistry* 37: 2648–2659), and several nodulation related ACP-like proteins (Epple et al. (1998) *J. Bacteriol.* 180: 4950–4954; Spaink et al. (1991) *Nature* 354: 125–130).

Overexpression of blmI in *E. coli*

To overexpress the blmI gene in *E. coli*, we directly amplified the blmI gene by PCR from the *Sv*. ATCC15003 genomic DNA and cloned it into the pQE-60 expression vector to give pBS1 so that BlmI could be produced as a protein with a native N-terminus and a $His_6$-tag at its C-terminus. However, no production of the BlmI protein was detected, as judged by sodium dodecyl sulfate-polyacrylamide gel electrophoresis (SDS-PAGE), upon introduction of pBS1 into *E. coli* M15(pREP4) under the standard overexpression conditions recommended by the manufacturer (Qiagen). We reasoned that the small BlmI protein with its native N-terminus may not be stable in the heterologous host, and hence moved the blmI gene from pBS1 into pET-29a to yield the second overexpression construct of pBS2. In the latter construct, BlmI should be produced as a fusion protein with 27 extra amino acid residues at its N-terminus, including an S-tag and the thrombin cleaving site, in addition to the His$_6$-tag at its C-terminus. Introduction of pBS2 into *E. coli* BL21 (DE-3) under the standard overexpression conditions recommended by the manufacturer (Novagen) indeed resulted in overproduction of BlmI. In fact, the bulk of the soluble protein was the overproduced BlmI, which was easily purified by affinity chromatography using Ni-NTA resin (Qiagen). It is noteworthy that fusion of the additional 23 amino acids to the N-terminus of BlmI as in pBS2 and change of the expression system from *E. coli* M15(pREP4) (pBS1) to *E. coli* BL21 (DE-3)(pBS2) dramatically improved the expression level of blmI.

In vivo 4'-phosphopantetheinylation of the BlmI Protein

To establish BlmI as a type II PCP, we tested if it could serve as a substrate for a PCP-specific 4'-PPTase. PPTases catalyze the posttranslational modification of an apo-PCP into a holo-PCP by transferring the 4'-phosphopantetheine moiety from co-enzyme A (CoA) to the conserved serine residue of PCP, and this reaction has been developed recently into a general method to prepare various holo-PCP, holo-ACP, or holo-ArCP from the corresponding apoproteins (Stachelhaus et al. (1996) *Chem. Biol.* 3: 913–9211; Gehring et al. (1998) *Biochemistry* 37: 2648–2659; Gehring et al. (1998) *Biochemistry* 37: 11637–11650; Weinreb et al. (1998) *Biochemistry* 37: 1575–1584). Therefore, we decided to investigate the 4'-phosphopantetheinylation of BlmI under both in vivo (Ku et al. (1997) *Chem. Biol.* 4: 203–207) and in vitro (Gehring et al. (1998) *Biochemistry* 37: 11637–11650; Lambalot et al. (1996) *Chem. Biol.* 3: 923–936; Quadri et al. (1998) *Biochemistry* 37: 1585–1595) conditions.

Figure 10A:
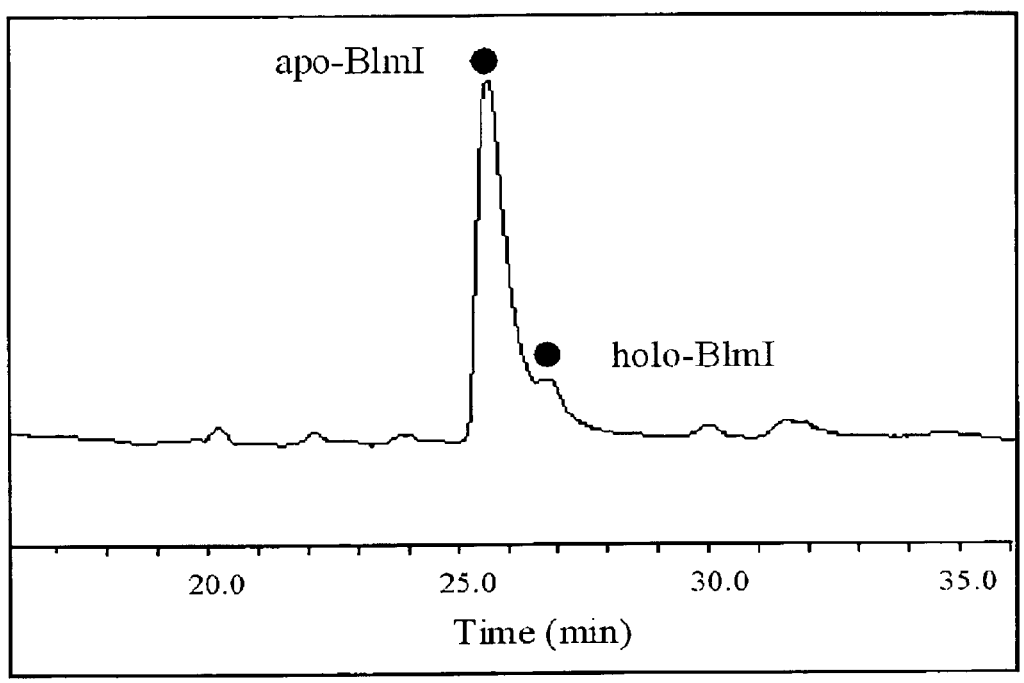
FIGS. 10A and 10B shows the HPLC analysis of BlmI purified from *E. coli* OG7001(pBS2) (FIG. 10A), and *E. coli* OG7001(pBS2/pDPT-Gsp) (FIG. 10B).
Figure 10B:
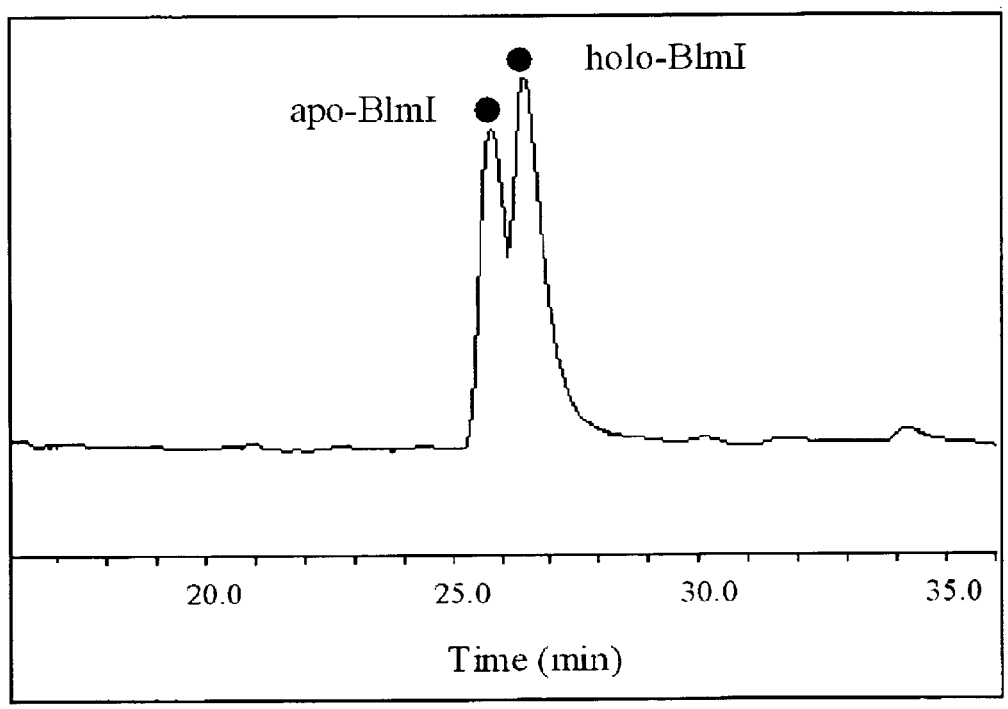

To examine 4'-phosphopantetheinylation of BlmI in vivo, we chose *E. coli* OG7001 as the expression host, which is a β-alanine auxotroph derived from *E. coli* BL21(DE3) by P1 co-transduction of the panD mutation from *E. coli* SJ16 (Epple et al. (1998) *J. Bacteriol.* 180: 4950–4954). Upon introduction of pBS2 into *E. coli* OG7001, blmI was exceptionally well expressed and the overproduced BlmI protein was readily purified. However, high performance liquid chromatography (HPLC) analysis showed that the purified BlmI was essentially in the apo-form (FIG. 10A), indicative that apo-BlmI was a poor substrate for the *E. coli* endogenous PPTases, such as EntD and ACP synthase (Lambalot et al. (1996) *Chem. Biol.* 3: 923–936; Walsh et al. (1997) *Curr. Opin. Chem. Biol.* 1: 309–315; Lambalot and Walsh (1995) *J. Biol. Chem.* 270: 24658–24661). To circumvent the poor endogenous PPTase activity, we next co-expressed blmI with the gsp gene, which was isolated from the gramicidin S producer *Bacillus brevis*, and encoded a PPTase that was known to 4'-phosphopantetheinylate heterologously produced PCPs in *E. coli* (Lambalot et al. (1996) *Chem. Biol.* 3: 923–936; Ku et al. (1997) *Chem. Biol.* 4: 203–207). We co-transformed pDPT-Gsp, in which the expression of the gsp gene was under the control of the T5/Lac promoter (Ku et al. (1997) *Chem. Biol.* 4: 203–207), and pBS2 into *E. coli* OG7001. BlmI was again very well expressed and the resulting BlmI protein was similarly purified. HPLC analysis showed that at least 60% of over-produced BlmI was modified into the holo-BlmI protein (FIG. 10B). (A PCP domain was similarly 4'-phosphopantetheinylated in vivo before by co-expressing gsp in *E. coli* using pDPT-Gsp, and approximately 80% of the PCP was produced in the holo-form (Ku et al. (1997) *Chem. Biol.* 4: 203–207).

We next cultured *E. coli* OG7001(pBS2) and *E. coli* OG7001(pBS2/pDPT-Gsp) in the presence of [3-$^3$H]-β-alanine, a known biosynthetic precursor of 4'-phosphopantetheine (Stachelhaus et al. (1996) *Chem. Biol.* 3: 913–921; Epple et al. (1998) *J. Bacteriol.* 180: 4950–4954). Specific incorporation of [3-$^3$H]-β-alanine into the 4'-phosphopantetheine moiety of holo-BlmI was determined by autoradiographic analysis. Thus, while fermentation of *E. coli* OG7001(pBS2) in the presence of [3-$^3$H]-β-alanine led to an IPTG-dependent overproduction of BlmI, little of the resulting BlmI protein was $^3$H-labeled, indicative of being produced in the apo-form. In contrast, fermentation of *E. coli* OG7001(pBS2/pDPT-Gsp) in the presence of [3-$^3$H]-β-alanine resulted in a significant increase of IPTG-dependent incorporation of the $^3$H-label into the overproduced BlmI protein, suggesting a specific incorporation of [3-$^3$H]-β-alanine into holo-BlmI, presumably in the 4'-phosphopanthetheine moiety. There were several additional proteins that were also weakly labeled by [3-$^3$H]-β-alanine. However, both their expression and their incorporation by $^3$H-label were independent from either IPTG induction or the presence of Gsp, hence these proteins were unrelated to BlmI. (Similar background labeling was reported before for in vivo 4'-phosphopantetheinylation of other PCP (Epple et al. (1998) *J. Bacteriol.* 180: 4950–4954)). We also purified the BlmI protein from *E. coli* OG7001(pBS2/pDPT-Gsp) and demonstrated that it was the holo-BlmI protein that was specifically associated with the $^3$H-activity. Finally, we confirmed the identity of holo-BlmI by subjecting the purified BlmI protein to MALDI-Tof mass spectral analysis (Weinreb et al. (1998) *Biochemistry* 37: 1575–1584). BlmI produced in the absence of the Gsp PPTase yielded a single peak with a molecular weight of 13,952, suggesting that the produced BlmI protein is in the apo-form (calc., 13,949). In contrast, BlmI produced in the presence of Gsp yielded two species with molecular weight of 13,969 and 14,303, respectively. While the species with the molecular weight of 13,969 represents apo-BlmI, a molecular weight of 14,303 unambiguously confirmed the other protein as holo-BlmI (calc., 14,289). The latter result indicated that the purified BlmI consisted of both the apo- and holo-BlmI proteins, in agreement with the HPLC analysis results (FIG. 10B).

In vitro 4'-phosphopantetheinylation of the BlmI Protein

To investigate 4'-phosphopantetheinylation of BlmI in vitro, we chose the Sfp protein as the preferred PPTase, which had been isolated before from the surfactin producer *Bacillus subtilis* (Nakano et al. (1992) *Mol. Gen. Genet.* 232: 313–321). (Overexpression of gsp in *E. coli* using pDPT-Gsp resulted in predominantly an insoluble Gsp protein (Ku et al. (1997) *Chem. Biol.* 4: 203–207). The Sfp PPTase was overproduced in *E. coli* MV1190(pUC8-Sfp) and purified to near homogeneity as described before (Quadri et al. (1998) *Biochem.*, 37: 1585–1595; Nakano et al. (1992) *Mol. Gen. Genet.*, 232: 313–321). Upon incubation of the purified apo-BlmI with [$^3$H-pantetheine]-CoA in the presence of the Sfp PPTase, we examined the covalent incorporation of the [$^3$H-pantetheine]-4'-phosphopantetheine moiety from CoA into holo-BlmI by autoradiographic analysis. Indeed, the apo-BlmI was quantitatively labeled by [$^3$H-pantetheine]-CoA, and no labeling was observed in the absence of either the apo-BlmI or the Sfp PPTase protein, demonstrating that the Sfp PPTase can recognize apo-BlmI as a substrate and specifically transfer the 4'-phosphopantetheine group from CoA into holo-BlmI.

In vitro Aminoacylation of BlmI

Once we established BlmI as a type II PCP that can be readily modified by PCP-specific PPTases into the holo-BlmI protein, we tested if the holo-BlmI could be aminoacylated in trans, requiring an A domain. Since BlmI has no cognate A domain of its own, we turned our attention to another putative biosynthesis gene cluster we have cloned previously from Sv ATCC15003, which encodes at least four NRPS and one PKS modules. We have established that this gene cluster is not clustered with the blm locus and is unrelated to BLM biosynthesis. From this gene cluster, we amplified by PCR a 1579 bp fragment encoding an A domain, named Val-A, which we predicted to have a molecular weight of 56,581 and a pI of 7.39. We cloned val-A into pET-28a to yield pBS3, in which Val-A would be produced as a fusion protein with a His$_6$-tag at the N-terminus. Introduction of pBS3 into E. coli BL21(DE3) under the standard overexpression conditions recommended by the manufacturer (Novagen) resulted in good overproduction of Val-A, predominantly in soluble form, from which Val-A was purified by affinity chromatography using Ni-NTA resin. The purified Val-A protein was active by the amino acid-dependent ATP-PPi exchange assay (Lee and Lipmann (1970) Method Emzymol. 43: 585–602; Ku et al. (1997) Chem. Biol., 4: 203–207). Among the 23 amino acids tested, Val-A specifically activated valine, an amino acid that is not required for BLM biosynthesis.

To carry out the aminoacylation in trans, we incubated the purified holo-BlmI and Val-A in vitro in the presence L-[$^{14}$C(U)]valine and ATP (Stachelhaus et al. (1996) Chem. Biol. 3: 913–921; Weinreb et al. (1998) Biochemistry 37: 1575–1584). The aminoacylated holo-BlmI-L-[$^{14}$C(U)] valine species was subjected to SDS-PAGE and specific attachment of L-[$^{14}$C(U)]valine to holo-BlmI was determined by autoradiographic analysis. Remarkably, the holo-BlmI was specifically labeled by L-[$^{14}$C(U)]valine in the presence of Val-A, indicative of the formation of the holo-BlmI-S-valine thioester. The in trans aminoacylation between the holo-BlmI and Val-A proteins appeared to be very specific. Neither incubation of L-[$^{14}$C(U)]valine with Val-A, the apo-BlmI, or the holo-BlmI protein alone, nor incubation of L-[$^{14}$C(U)]valine with the Val-A and apo-BlmI proteins, resulted in the detection of $^{14}$C-labeled BlmI protein.

Discussion

Figure 11A:
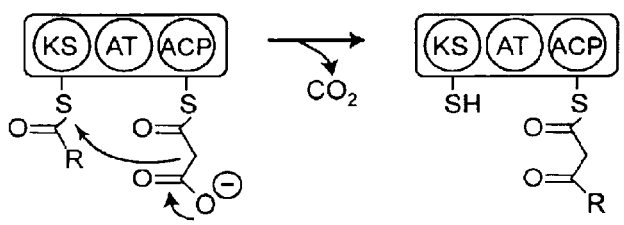
FIGS. 11A–11D show the enzyme architecture of type I and type II PKS and NRPS. A, adenylation domain; ACP, acyl carrier protein or ACP domain; AT, acyl transferase; C, condensation protein or C domain; KS, β-ketoacyl synthase domain; KSα, β-ketoacyl synthase α subunit; KSβ, β-ketoacyl synthase β subunit; PCP, peptidyl carrier protein or PCP domain.
Figure 11B:
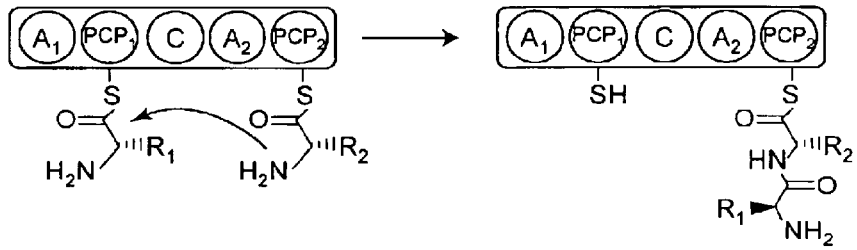
Figure 11C:
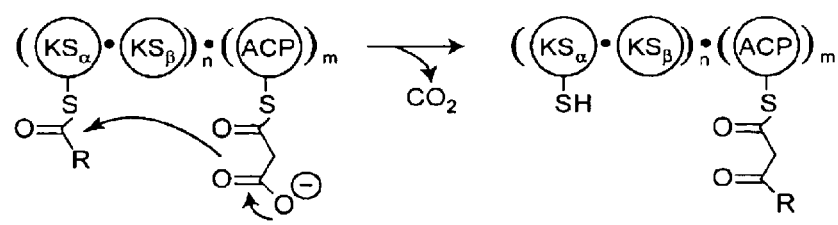
Figure 11D:
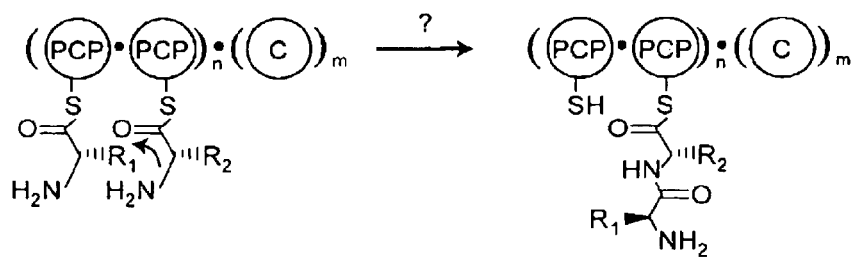
Figure 12:
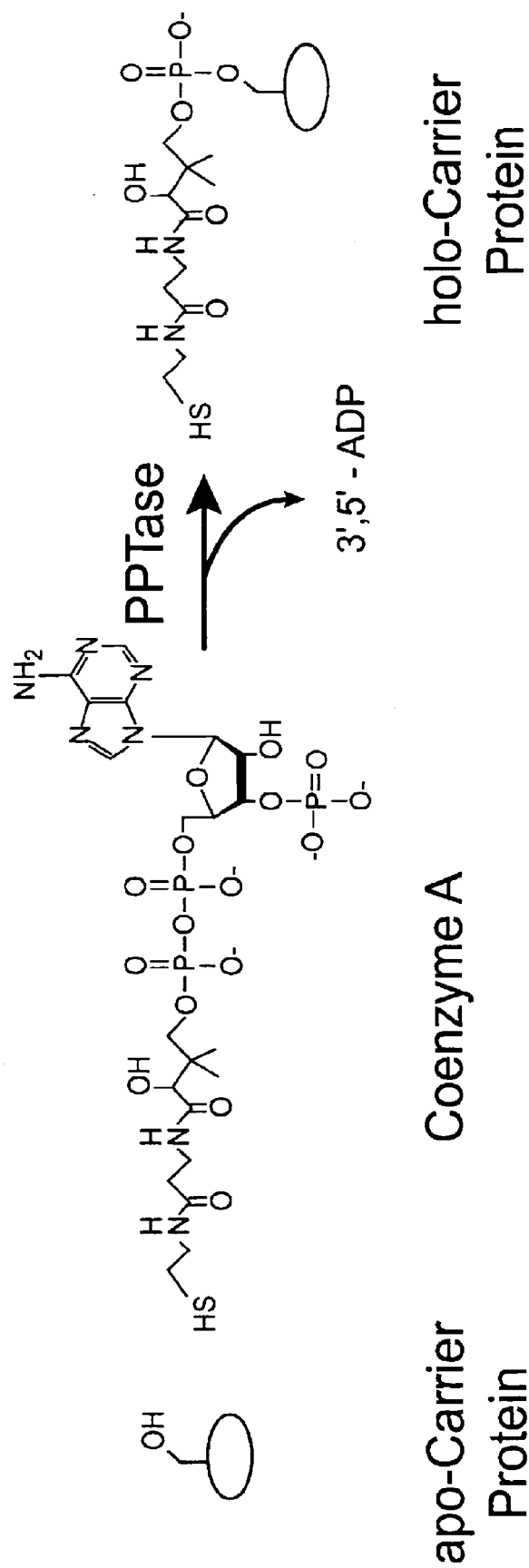
FIG. 12 illustrates the reaction catalyzed by phosphopantetheinyl transferases (PPTases).

Nonribosomal peptides and polyketides are two distinct classes of natural products yet are assembled from amino acids and short carboxylic acids by NRPSs and PKSs, respectively, in strikingly similar strategies (Cane et al. (1998) Science 282: 63–68). These fascinating multifunctional enzyme complexes have been classified into two types based on their gene organization and enzyme architecture. Type I enzymes are multifunctional proteins consisting of domains for individual enzyme activities, and type II enzymes are multienzyme complexes consisting of discrete proteins that are largely monofunctional. While both type I and type II PKSs (FIGS. 11A and 11C) have been well characterized to account for the vast structural diversities found in polyketide biosynthesis (Hopwood (1997) Chem Rev. 97: 2465–2497), all NRPSs studied so far are exclusively the type I modular enzymes (FIG. 11B) (Kleinkauf and von Döhren: H. (1996) Eur. J. Biochem. 236: 335–351; Marahiel et al. (1997) Chem. Rev. 97: 2651–2673; von D öhren et al. (1997) Chem. Rev. 97: 2675–2705). It is very tempting to speculate the existence of a type II NRPS that, analogous to type II PKS (Shen and Hutchinson (1993) Science 262: 1535–1540; Bao et al. (1998) Biochemistry 37: 8132–8138; Carreras and Khosla (1998) Biochemistry 37: 2084–2088), should consist of discrete proteins possessing enzyme activities such as the A (Stachlhaus and Marahiel (1995) J. Biol. Chem. 270: 6163–6169), the PCP (Stein and Morris (1996) J. Biol. Chem. 271: 15428–15435), or the C (Stachlhaus et al. (1998) J. Biol. Chem. 273: 22773–22781) domains of type I NRPSs (FIG. 11D). The fact that both the A (Stachlhaus and Marahiel (1995) J. Biol. Chem. 270: 6163–6169; Konz et al. (1997) Chem. Biol. 4: 927–937; Weinreb et al. (1998) Biochemistry 37: 1575–1584; Mootz and Marahiel (1997) J. Bacteriol. 179: 6843–6850) and the PCP (Stachelhaus et al. (1996) Chem. Biol. 3: 913–921; Weinreb et al. (1998) Biochemistry 37: 1575–15841; Pfeifer et al. (1995) Biochemistry 34: 7450–7459; Haese et al. (1994) J. Mol. Biol. 243: 116–122; Lambalot et al. (1996) Chem. Biol. 3: 923–936; Quadri et al. (1998) Biochemistry 37: 1585–1595; Gehring et al. (1996) Chem. Biol. 4: 17–24; Ku et al. (1997) Chem. Biol. 4: 203–207) domains of type I NRPSs can act as independent enzymes supports the hypothesis of a type II NRPS.

We have now cloned and sequenced the blmI gene, overproduced and characterized the BlmI protein as a bona fide type II PCP, and demonstrated that holo-BlmI can be aminoacylated by a completely unrelated A domain, providing for the first time genetic and biochemical evidence for a type II NRPS enzyme. We concluded BlmI as a type II PCP based on the following criteria. (1) The deduced amino acid sequence of the blmI gene is highly homologous to various PCP domains of known NRPSs, in particular at the signature motif of LGGXS within which the 4'-phosphopantetheine prosthetic group is covalently attached to the serine residue (Marahiel et al. (1997) Chem. Rev. 97: 2651–2673; Stachelhaus and Marahiel (1995) FEMS Microbiol. Lett. 125: 3–14). While the current boundaries for a PCP domain in the literature were defined arbitrarily (Stachelhaus et al. (1996) Chem. Biol. 3: 913–921) and varied from one PCP to another, we can now re-define a PCP domain for the type I NRPS as a 90 amino acid peptide with approximately 45 amino acids, each flanking the essential serine residue in the LGGXS (SEQ ID NO:81) motif, in light of this discrete BlmI type II PCP (FIG. 9). (2) The blmI gene has been successfully expressed in E. coli, and fusion of a short peptide to the N-terminus of BlmI dramatically improved its overproduction efficiency. While we cannot exclude the effect of different systems on gene expression, i.e., E. coli M15(pREP4)(pBS1) vs. E. coli BL21(DE-3)(pBS2), we attribute the increase in expression efficiency to the stability of BlmI as an N-terminal fusion protein instead of the otherwise labile BlmI protein with its native N-terminus. Since BlmI was produced predominantly in the apo-form in E. coli, apo-BlmI apparently was not a substrate for the endogenous PPTases, such as EntD or ACP synthase, excluding BlmI as an ArCP or ACP, respectively. EntD and ACP synthase are known to 4'-phosphopantetheinylate apo-ArCP and ACP, respectively, to their holo-forms efficiently (Lambalot et al. (1996) Chem. Biol. 3: 923–936; Walsh et al. (1997) Curr. Opin. Chem. Biol. 1: 309–315; Lambalot and Walsh (1995) J. Biol. Chem. 270: 24658–24661). (3) The apo-BlmI protein serves as a substrate for PCP-specific PPTases that transfer the 4'-phosphopantetheine moiety from CoA to apo-BlmI to yield the holo-BlmI protein. We have demonstrated this posttranslational modification for BlmI in vivo with the Gsp PPTase (Ku et al. (1997) *Chem. Biol.* 4: 203–207) and in vitro with the Sfp PPTase (Gehring et al. (1998) *Biochemistry* 37: 11637–11650; Lambalot et al. (1996) *Chem. Biol.* 3: 923–936; Quadri et al. (1998) *Biochemistry* 37: 1585–1595), both of which have been extensively used in preparing holo-PCPs. (4) The specific modification of apo-BlmI by 4'-phosphopantetheinylation has been monitored by HPLC analysis (FIG. 10) (Weinreb et al. (1998) *Biochemistry* 37: 1575–1584) and by specific incorporation of [3-$^3$H]-β-alanine in vivo (Stachelhaus et al. (1996) *Chem. Biol.* 3:913–921; Ku et al. (1997) *Chem. Biol.* 4: 203–207; Epple et al. (1998) *J. Bacteriol.* 180: 4950–4954) and of [$^3$H-pantetheine]-CoA in vitro (Gehring et al. (1998) *Biochemistry* 37: 11637–11650; Lambalot et al. (1996) *Chem. Biol.* 3: 923–936; Quadri et al. (1998) *Biochemistry* 37: 1585–1595), respectively, into the 4'-phosphopantetheine moiety of the holo-BlmI protein. The identity of BlmI was finally confirmed by MALDI-Tof mass spectral analysis that determined the molecular weight for both the apo- and holo-BlmI proteins.

While individual domains of type I NRPSs can function independently and several A (Stachlhaus and Marahiel (1995) *J. Biol. Chem.* 270: 6163–6169; Konz et al. (1997) *Chem. Biol.* 4: 927–937; Weinreb et al. (1998) *Biochemistry* 37: 1575–1584; Mootz and Marahiel (1997) *J. Bacteriol.* 179: 6843–6850) and PCP (Stachelhaus et al. (1996) *Chem. Biol.* 3: 913–921; Weinreb et al. (1998) *Biochemistry* 37: 1575–15841; Pfeifer et al. (1995) *Biochemistry* 34: 7450–7459; Haese et al. (1994) *J. Mol. Biol.* 243: 116–122; Lambalot et al. (1996) *Chem. Biol.* 3: 923–936; Quadri et al. (1998) *Biochemistry* 37: 1585–1595; Gehring et al. (1996) *Chem. Biol.* 4: 17–24; Ku et al. (1997) *Chem. Biol.* 4: 203–207) domains have been overproduced purified, and biochemically characterized, aminoacylation in trans has been successful only between PCPs and their cognate A domains (Stachelhaus et al. (1996) *Chem. Biol.* 3: 913–921; Weinreb et al. (1998) *Biochemistry* 37: 1575–1584). No aminoacylation between PCP and A domains from different NRPS modules has been observed. These results led to the conclusion that there is a specific protein-protein recognition between the A domain and its cognate PCP (Weinreb et al. (1998) *Biochemistry* 37: 1575–1584). Such domain-specific aminoacylation, in fact, should be beneficial in maintaining the fidelity of a type I NRPS by providing additional "gating" against misincorporation of non-specifically activated aminoacyl adenylate into the final peptide product. Since a type II PCP such as BlmI lacks its cognate A domain, we asked if BlmI could be aminoacylated by an unrelated A domain of a type I NRPS. Although we have yet to determine the biochemical role of BlmI in vivo, the fact that the blmI gene is located in the middle of the blm gene cluster suggests that it may be involved in BLM biosynthesis. To avoid the ambiguity of selecting an A domain that may potentially interact with BlmI in vivo, we preferred not to choose any A domain from the blm gene cluster to test if it could aminoacylate BlmI in trans. We reasoned that an A domain that is unrelated to BlmI should come from a gene cluster independent from BLM biosynthesis and should activate an amino acid not required by BLM. We chose Val-A because it satisfied both requirements. Val-A is an A domain of a type I NRPS from a gene cluster we have cloned previously from *Sv* ATCC15003 that has proven to be unrelated to BLM biosynthesis, and it specifically activates valine among the 23 amino acids tested. Remarkably, BlmI was efficiently aminoacylated by Val-A. The valine residue is specifically attached in a thioester linkage to the terminal —SH of the 4'-phosphopantetheine moiety of the holo-BlmI protein, as evidenced by the fact that the apo-BlmI was inactive under the identical conditions.

Aminoacylation of holo-BlmI by Val-A represents the first example in which an A domain aminoacylates a protein other than its cognate PCP domain. Since it has been suggested that an A domain of a type I NRPS can transfer the activated aminoacyl adenylate only to its cognate PCP domain because of the specific protein-protein recognition between the two domains (Weinreb et al. (1998) *Biochemistry* 37: 1575–1584), the fact that BlmI is aminoacylated by Val-A revealed a distinct feature of a type II PCP. It is very tempting to speculate that type II PCPs such as BlmI may have broad intrinsic substrate specificity toward either the aminoacyl adenylate, the A domain, or both. In fact, the latter feature is reminiscent of the type II PKS ACPs, which have been shown to be interchangeable among different PKS complexes (Shen and Hutchinson (1993) *Science* 262: 1535–1540; Bao et al. (1998) *Biochemistry* 37: 8132–8138; Carreras and Khosla (1998) *Biochemistry* 37: 2084–2088). The biosynthesis of D-alanyl-lipoteichoic acid in *Bacillus suntillis* (Perego et al. (1995) *J. Biol. Chem.* 270: 15598–15606) and *Lactobacillus casei* (Debabov et al. (1996) 178: 3869–3876) also involves a discrete ACP-like protein, the D-alanyl carrier protein, although the latter clearly is structurally and functionally different from PCPs.

The results strongly suggest the existence of a type II NRPS. In fact, we have already identified within the blm gene cluster two additional genes, blmII and blmXI (FIG. 1B), which encode type II C proteins based on sequence analysis (see Example 1).

Significance

All NRPSs known to date are exclusively the type I modular enzymes that are multifunctional proteins consisting of domains, such as A (Stachlhaus and Marahiel (1995) *J. Biol. Chem.* 270: 6163–6169), PCP (Stachelhaus et al. (1996) *Chem. Biol.* 3: 913–921), and C (Stachlhaus et al. (1998) *J. Biol. Chem.* 273: 22773–22781), for individual enzyme activities (Kleinkauf and von Döhren: H. (1996) *Eur. J. Biochem.* 236: 335–351; Marahiel et al. (1997) *Chem. Rev.* 97: 2651–2673; von Döhren et al. (1997) *Chem. Rev.* 97: 2675–2705), and control the structural variations of the resulting peptide products by the multiple-carrier thiotemplate mechanism (Cane et al. (1998) *Science* 282: 63–68; Stein and Morris (1996) *J. Biol. Chem.* 271: 15428–15435). While individual domains of type I NRPSs can function independently, aminoacylation in trans has been successful only between PCPs and their cognate A domains (Stachelhaus et al. (1996) *Chem. Biol.* 3: 913–921; Weinreb et al. (1998) *Biochemistry* 37: 1575–1584). We have cloned and sequenced the blmI gene, overproduced and characterized the BlmI protein as a bona fide type II PCP, and demonstrated that the holo-BlmI can be aminoacylated by a completely unrelated A domain. Our results provided for the first time the genetic and biochemical evidence to support the hypothesis of a type II NRPS, setting the stage for formulating new research concepts to study peptide biosynthesis. Genetic manipulation of type I NRPS has already been successful in generating novel peptides (Stachlhaus et al. (1995) *Science* 269: 69–72). An unprecedented type II NRPS should shed new light in engineering NRPS proteins, greatly increasing our ability to access peptides with even greater structural diversities.

Materials and Methods

General DNA Manipulations

Plasmids preparation and DNA extraction were carried out by using commercial kits (Qiagen, Santa Clarita, Calif.), and all other manipulations were carried out according to standard methods (Sambrook et al. (1989) *Molecular cloning: a laboratory manual*: (2nd ed): Cold Spring Harbor Laboratory Press: Cold Spring Harbor: USA). *E. coli* strain DH5α was used as the host for general DNA propagations.

Overexpression of blmI in *E. coli* and Purification of the BlmI Protein

The blmI gene was amplified from *Sv* ATCC15003 by PCR using a forward primer of 5'-CCG CCC ATG GGT GCT CCG CGT GGC GAG CGG ACC CGG CGC-3' (SEQ ID NO:82, the NcoI site is underlined) and a reverse primer of 3'-CCT AGA TCT CCG GTC CCG CTC CCC CGT-5' (SEQ ID NO:83, the BglII site is underlined). In order to create the NcoI site, the original starting sequence of "ATG AGC" has been changed to "ATG GGT", which resulted in the change of the second amino acid from serine to glycine. The first five codons of blmI were also optimized for overexpression in *E. coli*. The PCR-amplified 0.3 kb NcoI-BglII fragment was cloned into the similar sites of pQE-60 (Qiagen) to form pBS1. Digestion of pBS1 with NcoI and HindIII and cloning the resulting 0.3 kb NcoI-HindIII fragment into the same sites of pET-29a (Novagen, Madison, Wis.) yielded pBS2.

Expressions of blmI in *E. coli* M15 (pREP4)(pBS1) and in *E. coli* BL-21(DE-3)(pBS2) and purification of the resulting BlmI protein by affinity chromatography on Ni-NTA resin were carried out under the standard conditions recommended by Qiagen and Novagen, respectively. The incubation temperature was lowered to 30° C. to improve the solubility. The purification of BlmI was monitored by SDS-PAGE on 15% gel. The final pure BlmI protein was desalted on PD-10 column (Sephadex G-25, Pharmacia Biotech, Piscataway, N.J.) into 50 mM sodium phosphate buffer, pH 7.8, containing 200 mM NaCl, 10 mM $MgCl_2$, 2 mM dithiothreitol (DTT), 1 mM EDTA, 10% glycerol, and stored at −80° C. for in vitro assays.

HPLC Analysis and MALDI-Tof Mass Spectral Determination

Samples of BlmI (30–70 μg) purified from *E. coli* OG7001(pBS2) or *E. coli* OG7001(pBS2/pDPT-Gsp) were analyzed on a Nova-Pak C18 column (5 mm×10, Waters, Milford, Mass.) using a Rainin DMAX HPLC unit. The column was developed by a linear gradient of 0–50% acetonitrile in 0.1% trifluoroacetic acid in 25 min, followed by additional 5 min at 50% acetonitrile, with a flow rate of 0.6 ml/min and detection at 280 nm. MALDI-Tof mass spectral determination was performed on a Bruker Biflex IIII spectrometer at the Facility for Advanced Instrumentation of University of California, Davis.

In vivo Labeling of BlmI with [3-$^3$H]-β-alanine

The β-alanine auxotroph *E. coli* strain OG7001 (Epple et al. (1998) *J. Bacteriol.* 180: 4950–4954) was transformed with pBS2 and cultured under the same conditions as for *E. coli* BL21(DE3) (Novagen). For co-expression of blmI with gsp, pDPT-Gsp (Ku et al. (1997) *Chem. Biol.* 4: 203–207) was similarly transformed into *E. coli* OG7001(pBS2) and the transformants were cultured in 2×YT (Debabov et al. (1996) 178: 3869–3876) in the presence of kanamycin (25 μg/ml) and chloramphenicol (50 μg/ml). For in vivo labeling experiment, cells from 2 ml overnight culture of either *E. coli* OG7001(pBS2) or *E. coli* OG7001(pBS2/pDPT-Gsp) were harvested, washed with M9 minimal medium (Debabov et al. (1996) 178: 3869–3876), and re-suspended in 2 ml of M9 minimal medium. The latter were used as seed cultures (20 μl) to inoculate 1 ml M9 medium with kanamycin (25 μg/ml) or kanamycin (25 μg/ml) and chloramphenicol (50 μg/ml) for *E. coli* OG7001(pBS2) or *E. coli* OG7001(pBS2/pDPT-Gsp), respectively. The resulting culture was incubated at 30° C., 250 rpm to $OD_{600nm}$ 0.6 and to this was added 10 μCi of [3-$^3$H]-β-alanine (50 Ci/mmol, American Radiolabeled Chemicals Inc., St. Louis, Mo.) with or without IPTG (1 mM). Ttotal proteins were resolved by SDS-PAGE on 15% gels that were Coomassie blue-stained. To determine $^3$H-labeling of the overproduced holo-BlmI protein, gels were soaked in Amplifier (Amersham, Arlington Heights, Ill.) for 20 min, dried between two sheets of cellulose membrane (KOH Development Inc., Ann Arbor, Mich.), and visualized by autoradiography on X-ray films (Fuji Medical Systems, Stamford, Conn.).

In vitro Labeling of BlmI with [$^3$H-pantetheine]-CoA

Expression of sfp in *E. coli* MV1190(pUC8-Sfp), purification of the Sfp PPTase to homogeneity, and 4'-phosphopantetheinylation of apo-BlmI by Sfp in vitro were carried out essentially according to literature procedures (Quadri et al. (1998) *Biochemistry* 37: 1585–1595; Nakano et al. (1992) *Mol. Gen. Genet.* 232: 313–321). A typical 100 μl assay solution contained 26 μM apo-BlmI, 2.9 μM Sfp, 25 μM [$^3$H-pantetheine]-CoA (0.9 μCi, 40 Ci/mM), 10 mM $MgCl_2$, and 5 mM DTT, in 75 mM MES/NaOAc buffer, pH 6.0. After 30 min incubation at 37° C., the assays were stopped by addition of 5 μl of bovine serum albumin (0.2 mg/ml) and 0.9 ml of cold 10% (v/v) trichloroacetic acid (TCA). The precipitated proteins were collected by centrifugation at 14,000 rpm, 20 min, 4° C. (Eppendorf 5415C centrifuge), washed with 10% TCA three times, and resolved by SDS-PAGE on 15% gel. The $^3$H-activity incorporated into holo-BlmI was similarly determined by autoradiography as described for in vivo labeling of holo-Blm with [3-$^3$H]-β-alanine.

Overexpression of val-A in *E. coli* and Purification and Assay of the Val-A Protein The val-A fragment was amplified from *Sv* ATCC15003 by PCR using a forward primer of 5'-GGA ATT C CA TAT GGG CAC CAC CGT CGC CGC G-3' (SEQ ID NO:84, the NdeI site is underlined), and a reverse primer of 3'-GGC AAG CTT GGG ACC GGG CGT GGA GCG C (SEQ ID NO:85, the HindIII site is underlined). The PCR-amplified 1.6 kb NdeI-HindIII fragment was cloned in the similar sites of pET-28a (Qiagen) to yield pBS3. Expression of val-A in *E. coli* BL-21(DE-3)(pBS3) and purification of the resulting Val-A protein by affinity chromatography on Ni-NTA resin were carried out under the standard conditions recommended by Novagen.

Amino acid-dependent ATP-PPi assays were performed essentially according to the literature procedures (Ku et al. (1997) *Chem. Biol.* 4: 203–207; Lee and Lipmann (1970) *Method Emzymol.* 43: 585–602). A typical 100 μl assay solution contained 180 nM Val-A, 1 mM ATP, 0.1 mM PPi with 0.2 μCi of $^{32}$P-PPi (11.75 Ci/mmol, NEN Life Science Products, Inc., Boston, Mass.), 1 mM $MgCl_2$, 0.1 mM EDTA, and 1 mM L-amino acid in 50 mM sodium phosphate buffer, pH 7.8. After 30 min incubation at 30° C., the assays were stopped by addition of 0.9 ml of cold 1% (w/v) activated charcoal in 3% (v/v) perchloric acid. The precipitates were collected on glass fiber filters (2.4 cm, G-4, Fisher, Pittsburgh, Pa.), washed successively with 10 ml of 0.2 M sodium phosphate buffer, pH 8.0, 4 ml water, and 1 ml of ethanol, and dried in air. The filters were mixed with 7 ml of scintillation fluid (ScintiSafe Gel, Fisher) and counted on a Beckman LS-6800 scintillation counter to determine the radioactivity.

In vitro Aminoacylation of Holo-BlmI by Val-A

The aminoacylation of holo-BlmI was carried out essentially according to literature methods (Stachelhaus et al.

(1996) Chem. Biol. 3: 913–921; Weinreb et al. (1998) Biochemistry 37: 1575–1584). A typical 100 μl assay solution contained 180 nM Val-A, 1.5–2.8 μM apo- or holo-BlmI, 35 μM L-[$^{14}$C(U)]-valine (283 mCi/mmol, NEN Life Science Products, Inc., Boston, Mass.), 5 mM ATP, 10 mM MgCl$_2$, and 5 mM DTT in 75 mM Tris-HCl buffer, pH 8.0. The reactions were started by the addition of ATP and, after incubation at 37° C. for 30 min, were stopped by addition of 0.9 ml of cold 7% (v/v) TCA. The precipitated proteins were collected by centrifugation at 14,000 rpm, 20 min, 4° C. (Eppendorf 5415C centrifuge) and resolved by SDS-PAGE on a 15% gel. The radioactivity incorporated into the holo-BlmI-L-[$^{14}$C(U)]valine species was similarly determined by autoradiography as described for in vivo labeling of holo-BlmI with [3-$^3$H]-β-alanine.

Example 3

Cloning and Characterization of a Phosphopantetheinyl Transferase from the Bleomycin-producing *Streptomyces verticillus* ATCC15003

Multienzymes complexes exist for acyl group activation and transfer reactions in the biogenesis of fatty acids, the polyketide family of natural products (e.g. erythromycin, tetracycline), and almost all non-ribosomal peptides (e.g. vancomycin, cyclosporin, penicillin). All of these complexes contain one or more small proteins, ~80–100 amino acids long, either as separate subunits or as integrated domains, that function as carrier proteins for the growing acyl chain (acyl-, peptidyl-, and aryl-carrier proteins, abbreviated as ACP, PCP, and ArCP). They are converted from inactive apo-forms to functional holo-forms by the covalent attachment of the 4'-phosphopantetheine moiety of coenzyme A to a conserved serine residue of the carrier-protein substrate. This essential post-translational modification is catalyzed by a family of enzymes known as phosphopantetheinyl transferases (PPTases) (Lambalot et al. *Chem. Biol.* (1996) 3:923–936; Walsh et al. *Curr. Opin. Chem. Biol.* (1997) 1:309–315).

Research in the field of polyketide and non-ribosomal peptide biosynthesis has been hampered by the inability to fully modify and thus convert to the active form some polyketide synthases (PKS) and polypeptide synthetases (NRPS) when overproduced in heterologous hosts, presumably because the host PPTases are unable to effectively modify these overexpressed protein substrates. Our group is currently involved in the characterization of the gene cluster responsible for the biosynthesis of the antitumor drug bleomycin in *Streptomyces verticillus* ATCC15003. As bleomycin synthetase is a hybrid NRPS/PKS enzyme, we decided to obtain a PPTase from the producing organism in order to use it in vitro or in vivo by coexpression with the synthetase genes to produce properly modified, active synthetases for our studies.

Results and Discussion

Cloning of the pttA Gene from *S. verticillus* ATCC15003.

The similarities among PPTases from different organisms are reduced to two short motifs separated by 40–45 residues: (V/I)G(V/I)D (SEQ ID NO:87), and (F/W)(S/C/T)XKE(A/S)hhK (SEQ ID NO:91) (Lambalot et al. *Chem. Biol.* (1996) 3:923–936; Walsh et al. *Curr. Opin. Chem. Biol.* (1997) 1:309–315). Our previous attempts to amplify PPTase sequences from *S. verticillus* chromosomal DNA using degenerate primers according to the two conserved motifs were unsuccessful (unpublished results), so we decided to narrow our target. PPTases have been classified in two groups, according to their specificity for the carrier-protein substrate: PPTases involved in polyketide/fatty acid biosynthesis use acyl carrier proteins (ACPs) as substrate, while those for non-ribosomal peptide biosynthesis use peptidyl carrier proteins (PCPs) or aryl carrier proteins (ArCPs) (Walsh et al. *Curr. Opin. Chem. Biol.* (1997) 1:309–315). Several "NRPS-type" PPTase sequences were used to screen the databases to look for actinomycete homologues, and four proteins of unknown function were found: NshC from *Streptomyces actuosus* (Li et al. *Gene* (1990) 91:9–17); SC5A7.23 from *S. coelicolor* (GenBank AL031107), an unnamed protein from *Streptomyces* sp. strain TH1 (Mori et al. *J. Bacteriol.* (1997) 179:5677–5683), and Rv2794c (later renamed PptT (Quadri et al. *Chem. Biol.* (1998) 5:631–645)) from *Mycobacterium tuberculosis* (GenBank AL008967). The alignment of the actinomycete sequences showed the two motifs conserved in all PPTases and an additional motif—the "THC" motif: PXWPXGX$_2$GS(M/L)THCXGY (SEQ ID NO:86), located about 15 amino acids upstream of the (V/I)G(V/I)D motif (SEQ ID NO:87). The "THC" motif is not universally conserved in all PPTases, but it can be detected also in some non-actinomycete PPTases like EntD (Coderre et al. *J. Gen. Microbiol.* (1989) 135:3043–3055). Using a recently developed method of PCR primer design (the CODEHOP strategy (COnsensus-DEgenerate Hybrid Oligonucleotide Primer) (Rose et al. *Nucleic Acids Res.* (1998) 26:1628–1635), two primers were designed around the typical C-terminal PPTase motif (primers KEA-1: 5'-T GCA GCA GAA CAG GAG GCK NYC CCA NKG-3' (SEQ ID NO:88) and KEA-2: 5'-TG GGT CAG CGG GTA CCA NRC YTT RWA-3' (SEQ ID NO: 89, H=C+A, N=A+C+T+G, Y=C+T, K=G+T, R=A+G, W=T+A)), and one primer was designed from the "THC" motif (primer THC: 5'-C GGC ATG GTC GGC TCC HTN ACN CAY TG-3', SEQ ID NO:90, H=C+A, N=A+C+T+G, Y=C+T, K=G+T, R=A+G, W=T+A); this motif is not universally conserved in PPTases of all organisms). Using *S. verticillus* chromosomal DNA as template, no amplification product was detected using the THC and the KEA-1 primers. The set of primers THC/KEA-2 successfully amplified a single band of the expected size (about 250 bp), which was gel-purified and cloned. Eight individual clones were sequenced, and all of them resulted to be identical (except differences due to primer utilization) and highly similar to the putative actinomycete PPTases. The PCR fragment was used as a probe to screen a *S. verticillus* genomic library by colony hybridization. Of the 10,000 colonies screened, 25 positive clones were identified, and then confirmed by Southern analysis to contain the same 4.6-kb BamHI hybridizing band. The 4.6-kb DNA fragment was subcloned, and the nucleotide sequence of a 1,761-bp BamHI-SalI region was determined (SEQ ID NO. 3).

Sequence Analysis of the pptA Locus.

Figure 13:
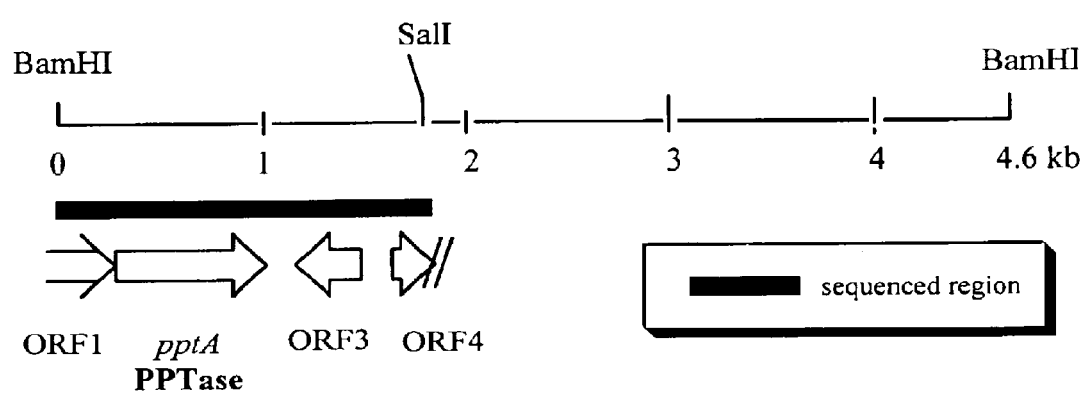
FIG. 13 shows a restriction map and gene organization of the pptA locus from Sv ATCC15003.

The sequence of the 1,761-bp BamHI-SalI fragment was analyzed for coding regions by using the CODONPREFERENCE and TESTCODE programs of the GCG package (Genetics Computer Group, Madison, Wis.). Two complete ORFs (pptA, orf3) and two incomplete ORFs (orf1, orf4) were identified within the sequenced region (FIG. 13). The first ORF from left to right (designated orf1) starts out of the analyzed area and ends with a TGA codon at position 248 of the sequenced fragment. Comparison of the deduced product of orf1 with proteins encoded by nucleic acids in databases showed similarities with Rv2795c from *Mycobacterium tuberculosis* (GenBank AL008967) and SC5A7.22 from *S. coelicolor* (GenBank AL031107), both of unknown function. The second ORF, pptA, contains the sequence amplified by PCR and used for the cloning of this locus. It comprises 741 nucleotides, starting with a GTG codon (position 245) which is coupled to the stop codon of orf1, and ending with a TAA codon. The starting codon of pptA is preceded by a potential ribosomal binding site (RBS), GGGAG. The overall (76.6%) and third codon position (93.9%) G+C contents and the codon usage of pptA are similar to those found in other *Streptomyces* genes, with the exception of the stop codon (TAA), which is most uncommon in this group of organisms (Wright et al. *Gene* (1992) 113:55–65). The pptA gene encodes a protein of 246 amino acids with a predicted molecular mass of 25,619 Da and a pI of 4.76, which contains the conserved PPTase motifs. Databases searches with PptA showed significant similarities to the putative actinomycete PPTases (39–52%/48–61% identity/similarity) and to confirmed bacterial PPTases such as EntD from *E. coli* (17%/24% identity/similarity) (Lambalot et al. *Chem. Biol.* (1996) 3:923–936). The third ORF, orf3, is separated from pptA by an apparently noncoding DNA region of 153 bp, and it is transcribed in opposite and convergent direction with respect to orf1-pptA. The gene orf3 comprises 240 nucleotides, starting with an ATG codon (position 1358) and ending with TGA. The starting codon of orf3 is preceded by the sequence GAAGG, a potential RBS. The deduced product of orf3 encodes a protein of 79 amino acids with a predicted mass of 7,555 Da and a pI of 7.17. The Orf3 protein shows similarities to the N-terminal region of SC5H1.35c, a protein of unknown function from *S. coelicolor* (encoded by nucleic acid sequence in GenBank AL049863). Analysis of Orf3 with the SignalP program (Nielsen et al. *Protein Engineer.* (1997) 10:1–6) predicts an N-terminal signal peptide which would be cleaved between residues 27 and 28 (ALA-DS), suggesting that the mature protein (52 amino acids, 5,099 Da, pI 4.31) would be secreted. Between orf3 and orf4 there is an apparently noncoding region of 251 nucleotides. The orf4 gene is transcribed in opposite and divergent direction with respect to orf3. It starts with an ATG codon at position 1610, preceded by a potential RBS (GGAGG), and ends out of the sequenced fragment. The deduced protein product (50 amino acids) of the incomplete orf4 contains a potential NAD/FAD binding motif, $GXGX_2GX_3GX_6G$ (SEQ ID NO:92) (Scrutton et al. *Nature* (1990) 343:38–43), showing low similarities to diverse oxidoreductases.

Heterologous Expression and Biochemical Characterization of PptA.

In order to test if pptA actually encodes a functional PPTase, we decided to overproduce and purify the PptA protein, and assay its catalytic competence on putative substrate proteins or domains. The pptA coding sequence was amplified by PCR and cloned into the T5-promoter-based pQE-70 vector, yielding plasmid pQEPPT, in such a way that a hexahistidine tag would be added at the C-terminus of the protein. Expression of the pQEPPT construct in *E. coli* M15(pREP4) resulted in the overproduction of soluble His-tagged PptA which was readily purified by affinity chromatography on Ni-NTA agarose under nondenaturing conditions. Because pptA belongs, by sequence similarity, to the subfamily of PPTases involved in nonribosomal peptide synthesis, we first assayed its activity using two different apo-PCPs as protein substrates. The first one, BlmI, has been previously characterized in our laboratory as a discrete peptidyl carrier protein, or type II PCP, whose gene is found within the bleomycin-biosynthesis gene cluster of *S. verticillus* (Du et al. *Chem. Biol.* (1999) 6:507–517). For the second PCP substrate we used BlmX, a bimodular NRPS protein encoded in the same cluster (FIG. 2), as a source of a type I PCP, i.e. a PCP included in a multidomain NRPS. For the production of this type I PCP, we amplified by PCR a 1,898 bp fragment encoding the adenylation and PCP domains from the second module of BlmX. This DNA fragment was cloned into pMAL-c2x to yield pMAL1617, in which the type I PCP would be produced as a maltose-binding protein (MBP) fusion, MBlmX-2, with a predicted molecular mass of 108.5 kDa. Introduction of pMAL1617 in *E. coli* TB1 resulted in good overproduction of MBlmX-2, about 40% soluble, which was purified by affinity chromatography using amylose resin. To test the PPTase activity, we incubated the purified PptA with BlmI and MBlmX-2 as putative protein substrates in the presence of ($^3$H)-(pantetheinyl)-CoASH, and the tritiated products were subjected to SDS electrophoresis and autoradiography. The well-characterized PPTase Sfp from *B. subtilis*, which exhibits a broad specificity for its protein substrate (Quadri et al. *Biochemistry* (1998) 37:1585–1595), was included as a positive control. In these experiments PptA exhibited a robust phosphopantetheinylation activity on both BlmI and MBlmX-2. Having demonstrated that PptA does in fact have PPTase activity on both type I and type II PCP substrates from nonribosomal peptide synthetases, we then proceeded to test two different acyl-carrier proteins (ACPs) as potential substrates. The first one, BlmVIII, is a monomodular multidomain polyketide synthase (PKS) which is encoded in the bleomycin-biosynthesis gene cluster of *S. verticillus* (FIG. 2). BlmVIII contains an ACP domain at its C-terminus, that is a type I ACP. For the second ACP substrate we used TcmM, a type II acyl carrier protein involved in the biosynthesis of the aromatic polyketide tetracenomycin C in *S. glaucescens* (Shen et al. *J. Bacteriol.* (1992) 174:3818–3821; Bao et al. *Biochemistry* (1998) 37:8132–8138). For the production of TcmM, its coding sequence was transferred from a construct previously made in pET-22b (Gehring et al. *Chem. Biol.* (1997) 4:17–24) into the pET-28a vector to yield pET28a-TcmM, in such a way that a hexahistidine tag should be added at both the N-terminus and the C-terminus of the protein. Plasmid pET28a-TcmM was introduced into *E. coli* BL21(DE3), and TcmM was easily purified by affinity chromatography using Ni-NTA resin. In vitro phosphopantetheinylation assays were performed as before, but using BlmVIII and TcmM as protein substrates, and PptA was able to posttranslationally modified both ACP substrates.

The pptA Gene is not Clustered to the Bleomycin-biosynthesis Locus.

Some bacterial PPTase genes have been found clustered, or close, to their respective "partner" NRPS genes: entD {enterobactin (Coderre et al. *J. Gen. Microbiol.* (1989) 135:3043–3055)}, sfp {surfactin (Cosmina et al. *Mol. Microbiol.* (1993) 8:821–831)}, gsp {gramicidin (Borchert et al. *J. Bacteriol.* (1994) 176:2458–2462)}, bli {bacitracin (Gaidenko et al. *Biotechnologia* (1992) 13–19)}, lpa-14 {iturin (Huang et al. *J. Ferment. Bioeng.* (1993) 76:445–450)}. To test the possible clustering of pptA to the bleomycin-biosynthesis (blm) locus, PCR reactions were performed using the THC/KEA-2 primers on several overlapping cosmid clones spanning the blm locus plus 30–40 kb upstream and downstream of its putative limits. No amplification product could be obtained in these reactions, showing that the pptA gene is not clustered with the blm locus.

Discussion

It has been suggested that in organisms containing multiple phosphopantetheine-requiring pathways, each pathway has its own posttranslational modifying activity (Walsh et al. *Curr. Opin. Chem. Biol.* (1997) 1:309–315). Our group has found that *S. verticillus* ATCC15003 contains several PKS and NRPS gene clusters, one of them being responsible for bleomycin production (a hybrid NRPS/PKS system) (Shen et al. *Bioorg. Chem.* (1999) 27:155–171; Du et al. *Chem. Biol.* (1999) 6:507–517). This suggested that the gene encoding the PPTase for the BLM NRPS could be also clustered, or close, to the NRPS genes. However, we have not found this gene after sequencing almost the whole blm NRPS locus. Because having this gene could be important for us in order to express functional NRPS modules from the blm cluster, we decided to clone the PPTase gene. Additionally, if the "one NRPS cluster—one PPTase" hypothesis was true, it seemed possible to use PPTase sequences as a new kind of probe to clone novel NRPS clusters.

We know that in *S. verticillus* there are several NRPS locus (maybe four), so we expected several "PCP-type" PPTases. However we have amplified only one, and it does not seem to be closely linked to any of the NRPS loci. Interestingly in the actinomycete *Mycobacterium tuberculosis*, whose genome is fully sequenced, there is only one PCP-type PPTase gene, which is not clustered with any of the two NRPS loci present in this organism (Quadri et al, *Chem. Biol.* (1998) 5:631–645). These and other indirect evidences suggest that the idea of cluster-specific PPTases is not the general rule at all but most probably the exception, especially in organisms containing multiple NRPS clusters. And there are strong evidences that at least some PCP-type PPTases can posttranslationally modify PCPs from different clusters and even different organisms (Quadri et al, *Chem. Biol.* (1998) 5:631–645; Gehring et al, *Biochemistry* (1998) 37:11637–11650). It is most likely that there is only one PCP-type PPTase in *S. verticillus* and that its gene is not necessarily clustered to any of the NRPS loci.

Biochemical characterization of the purified PptA protein confirmed not only its PPTase activity but also its broad specificity, comparable to that of Sfp. Different apo-PCPs (type I and type II) and a type-I apo-ACP from the bleomycin synthetase, and the type-II apo-ACP from the tetracenomycin PKS of *Streptomyces glaucescens* were efficiently used as substrates by PptA. These results suggest PptA as a good candidate for heterologous coexpression with NRPS and PKS genes to overproduce active holo-synthase enzymes.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated nucleic acid comprising a nucleic acid encoding a protein comprising the sequence of SEQ ID NO:115.

2. The nucleic acid of claim 1, wherein the sequence of said protein is SEQ ID NO:115.

3. The nucleic acid of claim 1, wherein said nucleic acid further comprises a nucleic acid encoding a protein encoded by SEQ ID NO:99.

4. The nucleic acid of claim 1, wherein said nucleic acid further comprises a nucleic acid encoding a protein selected from the group consisting of SEQ ID NO:113, SEQ ID NO:109, and SEQ ID NO:96.

5. The nucleic acid of claim 1, wherein said nucleic acid further comprises a nucleic acid encoding a protein selected from the group consisting of SEQ ID NO:107, SEQ ID NO:106, SEQ ID NO:102, SEQ ID NO:101, SEQ ID NO:100, SEQ ID NO:98, and SEQ ID NO:97.

6. An expression vector comprising the nucleic acid of any one of claims 1, 2, 3, 4, and 5.

7. A host cell transformed with an expression vector of claim 6.

8. The cell of claim 7, wherein said cell is a bacterial cell.

9. The cell of claim 8, wherein said cell is a *Streptomyces* cell.

10. The cell of claim 7, wherein said cell is a eukaryotic cell.

\* \* \* \* \*

SEQUENCE LISTING

```
<160> NUMBER OF SEQ ID NOS: 133

<210> SEQ ID NO 1
<211> LENGTH: 58857
<212> TYPE: DNA
<213> ORGANISM: Streptomyces verticillus

<400> SEQUENCE: 1
acccatctca taggtgtacg cgctggagca ttcggggcac gacggaaggt tctcggtcac     60
gagagcactg taagcccgaa cccgcaagga tgacgaattg caaaattgtg caagtcgcta    120
catgatggtc cggctgtgcc cgcaggtagc cgcgggcaca gcaccagacg ctgcctccgc    180
gcaccgcgcg ggaggcccgg tgaggcgaga ggctgaggtt ccgtgccggt tccgctgtat    240
caggcgaagg ccgagttctt ccggatgctg gggcacccgg tccgcatccg cgtactggag    300
ctgctgcagg acgggccgat gccggtgcgt gatctgctgg cggcgatcga gatcgagccc    360
tcggcgctgt cccagcagct ggcggtgttg cgccgctcgg gcatcgtgac ctccacccgc    420
acgggttcca cggtcgtcta cgagctggcc ggtggcgacg tggcggagct gatgtccgcc    480
gcgcgccgca tcctgaccga gatgctcaat gggcagcacg agctgctgga ggagctgagg    540
gaagccgagg tcagtgcccg gtgagctccc tcgccgtccg ggtgggagcc cgggtgcgtt    600
ccgtgctgcc cacccgcgcc gacctcgcgg gcatgggccg cagcccgcga cgtgatctac    660
tggccggtct gaccgtggcg atcgtggccc tgccgctcgc cctcggattc ggcgtctcct    720
ccggtctcgg cgcggaggca gggctggcca ccgcggtggt ggcgggcgcg ctggccgcgg    780
tattcggtgg gtcgaatctc caggtgtccg ggcccacggg cgccatgacc gtggtcctgg    840
tgcccatcgt cgcccggtac ggccccggcg gtgtcctcac ggtcggcctg ctcgccggac    900
tgatgctgat cgcgctcgcc ctcgcccgcg ccggccgcta catgcagtac gtgccggccc    960
cggtggtgga gggcttcacc ctcggcatcg cctgcgtgat cggcttgcag caggtgccga   1020
```

```
acgccctggg agtcgccaag ccggagggcg acaaggtcct cgtcgtgacc tggcgcgcgg    1080
tcgagacctt cgccggggcg cccaactgga ccgctgccgg actggcggca gcggtcgccg    1140
cggtcatgct gaccgcgcg cggtggcggc cggtcgttcc cttctccctc ctcgcggtga    1200
ccggtgccac cgtcgtggcc cagctgtgcc acctggacgc ggcccgcccg atcggggacc    1260
tgcccgcggg gctgcccgcc ccgtcgctgg ccttcctgga cctcggagca ctgggctcgc    1320
tgctggcgcc tgccgtggcc gtggcggccc ttgccgcgtt ggaatcgctg ctgtcggcgt    1380
ccgtcgcgga cggcatgacg gtcgggcaga agcacgaccc ggacaaggag ctgttcgggc    1440
agggtctcgc caacctggcc gccccgctgt tcggcggcgt cccggccacc ggcgcgatag    1500
cccgcaccgc cgtcaacgtc cgtaccggtg cgagctcgcg actggcggcc ctcacgcacg    1560
ccgcgatcct cgccgtcatc gtcttcgccc cgccccact ggtctcccgc atcccctgg     1620 ccgcgctcgc cggcgtgctg atcgcgaccg cgatccgcat ggtcgaagtg gcagcctgc    1680 gggcgatggc ccgcgccacg cgctccgacg gcctggtact gatcctcacg gcggtcgcca    1740
ccgtggccct ggacctcgtc tacgccgtca tcatcggcct gctggtcgcc ggcgcactcg    1800
ccctgcgggc cgtggccaag caggtccgcc tggaccaggt ctccttgaag gaggacctga    1860
ccggcgacca cagcgccgag gaacacgcgc tgctcgccga gcacatcgtg gcgtaccgca    1920
tcgacggtcc gctgttcttc gccgcggccc accgcttcct gctggaactc tcggacgtcg    1980
cggacgtgcg cgtggtgatc ctgcgcatgt cccgcgtgac caccatggac gccaccggcg    2040
ccctcgtcct gaaggacgcg gtcaccaagc tgaaccggcg cggcatcacc gtcctggcct    2100
ccggggtacg ccccggccag cgccgggtcc tcgactccgt cggcgccctc ggtctgctcc    2160
gggccgccac cggcgacgac tacaccggca ctcccgaagc catcgccgcc gcccgaagcc    2220
acctgcacgg cgccggtgtc ctggcccccg cctgcccggg cccgcctcct ccggtaccc    2280 caccgtgcgc tccgagtgcc cgacgatgag gagccgaccg aggtcctcct ccgtcacccg    2340
gacacccacg gttgcgccgc cccatgccgg cggtccctcc tgacggcccg tccgcggctt    2400 gaggcggcg tggacggcct gccgccgccg gcctcgggct gatcggcgtg atcaccgccc    2460
atgcgcgggt gggcgcccgc ggcatcgtgg gcgggaccgt gttcccggcc accgcggcgg    2520
ccggcctcgc gctgggcgtg gcctgccgcg gtgcctggta gcggcgggt ccggcggccg    2580 ggcctgtgct tcttcccgcc cgtccggcgg gtggcgccgc gccggcggtg acagggaaat    2640
atgaccggaa ctgggatgct cgcgtccact cgggtgtgtt taagtgccac gggggcttcc    2700
gacggcgcgt cgcgcgccgg cggttcgccc gatgatggtc gtgcggcgct gtgagccggg    2760
gagcctatgg cacaggacct gaacgactgg atcgaggacg aggtcgtccc ttacgaggag    2820
aagcctctcg aatggatctc ccagtaccac ttcttccgcg accgcgcgcg agccgcctat    2880
gtcgatcaca cctacttctt ctcaccggcc gatggcgcga tcgtctacca gaaagtagtg    2940
gatccccagg agtcgatcat cgacatcaag gggaagccgt actcgctggc cgccgcgctc    3000
cgtgacgaat cgttcggtca ccggtgcctg gtgatcggca tcttcatgac cttcttcgac    3060
gtgcacatca accggatgcc ttacggcggc cgtctctcct tcgcgctcaa ggagcccatc    3120
gggacgttca acctccccat gctggccatg gagcaggacc tgctcgaacg gctccgggtc    3180
aatccggctc acgcgaggta tctgcacctg aacgagcgga tggtcaaccg ggtcgacgcg    3240
ccgcggctcc ggggcccgta ctggatgctc cagatcgccg actacgacgt cgactccatc    3300
accccgttct gcagacggca gggaatgttc cgctcccagg ggcgccgctt ctcccagatc    3360
cgctacggat cgcaggtcga cctggtgatc ccgatggcgg ccgaccgcga gtacgtcccc    3420
```

```
gtggaggccg tcggccggca cgtgaaggcg gggctcgacc cgctcgtcaa gatccggtgg   3480
cgttgaagag cgcgtacgaa gcgatggcga actggaggga cacagcgtgg gtttccgtcg   3540
agcgcagagg gccggtgggc cgggagcggg ccggcgggag agcgcccggt tcaggccgga   3600
cgggccgtcg gcgccgcggg accgtccgtt acccctgtcc gccgggcagt tgttcgagtg   3660 ggtgttttgac aagctcgtcg acggagatct gagccaccag ccgacgattg tgcggctccg   3720
cggcccgctg aacaccgccg ccctgcggat ggcctacgcc cggctggtgc ggcgccacga   3780
gtgcctgcgc acccgcttcc ccgtgatcga cggggagccc gtgcaggtga tcgagggcat   3840
cgggaaagca gcgggggggcc cgctgccgct catcgatctg cgccacctcc cggaggcgct   3900
tcgcgcgcgc gagatcgcga ggatccgcga ggagacgctg tccacgccgg tccccttcga   3960
caagcggccg cccgtccgcg tggcgctgat ccgggcggcg cccgaggagc acctcttcct   4020
cgtcggcatc ccgcacatca ccgcggacct gtggtccgcg accctgctca acgacgagct   4080
catggcgcac tacagggcgg gggccgaggg gactccctcc cggcccccca ccccgtcgc    4140 gcagtacgcc gacttcgcgc agtggcagcg cgcgtggtgg aaccgggacc gcaccgagcg   4200
ggaggccgga cggtggcggg cgcggctgga cgggctgtcc gccgtggaac tgccctgga    4260 ccggccccgc cccgcgggcc gccggcggga ctgcttcctg atcgggaca ccttcgacgc    4320 cgaactgagc gaccggctgc gcgccttggc acgcaccgcc gacgtcacgc tgtacgtggt   4380
gctgctggcg gcgttccact ggctggtggg gcggatgtcg ggcgccggcc ggctggtgac   4440
cacctcgctc gtggccgccc ggcacggcag cgcggtacag gggatgaccg gcccgttctc   4500
ggactacctg gccctggtcg gggacctgtc gggcgatccg gacttcctgg agtccctgcg   4560
ccgcgtacgc gacgagtgcc tgaccgccca cgaccaccag cggcttccgt tctcacaggt   4620
cctcgaagtc atggaccccg gacgcgagtt gcaccccat ccgctggagc agctcgggtt    4680
caacctccac aacatccctc ccgcggtcat ggacttctcc ggcgacgtcg tcgtctcggc   4740
ggtgaacccg gagggggacg acggggagag cggcgacggg gagtacgtgc cctggaccgc   4800
cgacctgacc ttcgacgtct acgactacgg caccggccat atgccgttcg acgtgatact   4860
cgaccggcgg ctggccgatc cggcgacggc ccgggagtgg gccgggcact accggtcggt   4920
gctccgtgcg gtcgtcgccc accccggcgt gcgcctgtcc gccctcggca ccctgctgtc   4980
cctgccgcga ccgccgtccg ccacgtcctt cggcggccgg gagatcgacg tccggcgcgt   5040
cgaacgcgag ttggcggggc gcgacgggat caccgccgcc ctggtcgcgg tggcgccccg   5100
gcgcctggcc accgggctgc gcgtacggga actggtcgcc tactgcgccg tcgagggcac   5160
gccgcgtccg aacgcggccc acgacatccg cggccgcctg cgggagcgcc tgcccgacgg   5220
ctgggtgccg accgtgttcg tcgagcgccc gccggaggag atccggaagg ccctggccgc   5280
ccgggcggcg gcggcgaac gggcggagcc gctgccgccg cccgaggact gcgtcccgct    5340
tcccgaggag ggccggcccc cctcggaccc gtccgagcgg cggctggccg cgctctgggc   5400
cgagatcctg ggcgccccgc cgaagagcgt gaccgagccc ttcttccgcg tcggcgtcac   5460
cgataaggac gccctccgct tcctggcccg cgtggcggag gacttcggcg tcaccgtgcc   5520
cttcgccgac ttcctcagcg ctcccaacct gcgtatggtg aaggacaatt tggctgagaa   5580
acggagggtg taacgcgcaa tgagtgagtg gtagggtcgg aatcgaaccg cactgatcgg   5640
caatcttttc ggtcagctgt tccggatatt ccggggcgcg tcggcgctcc ctcgaccaag   5700
ggcgtacgcg gataagcgtg cgccgcccca cggctgcgtc tcgacgcctt catcggcgcg   5760
tcggacactt cgcggtgcca gtcggcacgc tcagagatca gtggaatgcc tcggtgtgcc   5820
```

```
cgaggtgcgc tcagtactgc tgtccacaca acgcgccaag ggagttggaa cgtgatggag      5880
acggcgaatt ccggctatcg ggtctcacct cagcagcggc atttatgggc catgctgacc      5940
cgcgggcggg acggcgggcg acgtgcgttc acccagtccg ccgtggtggt cgaccgttcc      6000
ctggacgccg cacgtctgcg cgccgcgctg gcctccgtgg tggccgccca cgagccgctg      6060
cggacgacct tcaccggtct cgcgggacgg accgcgccgg tccaggtcgt ccatgacccg      6120
gacgagcagc cgctgtccgt cgtcgacctg ccgcccgtcg cgccgacgg ctcgggcccg       6180 gaactggacg agctccggct ccgcaacgc gccgccctcg acccgcgcgg cgggcccgtc       6240
ttccgggccg ccctggcgcg ggccggcgag gaccgggcgg tgctggtgct caccgcgcac      6300
gccctggtcg cggaccggct ctccctccgg ctgctggccg ggcagatcct cgcggcgtac      6360
agcggggaga ccgtgtcccc cgatggcccg ccgcccttgc agtacgccga cttcgccgcc      6420
tggcaccacg acctgctcac cgccgaggac gccgcccccg accgcgcgca ctgggccgcc      6480
cacaccgcca ccgccggcac cgggccgctc ccggcgtcg tacggccggg cgcgcccccg       6540
ggtccgtggc gggcgcggga gtgggaactg cccgccgaac tggtggcggg gatcgacggc      6600
gtcgccggga agctgtccac cgatcccgcc accgtgctgc acgccgcctt ccgtatcgcg      6660
gtctggcggc tcgccggcga gcggaacctg cccgtcgccc tcactcgtga cggccgttcc      6720 cacccgaac tccgcaccgc gatcggcgcc ttcgagcgtg agctcccgct cgtccacgag       6780
atccgtcacg agacggcgtt cgcggaatac gcgcgcgctc tggacgcgct cgtcgccgag      6840
ggcgaggaac tcctcgacca ttgcgacccg gaactgctcg gcagcctcga cggcaccgcg      6900
gaagggccct gcttcaccct cacccaccac caggccgaaa caccggtccg gcgggccggc      6960
atcaccttta ccaccgtcca tcaggattcg ggtacgccga ttcccgtccg cctgaccgcc      7020
cgacgcgacg gcgcccggct gcgcatggaa ctgggatacg acgagggccg tatcgacgag      7080
acgtttcccg agaacgccgc cgcctgcctc acccgcattc tcgaaggcgt cgtctccgcc      7140
cccgagggcc cggtcggcga catccgcatg ctgtcggacg agaccgcacg gctgctccgg      7200 gaagcgggc tgggcccccg cgtggaactt cccggcaagg cggtccacga actcttcgcc       7260
gagcaggccg cgcgcacccc cggggcggtc gcggtcagcg cgggcgagga cgccctcacg      7320
tacgccgaac tcgacgagcg gtccaaccgc ctggcacacc acctgaccgg gctcggggtg      7380
acacccggcc ggcacgtcgt ggtctcggtc ggccgctccg ccgagctgct cgtcgggctg      7440
ctcggcgtgc tcaaggcggg tggcgccttc gtccccgtcg acgtgggctt ccccccgcaaa     7500 cggctggagt tcgtgctccg ggagaccgcc gcgccggtcc tgctctgcac cgccgacgta     7560
cgggaccgca tcggcactcg gaccctcgac gacgccgggg tgacacccgt cgcgctggac     7620
gccgaccggc ggcgcatcgc cgcacacccc gccggcccca ccggcatcgc caccaccccc     7680
gacgcccccg cgtacgtcgt ctacacctcc ggcaccaccg ggaagcccaa cggcgtacgc     7740
gtcccgcacc ggggcctcac caactacctc acctggtgca ccggcgccta cggactcgac     7800
gggggcaccg gcaccctcgt gcacacctcc atcagcttcg acctcaccct caccaccctg     7860 ttcgccccc tgctcgccgg cgggcaggtg gtcatgctct ccgagaccgc cggcgtgacc      7920
ggcctgatcg ccgcgctgcg ctcccggcgc gacctcaccc tggtcaagct gaccccgacc     7980
cacctcgacg tcgtcaacca gctgctcacc ccgacgagc tgcgcggcgc ggtccgcacc      8040
ctcgtcgtcg gcggggaggc ggtgcgggcg gagagcctgg agccgttccg ggcctccggg     8100 acgcgggtc tcaacgagta cgggcccagc gagacggtcg tcggcagcgt cgcgcacgtc      8160
gtcgacgccg ccacgccccg taccggcccg gtgcccatcg gccggccgat cgccaacacc     8220
```

```
accgtccacc tgctcgacca gcggcggcgg cccgtcccg acggcgtcgt cggcgagctg    8280
tggatcggcg gcgccggtgt cgccgacggc tacctggggc ggccggaact caccggcgag    8340
cgcttcctcc ccagcgacta cccgccggac ggcggccggg tctaccgcac cggcgacctg    8400
gcccgccggc gcgccgacgg caccctggag tacctcgggc gcaccgacgc gcaggtgaag    8460
atccgcggcg tccgggtgga gcccgccgag accgaggccg tcctcgcctc ccaccccggc    8520
gtcggccagg ccgtcgtggt cgcccggctg gacgaggacc ccggccgttc gtcgccgctc    8580
gccggcgagc tgacgctgac cggctacgtg gtcccggccc gcggtgccca ggcgcccccg    8640
cacgaggagc tcatcgcgta ctgccgggag cggctgcccg agcacttcgt cccggccgtc    8700
ctcgtcaccc tcgacgccct gcccgtcacc ggccacggca agatcgaccg cggtgcgctg    8760
cccaagccgc acgccgggc ccgggacggc gcggcgtacg tcgcgccgcg caccgccacc    8820
gaggagatcc tcgcggccac cgtcgcgaag gtgctgggcg tcgagcgcgt cggcatcgac    8880
gacaactact tcgtcctggg cggcgactcc atccgcagcg tcatggtcgc cagccgggcc    8940
caggcccgcg gggtcgaggt caccgtggcc gacctgcacc ggcacccac cgtccgggcc    9000 tgcgccgcgc acctggacgc ccgcgaggac ctgccgcgga cgcccgtcac cgaacccttc    9060
gcgctgatct ccgccgagga ccgggcgctg gtgccggacg acgtcgagga cgccttcccg    9120
ctgaacctgc tccaggaagg catgatcttc accgcgact tcgcggcgaa gtcggccgtc    9180
taccacgcca tcgcgtccgt gcggctgcgc gccccgttcg acctcgccgt gctgcggatg    9240
gtcgtgcgcc agctcgtcga gcggcacccg atgctgcgca cctccttcga catgagccgc    9300
ttcagccgcc cgctgcaact ggtgcaccgc gagttcgccg atccgctgca ctacgaggac    9360
ctgcgcggca ggagcgccga ggagcaggac gcccgcgtcg aggagtggat cgagcgggag    9420
aaggaacgcg gcttcgagct gcacgagttc ccgctgatcc gcttcatggc gcagcgcctg    9480
gaggacgacg tcttccagtt cacctacggc ttccaccacg agatcgtgga cggctggagc    9540
gaagccctga tgatcaccga gctgttcagc cactacttct cggtgatcta cgacgagccg    9600
atcgcgatca agccacccac cgccggcatg cgcgacgccg tcgccctgga gctggaggcc    9660
ctcgcggacc gccgcaacta cgagttctgg gactcctacc tcgccgacgc caccctgatg    9720
cggctgccca ggcccggcac cggaccccgg gccgacaagg gcgaccggga catcacccgc    9780
atcgccgtcc ccgtccccac cgaactctcc gacggcctca agcgggtcgc cgccacccac    9840
gccgtcccgc tgaagaccgt gctcctggcc gcgcacatgg tggtgatgtc cctctacggc    9900
ggccacgagg acaccctcac ctacaccgtc accaacggcc gccccgagac cgccgacggc    9960
agcaccgcga tcgggctgtt cgtcaacagc ctcgcgctcc gcgtccggat gaccggcggc    10020
acctgggcca acctgatcac cgccacgctg gagtccgagc gcgcctcgat gccgtaccgg    10080
cggctgccga tggccgaact caagcgccac cagggcaacg aaccctggc cgagacgctg    10140 ttcttcttca ccaactacca cgtcttccac gtgctcgacc gctggatcga ccgcggcgtc    10200
ggccacgtcg ccaacgagct ctacggcgag tccaccttcc ccttctgcgg catcttccgc    10260
ctgaaccggg agaccggcga gctggaggtc cgcatcgagt acgacagcct gcagttctcc    10320
gacgccctca tggagagcgt ccgcgacagc tacgcccgcg tcctcgcggc cctggtcgcc    10380
gaccccgacg ggcgctacga ccggcacgag ttccgctccg accgcaccg gccgcactg    10440 gccgtcctca cccgcgggcc cgaggcgccg gcggccgacc ggtgcctgca cgacctggtg    10500
gcggaccggg cggcggaccg ccccgacgcc ccggccgtcc agctggacac cgacgtgctc    10560
agctacggcg agctcgaccg ccgcgccaac cggctggccc accacctgcg ttcgctcggc    10620
```

-continued

```
atcggcccgg agagcgtcgt cggcgtcctg gccgaacgct ccctcgccca gatcatcggc    10680
ctcctcgcgg tcctcaaggc gggcgccgcc tacgtcccgc tcgacccggc ccagcccgac    10740
gagcgcctcg ccgccgtcat cgccgggagc ggggccgccg ccgtcctcca ccggcccggc    10800
ctcgaagggc ggctgcccgc gggcgtccgc gcgctcccca ccgacgccgc cgacggcagc    10860
accgccacgc acgaccccgg gcccaccgcc acgccccgca acgccgcgta cgtgatgtac    10920
acctccggat ccaccggaga gcccaaggqc atcgtcgtcg aacaccgcaa cgtcgtggcc    10980
tccctcgccg cccgcggcgc ccactacgcg gccggacccg gccggttcct gctgctgtcc    11040
tccttcgcct tcgacagctc ggtcgccggc atcttctgga cgctgaccca gggcggcacc    11100
ctcgtcctgc ccggcgaggg acagcaactc gaccccgccg cgctggtgga gaccatcgcc    11160
cggcaacggc ccaccacac cctcgccatc ccctccctgc tggcgcccgt cctggaccag    11220
gccgccccg gcgacctcgc ctccctgcgc acggtgatcg ccgcgggcga gtcctgtccg    11280
gccgaactgg ccgccgcctg ccgggacctg ctgcccggga gcaccttcca caacgagtac    11340
ggccccaccg agaccaccgt gtggagcacc gtctggtccc aggagaacga gcacgacgga    11400
ccccacctcc ccatcggccg gccggtcgcg ggcacctggg tgcaccccg cgaccaccgc    11460
ggacgcaccg tccccctcgg cgtcgccggc gaactctcca tcggcggcgc cggcgtggcc    11520
cgcggctacc tcgggcgccc ccgggacacc gcggccgcct tccgccccga ccccgaggcc    11580
acggctcccg gcggccgcgc ctacgccacc ggcgacctcg gccgctacct ccccgacggc    11640
aacctggagt tcctcggccg cgccgaccac caggtcaaga tccgcggctt ccgggtcgag    11700
ctcggcgaga tcgaggccgt cctcgacacc cacccggagc tccagcggac catcgtcatg    11760
gcacgcggcg accaccccgg cgaccaggtg ctcgtcgcct acgtcctccc cgccccggc    11820
cggcggcccg aacccgccga catccagggg tacgtccgcg accggctgcc ccgctacatg    11880
gtgcccaccg cggtgatcgt cctcgacgcg gtaccgctga ccgccgccgg caaggtcgac    11940
cgggcctcgc tccccgcccc cagccacgcc cagctcaccc gggaccagga gtacgtcgag    12000
cccggcaccg acaccgagcg ggcgctcgcc gccatctggg ccgacgtcct caaactggac    12060
cggatcgggg ccggtgaccg cttcttcgac gtcggcggcg aatccctgcg cgcgatgcag    12120
gccaccgccg cggccaacaa gatgttccgc acccgcgtct ccgtccgccg cctcttcgag    12180
gcgccctccc tgcgggagtt cgcccacgag atcgacaagg cccgctcgc gggcggcggg    12240
accggcctca ccggccccgc ggccgccccg gccaccggag gtgccgccga atgaccccgg    12300
ccgccgacac cacccaccg ctctcgccgg cccagcgcag catgtggttc ctgcaccggc    12360
tcgcgcccga ggtgcccgcc tacaacatct gcaccgccat cgagctcacc ggcacaccgc    12420
gcccggcgg gctgcgggac gtggtacggc ggctcggccg caggcacgag gcgctgcgca    12480
cggtgttccc gtcggtgggg gagacccccc gccaacgggt caccgaccgg cggcgccc    12540
tgcggaccgt ggacctcacc cacctgaccc ccgccgccgc cgaggccgag accgcacgga    12600
cgctacggtg cgccgccgcc cggccgttcc ggctcgacac cggccccctg cggaatgga    12660
ccctgctgcg ccgcgccccc ggccacgcgc tgctcgtcct ctccgtccac cacatcgtct    12720
tcgacggcgg ctcgctccac gtggtctgcc gcgaactgga ggaggcgtac ggagcggccc    12780
tcgccgggcg cccggacccc ctcggcacac ccgcgcgggg ctacgacgg cagtgccgga    12840
cgcgggcggc ggaacaggac gaggccgggc gggagttctg gcgccgcgaa ctgtccggcg    12900
cgccaccccg cacgaccgtc ttccggggca cggccggcc cgccggaccg cccgcccgcg    12960
ccaccgtcca ctacggcacc gacgatccgg ccccgaccgc ggacttctgc cgcgagcacg    13020
```

```
ccgtcaccgg ctacgtgctg ctgctcgcgg ccctcgcctg cctggtcgcc cggtacaccg    13080
gccggacgga cgtggtgatc ggctcacccg tcggactgcg cgaggacccc gaagggctcg    13140
ccaccgtcgg cccgatgctc aacctgctgc cgctgcgcct ccggctgcac ggcgaccccg    13200
gcttcggcga ggtcctggcc cgcacccggg agacgctgct cggcgcgctg gagcaccgca    13260
ccacaccgtt cgaggacatc gtcgacgcgg tgggcgccga ccgggacccg gacgtcagcc    13320
ccctcttcca gatcctcttc gcccacgaac gccccccggc cccacccgcg ttaccgggcg    13380
tccgtgcccg cgtcgtaccc gtccccgctc cggccgccaa gtacgagctc gccgtcaccg    13440
ccaccgagac gcccgacggg ctccggctga tcgtcgaggc ggagcacgga cacggggaac    13500
cggccgaact cgccgccttc gcccgccact tcggcgtcct gctggccgcc ggggtccgcg    13560
cgccggacac accgctgagc cgcctgccgc tgctcaccga cgaggagcgg cgccggctca    13620
ccgacaccac ggcccccggc accgcgccgg aggcccccta ccgcccccctg caccggctgg    13680 tcgaggagtc cgccgcccgc cggcccgacg ccctggcggt cgtcggcggc acgcgtcacc    13740
tcagctaccg ggagctgaac tgccgcgcca accggcgtgc cgcctggctg cgccgcgctg    13800
gcatcggcac cgaggacgtg gtcggcgtcc ggctggaacg cggcccggaa ctcctcgtct    13860
cgctcctcgc cgtcctcaag gccggcgccg cctacctgcc cgtcgacccg gcgctgcccg    13920
ccgagcgggt acggctgatg ctcgacgacg cccgggccgc gctgctgctc accgagaccg    13980
cgctcggcac cccgccggcc ccggccggca ccccccgtgca ccacgtggac ggaccgccac    14040
cgccgacccg gcccggggac gacgccgacc acaccggccc cgacctgccc accagcctcg    14100
cctacctcct ctacacctcc gggtcgacgg gccggcccaa ggccgtggcc ctccagcacg    14160
acagcgccgc ggcgttcctg cgctgggcgg gccgcgcctt cgacggcggg gagctggccg    14220
ccgtcctggc caccacctcc gccggcttcg acctgtcggt cttcgagctg ttcgcccccc    14280
tggcccacgg cggcaccgtc gtcctcgccg acagcgccct gcacgtgccc gccctgccct    14340
gggcgcccgc ggcgacgctc ctgaacaccg tgccctccgc ggccgccgcc ctgctggacg    14400
ccgacggcct gcccgacggt ctgacggccg tcaacctggc gggcgagccc ctgaccgcgg    14460
agctggtcgc ccggctgcac gcccgcctgc cgaaggccgc cgtccgcaac ctctacggcc    14520
cctcggaggc caccacctac gccaccgcgg ccctcgtgcc cgcgggcggc accgaggcgc    14580
cggccatcgg ccgggcgctc ggcgcggccc gcgtgtggac cgccgacgac cggcagcgcc    14640
ccctccccgg cgcggtcgtc ggtgaactcc tcatcggcgg tacggccccg gcccgcggct    14700
acctcggccg gccgggaccg accgccgacg ccttccggcc cgatccgacg ggaccgcccg    14760
gctcccggct ctaccgcacc ggggacctgg ccgtacgccg ccccgacggc cggttcgtgt    14820
tcctcggccg caaggacgag cagatcaaac tccgcggggt gcgcatcgaa ccgggcgagg    14880
tggaagccgc tctccgccag tgcgcgccgg tgccgcgggc cgccgtcgtg ctcgccggga    14940
ccaccgcgga gaaccaccgc ctcgtcggct tcgtcacccc ttcgcccggc gcccgcgtcg    15000
accccgagcg cacccctcgcc gcgctgcgtt cgcgcctgcc cgccgccctc gtgccgccg    15060 cgctggtggt gtgcgacgcc ctgccgctga ccgccaacgg gaagaccgac cgggccgccc    15120
tcgcccggcg ggcgcgcgga caccggccgg accacggccg gtacgccccg ccccgcaccc    15180
gcgtcgagaa ggcggtcgcc gcgatctggc gcgaggtgct cgggaccgaa cgggtgggga    15240
tccaccaggg gttcttcgac gcgggcggca cctccctgtc gctgctgcgc cttcaccacc    15300
```

```
ggctggtcgc gtccgtccat cccggcctcc ggctcgccga cgtcttccgg ctgccgaccg   15360
tcgccgcgct cgccgcgttc gtggacgggc aggaggacgc gcgcgagacg gccgtcggcg   15420
acgcggccct ccgggccggc cggcgccgcg ccgcggtggc cgcgcgccgc aggaaaggcg   15480
gcggacgatg agccatgccg acgcgggcga cgggctcgac gcggctgaca cgactgacgc   15540
ggccgacggg atcgccgtga tctcgctggg cggacgcttc cccggagcgg accgggtgga   15600
ccgcctctgg acgaacctgc tcgaccgcga ggacgccatc agccacttca ccgccgacga   15660
acgcctcgcc cggggccgcg accccgaact ggtgcgccac ccgcggttcg tcggcgcgga   15720
aggcgtcctc ggcgacgtct ccctcttcga cgccgagttc ttcggctgct cgccgcgcga   15780
ggccgaagtc atggacccgc agcaccggct ctgcctggag gaggcgtggc acgtcttcga   15840
caccgccggc tacgacccgg cggcgacggg caccgcggtc ggggtgttcc tctccgcgag   15900
cctcagctcg tacctgatcc gcaacgtcct gcccggcggc gcggcacagc gcctgctcgg   15960
cggcttcccg ctgctgatcc acaacgacaa ggactttctg gccaccaccg tgtcccacaa   16020
actgggcctc accgggccga gttacgccgt cggctcggcc tgctcgtcct ccctcgtcgc   16080
ggtgcacctg gcctgccaga gcctgctcac cgaggaatgc gacatggcgc tggccggcgg   16140
ggtctcgctc caagtgccgc agggccaggg gtacgtgcac gccgacgacg gcatctactc   16200
acccgacggg cgctgcgccc ccttcgacgc cggcgcggcg ggcacggtgg gcggcagcgg   16260
cgtgggcctc gtcctgctca agcggctcgc cgacgccgtg cgcgacgggg accgcgtcca   16320
cgcggtgatc ctcggctcgg cggtgaacaa cgacggcgcc gacaaggtcg gttacacggc   16380
gcccggcgtc accggccaga gcgccgtcgt cgccgaggcc ctggcggtgg ccgggatctc   16440
cgccgcgacc gtcggcgtcc tggaggcgca cggcaccggc acccggctgg gcgatcccgt   16500
cgaagtggcc gcgctcaccc gggcgttccg cgcccacacg gaccgcagcg gcttctgcgc   16560
gctgggctcg gtgaaggcca acgtgggcca cctggacgcg gcggcgggcg tcaccgggct   16620
gatcaaggcc gtgctggcgg tccgcgaggg cgtcatcccc ggcaccccgc actaccgttc   16680
gcccaacccc gccatcgact tcgccaccac acccttctac gtcaccgccg acaccctcgc   16740
ctggccggag gcggaccacc cccgccgggc cggcgtcagc tccttcggca tcggggcac   16800
caacgcccac gtgatcctgg aacaggcccc gccggccgcc cccgcgcgg accggaccgc   16860
cggggtgccc atgccgttgg tggtgtccgc ccgcacccgc gaagcactgg cggaggccgt   16920
ccgggacctg gcggcgtggt cggccccgga gccggggacc cggctcgccg atctcgccgc   16980
cacgctggcc gggcgccggg ccttcccgta ccgcgccgcc gtcgtgtgcc acgacctgcc   17040
cgaggccgcg cgcctgctgg gcggcgcgcg cggcgagacc gcgctccccg gcagggaggc   17100
cgtgttcctc ttccccgggc agggcaccct cccgccggac accgggcgcg gcctgtacgc   17160
ggacgtgccg gcgttccgcg cccacttcga cgcctgtgcc gaagggttcg cccgctcgg   17220
caccgacctc cacgccgcgc tcgggcccc ggccgacgac accagggccg cgcaacccgc   17280
cctcttcgcc gtcgagtacg ccctcgcccg caccctgatg gactggggtg tgcgcccggc   17340
cgcgatgctg gggcacagcc tcggcgagta cgtcgcggcg acgctggccg gggtgctgtc   17400
cctgccggac gcgctgacgc tcgtccgggc ccggcggaa gcgcagcaca ccatgccgcc   17460
cggccgcatg ctcgcggtcc cgctcacgcc ggacagacctg cgcccgctgc tgccccggga   17520
ggtggagttc agcgccttca acgcccccgg ccgctgcgtc gtcggcgggc cccggagcc   17580
ggtgcggag ctgcgcgccc ggctggcgcg gcgcggagtg ccggccgccg aactggccac   17640
cgcgcacgcc ttccactcgg cggccgtcga accgctgctg acggcttcc ggggcgtgct   17700
```

```
ggaaggcgtc cgactgcggc cgccccggct gcggtacgtg tcctccctca ccggcgactg    17760
ggccgacgcc gcggtcacca cccccgcgta ctggctcgcc cacctgcgcc ggcccgtccg    17820
cttcgccgac ggcctgcggc gctgcctgga cctcggcccc gtcgccctgg tcgagaccgg    17880
gccgcgggcc ggactgaccg gcctggcccg ccgcgccgg ggccccggcg agccccctta     17940
caccgtccgc tgcctggccg cccccgacga ggcggcttcg ctgacccacg cggtcgccgt    18000
actctggcgc tcgggctgcg ccgtcgactg gacggcgttc caccgccccg ggcgcccccg    18060
ccgcaccacc gtgcccggct accccttcca acgggtacgg cactggatcg acgcgccgga    18120
cgagtccgaa cccacggacc tcgccaccgc cctgcgcgcg gagttgcgga cggacggcga    18180
tccgccgctc gccgtcgatc agcggcccgg actgcgcacg gggctgaacc ggctgtgcgc    18240
cgccctggcc cgcgactacc tggccaccgg cgtcgaagcg agcggggtcc tgcccggatt    18300
ccaccgcttc ctggactacc tgcgcaccct ggccgcctcc gcaccggccg cggacgacgc    18360
ggggacgatc gccgcggaga tcaccgcggc ccacccgtcc ttctccgggc tcgtcgacct    18420
gctccggcac tgcgcccagg gctatccgcg cgccctgtcc acccccggag ccgcactgga    18480
cgtcctctat ccggccggca gcggcgacct cctgcgccgc accctgggcg agggcaccgc    18540
cgaccaccgc gccaccggcc gcctcacccg gctggccggc tccctgctcg accggctcgc    18600
ggccgaccgg gaacccggcc gcccgctgcg cgtcctggag gccggagcgg gcgcgggcag    18660
cctcacccag gccctggtca cccgggcccc cggccggctc gactaccacg ccaccgacat    18720
ctcccggcac ttcgtgaccg cactcggccg ggaggccgcc cggcgcggcc tggacttcgt    18780
ccgcgcacgc gtcctcgaca tcgcccgcga cccaggcgaa cagggcttcg ccggcgagcg    18840
gttcgacgtc gtctgcgggcc tcgacgtggt ccacgccacc cccgacctgc gcaccacgct    18900
cggccatctg cgctccctga tggcaccgga cggcaccctc gcgctgatcg agaccaccgc    18960
cgacgacccc tggctgacga tgatctgggg cctgacggac ggctggtggc accacaccga    19020
ccggcgcacc cacggcccgc tgctcgacgc cgccggctgg cgcgccctcc tggccggcga    19080
ggacttcgcc acggccgatg tgatcgtgcc gcccgacggc ccccaggacg cggccctgct    19140
gctcgcccgg cagacccccc ggccggcggc ggccgcaccg tccgtcggca agcgggacgt    19200
cggcacgtgg tgctacgccc gcggctggcg gcacgccgcg cccgccgacc ccgcccccgct    19260 gacgggcggc tgcctgctgc tgggcgacgg ggacacggcg aaggccgtcg cgagccggct    19320
ggaggccctc ggcgtgcccg tcaccaccgt cggcggcggc cgaccgccgg gccccgagcg    19380
gtaccgggaa ctcgtcggcc ccgccacccg cctggccgtc gacctgtggc cgctgcgcga    19440
cgcgtcccac cgcggccgcg ccgccggcgc cgccggcgta cggaccgccc aggacgccgc    19500
gctgcacaac ctgctccacc tcgcccgggc cttcggcgcg ctggaggagc gccacccgcc    19560
ccgcgtcgtg accgtgacca ccggtgccca cgacgtgctc ggcgacgacc tcgcccaccc    19620
cgagcacgcc accgtcccgg ccgcggccaa ggtgatcccc cgggagtacc cgtggatcgc    19680
ctgcaccgcc ctggacgtgg agccgggcct ggacgccgag cggctggcgg acctgatcgt    19740
ccgggaactc ggcgcggcgc gcgagaccac cgtcaccgcc tgccgcggcc gacgccgctt    19800
caccccctgc cccgtccggc agcccctccc cgccgcaccg gaacgcccgg cggtccggcc    19860
cggcggcgtc tacctcgtct gcggcggcct cggcggcatc ggcctccacc tcgccgagta    19920
cctgggccgc gccgcacca ccgtcgtcct cacccaccgg cggcccttcc cgccccgg      19980 cgcgtgggac gggctgcccg cgggacaccc ggaggcggcc gtcgtccggc ggctgcgctc    20040
cctcgccgcc accggcgcca cggtcgtcgt ccgccgggcc gacctcaccg accacgacgc    20100
```

```
gatgcgcgcc ctcgcggacg aggtggaaca ggcccacggc cccgtccggg gggtggtgca   20160
cgcggccggg gtgcccgaca ccgccggcat gatccagcgt cgcgaccgag ccggcacgga   20220
cgccgccctc gccgccaaac tgaccggcac cctcgtcctg gacgaggtgt tcgcccaccg   20280
cgacctcgac ttcctcgtcc tgtgctcctc gatcggcacc gtgctgcaca agctgaagtt   20340
cggcgaggtc ggctacgtgg cgggcaacga gttcctcgac gcctatgccg cccaccgcgc   20400
ggcccgccgc cccggcagaa ccctgtcgat cgcctggacc gactggcggg agtcgggcat   20460
gtgggccgcc gcccagcgcc gtctgaccga gcgctacggc accggcgccg acctgcccgt   20520
accgccgggg ggcgacctgc tcggcgcgat cagccccgag gagggcgtcg acgtcttcgc   20580
ccggctgctc gccgccgaca ccggcccgaa cgtcatcgtg tcggcccagg acctcgacga   20640
actcctcgcg cggcacgcgg cgtacaccac cgacgaccac ctcgccgccc tcggcgacct   20700
gaggatcgcc gccgcccggg accgctccgc gccgccgcg ccgtacgcgg cccccacac   20760
gcccgcccag cggcggatcg ccggctggta ccgcgacctg ctcggcgtcg aacacgtcgg   20820
cctcgacgac gacttcttcg cgctcggcgg ggactcgctg ctcgccctgc gcctgctgtc   20880
gcagctgcgg gacgcctacg gggtggagat ctccgtcgcc cgcatgttcg acgagcccac   20940
ggtggcggcg ctggccgccg ccaccggccc gccgccggaa gagacgcccg gccaggaaga   21000
ggtggtgctg tgaccacgcc ccgcatcacc gacctgctca ccgagctccg cggccggcag   21060
gtgaccctca cggccgacgg ggaccggctg cactgccgcg cgccccgggg cgcgctcacc   21120
gacgagctcc tcgccaccat ccgcgcccgc gcgacgaaac tcctgcccca cctgcgcgcc   21180
gaccgccgca tcccgcgcca cgacgggccc gcgccgctgt ccttcgccca ggaacggctc   21240
tggctcctcc accagttcca cccgcacgac agcgcctaca acatccccct gcacatcgcc   21300
ctgcgcgggc ccctgaaccc ggccgccctg cgcgccgccc tggccgaggt ggtacggcgg   21360
cacgacgtcc tgcgcacccg gtacgccatc agccgcggcc tgccccggcc cgtcgtcgaa   21420
ccggcccaca cgccgccgct gcccctgacc gacctgaccg ggctcccccgc acaccaccgg   21480
gacgccgaac tcgcccggct ggccgcccag gaggccaggc ggcccttcga cctcgcccag   21540
ggcccggtgc tgcgggcccg gctcctccga acggcccccg aggagcaccg gctgctgctg   21600
acccgccatc acatcgccag cgacggctgg tcgctcgaca tcctgctccg cgaactgggc   21660
acgttctacc gggcagggcg ggacggcaca cccgccggcc tcgacgccct gccgctgcgg   21720
tacgccgact tcgccgcgta ccagcgcgaa caggccgaac ggccggagac ggccgagcgg   21780
tcgacccgct gggcacggca cctgaggggc gccccgcga cactcgacgt cctcgggccc   21840
ccgcccgccg aaccctccca cgcgccggcc ggcaccgtac ggacggacct tcccgccgcc   21900
ctcgtcaccg gcctgcggca gctgggcggc cgggcccgca ccacgctctt cccgctcctg   21960
ctgagcgcct tcggcctcgc cctggccggc ccgcccggcc cgtacgacgt catggtcggc   22020
atccccgtcg ccgcccggcc gcgcaccgaa ctggagccgc tcatcggctg cttcgcgacc   22080
atcgcgccga tgcggctgac gagcgacggg accgagccgc tgacccggct cgccgcccgc   22140
gcccagcagc acgtccagga cgcgctggac ggacccgacg tccccttcga gcggctcgtg   22200
cacgcgctgc gtccggagcg ggacctcgcg gagaaccccc tgttctcggc gtcgttcgcc   22260
ttccagaaca ccccgcggac cgccgtcgcg ctccccggcc tggacgccga ggtgctgccc   22320
tcgccgcccg tggcccccaa gttcccgctg ccctcaccg cgacggcgcg ggccgacggc   22380
ggaatgggcc tggagctgga gttcgaccgg gaccggatcg ccgagccggt cgcgcggggg   22440
atcctcacgt ccttccacgc cgccctcgcc cgcgcggtcg ccgaccccga ggccccggcg   22500
```

```
gcgcccgtac cggccgccgc cgtggaccgg cggcccgggc gcgaaggaca cgagtgcctc    22560
cacgagccgg tggcgcgggc ggcggcacgc caccccgacg ccgtcgccgt cagctgcggc    22620
ggcacccagc tcagctacgg ggcgctcgac acccgcgccg aacggctggc cgcggtgctg    22680
cgcgcccacg gcgccggccc cgagcggctg gtggccctgt gcctgccgcac cggccccgaa    22740 tgggtcgtcg gcgccctcgc catcctcaag tccggcgccg cctacctgcc gctcgacccc    22800
ggcgacccgg ccgagcgccg cgcctccgtc gccgccgacg cgggagcgac gctgatcgtc    22860
tccgacaccg cgcttccccc gctccaccgc gtcgacgtca cggccaccct cccggacggc    22920
gcccccgagc ccaccgcccg ggccgtcctg cccggcaacc tcgcctacgc cgtctacacc    22980
tccggctcca ccggcggccc caagggcgtg ctcgtcaccc atgccaacgt caccgggctc    23040
ctggccgcgt gccgtgaggc cctgcccgcc ctggacgccc cccggacctg gtcggcgacc    23100
cactcgccgg ccttcgactt ctccgtctgg gaggtctggg gcccgctgac cgccggcgga    23160
cgcctcgtcc tcgtgccccc ggacgtggcc cgggcccgg acgaactgtg ggacaccctc    23220
cgcgacgaac aggtcgaagt cctcagccag accccagcg cgttccacca cctcctgccc    23280
accgccgtgc gccgggcggc ccaggccacc gcgctcgaac tcgtcgtcct gggcggcgag    23340
gcgtgcgagc ccgcccgtct gacgccttgg tgggacgccc tgggcgaccg gcgcccggcc    23400
gtggtcaaca tgtacggcat caccgagaac accatccacg tcaccgtccg ccggatgacg    23460
gcggcggacc ggtcgggcag tcccgtcggc cggccgctgc cggggcagcg cgccgacctt    23520
ctcgaccccc acgccggcc cgtcgcgccg ggcgggcggg gcgaactgtt cgtcggcggc    23580
gtcggactgg cccgcggcta cctcggccgg cccggcctca ccgcccggag cttcctgccg    23640
gacgacaccc ccggctggcc gggcgcgcgc cgctaccgct ccggagacct ggcccggctg    23700
ctgcccgacg gcggcctgga ctacgcgggc cgctccgacg cacaggtcaa ggtccgcggc    23760
taccgcgtcg agcccgccga gaccgaagcc gccgcgctga cccatcccgc cgtgcgccac    23820
tgcgtggtcg tgccacgcgg cgacggcgac cggcgccatc tcgcggcgta cgtcgtcgcc    23880
gacacccgcg cctgcgacgg gcccgggctc cgcacccacc tggccgagcg gctgccccgc    23940
cacctggtgc cggcctcggt ggtcttcctg aagcggatcc cgctgacccg caacggcaag    24000
ctcgacgtgg cggccttgcc cgaccccggc gcccaccgcg cacccgcccg cgaacgcccg    24060
cgcaccgcga ccgaacggac cctcacccgg ctgctcgccg ccctcctgaa ggcgccaccg    24120
gagaccatcg ggacgcacga caacctcttc gacctgggcg gcgactccct gacggtcacc    24180
cagttccact cccgggtggt ggaggagttc gccgtggacc tccggtgcg ccgggtctac    24240 caggccctcg acatcgcgac gctcgccgtg accgtggacg acttccggcg ccgcgccgaa    24300
cgcaccgcgc tactgcgcgc cctcgcggcg gcggaggcga tggaacccgg cggtacggcg    24360
ggggagtccg gcggtaatcc ggaggagtcc gccgctacgg cgcgggggcc cgccgtcgcg    24420
gcgaacgaac ccgcgctgc ggcgcgtgag tccggcgccg cgccggtgga gcccgccgtc    24480
gcagtacagg agtccgccgc tacgaagggg gagcccggca ccgcagcgaa tgaactcggc    24540
gctgaggcac gggagcccgg caccgcagcg caggaacccg gcaccgaccc ccggccaccc    24600
gccgccacac cgcaggaccc ccgcaccaca ccgcaggaag gacagccgtg cccgcgtccc    24660
gaatgagccg gccggccggc atcgtcgaca tcgcgcgccg tcacgccgag cgcacccccg    24720
cccgtcccgc gtacgcgttc ctgcccgacg gcgagacgga gagcgtccgc ttctccttcg    24780
ccgacatcga ccggcgggcc ccgcgccgtgg ccgccgtcct ccaggaccgc ggcctggccg    24840
gggagcgggt cctggtcgcc tatccctccg ggcccgagta cgtccaggcg ttcctgggct    24900
```

```
gcctgtacgc gggcgtggtc gccgtcccct gcgacgagcc gcgctccggc ccgagcgcgg   24960
aacggctcgc cgggatccgc gccgacgccc gccccgcccc ggccctgacc gccggcgccc   25020
ccgaggccgg gctcgccggc ctggccaccc tggacgtggc cggcgtcccc gactccgccg   25080
ccggggcctg gaccgacccc gtcgcgggac cggacgcccc ggccttcctc cagtacacct   25140
ccggatcgac ccgccgcccc cgcggcgtca tggtcggcca cggcaatctg ctggccaacg   25200
agcgctgcat cgccgccgcc tgcggccacg accgggactc caccttcgtg ggatgggcgc   25260
cgttcttcca cgacatgggc ctggtcgcca acctcctcca gccctctac ctcgggtccc   25320 tgtcggtgct gatgccgccg atggccttcc tccagcgccc ggcccgctgg ctgcgggccg   25380
tctcccgcta ccgggcgcac accagcggcg gccccaactt cgcctacgac ctgtgtgtcg   25440
accgggtcgg cgaggacgag cgggccggac tggacctgtc gggctggaag gtcgcctaca   25500
acggcgcgga acctgtacgg gccgacaccc tgcgacggtt caccgaccgc ttcgcccccc   25560
acggcttcac ccccggcgcg cacttcccga cctacgggct cgccgaggcg accctgctcg   25620
tcgccaccgg ccccaaggga gtgccgcccc gcaccctgac cgccgaccgc gccgccctgc   25680
gcgccggccg gctccggccc gccgggcccg gcgaggccgg cctggaactg gtcggcaacg   25740
gcaccgccgg cctcgacacc accctccgga tcgtcgaccc cgcgaccgcg cgggagtgcc   25800
cgcccggaga ggtcggcgag gtctgggtgc gggcccggg cgtggcacgc ggctacttcg   25860
gccgcccgcg cgagtccgcg ccgctgctcg ccgcccgcct gccggcggc gaaggaccgt   25920 acctgcggac cggggacctg ggcgcccgc acgacgggga actcttcctc accgacgcc   25980 acaaggacct catcgtcatc cgcggccaga accaccaccc gcacgacctc gaacggaccg   26040
ccgagcaggc ccaccggcg ctccgcccga cctgcgccgc cgcgttcgcg gtgcccgggg   26100
acggcgcgga gcggctcgtg ctcgtctgcg aactcacctc ctaccgcgcc gtcgacccgg   26160
ccgccgtcgc cgaggccgtc cgggccgcgc tcgccgcgcg gcacggcgtc gccccgcaca   26220
cgctggtggt gctgcgccgc ggcggcatcc ccaagaccac cagcggaaag gtgcggcgcg   26280
gccactgccg gacggcctac ctcgacggaa cgctccccgt tcacacgcc gtccgcctcc   26340 cggcggggga ggagggcacc gaggcccttc ccctgaccac ggaccccggt cggctggcca   26400
cggcgctgcg cgacctggcc gccgcccacg cgggcctggc cgggcccctc ccgcaccg   26460 acgagccggt gagcgccctc ggcctggact cgctcgcctc cctgcggctc caccaccacg   26520
tccagtccgc ctacgcgtg accctgcccg tcaccgccct gctcggcgac accacttacc   26580
gccggctcgc ggagctgacg ctcgccgccc ccgcccggc ccgggcgccc gaggggcaag   26640
tcaccggcgt ctggcggccg ttgacgcacg gcagcgcgc cctgtggtac gaacaggcgc   26700
tcgccccgca cgcggccgcc taccacctcg tccgcgcgct ggcctccgc ggccccgtcg   26760 acgaggaggc cctcgccgag gcggtccgcc gcgtcgtccg ccgccacccc gccctgcgga   26820
cccgcttcgc gctccgcgac ggcgaaccgg cgcgccggac cgagccgtac ggaccggagc   26880
tggacgtacg cgacgccacc ggcctgccgg cggaccggct ccgcgaacac ctggccgcgg   26940
cgggcgaccg ccccttcgac ctggccgccg gcgacaggcc cgtgaggctg acgtctacc   27000 gcacggacgg cggccacatc ctgctgctgg tcgcccacca cctggtcgcc gacttctggt   27060
ccctcgtcgt cctcctgggc gacctcgccc gggcccacgc gggcgaggac ctgccgcccc   27120
cgccggaggg ggaccccggc gacgaggcga cggacgcgga ccggacgtac tggcggcacc   27180
ggctcgccga cgcgccaccc gccctcgacc tgcccaccga cctcccccac ccgccgagc   27240 gcggcttcgc cggcgccacc cacgccttcc ggctgccccc ggacctcacc gcccggctga   27300
```

```
ccgccctctc ccgggaacgg cactgcaccc tcttcaccac cctcctcgcc gcccaccagc  27360
tactgctcca ccgcctgacc gggcaggacg acctcgtcgt gggcaccctc ctcgcccgcc  27420
gcgacaccgc cgaagcggcc ggcgccgtcg gctacctggt caacccgctg ccgctgcgct  27480
ccgtacggga gccgggggag accttcacgg aactgctgcg ccgcacccgg cggaccgtgc  27540
tggacgcggt cgcgcacggc cgccacccct tcgggccgct cgtctcccgt ctcgcccccg  27600
cgcgcacgcc cggccgcgcg ccgctcctgc agagcctgtt cgtgctccag cgcgagtacg  27660
gcgacgaggc ggacgggtac cgcgcgctcg ccctgggcgt cggcggccgg ctgcgcgtcg  27720
gcggactcga cctggaggca ctcgcgttgc gcgccgctg gtcgcagctc gacctctcgc  27780
tgagcatggc gcggctcggg gacgggctga cggggtgtg ggagtaccgc accgacctgt  27840
tcaccgaggc cacggtcgcg gagctgagcg aggcgttcgt ccacctgctg cgggcggccg  27900
tcgaggaccc gggcgcgccc gtggagacgc tgccgctcac cggcggccgg gagaccgggc  27960
cgcgccgcgg cccgtcggcg gcccggcccg ccctcccgct gcaccggctc gtggccgcgg  28020
cggcgcgccg cgatcccgca cggacggcgg tcgtcgcact cgccccggac ggcaccgccc  28080
accacatcag ccacggagcc ctgcaccgcg cggccaccac cctcgccgcc cggctccgcc  28140
gggagggcgc cggccggag cggcccgtcg ccgtgctcgt cgagcggggc ccctggctgc  28200
ccgtcgccta cctcggcatc ctgcacgccg ggccaccgt gctgcccctg gacccggagg  28260
accccccgca caggctcgcc cggacgatcg cgaactcggg ggcgcggctg ctgctcaccg  28320
agaccgggac cgcctcgcgc gcggccgagg cggccggtcc cggcgtacgc gcgctgaccg  28380
tgcgtgaggg tgccaccggc ggcgagcggt tctcggcgga cgtccacccc gagcagtccg  28440
cgtacctgct gtacacctcc gggtcgacgg gcgaccccaa gggcgtgctc gtcccgcacc  28500
gggccatcgt caaccgcctc ctgtggatgc aggagaccta ccggctgcgc ccggggagc  28560
gggtcctgca caagacgccg gtgacgttcg acgtctcgat gtgggagctg ctgtggccgc  28620
tgaccgccgg ggcgaccgtc gtcatggccc ggcccgggac ccaccgcgac cccgcgcgac  28680
tcgtccggcg gatcgcccgc gaggccgtca ccaccgtgca cttcgtcccc tcgatgctca  28740
ccccgttcct caccgagctc gcccgcggca cgacgcggct gcccgcgctg cggcgcgtgg  28800
tgtgcagcgg ggaagagctg cccgcggccg cggtgaaccg cgccgccgga ctcctcgacg  28860
cccggctgta caacctctac ggcccgaccg aagccgccgt cgacgtcacc gcctggccct  28920
gccgcccgcc cgagccgggg ccggtgccga tcggcctgcc catcgccaac accaccaccg  28980
aggtcctcga cggccggctg cgcccgctgc cccgcccggt gccggcgag ctgtacctgg  29040
gcggcgcctg cctggcccat ggctaccacc acgaccgc cctgaccgcc gcgcgcttcc  29100
ttccggcccc cggcggcggg cgccgctacc gcaccgggga cctcgtccgc caacgggccg  29160
acggggcact ggtgttccgg ggacgcacgg acgaccaggt gaagatcggc ggcatccggg  29220
tcgagcccgc cgaggtggcg gaggcgcttc gggccctgcc cggcgtcgcc gacgccgcgg  29280
tcgtcccgca cgacgggcgg ctggcggcgt acgcggtcgc cgacccggtc ggcccggccc  29340
cggcggcgga cgcccgtgcgg gacgcgctgc gcaggcggct gccgccac ctggtgcccg  29400
ccgccctcac cctgctggac cggctgcccc tcaccccggc gggcaagctc gaccgccggg  29460
cgctgcccca ccgtcggcc ccgccccgg acggcggacg gccgcccacg accgggaccg  29520
aacggctcgt cgcccgggtg tgggccgaac gcctcggacg ggaagtcgtc ggcgtggacc  29580
gggacttctt ctccctgggc ggcgactccg tcgggcccct cggcgtgacg gcggccctgc  29640
gcgccgccgg gctcccggtg acggtcaccg acctcctgcg cctgcccacc gtggccgccc  29700
```

```
tcgcccgcca cgccgacgag cgggcggatc gccgaccggc gcgacaggag acgccccccg   29760
ggccgttcgc cctctgcccg gaagccgccg gcgtgcccgg cctggaggac gcctaccgga   29820
tgtcgatggc ccagcgggcc gtgctcttcc accgtgacca caaccccggc tacgaggtct   29880
acgtcaccag cgtcgccgtc tccacgcccc tggaccgcac acggctcgcc gcggccgtgg   29940
accggctgct ggaccggcac gcctatctgc ggtcctcctt cgacctcgtg tcccacccgg   30000
agcccaccca gctcgtctgg acccacctgc ccaccccgct cgaggtggtg gagtcgtccg   30060
accccgccgg tttcgacgcg tggctgcacg ccgaacgcaa gcgcccctc gacgtcggca   30120 ccggaccgct ggcccggttc accgcgcacg acgcgggagc cgccggattc cggctgaccg   30180
tcagcagctt cgccctcgac ggctggtgcg tgccaccgt gctcaccgaa ctgctccgcg   30240
actactggtc cgcgctgcgc ggcgcgcccc tcagcctccc ggcacccgcc gcctcctacc   30300
gcgagttcgt cgccctcgaa cgcgccgccc aacacgatcc ggcgcaccgg gagttctggc   30360
ggacggagct cgccggtgcc cggccgcatc cgctgccccg ccgccggtg ccaccgcccg   30420 ggccggacgg gatccgccag caccgtcacg tcgtccccgt cgaggacacc gtcgccaagg   30480
gcctgtcggc gctcgccggc gagctggtg tcgggctcaa acacgttctg ctcggcgtcc   30540
acctgcgggt cgtccgggcc ctgtccggcg accccgacgt catcacggcc gtggagaccc   30600
acggccgcct cgaacggcac gacggcgacc gcgtcctcgg ggtgttcaac aacatcctgc   30660
cgctgcggca gcgggtggac ggcgggagct gggccgacct ggcccgcgcc gcgcacgccg   30720
cggaggcgcg gacgggggag taccgccgct atccgctggc ccaggcacag cgcgaccacg   30780
gcgcggccgg gctcttcgac accctcttcg tgttcaccca cttccacctc taccgcgcgc   30840
tggccgacct ggacggcatg gcggtctccg acctgcgggc ccccgaccag acctacgtac   30900
cgctcaccgc ccacttcaac gtcgacgcca cggacggcgg cggcctgcgg ctgctgctgg   30960
agtcggaccc gcgggagttc cccgacgagc aggtcgcgga gttcgccgcg tactaccgcc   31020
gcgcgctgcg ggccgccgcc gacgccccgc accggccgta ccgggacacg ccgttgacgg   31080
accggccggc cggtccggcg ccgcaccgcg cggagcgctc cgtccacgcc ctgttcgcgg   31140
ccccggcccg gaaccacccg gaccggatcg cgctcgacgg cgaggacggg ccggtcagcc   31200
acggcgccct ggcccggcgc gccgcccgcc tcgccggaac gctgcgggcc gcgggcgccg   31260
ggccggacac cgtcgtcggg atctgggcgc gcgccgcgc cgacgccgtc gtggcgctgc   31320
tggccgccct ccacgccgga gccgcctacc tgccctgga cccggtccac ccgcccggc   31380 ggcagcggca ggtgctcacc gaggccggcg cccgcctgct cgtcctgccc gccggcctcg   31440 acacccgct ccgggcctgc ggcctgcccg tcgtggcccc ggacgacctc ggcgcgccca   31500
tcgcccccgt gtccgtccac ccggagcagc tggcggcggt catggccacg tccggctcca   31560 ccggacgcc caagacgatc ggcgtccgc agcgcgccct ggccggctac ctccgctggg   31620
cgatcggcca ctaccgcctc gacgaggaga ccgtctcccc ggtgcactcc tcgctgggct   31680
tcgacctgac cgtcaccgcg ctgctcgcac cgctggccgc cggcgggcag gcgcggctga   31740
ccgactccgg cgaccgggt gcctcggcg cggcactggc cgccggccac cacacccctgc   31800 tcaagatcac cccggcccat ctggccgccc tcgcccacca gttgggcgcg ccgaccgcac   31860
tgcgcaccgt cgtggccggg ggcgaacccc tgcacgccgg ccacgtccgc gcctccgcg   31920 ccttcgcgcc cggcgccgg ctcgtcaacg agtacgggcc gaccgagacc accgtcggct   31980
gctgtgccca cgacgtcgca ccggacccg gcgaggcgcc catccccgtc ggtacccga    32040 tcgcgggcct cagcgcgtgc gtcgtcgacg acgcgctgcc cgcaccgccc ggcgtgcggg   32100
```

| | | | | |
|---|---|---|---|---|
| gcgagctgta | catcggcggg | acgggcgtca | cccgcggcta | cctgggccgg cccgcggcca 32160 |
| ccgccgccgc | ctacgtgccg | gaccctgccg | ccccggcgc | ccgccgctac cgcaccggcg 32220 |
| acctggcacg | ccggctgccg | gacggcaccc | tgctcctggc | ggggcgcgcc gaccgccagg 32280 |
| tgaagatccg | cggccaccgg | gtggaaccgg | gggaggtcga | gcaggtgctc ggcggccacc 32340 |
| ccggggtgcg | ggaggcggcg | gtcgtcgccc | acccggcacc | cggcggcggc cgccggctgg 32400 |
| tcgcgtactg | ggtaccggcc | gaaccggccc | ggccaccgtc | cgcggacgcg ctcaccgcgc 32460 |
| tgctcgccga | ccggctgccg | ccgtacgcgg | tccccgccga | actcgtccgc ctgcccgccc 32520 |
| tgcccaccac | ccccaacggc | aaggtcgacc | acacccggct | gcccgcggcc ggacgggacc 32580 |
| ggcgactggc | ggaactgctc | gaccggatcg | aggcactgtc | cgacgccgag gcggcctcgg 32640 |
| cactgcgcga | cagccggccc | gcacccggga | gtggcgatga | ccgagcatga cgaccacccg 32700 |
| ccggcccgcc | ggggccccgc | cggttccgct | ggcccggcg | gaagcccgcc cgtcccgcac 32760 |
| gtgccggtgc | ccgggcatga | cgaccgcgtc | ggacggctgc | cggcggaccg gagcgtcccg 32820 |
| ccgacccgcc | gattctctgg | ggaccccgcc | ggttccggtg | gtggcccgcc cgtcccgcac 32880 |
| ccggaggtgc | cgatgcgcgg | gcatgacgac | cgcgtcggac | ggctgtcggc ggactggagc 32940 |
| gtcccgccga | cccgcctgcc | cgccggggac | ccggccggtt | ccgtcggccc cggcggaggc 33000 |
| ccgcccgtcc | cgcacgagga | ggtgacgatg | tcggagtatg | acgaccgcct cgcgcggctg 33060 |
| tcggacaacc | agcgcgccct | gctggaccgc | tggctcgccg | aggaccccgc cggcggtgcc 33120 |
| ggcccgcttc | gccccgacgg | ccgcccgccc | cgcaccgagg | ccgagcggat cctggccggg 33180 |
| gtctgggagg | aggtgctgga | gaccggcggg | atcggcgccg | acgacgacta cttcgcgctc 33240 |
| ggcggagact | ccgtccacgc | catcgtcatc | gtggcgaagg | cccggcaggc cggactcgcc 33300 |
| ctgaccgccc | atgacctctt | cgaggccagg | accctcgcgg | ccgtggcgcg gagagccgcc 33360 |
| ccggccggcc | ccgccgagcc | cgtccccgac | gcgggcggcg | gcgcggtccg gtacccgctg 33420 |
| accctatgc | agcagggcat | gctctaccac | tcggccggcg | gcagcacgcc cggcgcctac 33480 |
| gtggtgcagg | tgtgctgccg | gctgacgggg | gacctcgacg | tggccgcctt ccgcaccgcc 33540 |
| tggcaggccg | tgctgtccgc | caacccggcg | ctggccgtct | ccttccactg gtccgacggc 33600 |
| tccccgcccg | agcaggtggt | ggaccccgac | gcgcgcgtca | ccgtcgacac ggccgactgg 33660 |
| cgggaccgca | ccccggccga | gcgggacgat | gccttcgccc | gcttcctgga caccgaccgc 33720 |
| gcggcgggct | tcgacctcgc | ccgcgccccg | ctgatgcggc | tgacgctctt ccgcgagggc 33780 |
| gagcacgcgt | accgctgcgt | gtggaccac | caccacctcg | tcctcgacgg ctggtcccag 33840 |
| cagctcgtcc | tgcgcgacgt | cctcgactgc | tacatgcgcc | tgcgcgccgg acgcggcgcc 33900 |
| gagccgcccc | ccggccgtc | cttcaccggt | catctgcgcc | ggctggagcg gcaggacggg 33960 |
| atcgacgagg | agttctggcg | cgaccacctc | ggcggcctgc | ccgcacccct ccgcgtcgcc 34020 |
| ggtcccggct | gccgcgacgg | ccgggtggtc | gccgtacggc | gcgccgagca ccggcaccgg 34080 |
| gtctccgcgg | cgacgggccg | ggagctgacc | ggcttctgcc | gccgccacgg gctgaccccg 34140 |
| gccgccgtgc | tgcacggcgg | ctgggcggtg | ctgctgtccg | tgcactgcgg ccaggacgac 34200 |
| gtggtcttcg | gcaccaccct | ctccggccgc | cccgaggacc | tgcccggcgt gaccgagtgc 34260 |
| gtcggcctct | tcatcaacac | gcttcccctg | cgggtccgtt | gcgggagga cacggacgtc 34320 |
| gtcgactggc | tccacggcgt | ccaaagcgac | ctggccgccc | tgtgggacca cgcgcacgtc 34380 |
| ccgctcagcc | gcgtcgagcg | cggtctcgga | ctgggccggg | gcggcgggct gttcgacagc 34440 |
| atcatggtcg | tcgagaactt | ccccgccgcc | gtcgccgacg | gccacgaggc gggcgggctg 34500 |

```
cgggtgacgg agccccgggc actcgtcgac gagggctacc ccctcgtact ggaggccacc      34560 accgggacc  ggccggtgct gcacgcccgc tacgaccccc accgcctcgc cggcgggcgg      34620
gtccaggcgc tgctcgccgc cttcgacgac tacctccggg cggtgaccgc cgacccggcc      34680
cgcccgctgc cggacctccg cgcggtcctg gcccgcgacc acgcgcgccg ggacggcgcg      34740
gcacgcgggc ggcgccgcgc cgcggaccgc acccgtctga cgctggcccg ccgccgcccg      34800
gcgacgacga ccgagggaga gacaccgtga catggaccgt ggtgaccgga gccggcggct      34860
tcatcggctc ccacctcgta cgccgcctcg tccgggacgg gcaccgggtc cgcggcgtgg      34920
acctggtgcc gccgcgctac ggccccgcg  aggcccagga gttcgtcatc gccgacctgc      34980
gcgacgcggc gcaggccgcg cgggccgtcg ccggcgcgga ctccgtcttc gcgctcgcgg      35040
ccaacatggg aggcatcggc tggacccaca ccgcgcccgc cgagatcctc cacgacaacc      35100
tgctgatctc caccccacacc atcgaggcat gccgggccgc cggcgtgcgc accaccgtct      35160
acacctcctc ggcctgcgtc taccccgcgt ccctgcagcg cgagcccgac gccgcgccgc      35220
tggccgagga cccggtcttc cccgcggaac ccgacatgga gtacggctgg gagaagctga      35280
ccacggaaat cctgtgcggc gcctaccgcc gcagccacgg catggacatc aagacagccc      35340
ggctgcacgc catctacggc cccctcggca cgtacaccgg gccccgcgcg aagtccctgt      35400
cgatgctctg cgacaaggtc gcccggatac ccggcgacga gggggagata gaggtctggg      35460
gggacgggac gcagacccgc tcctactgtt acgtcgacga ctgtgtcgaa gggctgatcc      35520
ggctcgcccg ctccgacgtg gcggaaccgg tcaacatcgg ctccgaggag cgcgtcgaca      35580
tcgcgtcgct cgtcgagcgg atcgccgggg tcgccgggaa gaaggtgcgc tgcgccttcg      35640
cccccgaccg cccggtcggg ccccgcggc  gcgtctcgga caacacccgc tgccgcgaac      35700
tgctcggctg ggcaccggag acgtccctcg cggccggcct ggagcgcacc tacccgtgga      35760
tcgagcgcca ggtcctcgcc gaggccggga gggccgatgc ctgagcaccg cacaccggtg      35820
aaggacctcg gccggctgct gctcgggcac gccgcgcgct tccggggccg cgagctgcag      35880
gacgtcgcca cccgggcgct gcgggcctcc ggcggggaga acgcctgggt ggtgtccgtc      35940
gtcaacacca gtctccgcgc ccgccaggcc gtggaccacg cgctgcggct cgcccccgc      36000 cgcgggctct cccggctgcg ctacccgttc tccgccgccc accacggcc  caccccgccc      36060 cggaccctgt cgctgctgtg cccgacccgc gaacgcgtcg gcaacgtcga acgcttcctc      36120
gacagcgtcg cccgcaccgc cgccgcgccc ggccggatag aggccctctt ctacgtcgac      36180
gacgacgacc cccaactccc tgcctaccac gagctgttcg agcacgcccg gtggcgctac      36240
ggacggatcg gccggtgcgc cctgcacgtc ggcgccccg  tcggcgtacc ccacgcctgg      36300
aaccacctgg cccggaacgc ggccggcgac gtgctgatga tggccaacga cgaccagctc      36360
tacatcgact acggctggga caccgccctc gacgcccgcg tcaccgaact gagcgccctg      36420
caccccgacg gcgtcctgtg cctgtacttc gacgacggca gtaccccga  gggcggctgc      36480 gacttcccga tggtgacacg gccctggtac ggcaccctcg gctacttcac cccgacgatc      36540
ttccagcagt gggaggtcga gaagtgggtc ttcgacatcg ccgaccggct gcaccggctc      36600
taccccgtcc ccggcgtcct cgtcgaacac cggcactacc aggactacaa ggcacccttc      36660
gacgccacct accagcggca ccggatgaca cgggagaagt ccttcgccga ccacgccctg      36720
ttcctgcgca ccgagccgga ccgcgaggcg gagacggaca ggctgcgggc cgtcatcgcc      36780
cgggcaggga acaccccgga cgccgaccac gccgaccatg ccgttcacga cgcggagacc      36840
ttctggttca ccggcctcct gcgcgagtcc cacgccaagc tgctcgcgga actcgacgac      36900
```

```
gcgccgggcc cggccgccgg agccgtgctc ttcgccgacg gctcctggac cggcgtcgcc    36960
taccgcaccc acccgctggc caccgccctg ctcgcctcga tccccgaggc caccctcgac    37020
tccggccgcg ccgacctcct cgtcgtcccg cccggcgcgt cccaccacca ccccgacggc    37080
accgtcgact ccgcgttcgg ctccgacgcc ggcctccgcg tcctgttcgg actgcgcgtg    37140
ccggacgccg cgcaactccg cgtcggcgac ggcccggtgc cctggggcaa tgggcaatgc    37200
ctgatccacg acaccgccgc accgagcacc ctgcgcaacg acggcaccga atctctggcc    37260
gccctcacct tcgtggtgcc gcgcccggca ccggggagt gaggcccgtg tgcggcatcg     37320
tggcgatccg ctccgccgac ggcggactcg acggcggtga actcaccgcg ccgatggccg    37380
acctgcgccc gcgcggcccc gacggcgaag gcacctgggt ctcgcccacc ggccgggccg    37440
ccctcggcca cacccggctc gccgtgatcg cccccgacgc cggacgccag ccggtcgccg    37500
gcccggacgg caccgtccgg ctcgtcgtca acggcgagtt ctacggctac cgggagatcc    37560
gcgcggaact gcgcgccgcc ggctgccggt tccgcaccgg cagcgacagc gagatcgccc    37620
tccacctgta cctgcgggac ggccggcggg cactggagcg gctgcgcggc gagttcgcct    37680
tcgtcctctg ggacgaacgc cgcgccaccc tcttcgccgc ccgcgaccgg ttcggcgtca    37740
aacccctcta ctacaccgag cgcgacgggc ggctctacgt cgcctcgacg gtcagggccc    37800
tgctctcctg cggcgccccc gccgctggg acaccgccgc cttcgccgcg cacctgcagc     37860
tcggcctgcc ccccgaccgc accctcttcg ccggcatccg gcagctcccg cccggctgcc    37920
acctcatcgc cgacgcccac ggcacccgcg tcaccccta ctgggacctc gactaccgc      37980 ccgccggcga actcgccgcc cggggaagcc tggacgacca cctggacgcg gtacgcgaac    38040
ggaccgacga ggccgtacgg ttgcgtaccg tcgccgacgt gccccgcgcc tgccacctca    38100
gcggcggcct ggactcctcc gccgtcgccg cctccgccgc ccgccacacc cggctcaccg    38160
ccttcaccgt ccgcttcgac gaccccgcct tcgacgagag cgccgtcgcc cggcgcaccg    38220
ccgcccacct ggccatcgac caccgcgaag tcgcctcgga acgcgcccac ttcgcggacc    38280
acctgcggga cgtcgtccgc gccggcgaga tggtgcagga gaactcgcac ggcatcgccc    38340
ggtacctgca cagcgcgcac atcaagaagg cgggattcac cgccgtcctc gccggggagg    38400
gcggggacga actgttcctc ggctaccccc agttccgcaa ggacctgacg ctcagcctgt    38460
ccgccgacgc ccgcgacaag gccgaccgcg gctacgcccg gctggtcgcg gccgggctcc    38520
tgccgccgta cctgcgcacc ctcctcggca ccctcggctt cctgccctcc tggatcgtcg    38580
accgccacct ggccgtcacc cagcccgtcg ccgccctgct ccgccccgac ttcgccgccg    38640
aactggcccg cgccgacgcc gccgcgcccc tgctcgccgc cggcgccggc ctgctcgccg    38700
ggcgcgcccc ggcgcaccag gccacctacc tcttcgccaa gacctggctg cccggctacc    38760
tgctcgccgc cgaacgcctc gacgcggccc aggccgtcga ggtgcggctg cccctcttcg    38820
accaccacct cttcgacctc gtccggcaca ccccgccggc ctggtacgac aaggacggca    38880
ccggcaagta cccgctgcgg gccgccatgc gccaccggct gccgcgcgag gtgaccgagg    38940
gccgcaaaca gggcttcctc gcacctccga tggccgacga cgacaccctc ctcgacgccc    39000
tgcgcgaacg cctcgccgga ccgggcgcgg gcgacgaccc cttcttcgac ccgcacgccg    39060
tccgcgccct gctggaccgg ctggccgccg caccccggg gcagcggtcc ggcggcgaga    39120
aactcctcca actcgtcgcg agcaccgccg aactggccga cgagttcggc ctcaccaccg    39180
cccccagcgg gcagaaaggc ggcaacggtg gctgacctcg atcccggcac gctctccgag    39240
gccgagctga ccgcccggat cgccgccctg tccccgaac gccgggcggc gttcgagaag     39300
```

-continued

| | |
|---|---|
| atgctgcacg gcgccgcgca ccccccgcccc ggcatcccgc gccgcggcgc caccgcggca | 39360 |
| ccggcctcct acggccagga acgcctgtgg ctgctcaccg ggctgctgcc caccgcctac | 39420 |
| aactacgcca ccgccctgcg gctgcgcggc gacctgtccg tccccgcgct gcgcggcgcc | 39480 |
| ctgcgcggca tcgtccgccg ccacgaggtg ctgcgcacca ccttccggct ggacggcgac | 39540 |
| gacctcatcc aggtcgtcca ccccacggcg gacgtccccg tgcgcctggc cgacctcacc | 39600 |
| ggacgctccg ccgacaccgg gcggctgatg cgcgaggagg cccgccgccc cttcgacctg | 39660 |
| gagcacgggc cgctgctgcg gctgacccte ttccggctcg ccccccgcga ccacctcgcc | 39720 |
| ctgctggccg tccaccacgc cgtcaccgac ggctggtcca acggcgtcct cgtgaccgaa | 39780 |
| ctcgccaccg gctaccggga actgcgcgcc ggacgccccg accggcggcc cgccccgccg | 39840 |
| gtccagtacg gcgactacgc gcactggcag cgcgagcggc tgaccgggcc cgaactgcgg | 39900 |
| gccctggagg actactggcg caccgccgta cgcgacctgc ccaggacgga cctgcccacc | 39960 |
| gaccgccccc gccccgccgc ccggcgcggc gagggcgcca ccacgcccct gctgctctcg | 40020 |
| ccggagctga ccggccggct cgccgacctg cgccgccgcg agggcgggtc gctgttcatg | 40080 |
| ctcgtgctct ccgcgctcct ggtcgtcctg cgtggcaccg gcggccggga ccggctcgcc | 40140 |
| gtcggcaccc tcgtcgccgg ccgcacccgc cccgaactcg agccgctcat cggctacttc | 40200 |
| gtcaacgtcc tgctgctgcc cttcgagacc ggcggccgga cctccttcgc cgagctgtgg | 40260 |
| cggcgggtcc gcggccggct ggtggaggcg tacgcccacc aggaactgcc gctggagaag | 40320 |
| gccctggagc tgctgcgcgc cgacggcacc gccccgccg accgccggt cggcgtggtc | 40380 |
| tgcgtcgccc agcagcccgc ccccgcgatc accctgcccg gactcgacgc gagcgtcgag | 40440 |
| gacgtcgacc tgggcaccgc ccagttcgac ctcgtcgtcg aggtgcgcga acggccggaa | 40500 |
| ggcgtgcaga tcgccttcca gtacgaccgg gacctgttcg acgcggccac ggtccggctc | 40560 |
| ctcgccgacc acgtgcacgc cgtcctcgac caggccgccg ccgacccac cctgccctgt | 40620 |
| gccgagctgc ccgccccgcc ggccccgcg gccccggccc gcacggccgg cgccacgacg | 40680 |
| ctgcacgccc tgttcgagtc ccgcgccgcg aagagcccg acgcggtcgc cctcgtcgac | 40740 |
| ggcggccacc gcgtcaccta ccggaccctc aacacccgcg ccaaccggct cgcccgccac | 40800 |
| ctgcgcgcgg tcggcgtgcg taccgaggac cgggtggcgc tgcgcctgcc ccgcggcacc | 40860 |
| gacgcggtga ccgccaccct cgccgccctc aaggccggcc ccgcgtacgt accctcgac | 40920 |
| cccgccctcc ccgaggaacg gctgaccccg gtcctcgccg acgcccgccc cgccgtggtc | 40980 |
| ctcacccccg cgtatctgca cgaccggtcc gccgagatca ccgcccacgc cggccatgac | 41040 |
| ctcaacctcc ccgtccaccc cgacaacctc gcctacctcc tccacacctc cggatccacc | 41100 |
| ggcacccca agggcgtcct cggcacccac cggggcgcg tcaaccgcgt cgactggatg | 41160 |
| agcaccgcgt acccgttccg gaccggcgac gtggccgtcg cccgcaccgc gcccggcttc | 41220 |
| gtcgacgcg tctgggaact cttcggcccc ctggccgccg gcgtcccct cgtcctcctg | 41280 |
| ccgaccgacg aggcgcgcga cccggccctg ctgacggcgg cgctggaacg gcaccgggtg | 41340 |
| agccggatgg tgacggtccc gtcgctgctg accatgctcc tggacgagtc cgcccgcgcg | 41400 |
| acggacctcg gcaccgcct ggcctgcctc cgcacctgga tcaccagcgg cgagcccctg | 41460 |
| ccgcccgcgc tcgcccggcg gttccacgac cgcctgcccg gccgcaccct gctgaacctg | 41520 |
| tacggctcct ccgagaccgc cgccgacgcc accgcggccc gcatcgaccc ggcgcccggg | 41580 |
| actgcgctcc cggagcggtc cccgatcggc acgcccatca ccggcgtcag cgccctcgtc | 41640 |
| cgcggcccgg acctgcgccc gctgcccgcg ctgatgcccg gcgagctgta cgccgggggc | 41700 |

```
gcgtgcgtgg cccgcggcta ccacgcccgt ccggccgaga ccgccgcggc gttcccgccg    41760
gatcccgacg gcgggcccgg cgcccggatg ttccgtaccg gtgacagggc ccggctgcgg    41820
gccgacggcc ggctggaact cctggggcgc gtggaccggc aggtgcagat ccgcggccag    41880
cgcgccgagc ccggcgaggt cgaacacgcc ctgctggccc acccggccgt acgggccgcc    41940
gccgtcacgg cgaaccccga cgccaccggc ctgtgggcgt acgtgcggct cgctcccggc    42000
ccgttcgccg ccggctcccc ccagaccgag ctgaccgcct tcctgcgccg cacgctccct    42060
gcccacctcg tgcccaccgc cgtcaccgtc ctggacgagc tgccggtgac cgcgcacggc    42120
aagaccgacc acgcgcggct gcccgccccc gaccccgggg ccgggcgccc cgccccgacc    42180 gcccccccgca cccccaccga gcgtacggtc gccgacgtct tcgccggggt gctcggcctg    42240
gaggggccgg tcgcgcgcgca cgacgacttc ttcctcctcg gcgggcactc cctcctcgcc    42300
gcccgcagtc gcggcggaac tccgcgcccg ccgcggcgtc cggatcgggc tgagcgacgt    42360
cttcgcggcc cccaccgtcg ccgcagcgtc gccgcccgga ccgacgccgc ccggcccggc    42420
accggccccg agcacacccc gttcgtcacc gaccccggcg cccggcacga gccgttcccg    42480
ctcaccgacg tccagcgggc ctactacgtg ggacgcgagg gcgggttcgc cctcggcggc    42540
gtctccaccc acgcctacct ggagatcgag gccccgcgga tcgacgtcgc acggtttacc    42600
ggcgcgctgc gcggggtgat cgcccggcac cccatgctgc gcgccgtgat ccgtcccgac    42660
gggctccagc aggtgctcac cgacgtcccc ccgtacgacg tggccgtgca cgacctgcgc    42720
gacctggacg agcccgcgcg gcagcgccga cgcgccgcgc tgcgcgagga gatgtcccac    42780
caggtggtgc ccgccgacct ctggcccctg ttcgacgtcc gcgtctccct cggccccacg    42840
gacgccctcg tccacgtggg ggtggacgcg ctgatctgcg acgcccacag cttcggcctc    42900
gtcctggccg aactcgcggc ccgttacgcc gaccccgcac gccgcttccc gcccctgacg    42960
gcggacttcc gggaccacgt cctccatcag gaggcgctcc gcggaaccgc cgagtacgcg    43020
gcggcggagc ggtactggcg cgaacgcctg cccgagctgc cgcccggccc cgaactgccc    43080
ctggccgtcg cgcccgagac cctcggcacc ccgcgcttca cccgccgctc cggccggctg    43140
gacgcggcct cctggacggc ggtcaaggac cgggcccgcc gcgccgggct cagcccctcc    43200
ggcgtactgc tggcggcgtt cgccgaggtg atcaccgcgt ggagcggccg gccgcgctac    43260
tcgctgatgc tgacggtctt cgaccgcccg ccgctccacc cggacctcgg gcggatcgtc    43320
ggcgacttca cctcgctcag cctgctggag gtcgaccaca gtcggccggg cgacttcacc    43380
gacagggccc gcgccctcca gcgccgcctg tggcaggacc tcgaccacct ggcggtcggc    43440
ggcgtgacgg tgacacggga acgggcgctg cgccacgacg cccgaccggg tctgctcaca    43500
cccgtcgtct tcacctccga cctgcctgtc ggcgagaccg cggccgagga cgcggacggg    43560
ggagagggat gggcgctcgg agagcccgtc tacggcgtca gccagacccc gcaggtccat    43620
ctcgaccatc aagtcgccga agaccgaggg gagttggtct tcaactggga cgccgtggaa    43680
gacctgttcg ccccgggcgc cctggacgcc atgttcgccg cctacaccgc ctcgctgacc    43740
cgcctggccc ggagccccga agcctggcgg cggcccggca cgccgccgct gcccaccgcc    43800
caggcggccg tgcgccggcg caccgccgcg accgaggcgc ccctgccgc ccgcctgctg    43860 cacgaggccg tcgcgacgc ggcccggcgc cacgccgacc tgaccgccct ggtcgacggc    43920
gacacccgga tgacctaccg gcgactgacc gagcacgccc ggcgcgtcgg ccgcacgctg    43980
cgccgcctcg gcgcccgccc cggccgcctg gtccggtgg tcgcccgcaa ggggtggcgg    44040
caggccgtcg ccgcgctggg cgtcctggag tcggggggcgg cgtacctgcc cctggacccc    44100
```

```
gaactgcccg ccgaacggct cgtccacctc gtacggcgcg ccgaagccgc cctcctcctc    44160
accgaacgcg ccctgctgga cacgctcgcc gtccccgtcg gcgtcaccgt gctcgcggtg    44220
gacgacgacg cggccctcga cgccgacggc ggcccgctgc agagcgtgca gaacctcacc    44280
gacctggcgt acaccatctt cacctcgggc tccaccggcg aacccaaggg cgtcatgatc    44340
gaccacctcg gcgcggccaa caccctggaa tgcgtcaacc gccgcttcgg caccggcccc    44400
ggcgacgcgg tcctcgccgt ctcctccccg agcttcgacc tcgccgtcta cgacctgttc    44460
ggcgtgctgg ccgccggcgg caccgtggtc gtccccgccc acgaccgccg gcgcgacccc    44520
ggacactggg ccgagctgat ccggcgcgag cgggtcaccc tgtggaactc cgtccccgcg    44580
ctgggcaccc tgctcaccga gtacgccgag gccctcgccc ccgacgccct cgcgcaccctg   44640 cgggcggtgc tcctcagcgg cgactggatc ccctcggac tgcccgaccg gatccgcgcc    44700
ctgtccgccc ccggcgccac cgtgatgagc ctcggcggcg cgaccgaagc ctccatctgg    44760
tcggtctggt acgagatcgg gaaggtgcac gaggcgtgga gcagcatccc ctacggcacc    44820
cccatggcca accagcggct ggaggtcctc gacgagcagc tgcggccccg gcccgactgg    44880
gtgcccggcg agctgtacat cggcggcacc ggcgtcgcca agggctactg gcgcgacccg    44940
gaacagacct ccctgcgctt ccccgtccac ccgggcagcg ggcaacgcct gtaccgcacc    45000
ggggacttcg cccgccacct ccccgacggc acgctggaat tcctgggccg gcaggacgac    45060
caggtgaaga tcggcggatt ccgggtcgaa ctgggcgagg tcgaggcggc cctcggccga    45120
ctgcccgacg tcgccgccgg cgcggtgatc gccaccggtg accgcggggg cgaccgccgc    45180
ctcgtcggct tcgccgtacc ggcccgggag ggcggcttcg acgcggccgg gctccgacgg    45240
caactcgccc ggcggctgcc cgcctacatg gtccccacga ccctgctgcc cctggaccgg    45300
ctgccgctga ccgccaacgg caaggtcgac cgggccgcac tccaacgcct cgtccccggc    45360
cgcgcaccgg ccccggcgga acccgccacc gccccacctg cccgttcccg cgccgtcccc    45420
gtgcccggct ggctcgccga cctgtggtgc gaactcctcg acgtgccgga ggccgacccc    45480
gacgcgaact tcttcgccct cggcggcacc tcccgggtcg cgatcaccct ggtcacccgg    45540
atcgaggccc gactcgccgt ccgggtgccc ctcgcccgcc tcttcgacgc ccgcaccctg    45600
ggcggcctcg ccgagacgat cgccgaactg tcggccgccg ccgaggagga gccggcaccc    45660
gccgagcccg tgtacgcccc cgaccccgcc accgccacg agccgttccc gctcaccgac     45720
atccagcgcg cctactggct cggccggcac cgctccctct cccttggcgg cgtcgccacg    45780
cacacctacc tcgaactcga cgtcgaggac ctcgaccccg gccggctcca gacggccctc    45840
cgccggctga tcgaccgcca cgacgccctc cggctcgtgg tcctccccga cggccggcaa    45900
cagatcctcg gcgacgtacc gccgtacctc ctcgcccaca ccgacctgcg gggcagggcg    45960
gacgccgagg ccgaactggc ccgcgtccgc gagcacatgt cgcacgaggt gcgcgacgcc    46020
tcccgctggc cgctgttcga cgtacggacc caccgcctgg acgacgtccg cacccggctg    46080
cacctgagct tggacctgct catcgccgac gcccacagcg tccacgtact caccggcgac    46140
ctgctcacct tctacgccga ccccgacgcg gccctgccgc cctcggctg ctccttccgc     46200 gactacgtcc tggccgtccg cgccacgcc gagggcgagc cgcgccgccg cgccctcgac    46260
cactggcggg cccggctggc cgacctgccg ggcccgcccg gctgccgct gcggtgccgg     46320 cccgaggagc tgaccgcgcc gcggttcgcc cgcctcacca ccggactcgg cccgacgcc     46380 tgggcacggc tgcggcgcgc cgcggcggcc ccgaactca ccccgccgc actgatctgc      46440 gccgccttct gcgacgtcct cgcccagtgg agcgacaccc ccgcttcac cctcaacctc     46500
```

```
accaccttcc accgccccgc cctgctcccc ggcgtggacg acctcgtcgg cgacttcacc    46560
accacgaccc tgctcggggt cgacggcgag ggggacacct ccgggaccg ggcccgccga    46620 ctccaggacc gcatctggga ggacctcgaa caccgcgtcg tcagcggcgt cgaggtcctg    46680
cggatgctgc gccgcgagcg gggcacccac gacgccgtcc ggatgccggt cgtcttcacc    46740
agcaccctgc gggccgccgg ccccgccccc cggacggccc cgcccgcctg gcgggtacgg    46800
cccggctacg cgatcagcca gaccccgcag gtcctgctcg accatcaggt gagcgagagc    46860
gacggccgac tggtctgcac ctgggactac gtcgcggacg cctacccgcc cgggctgatc    46920
gaggccatgt tcgggccctt cgaggcgctc ctcgcctcgc tcgccggtca cgacgacgac    46980
gccggccacg acgacgacgc cggccacgac gacggccccg ccacgacga cggccccggc    47040 cacgacgacg cccccggcca cgacgacggc cccggccacg acgacggccc cggccgcgac    47100
gacagtgccg atcacggcca cagtgccacg cacgacgaca cgccgcccg aaacgacaga    47160 gagggaggtg gaccggagtg acgagcgccc ggcccacgcc gacactgctc cccgccgacc    47220
agcgggagct gctgcggatg atgaacgacc gcaccgcacc cgtgcccgcg cacaccctca    47280
ccgcccaact ggccgacgcc gcgcgcacgc acgaccgggc tctggcactg gtggcaccgg    47340
gtctgacact gagccacgcc gaactggacg cccgggcggc cgcggtggcc gcccggctca    47400
ccgccgcggg cgtcatcccc ggggaccggg tcgcctcgc cgtcgagtac ggctgggagc    47460
aggtcgtggg cgccctggcc gcgctccgcg ccggagccgt ctgcctgccc gtcgccccg    47520 ggctgccccg gcccgcccgc tggcagcacg ccacccgggc cggggcgacg gccgtcctca    47580
cccagtcctg gctcacccag cgcatcgact ggccgcagga actgcccgtc ctctccgtgg    47640
acgaacccgg gccgccggta ccacccacca ccgccccggc cgacggacgg tccgcgaccg    47700
acgccgccta ccggctggac gccccccgtca gccaccgcgc gatcaccacc gccgccctgg    47760
agatcgaccg cgccttccgc gtcggacccg gcgaccggct cctggccctg gccccgccg    47820 actcgccgct cgctctctac gaactgttcg ggcccctcct ggccggtgcg gccctcgtcc    47880
tcacccggga catcgacctg cgcgatcccg gagccctgca cgaggcgctg cgcacccacg    47940
gcgtcaccct ctggcactcg ccgcccgccc tcctcggcct cctcctcgac cacctcgccg    48000
accggggcgg caaactgccc gagtcgctcc ggctggtgct gctcggcggc gaacgcctcg    48060
accccgccct cgtccgccgc gtccgcgaga gcgccccgca ccagccggcc gtcgcccacc    48120
tctcctcggc cacccgtcc ggccctgga ccacctgcct ggagaccggc gacctcgccc    48180
cggaatggcg ctcggtcccc gtcggcgcgc ccctgcccaa ccagcgggcg cacatcctgt    48240
ccgagaccct gcggccctgc ccggtctggg tcaccggccg cctccactac ggcggcgtcg    48300
ccgccgagcc ccccaccgga gaggagcacg caccccgcgac cgtccccgcac ccggagaccg    48360 gcgaaccgct gctgcgcacc gggctgttcg cccgcctgct gcccgagggc ctgatcgacg    48420
tcgtcggcga cgagaccgcc cggatcagcg tccgcgaccg gccctgaac ctccaggaca    48480 ccgagaccgc cctcgccgcc cacgaggacg tgcactccgc cgtggtcgtc cccgtcgggc    48540
ggggagacga gtcgctcgcg cgggtacggc tccaccccgg cgccacgcc ggccccgacg    48600 aactcctcgc ccatctgcgc cgcaaggtct ccccttacct gctgcccggc cacatcgagg    48660
tgggcggtcc gctgccgctc acccgggacg ggcgcgtgga ccgcgcgcgc gtcaccgccg    48720
aggcccccgc ccccgctgcc gtgcccgccg ccgcgccggc ggcgtcggca cccgcgcggg    48780
acgaggccga actcctcgcc caagtggccc gggtgacctg ccgggtgctg ggaatcggcc    48840
ccgtcgaacc cgatatgaac ctgctcgacg ccggtgccac ctccgtcgaa ctcgtccgcc    48900
```

```
tggcgaccgc tctggaggag gaactcggcc tcgacaccga catcgaggaa ctgctggcct    48960
tcccgtcggt cgccgtgatc gtcggccgcc acctcggccg ccggacggca ccaccggccc    49020 gggacccect gccgcccgcg tccgtagcgt tcgcacccgg gtccgtactg cccgcgccgc    49080
ccgcgcccgg acccgtgccg cccgcgtccg tgccgcccgc acccgcgtcc gtaccgcccg    49140
cgtccgagtc ctcaccgctc gcgccgcccg cacccgggcc cgtgccaccc acgcccgtcc    49200
cgcccgcctc cgtcccgccc gcgtccgggg ccgcgccgca cgtaccgccc gcgccgcccg    49260
cacccatccc cgcgcctcc gtgcccccg cgcccgccc ccaaccgccc ctgctcaccg    49320
gcatcggcgc ccgccaggcg ttcaaggacg cccaccacgg catccggcac gagttcgacg    49380
ccaccgacgg cgtcgccctc agcggcccgg acgaccacca cctcaccgcc cgtcgcagcc    49440
accaccgctt cgaccccggc cccgtgacgc tgccggacct gccgccctc ctcggggccc    49500 tccgccgggt ccgcggcccg ggaggcgaac ccaaatacgc ctatccgtcg gccggttcct    49560 cctacccgt ccagacctac ctgctcgtcc acccggggaa ggtgaccgga ctgcccggcg    49620
gcagccacta cgtccacccc gcgcgcaacc gcctggtgag catcgacccc accgcgaccc    49680
tgcccgccga cgcgcacgcc gagatcaacc gcgccgccta cggggaggcg gccttctccc    49740
tctacctcat cgccgcgatc gacgcgatca caccgctcta cggcgatctc tcctgggact    49800
tcaccgtctt cgaggccggt gccatgacce agttgctgat gcggaccgcc gtcggcaccg    49860
gcatcggcct gtgccccgtc ggcacgatgg accccgcgcc gctgcgccgc gcgttcgccc    49920
tcaccgaccg gcaccgcttc gtccacgccc tcctcggcgg gcggccccgc acggaggccc    49980
cgtgaaccgg cacggccccc tggcgggccg gcggcagagc gtcgacaccc gcagcgccgc    50040
gtgggtggcg ccgacgggca cccgggggct gccgctggag gtggccgcca cccgggacgg    50100
cgtcgacccg gccgaatggg cccgcaccca cctcgacacc gtcaccggct ggctgcaccg    50160
tcacggagcc gtcctgttcc gcggcttcgg cgtcggcctc gacggcttcg gcgacgtcgt    50220
ccacgccctg gccggatccc ccgaggcgta cgtcgaacgg tcgtcgccgc gcaccgccct    50280
cgggcatcac ctctacaccg ccaccgacca ccccgccgac cagcccatcc ccccgcacaa    50340
cgagaactcc taccaactcc gcttccccgg acggctggtc ttcggctgcc tcaccccggc    50400
ccggaccggc ggcgcgaccc cgctcgccga cacccggcgc gtcctgggcc gcctcgaccc    50460
cgccctcgtc gccgccttcg cccgccgcgg ggtgctctac cagcgcaact acggcgacgg    50520
gatcggcatg tcctggcagg acgccttcca gacccgcgac aaggcggccg tcaccgccta    50580
ctgcgccgcc cgccgcgtcg acgtcgaatg gaaacccgac ggcgggctgc ggaccaccca    50640
ggtccgcccc gccctcgccg tccacccggc gacgggggag cgggtgtggt tcaaccacgc    50700
cgcgttcttc cacgtctccg cccggccgcc ccgcgctgcgg gacgccctgc tggcccagtt    50760
cgacgaacgc gacctgccga gccactcctg ctacggcgac ggccggccca tcgaacccgc    50820
cgtcatggag gaactgcacc acgcctacgc cgccgaactg gtggcgcccg cctggcgggc    50880
cggcgacgtc ctcctcgtcg acaacctcct caccgcgcac ggcagggaac ccttcaccgg    50940
cgaacgccgc gtcgtcgtcg gcatggcaca gccgctggac tgggacgagg tgagcgcgtg    51000
accgcccccg gcacaccgct gccgcgacc ttcgtccagc gcggcctgtg gccgtccact    51060
cgccacgccc gccggcgga ggtcacccac gtccgcgccc tgcgcctgac cggggacacc    51120
gacacggcgc ggctcaccga ggccgtccgg cgggtcaccg ccgccctccc cgccctcacc    51180
gccgaactct ccggcgacga ggaacccgc ctgaccctcc ggccggacgc ccccgaggtc    51240
accccggtcg acctgcgcgg agccccgtcc gccggacgcg acgccgtctg cgtggcgctg    51300
```

```
ctgcgcgccg accgggacca ccctcgcgcc ggacgccacc gggcccgctt ccacctggtg    51360
cggctccacg acgacgagac ggtgctcgcg ctcacggccc acaccctcct cctcgacaca    51420
ccgtctctct acgccgtgct cggcgcggtc tgccaggcgt acgccggccg cttccgcccc    51480
gagcactacc gcgacgccac caccctgccc gacgcgcccc acgcccccct ctccggtcgg    51540
gcccgggcct cccgccggcg ctggtggcac cggcgcctgg ccgccctgcc cggcccggcc    51600
ccggcccccg ccggcccgcc ccgcgaccgg gtgaccgaaa cccaccggct gcgcatcccc    51660
gcagcgcgct ggaaagccct gaccgccctg accgccctgg gcggccccct cggcggcaac    51720
ggctcgctcg ccgtcatggc cctggccgcc tggtgcctgc gcgccccgga ccaccgggga    51780
ccggcccgct tcaccaccgt cgtcgacctg cgcgaccacc tcggactcgg gcccgccgtc    51840
ggcccgttca ccgaccgcct cgtcttcggc gccgacctcg gcgaagcgcc gcgcccctcc    51900
ttccgggacg tcacgctgcg cgcccagtcc gggttcctgg acgccgtcgt gcactacctc    51960
ccctacggcg acgtcgtgga actcggcagg gaactgggcc gcgtcaccgc gccccgcacc    52020
gccgcgcact gggacgtggc gctgaacttc tgccgcaacc cgcccaccag cgccgccacc    52080
cgcggcgaac gcaccctcgc cgaacgcggc ctgtccatcg agctgttccg cgaggccgac    52140
ctgctcggcg cggccggcac cggtcccgcg caccggtggg acggcacggt gctcgccctc    52200
tccctaggcg aactcggcga cgacaccgtg ctggtcctcg acgccgaccg cgaccacccg    52260
caccacggaa ccgccgaccg gctgctccac cggatggacg aagcgctcct ggcggccgtc    52320
gccgacccgg acgccccccct gcccccttg cccgccccccg cgcacaccac gaggagccac    52380
cgatgaccac gaccccgcgg accgccgccg agcccaccta ccacgtggtg gtcaacgacg    52440
aggagcagta ctcgatctgg ctcgccgaac aggagatccc ggccggctgg cgggccaccg    52500
gaacctccgg cacccaggag gagtgcctgc gccacatcga cgaggtgtgg accgacatgc    52560
gcccccgcag cctgcgcgag gccatggccg cggcggagca cgcggagccc gctcccgccc    52620
cggccccggc cgaggaggag ccgagcctcg tcgaccggct ctgcgcgggc gaccagccgg    52680
tggagtcggt cctccgcccg gagcgcacgg ccgccgccct gcgggaggcc gtcgaccgcg    52740
gctacgtctt cgtccgcttc gccgccaccc gcggcggcac cgaactcggc gtcgccgtcg    52800
accccgcggc gaccaccatg gacggcaccg agctgcgcct gaccggcacc ctcaccctcg    52860
acttcgaacc ggtccgctgc cacgcccgcg tcgacgtgac caccttcacg ggcgagggcc    52920
gcctggagcg cgtgtccggc acctgacccc cgccggccac ccggccgtga ggcgcggctc    52980
gggaccgggc cgccgaccca ccgaagggag ggaccccatg accaccccca tgaccacccc    53040
cacgaccacc cgcaccacca cccgcaccgc cgtcttcgcc cacctccgcg ccccccggcct    53100 cggcgaccctc ctccagcgca acatcggcct cgccctcgtc cgccgcgccc gccggcgac    53160 ggcggtcacc ctggtcgtcg gcgaggacct ggcggcccgc ttcggtccgg cactcacccg    53220 ccacgtac gccaccgacg tgctgccctg ccccagcgg ggcgaggccg accccggtg    53280 gcccgccttc ctgcgcaccc tggccgaccg ccgcttcgcc ctcgccgtcg tcgacccgga    53340
cagccagggc ctgcacgccg ccacgcccg ggccgccgg gtgcccgagc ggatcggcct    53400
gccgcaggac cggcccggag acgaacacat cacccatccc atccgcctcc cacgtcccct    53460 gtggggacc ccgaccctgt acgagtacgc cactgccctc gccgccgcgc tgggcctgcc    53520
cgcaccgccg cgcccggg acgtcctgcc ggagctgccc cgcacccgcg gcgtccgccc    53580
gccgacggcc ggtctgcccc gtccgctcgt cgccgtccac cccggcgggg caccgcactg    53640
gaacaggaga tggccgctcg agcactacgc ccggctctgc gcccgcctcg cggccgaact    53700
```

```
ctcggcctcc ctctgcctgc tgggcgacga agccgaacgc cccgagctgg aactgctccg   53760
gcacgccgtc ctgacgcggt ccccgcgagc cgtcgtccac ctcgaggcgg gcgcggacct   53820
cgaccggacc gcgaacgtcc tcgccgacgc cgacctgctc gtcggcaacg actcctcgct   53880
cgcccacgtc gccgccgccg tccgcacccc gtccgtcgtc ctctacggcc cgaccggcac   53940
cgagtacctg tggaccagga tctacccgta ccaccgcggg gtctccctgc ggtggccgtg   54000
ccagcggctg cggcacgccg caggcgaact cgccggccgg cggtgcgcgc acggctgcgt   54060
cctgccctac cagggcccgg ccggcccgta tccgcgctgt ctggccgacc tgccggtgga   54120
cagggtctgg ccggcggtga ccgcccgatg ggcgagcccc accccgtgac gatcaggag   54180 taccccatga gcgccgaccc gtcccgggtg cggacgatcc tctccgtcaa cttcaaccac   54240
gacggctccg gcgtgctgtt gcgggagggc aggatcgccg gctacgtcac caccgagcgc   54300
cgctcccgcc tcaagaagca cccgggcctg cgcgaggagg acctcgacga actgctggac   54360
caggccgggg ccgacctctc cgacatcgac cacgtcatgc tctgcaacct gcacaccatg   54420
gacacacccg catacccccg gctgcacggc tccgacctca aggagacctg gctcgcgttc   54480
tgggtcaacc agcgcaacga cgaggtgagc ctgcgcggcc gccgcatccc ctgcaccgtc   54540
aacccggacc accacctcat ccacgccgcc accgcctact acacctccgg ctacgactcg   54600
gcgatggccg tggccatcga ccccaccggc tgccgcgcct tcgccggcaa gggcagccgc   54660
ctctaccccc tgcgccgcga cctcgacgcc tggttcaacg ccaacatcgg ctactgctac   54720
gtcgccgacc tgatgttcgg ctccagcatc gtcggcgccg gcaaggtcat gggcctcgcc   54780
ccctacggca gacccgccga cggcgccggc cccgacgagg aaccgcccga gaccgtgcgc   54840
gacttcgccg ccctggtggc cctggccgac cggcacccgc gcctcgtcga cgtcgacggc   54900
aggaagctca acgccaccct cgcccactac atccagctgg gcctggaacg ccagctgacc   54960
gccgtcttcg ccgagctcgc cccgctgtgc gcccgcaacg gcatcgcacc ggacatctgc   55020
ctctccggcg gtaccgccct caacgccatc gccacccaac tcgccttcga gtcgaccggc   55080
ttcgagcgca tgcacctcca ccccgcctgc ggcgacgacg gcaccgcgat cggcgcggcg   55140
ctctggcact ggcaccacgt cctgggccac ccccggctcc accacaccaa cgccgacctc   55200
atgtactccg tccgtgagta ccccgagcac accgtccggc gggccgtgcg ggaccacgcg   55260
gccgacctcg tcgtcgagga gaccggcgac tacgtcgcca gggccgccga actggtcgcc   55320
ggcggcgccg tcatcggctg gtacgacggc gccggcgagg tcgggccgcg ggccctgggc   55380
caccgcagca tcgtcgccga cccgcgcgac cccgccatgc gggaccggct caactcccag   55440
gtcaagttcc gcgaacactt ccggcccttc gcgccgtccg tgctcaagga gcacgccgcg   55500
gagtggttcg gcctctccga cagcccccttc atgctgcggg ccaccccgt cctcaagccc   55560 ggcgtgcccg ccatcaccca cgtcgacggg acgtcgagga tccagtcggt caccgccag   55620 gacaccccg ccttccacga cctcatccac gccttcaagg accgtacggg gatccccatg   55680
gtgctcaaca ccagcctcaa caccaagggc gagccgatcg cggagacacc cgaggacgcc   55740
ctgcgcaccc tgctcggctc ccggctcgac cacctggtgc tcccgggcct catcgtcagc   55800
ggccggacgg cggccgcgtc atgagcgccc gcggggcga gcggaccccgg cgccgcgcgc   55860 tcgaacgcga catcgccgcg atctgggccg agacctcgg cagggacagc gtcggccgc   55920 acgaggactt cgccgcgctg ggcggcaact ccatccacgc catcaagatc accaaccggg   55980
tggaggaact cgtcgacgcc gagctgtcca tccgcgtcct gctcgagacg cgcaccgtgg   56040
ccggcatgac ggaccacgtc cacgccacgc tcacgggggga gcgggaccgg tgaacaccga   56100
```

```
cctgccccgg ctgctcgacc ggatcgccgg cctgcgcgtc ctcgtcatcg gcgacgtcat    56160
cctcgacacc tacgtctggg gagccacctc gggcctgtgc cgcgaatccc ccgtccctgc    56220
cgtcaccctg acctccgtcg cccaccagtg cggcggcgcc gccaacgtcg ccgtgaacct    56280
ccgggcgctc ggcgccgaac cggtgctgct ctccgcgacg ggtgacgacc gcgccggccg    56340
ccggctgcgc gaagccctcc gtgcgcggga cgtcgacacc ggcggactct tcgtacagcc    56400
cggccggacc acggtcacca aacgccgcgt catggccgac ggacagatgc tgctccgcct    56460
cgacgagggc ggcgaacacc cgttgcccgt ggcgacggac accggaagcc gcctgctcga    56520
acgggccgcc ggcctgctgc ccgccgtcga cgccgtgatc gtctccgact acgggtacgg    56580
cgtgtgggag cccgacaccg tcgcccggct cgccgcacac cgcgaactcg gcccgtccac    56640
cctggtcgtc gactcccgcc ggcccgcgcg cttcaccgcg ctgcgggcca cgccgtcaa    56700 acccaaccac gcggaggcgc tgcgcctgct cgacgccggc gaaccccgc ccggcccggc    56760 cagggcggac tgggcggccg ccctcggcga ccggctcctg cgcctgacgg gagccgaacg    56820
ggtcgccctc accctggacg ccgacggatc actgctcttc gaacgcgacc ggccccggt    56880 ccgcacgttc gcccggggca gccgggcacc ggtcacggcc gccgtcggcg ccggcgacg    56940 cttcaccgcg gccctcaccc tcgccctcgc cgccggcgcc gactccgcgg tcgccgccga    57000
actggcctcc gccgccgccg gcacggccgt cgccaccccc ggcaccagca cctggcacgc    57060
cgacgaactg cgccgactgc tcggcggcac cggcaaggtc tgccggaccg gcaccctgcc    57120
cgcccggctc ctcgacccgg ccgcccgcga ccgccgggtc gtcttcacca acggctgctt    57180
cgacctcctg cacggcggcc acgtctcctg cctgagccgg gccaaggaac tgggcgacct    57240
gctcgtcgtc ggcgtcaact ccgacgcgag cgtccgacgc ctcaagggcc ccgtcgccc    57300 ggtgatcccc ctcgccgaac gcatgcgcgt cctcgccgcc ctgagctgcg tggacctcgt    57360
cgtgcccttc gacgacgaca gccccgccgc cctcatcgag gccctccgcc ccgaggtcta    57420
cgccaagggc ggggactaca ccctcgcgac cctgcccgaa gcacccctcg tccaacggct    57480
cggcggcgtc gtccacctgc tccccagcgt cgccgacacc tccaccaccg acatcatccg    57540
gcgcatccac gccctgtcca ggaccggcga gggagacacc ccatgagcca cgccatcgga    57600
ccgagccggc tgatccccgc catccgcgaa gcgctcgggg acgagaagga ccccccggctc    57660 gccctctacg tccacgtccc cttctgctcc tccaagtgcc acttctgcga ctgggtcacc    57720
gacatccccg tcgcacgcct gcgcggcgac agccgggaac gctcgcccta cgtcaccgcc    57780
ctctgcgacc agatccgctt ctacggcccc cagctcaccc ggctcggcta ccgccccgag    57840
gtcatgtact ggggcggcgg caccccacc cggctcaccg gcgacgagat gacgccgtc    57900 caccaggccc tcgacgacgc cttcgacctg acgggactcc gccagtggtc ggtggagagc    57960
accccgaacg acctcgaccc cgccaccctc gacaccctgc gcggcctcgg cgtcacccgc    58020
gtcagcgtcg gcgtccagtc gctcaacccg taccagctgc gcaaggcagg ccgggcccac    58080
tcgcgcgaac aggccctggc cgccgtcccc ctgttgcgcc gcgccggcat cgacgagttc    58140
aacgtcgacc tgatcgccgg cttccccggc gaagccgtca gtccttcga ggagaccctg    58200 cgcaccgtcc tcgcgctcga cccgccgcac gtctccgtct accctaccg cgccacccc    58260 aagacggtca tggccatgca gctcgaccgc gagttcgtcg aggcccggaa ccgggacggc    58320
atgatcgacg cctatgaacg ggccatggcc gcgctcggcg ccgccggcta tcacgagtac    58380 tgccacgggct actgggtgcg cgacgcgcgc cacgaggacc aggacggcaa ctacaagtac    58440
gacctggccg gcgacaagat cggctttggc agcggcgccg aatcgatcat cggtcaccac    58500
```

| | |
|---|---|
| ctgctctgga acgagaacag cgcctacgcc cgctacctgc tcgcccccg cgagttctcc | 58560 |
| gccgcccacc ggttcaccac cgccgaaccc gaccgcctga ccgcccccgt cggcggcgcg | 58620 |
| ctgatgaccc gtgaaggcgt ggtcttcgcc cgcttccgca gactgaccgg cctggacttc | 58680 |
| gcggacgtcc gcgccacacc gtacttccgc cagtggttcg agctcctgga gcgctgcggc | 58740 |
| ggccgcttcg tcgagacgcc gtacagcctc cgcctggagc cgtccaccat ccaccgcgcc | 58800 |
| tacatcaccc acctcgccta caccatggcc catggcctgg ccccgaacg cgcctga | 58857 |

<210> SEQ ID NO 2
<211> LENGTH: 18660
<212> TYPE: DNA
<213> ORGANISM: Streptomyces verticillus

<400> SEQUENCE: 2

| | |
|---|---|
| gtgaccgaga accttccgtc gtgccccgaa tgctccagcg cgtacaccta tgagatgggt | 60 |
| gcgctcctgg tctgccccga atgcggccac gagtggccgc ccgcgaccgc cgagtccgcg | 120 |
| gacaaccccg aagacggcgc gatcagggac gcggtcggca acgtactcgc cgacggcgac | 180 |
| accgtcacgg tggtcaagag cctgaaggtc aagggccacc cgaccggcat caaggccggc | 240 |
| accaaggtgc gcaacatccg cctcgtggag ggtgtggccg ccacgacat cgactgcaag | 300 |
| atcgacgggt tcgcgccat gcagctcaag tccagcgtgg tcaagaaggt ctgaccggtt | 360 |
| acgccggccc aggccctgcc caggctccac tacgccgcgg cgcaaccgag ccggaacggg | 420 |
| gcccgggccc gctccaagtc ccgttccgtg cgcggccgcg gcagccaggc cgtgttcacc | 480 |
| ctggggtcgc cgtccccgtt cgcacgcgtc gtacacgcca ccacgcacgg cacggaactc | 540 |
| cccgaactcg ccacgttccc caagtccccg cgtgcccgga tccgcccgga ccggcgtcgg | 600 |
| tccgcccgcc gggccgcggc cgggtccccg ggccgcggcg ggagggggtc tcgcgccgtg | 660 |
| gaacgccggc cggaaatta cgtataggta gagatcccgg cgaagcgatc ggcgcgttat | 720 |
| ggcagcatcc gcgccggccc gccgcgcagt tcctcggtcc cggaccgatg gcgtcaaaag | 780 |
| tgagcgacga aatcgccgga tcgcgcgagg accgtcgcgg gccgcacgag gacaaccggg | 840 |
| ggatatatca gcgcattccc aggtcacgcg ttgactggaa atcgcctact tatcgcgtca | 900 |
| cgcctgtagg gatcatggcc gggaatggcc tcagacgctt tgagtgccca ccttgaggtt | 960 |
| tccgactgtc ggcagcgcgg ggggatcacg gtgacgaatg acggatctga actcgccggg | 1020 |
| caaaacgtgg cggcggtccg cttcgagcgg tattccgcga tcgcgccgga gcggaccgcc | 1080 |
| atcctgcaca aaggtgccgc gaccggttac gacgagctca accgccgggc cgagctgaca | 1140 |
| gccacgcgcc tggcggacgc gggcgccggc ccctcgaccc tggtggcagt ggccctccca | 1200 |
| cgcgatcccg acctcgtcgc cacctgtgc gccctgctca aactgggtgc cgcatgcctt | 1260 |
| cccctggatc ccggcatacc ggccgggcgg ctgcgcgaga tcatggccga cgcgtccccc | 1320 |
| gacgttctcg tcaccacccg tgccgtcgct ccggcattca ccggtgacgg accgtcctt | 1380 |
| ttcctggacg acgctcctcc gacctgctcc gccgtcctc acggcactc agcggggacc | 1440 |
| gcgtcggaaa tcgcctatgt gctgtacccg acgactcctg acgagaagtc cgaaaattcg | 1500 |
| gtcgtctcct atcgtgatat ggcgcgctac cttgacgacc ccactgccgg gattccggcg | 1560 |
| agggcggaga ttctccggct ggtcgcgccg ctcctgtccg gcggtcgtct ggtgctggac | 1620 |
| gccgacgaga cccggccccg gccggtcacc cgtgaggcgc cgcgcgacat ggtggaggac | 1680 |
| gtcgtggcgc aggtctggtg cgccgtgctc ggcgtggacc gggtgggcgt gcggaccgc | 1740 |
| ttcttcgacc tgggcggcaa gtcgctggcg gcggtccagg tggtggcgcg cctgcggaag | 1800 |

```
ctgctcggcg tcgagctgcc gctgcgggcc ctgttcgacg cgccgacggt cgaggagctg    1860
gccgcccggg tgcgggccga acaggccggc ggccagggcg tccggagga ggcggcgctc     1920
gagccggtgg gccggagcga gccgctgccg ctgtcgttcg cacagcaacg cctgtggttc    1980
ctggaccgct tgatgcccga ccgcgccttc tacacgatgt gcgacgcgtt ccgcgtccgg    2040
ggcgggatcg acctgggtgc gctgcggcgg gccctgcgga tgctggtggg acggcacgag    2100
acgctgcgga cggcgttcgt cgagcgggac ggtgtgccgt accagctcgt cggtccggcc    2160
gacgggcccg gtgcgcggcg cgtggccgct cccacgcggg tcgacctgtc gctgctggag    2220
cccgccgagc gggaggaggc ggtgcggaac ctggtggcgg cggaggcgcg accccgttc    2280
cggccggcgg acggcgcgct gctgcgcgtg tggtggccc ggctggcgga cgatgatcac    2340
gtgctggtgg tcagcacgca ccacatcgtc tccgacgcct ggtccgtggg tgtgctggtg    2400
gacgaactcg gacggctgta ccgcgagtgc gtcaccggag atcccgccgc gctgcccccg    2460
ccggccgtcc agtacgccga cttcgcggtc tggcagcggg cctggatggc cggtccggtg    2520
caggaggagc atctcgcgta ctggaagcgg gccttggacg gcgctccctc ggtgctgcgg    2580
ctgcccatgg accaccgcg gcccgccgtg cagtccgagc ggggcgagac ggtcgggttc    2640
gcgctgcccg acgcgctggt cgccgcgctg gagaagctgg gccgggagca gggcgccacc    2700
ctgttcatga cgctgctcgg cgccttccag gtcctgctgg cgcgtcacgc cgggcaagag    2760
gacatcgtgg tcggcgtgcc ggcggcgggg cgcacccgga ccgagacgga acctctggtc    2820
ggcttcttcg tcaacacgct tcccttgcgg gcgatctgcg ctccgggcct gtcgttccgg    2880
gacctgctgg accaggtgcg cgaggccgcc ctcggcgcct tcgcccatca ggacctcccc    2940
ttcgaggcgc tggtcgaggc gctcgcaccc gagcgcgacc tcggccacaa tccctcgtc    3000
caggtcacct tccagctcct gggcacaccg gcggcgcggc cggacctgat cgggacggag    3060
gtcgagcggt acccggtcca ggaggccgtc tcgcagttcg acctgtccct ggacatcaag    3120
cgggccgacg acggttccta ccgggggatc ctgaactact gccccgacct gttcgaccga    3180
cgccgcatgg aggtgctggt cggccactac ctgacgctgc tcggcgccgc cgccgcggac    3240
ccgggccgcc cgatcggtga gctgccgctg tccgacgggg ccgaacggct gcggctgctc    3300
gacgggttcg ggaagcggga cgcggcgtac gccgggccgg gaagcgttcc ggagcggttc    3360
gcggaggtgg cgcggacggc accggacgcg cgggcggtga cgtgtggcgc gacaacgctc    3420
accttcgccg agctgaacga ccgggtggag cgcctggcac aggcactgct cggcgccggg    3480
gtcacccgcg agacgccggt cgcggtccgc ctgccccgtt ccaccgacag cgtcgtcgcc    3540
ctgctggccg tcatgcgggc gggcggcgtc tacgtccccc tggacccga ctggcccgcg    3600
gaccgcaccg cctacatcct ggacgacacc gcggcctccg tcgtcatcac ccgcgacctg    3660
cccgcactcc ccgtcgcct ccacgtcgac ccgcgccggc ccgcggccga cggcctggta    3720
cccgcgcccc gcatcgaccc cgatcaggcc gcgtacgtca tctacacgtc cggctcgacg    3780
ggcgcgccga agggcgtcgt cgtccggcac cgctccctga accacctcac cagcgccctg    3840
caggccacct ttctcggcca cgacccgtat ctcgccgggg ccgacggcgt accgcccggg    3900
gacgcgaagc tgcgtacgac gctcaccgcg cccttcacgt tcgacgcgtc catggagcaa    3960
ctgagctgga tgctggccgg tcacgagctg ttcatcgtgc ccgaggacgt gcggcgcgac    4020
ccctcggcgc tggtccggtt cgtccgggag caccggatcg acgtcatcga cacgacctcc    4080
tcgcagctcg aactcctcgt atcgcacggg ctgttggacg gagagtgggc gccgtccatg    4140
gtcatggtgg gtggcgaggc ggtctcgccg tcgctgtggc ggaccttgcg ggaccagcgg    4200
```

```
cgcactcgct gtttcaacct gtacgggcct acggaggcga cggtcgacgc cacctgccac    4260
gacctgtccg accccgccga cgtccccgtc atcggcaccc cactccccca cacccacgtc    4320
cgcgtgctcg acgaccgact gcgacccgta cccgtgggcg tcgccggcga gatctacctc    4380
ggcggaaccg gcctggcccg cggctacctc aaccgccccg ccctcaccgc ccgacgcttc    4440
gtcgccgacc cctaccccga cacccccggc agccgcctgt accgcaccgg cgaccgcgcc    4500
cgctggcgcc ccgacggcac cctcgaatac ctgggacgca ccgacgacca aatcaagatc    4560
cgcggcttcc gcgtcgaacc cggcgaaatc gaggccgtcc tcacccacca ccccgccgtc    4620
aaggaagccg ccgtcgtcga cgacgcgcac gcgcggctgg tcgcctacgt cacgctcgcg    4680
gaaggcggcg gcgccggccc caccgacgta cgccggttcg cgcaggggcg gctgcccgcc    4740
cacatggtgc cgtcggcggt ggtcgtcctg gaggcgctgc cactgacgtc gaacggaaag    4800
ctggaccgcg cgcgcctgcc ggcgcccgcg gcgggcagac cggaactgga tgtccgcttc    4860
gtggcgccgc gcgacatggt ggaggaggtc gtggcgcagg tctggtgcgc cgtgctgggc    4920
gtcgaccggg tcggtgtgca cgacgacttc ttcgagctgg gcgggcactc gttgctggtg    4980
gtccaggtga tgacccggat acgaaagctg ctcggcgtcg aggtgccgtt gcgggagctg    5040
ttcgacgccg cgacggtcga ggagctcgcc gcccgcgtcc gcgccgcacg gaccgagggc    5100
ctcggccggg gggccgcccc gcccctcggg ccggtggacc ggagcgggcc gctgccgctg    5160
tcgttcgcgc agcaacgcct ttggtacctc gatcagttgg cgcccgacag tgtctcctac    5220
aacatgtgcg acgcctaccg ggtccgcggc cctctcgacc tggacgcgct gcggcgggcg    5280
ctgcggacgc tggtcgagcg gcacgagacg ctgcggacgg cgttcgtcga gcgggacggg    5340
gtgccccacc aggtggtctc ggcgcccgac gcgccggccg cgcggcgcgc ggcggaggtc    5400
gtgcggatcg aggcggccgg gcggaccgac gaggcggtgc gggacctggt ggccgcggag    5460
gcgcgcaccc cgttccggcc ggcggacggc gcgctgatgc gcgtggcggt ggcccggctg    5520
gcggacgacg atcacgtgct ggtggtcacc acgcaccaca tcgtctccga cggctggtcg    5580
gtcgacatcc tggtggacga attggggcgc ctgtaccggg aacacgtcac gggtgacccc    5640
gccgggctcc ctccgctcga cgtccagtac gccgacttcg ccgtctggca gcggtcctgg    5700
atgaccggcc ccgtgcggga ggagcacctc gcgtactgga agcgggccct ggacggggca    5760
ccctcggtcc tgcggctgcc ggcggaccat ccgcgtcccg ccgtccagtc ccagcggggc    5820
gagaccgtcg agttcccccct gcccgcacca ctggtcgcgc ggctggaagc gctctgccgg    5880
gagcagggcg tcaccctgtt catggcgctc ttcgcgcgt tccaggtgtt gctggcgcgc    5940
tacagcggtc aggacgacgt ggtcgtgggc gtgccgacgg cgaaccgcac ccgcgcggag    6000
accgagcccc tggtcggctt cttcgtcaac acccttccgg tacgggtcgc gtgctcgccg    6060
gagctgtcgt tccgcgccct gctcgaccgg gtccgcgagg ccgcgctggg cgccttcgcc    6120
catcaggacc tgcccttcga ggcgctggtc gaggcgctcg cgcccgagcg cgacctgggc    6180
caccaccctc tcgtgcaggt caccttccaa ctcctcgacg ctcccgacga gaggctcgtc    6240
ctgcacggca cggactgcgt ctcgctcggc ttcggcggtg tgaccagccg gttcgacctg    6300
tccctcgacg tcgtctcggg gcggcggggg aagcggtgcg tgctgacgta ctgtcccgac    6360
ctgttcgacc ggccccgcat ggaggtgctg gccggccact acctgaccct gctcggcgcg    6420
gcggccgacg atcccggtct ccgcgtcggc gacctcccgc tgagcgacga cgtcgaacgc    6480
ctgcgccctgc tgggcgggtc ccgccccgcg tacctgcccg cgcccgggc ggagaccgtc    6540
cctgacgcct tcgccgcgca ggtgcgggcg acaccggacg cgcccgcgct ggtccacggg    6600
```

```
gactcgacgc tgacgttcgc cgagctggac acccgggtca ccgccctggc cgtgcggttg   6660
cggcgctgcg gcgtggccgc cgagacgccg gtcgcggtgt gcctgccgcg ctccgccgac   6720
gccgtcgtgg ccctcctggc cgtcctgcgg cggggcggcg tctatgtgcc agtggatccg   6780
gagtggccct ccggccgcgt cgcccacgtc ctcgacgaga ccgcggcccc cgtcgtcatc   6840
acccgcgacc tgcccgccga tcccggccgc gtccacctcg acccgcgcca ggccccggcc   6900
gacgaccggg atccctgcc gcgcctccac cgcgaccagg ccgcgtacat catcttcacc   6960
tcgggctcca ccggcgcccc caagggcgtc gtcgtccgac acggctccct gtaccacctc   7020
ctgggccacg tacggcgcat ggcggagggc ggccccggc ggaacgtcgc gcacaccacc   7080
gcgatgacct tcgacccgtc gctggaacag ttcctgtggc tcgtcgccgg acacaccctg   7140
cacgtcgcgc ccgaggaggt gcgccgcgat cccgaggcgc tggtggccct ggtgcggcgc   7200
gccgcgatcg acgtcctcaa cgtcacccg tcccacctga ccctgctgat cgaggccggg   7260
ctgctggagg cgaccgggt gccgggtacg gtcctggtgg gtggcgaggc ggtgcccgcg   7320
gcgctgtggc ggaccctgcg cgaacggacg ggagccaccc gcttcttcaa cctgtacggg   7380
cctacggagg cgacggtcga cgccacctgc cacgacctgt ccgaccccgc cgacgtcccc   7440
gtcatcggca ccccactccc ccacacccac gtccgcgtgc tcgacgaccg actgcgaccc   7500
gtacccgtgg gcgtcgccgg cgaaatctac ctcggcggaa ccggcctggc ccgcggctac   7560
ctcaaccgcc ccgccctcac cgcccaacgc ttcgtcgccg acccctaccc cgacaccccc   7620
ggcagccgcc tgtaccgcac cggcgaccgc gcccgctggc gccccgacgg cacccctcgaa   7680 tacctgggac gcaccgacga ccaaatcaag atccgcggct ccgcgtcga acccggcgag   7740 atcgaagccg tcctcaccca ccaccccgcc gtcaaggaag ccgccgtcac cgtggccacc   7800
gacgacggtg ccgccccggct ggtcgccctc gtcgtccccg cccccgcgc cccgcacggc   7860 gattcggccg acggcgcccc ggacgcccag gtcgaggagt ggaacgccgt cttcgaggcg   7920
acccacaccg acgccgccga cggcgaactc accttcaaca tcaagggctg gaacgacagc   7980
ctcaccggtg cgccgatccc cgccgaacac atgcgggaat gggtcgacac caccgtcgcc   8040
cggctcctgg aacggccggc cgagcgcgtc ctggagatcg gcagtggcac cgggctgctg   8100
atgtggcggc tgctgccgca cgtcaccgag tacaccggaa ccgacttctc gcggcccgcc   8160
gtggactggc tccgggacgg gctgcgccgc cgccccgcgc accgggtacg gctgctgcac   8220
cgcgaggcga ccgacttcac cggcgtccgc gccgcgtcca ccgacctcgt cgtcgtcaac   8280
tcggtcgtcc agtacttccc cgaccgcgcc tacctcgaca ccgtcctggc ccgcgccctc   8340
gacgccacgg ccgaccgagg gcgcgtcttc gtgggcgacg tgcgcaacct ggccctcgcc   8400
ccgcagttct acgcccgtca ggccctcgcc cacgccggtc cgggcgcggc ggcgcgggac   8460
gtggcgcgcg ccgccggcga gttcgcggcc atggacggcg agttgctggt gtccccgcg   8520 tacttcgccg cgctcgccgc ccgctcgccc gcgtcaccg gcgtcgagat cctgccccgc   8580
cggggacggc accgcaacga gatgagcctg taccgctacg acgtggtgct gcacgtgggc   8640
ggtgaccgcc cggcggcccc ggaggcggag gtgctcacct ggggcgacca ggtgcacgac   8700
ctcgcgtcgc tgtccgcccg cctcggccgc gggggcccgg acgccctgct cgtgcgcggc   8760
gtcgccaacg accgtctgac gcgggacaac gagctgctcg acgcaccgc ccgcacgacg   8820 gccgtcgagc ccgaggacct gtgggggctg gcggactcca ccccctaccg ggtgagcgtc   8880
agctgggccg ccgccgatcc gcggggcgcg atggacgtcc tgctggtccg gcgggacgcc   8940
cacgacgacg gtccgctgct cgtccccac cccgtaccgg agccctcggc accgctgacg   9000
```

-continued

```
aacacgccga cccggcaccc gtccgcgcgg caaggggggct cggccgcgga cgggctgcgt    9060
tcctggctcg ccgagcggct tcccgcgcac ctgctgcccg cgaggatcac cgaggtggac    9120
gcgctgcccc gcaccggcac cggcaagctc gaccggggcg cgctcggcgg actcgtgacc    9180
gcgggccgtg gcgcccgggc gggcgaccgc cccgccaccg ccccccgtac gggtctcgaa    9240
cggaccctgg ccgacgcgtg ggcgcgggtg ctcggcctcc ccgaagtcgg cgtgcacgag    9300
aacttcttcg ccctcggcgg cgactccctc ctcgccgtca gggctgtcgc ccggtgccgc    9360
cgtgccgggg tccgactgac cgtccggcag ttgctgagcg agcagaccgt cgccgcgctc    9420
gcggcggccc tcgaggagga gtctcaatga tgaagtcaag ccgcttgcgc gaccggcagc    9480
tcggggtga agaccggtt gtcgcgcagg agagcccaca ggacgctggc ccgacgccgt    9540
gccagggcga tgacgcttg aacgtgtttg cagccctcgc cgcgcttctt gaggtagaag    9600
tcccggttcg gcccctcccg catcatgctg gtttgggccg acatgtagaa cactcgtcgc    9660
aggcggcggc tgtagcgctt gggccgatgc aggttgccag tgcgacgacc ggagtcgcgg    9720
gggacgggca ccaggccggc cgccgaggcc aggtgaccgg cgtcggcgta ggccgtgagg    9780
tcgccggcgg cgacgacgaa ctcggcgccg aggatcggcc ccatgcccgg cagagactcg    9840
atgatctcgg cctgtggatg gctgcggaac gtctcgcgga tctgctggtc aatccgcttc    9900
agacggtcgt ccagggccag gatctgcgcg gccaggtcag ccacgatctg ggcggcgacg    9960
tcctccccgg gcagcgcggt ctgctgagcc tgggcagcct ccagcgccgt cgcggcgacg    10020
gcgtcggcac cgcgcacgcc tcggttggcc agccaggccg tcagccgggc ccggccgcgg    10080
cggcggagag ctgccggggt ctggtagccc gtcagcagga ccagcgcgcc cttctgcgag    10140
ctgtagtcga aggcccgttc cagcgcgggg aagacgccgg tcagcgtgtc gcggagacgg    10200
ttgatcatcc tgacccggtc ggccacgagg tcggaacggt gggcggtcag cagcgcgagg    10260
tcggcggcca gctgggcggg cacgtcgatc gacgcgaagt cccgtcggtt gcgggcggtt    10320
tcggcgatga cgtaggcgtc gcgggcgtcg gtcttcgcct cgccccggta agcgccggac    10380
atgcggttga ccgtgcggcc gggcacgtag acggcctgct ggccgtgggc cgcgagcagg    10440
gccagcagca gcgcggagga cgtgccggag atgtccactg cccagtggac ctcgtcggcc    10500
aggtcgagga tctcacccat ggcggtcagg atcgccgact catcgttgcc gatcttcttc    10560
gaccacagcg tcacaccggt ctcgtcgacc accgccgccc agtgatgccc cttgcccgcg    10620
tcgatcccgg cccagacccg ggcccgtcgc tcgcccactc gccccctcctc actccgaaca    10680
gcatcccgtc gacccgagga acaccccgct gtcatctccg taaaaagcga ccgaagcgca    10740
catctcaatc agcagccagg gcgccccgga gaaccgggcg gccactcctt gtaagccact    10800
gacggcagag aaccataagc cacacccggc cctcccgggc cgcctaacaa cttacggaga    10860
accatgactg acctgccgtt gcgtaccgtc gcactcaccg gtgaggagag cgcggaggtc    10920
gacgacctgc tgcgcacgct ggccgacgtg ccggtcgact ccaccgtggg actgctgcac    10980
cgcacccggc tcgccgcaca ggaactgccg ctgcgcatcc gcgccgagct cacggggatg    11040
cggctctacg acagcccgcg cgccctcgtc gtcacgggct cggcgtcga cgacgaacgg    11100
atcggaccga ccccgcggc ccgtcccgcc ccggatcccg agcggacccg cgacctggag    11160
ctgctgcttt tgctgcacgc ggccctgctc ggcgaggcgt tcggctgggc gacccagcag    11220
aacggccggc tcgtccacga cgtgctgccc gttcccggtg aggagaccgc gcagatgggt    11280
tccagcagcg agaccgagct gctgtggcac accgaggacg cgttccaccc gctgcgctgc    11340
gactacgtgg gcctgctgtg cctgcgcaac caccagcgcg ccgcgaccac cgtgggctgg    11400
```

```
cccgacctgt cccggctcac caccgaggac cgtgccgtgc tcctcgaacc ccgctatctg   11460
atccgcccgg acacctcgca cacgcccgcg cagaacgcga cgggcacgcg gtccgccgag   11520
cgtttcgcgg cgatcgccga gatggacgac gccccggagc gcgtcgccgt cctgttcggc   11580
gaccccgagg acccgtacct gcggatcgac ccggcctaca tgagcccggc ccccggggac   11640
gcggccgccc ggcgggcgta cgacaccgtc accgcgctca tcgaggacga gctgcggcac   11700
gtcgtcctgg acgccggttc actgctgctg gtcgacaact accaggcggt gcacggccgc   11760
aagccgttcg ccgccgccta cgacggccgc gaccgctggc tcaaacgcgt caacatcacc   11820
cgcgacctgc gccgttcccg gtccgcgcgg cggtcggcca cctcgctgct ggtgtgaggg   11880
aggcaccatg gatttccccc tcacccgcgt caaccctggg ttcagcggcg gctgcgacgg   11940 ccgccccgg gtgcggctgt gcgcgctgcc gtacgcgggc ggcaccgccg ccgtcttcaa   12000
ggactggccc gccgcgctgc cccccggagt ggagctgctc accgcgcacc tgccgggacg   12060
cggcgaccgg ttcaccgaac cgcccccggc caccctggag gagaccgccg agcggctgtg   12120
cgaggcgctg ccgccgagtg acctgcccac ggtcgtcctc ggccacagca tgggcgccct   12180 gctgggggtac gaagtggcgg cgcggctcgc ggcgcggggc cgcgccccca acctgctgat   12240
cgccgcggcc tgccgtcccc cgcacgttcc gccggacgcc tccggtccgg tgaccgaggc   12300
cgagctggcg gccaccctgc gggccgaacg cccatgggac acggccctga gggacgagga   12360
actgatggaa gcggtgctgc ccgccctggt cgccgacatc acggccggcg accgctacca   12420
ccgcccgcgg ccccgcccgc tcgacctccc gctgaaggtc tacatcggcg ccgacgacga   12480
cggcaccgac tggcgcacca ccctgggctg gcgcgcgtgc accgcccggg actgcgaggt   12540
cgtcgtcctg cccggcggcc actacttcct ggagaccgac cgcgcggccg tcctcacccg   12600
cgtcgccacg gacctcgccg aagccgaggt aggggcatga ccgcgcgcgt cgacgccaca   12660
cccacctacc tggcggtgct ggcggtgcgc gaggcccgcg ccccgctcct cggcagctgc   12720
ctggcccgca tgtccttcgc ggtgctgccg ctcgccctgc tgctgtcggt ccgggacgcg   12780
acggggtcgt tcgccgtcgc cggactgacc tccggcgcgc tgtcggccac gctcacgctg   12840
ttcgcgcccg cccgcgcccg gctgatcgac cgccggggct cacggtccgg actggtccgg   12900
ctgaccgtcc cgtacctgct ggggctcgcc gtgctgatca cattggccga gcggaagcg   12960 cccaccgcgg cgctgctcgt cgccgccgcg gtcgcgggcg tgttcgcgcc gccgctcggt   13020
ccgaccatgc gcgtgctgtg ggcgaggatc ctgcacggcc gtcagcccct gctgcacacc   13080
gcctacgccc tcgactccgt caccgaggag gtggtcttca ccgtggggcc gctgctggcg   13140
ggcggcctga tcgcggtcgc ggcaccgctc gcgtcgatga tcacggtcat ggtgctgatc   13200
gcggccggta ccgcctgctt cgtgctgtcc ccgcgaccg ccgccgcccc cgcgtcgggc   13260
gaagccgacg aggaccggcc gcacggccgg cccatggctc tgcccgggat gcgcacgatc   13320
gtgctgtcct tcgcggccgt cggcctggtc gtcggggtgc tccaggtcgt cctgccgttc   13380
atcgccgacc acgcgggctc gcccggcgcg ggcggcatcc tgctgtccat gctgtcggcg   13440
ggcagcgcgg tcgcgggcct cgcctacggg cggatcgcct ggcgctcgac gcccgtgcgg   13500
cggttcgtgg tgctcgtcac cgggttcacg ctggcggtgc tgccgctgtg cctgaccgcg   13560 agccggtgc cggccgggc cttcgccctc tcgtggaca tctgcctcgc cccgctgttc   13620
accaccgcct acctgctggt caacgacctg gtgacggcgt cggggaccgc acccaccgag   13680
gccaacacct gggtctccac ggccaataac ggagggttcg ccgcgggcag cgccgccgcc   13740
ggtgtgctgc tcgactcccg ggccccacc gtcaccgtca ccgccgcgtt cgcggtcgcc   13800
```

-continued

```
gccgcgaccg ccgtcatgac cgttctgcgc cgccggaccc tgctcctcgg cgccggacac      13860
cccgaaccgg ccgccgccac acccgccgac cgcaccgcac ccgccgaagc cgaggagtga      13920
accgatcgtg tccaagaacg cggcgcactg gtcgcgcatc cgcacagggg acgcccccgg      13980
cgtcgtactc gccgtggact tctacggaac gggccgccag gaagccacct tccgccacct      14040
gtgcgacctg ctcacggatc cggtcgaggt ctggcacgcg gtcccgcccg ccccggacgg      14100
cgactggtcc acgccaccg gcgccggtca cctgcgctgg tggaccgagg ggctcgacac       14160
ggtcctcgcg ggacgccgg tgcgggccct cgtcggctac tgcgcgggcg gcgtcttcgc       14220
ctcggccctc gccgacgccc tcgtcgaacg ggagggccac cggccgcggg tcgtgctgtt      14280
caaccccagc gcgcccggcg tcgccacgct cacccgcgac ttccgcggtc tgatcgccgg      14340
catgaccctc ctcacggacg gggaacgcgc cgctctgctg gccgagacga ccgcgatccg      14400
gcgggcacac gccccgacg cgctggtacc ggtcgccgaa cgctacgccg ccctgtaccg       14460
cgagggctgc gacctcctgt gcgagcggct cggcgtggac gcctccttcg gcgccgaact      14520
ggccgccgtc ctccactcct acctggccta cctcacggcg gcgctcgacg tgcccccac       14580 cccgctgtgg cgcggcgccg tctcgctcac ctcccgcgag caccagggca ccgacttcac      14640
cgacgtcgag cacggcttcg acgtcgcccg tgccgaactg ctgagctccc cccaggtcgt      14700
cgcggcgctg accgcgctcc tccgcgaaca cgaggcgagc cgatgaccct caccctgcgg      14760
gacgccttcc tcgaccaggc cgcccggacc cccgacgccc acgccgtcgt acacggcgac      14820
actgtatgga cgtaccgcga actggaactg cgggccggcc gcatggcccg gacgctggcc      14880
gcacgcggcg cgggccccgg cacgctggtg gcggtacgcc tgccgcgcgg tcccgaaccg      14940
gtcgccgcgc tcctcgcggt cgtgctgacg ggagcgggct acgtgccgct cgccgacgac      15000
gacccgccgg accggtgccg gcacatcctc gacgactgcg ccgccgcgct gctgctggcc      15060
gagcacccct cgcgggacgg acgcaccctc accccggacg aggcgctggc acccgcccgc      15120
ccgttcgacg cggcccccggt gcgggccggc gaccccggcgt acgtgatcta cacctccggc      15180
tccagtggcc gtccgaaggg cgtgctggtc gaacagggcg cgctcggcgc ctacctggca      15240
caggcccgcg cgcgctacga cgggctgtcc ggacggacgg tgctgcactc ctcgctgtcc      15300
ttcgacatgg ccgtgaccag tctgtggggc ccgctcgtca gcggcggcgc gatccacgtg      15360
ctcgacctga aggcgatcgc ctccggcacc cagccgccgc ccgccgcctc ggcacgtccg      15420
tccttcctca aggtcactcc gtcccacctg ccgctgctgg gcctgctgcc ggactcctgc      15480
ctgcccaccg ggcaactcgt gatcggcggc gaggcgctga ccggctccgc gctcggaccc      15540
tggcgcgccg cgcaccccga cgtcacggtc gtcaacgagt acgggcccac cgaggcgacc      15600
gtcggctgct gcgcgtacac cgtccgcccc ggtgacgccg tggacccggg tgccgtcccc      15660
atcggacggc cgttcgcggg cacccgcctg tacgtgctcg acgcggacgg cgagccggtc      15720
gccgtgggcg gtgtgggtga actgcacatc gcgggcgacc agttggcgcg cggatacctg      15780
gggcgcccgc ggctgaccga ggaacgcttc gtcccggacc cgttcgccgc cgacggctcc      15840
cggatgtacc gcaccggcga cctggtgcgc gaacgcccgg acggcgacct ggagtacctc      15900
gggcgcgcgg acgggcaggt gaaggtctcc gggtaccgga tcgagcccgg cgagatcgag      15960
gccgtgctcc gcggccacgc gggggtgagg gactgcgcgg tcgtcgccgt cggcgaggcg      16020
gacgcccgcc ggctcgtcgc ctacgtggta ccggacccgg actccccgcc cggcaccgcc      16080
gcgccggcgc ggcacgcggc cgaggcgctg ccgccgtaca tggtgccggc gacgttcgtc      16140
accgtgcccg aactgccgct caccccaac gggaagctcg accgggacgc gctgcccggc       16200
```

```
ccccctgccg gcgacgccgg gccgggcgac cgcaccccgg ccgagaccct gctgtgcgag    16260
ctgctggcac gggccctggg catcccggag atcgacgccg acgccgactt cctgacgtcc    16320
ggcggcacca gcatcaccgc gctgaagctg gtcgccggcg cccgccgggt cggcatccgc    16380
ctcgaactca ccaccgtcct gcgcgaacgc acggtgcgcc gcatcctggc ggcccagccc    16440
gacgccgcct cgcccctcgc cgaaggagtg cccgagtgac cggttccgta acgctcaccc    16500
ccctcggcgg gatcatcccc aggccccgcg gcgaggggct caccaccggc gccgagtacg    16560
acctggggcc gctcggcgac gcgggccccg actgggtgcg ggcccacggc ccgcgactgc    16620
gcgagcgcct cgccaccgac gggctgatcc tgctgcacgg tctgcccacc gacgcgagacg    16680 gcgtcgacgg cttccacgac gtcgtcggct ccgtcggcgg cgacccgctg ccctacaccg    16740
agcgctccac cccgcgcagc gtggtcaagg gcaacatcta cacctcgacc gagtacccgg    16800
ccgaccagcc catcccgatg cacaacgaga actcctacgc cgcccattgg ccgtccacgc    16860
tctacttctt ctgccacacc cgcgccggaca ccggcgggc cacgccgatc gccgacggcc    16920
gcgccgtcct cgacctcatc ccggccgagg tcaggcggcg gttctcccaa ggggtcgtct    16980
acacccgtac gttccgcgcc gacatgggac tgagctggca ggaagcgttc cagaccgagg    17040
accgcggcga cgtcgaacgc cattgccgcg cccacggcca ggagttctcc tgggacggcg    17100
acgtcctgcg cacccgccac caccgcccgg cgaccgccgt cgaccccggc accggagccg    17160
aggtgtggtt caaccaggcg cacctgttcc acccgtccag cctggatccc gacctgcgcc    17220
aggtgctcct ggagacgtac ggcgagaacg gcctgcccccg cgacgccctg ttcgccgacg    17280
gcaccccgat ccccgacgcc gacctggcaa cggtccgcgc ggcctacacc cgcgccgcgc    17340
tcgcgctgcc gtggcgagag ggcgacatca tgctggtcga caacctgagg atggcccacg    17400
gccgcgagcc cttcaccggc gagcgccgcg tactcgtcgc gatgacctcg gcggactcat    17460
gagccgtgcc gacgcatcgg cacgccgtcc tcccgtcggg gcgctaccat cgccgctgtc    17520
tcggccatca ccccacccgg gcggaggcaa ccggccgtgc acatccccgc cgtggtcgcc    17580
acggcacgcg cgatcacccg cgccatgacc gcccagcccg ttgtcacatc tgcggaggcg    17640
ccgcgatgac agaggtccga ggtgaactga tccgggcgct gccgggtgtg ctggaggcgc    17700
gtgcggcgcg ggcggggcac acgaccgcct tcctcgacgc acgacggtgt gtcacgtacc    17760
gggagttgga ggcgcgcacc cgccggctgg cggggtcacc tggtgcggtt ggggtgcgc    17820 agggggcagac cgggtggcgc tcgtcaatgg gcaaccgggg tggagatggc ggagggttcc    17880
ctccccggtg ctgcgggccg gagcggtagg ggtgccgctc gattccgggg ccacggacgc    17940
ggagctcgcg tacttcctcg acgactgtgg agcggtggcg gtggtcaccg aggagacgct    18000
gctgccgcgg gtctcgcgat cggcgggcgt acggatcctg gtggggggtt cggacgccgt    18060
cccgagggga gcggctgccg gcatccactc cttcgagcgg ctcgcggcgt cggatccggg    18120
gtgcgcgcca cgggacgacc tcggcctcga cgagccggcc tggatcctct acacgtcggg    18180
gaccacgggc cggagcaagg gcgtggtctg cggccagcgc gccgcgctgt ggtccgtggc    18240
ggcggcgtac gtgccgtcgt ggggtctggg gccgcaggac cggctgttgt ggccgctgcc    18300
catgttccac gcctacgcgc actcgctgtg cctgctcggg gtggtggccg tgggcgcgag    18360
cgcgtacctc ctcgaccggg gcgcgagcgt cgtccgggcg cttgaggaac agcggtgcag    18420
cgtcgtggcc ggtgtacccg ccacctaccg cctgctcacg agcgccttcc gcgacgcccc    18480
ccggccaccg gccggcctgc gactgtgcgt caccgggggc tgcgccgtgc ccgccggggc    18540
```

```
tgcgggcgga cgttgaggag ctgctgggcg tcccgctgct cgacggttac ggcagtaccg    18600
agacctgcgg caagatcacg gttgagcggc tcggcggctc ccgggagggc ggttgccggg    18660

<210> SEQ ID NO 3
<211> LENGTH: 1761
<212> TYPE: DNA
<213> ORGANISM: Streptomyces verticillus
<220> FEATURE:
<221> NAME/KEY: CDS
<222> LOCATION: (245)..(982)

<400> SEQUENCE: 3
ggatcctgcg ctaccggac ttcgcccagt ggtgcggcac cgagctcacc gccgactggc      60
acgtccgctt ccgggccgcc gccgcggtct acgggcatct gcacatcccc cgcgtgaccc     120
ggtacgacgg cgtccgcttc gaggaggtgt cggtcggcta cccgcgcgag tggcggcccc     180
ggccgccccg cgagccgctc cggcagatcc tgccccagcc cgtcgacgag ccggagcccc    240 tctg gtg atc gcc gcc ctc ctg ccc tcc tgg gcc gtc acc gaa cac gcc      289
     Met Ile Ala Ala Leu Leu Pro Ser Trp Ala Val Thr Glu His Ala
     1               5                  10                  15 ttc acc gac gcc ccg gac gac ccg gtg agc ctc ctc ttc ccc gag gag      337
Phe Thr Asp Ala Pro Asp Asp Pro Val Ser Leu Leu Phe Pro Glu Glu
             20                  25                  30 gcc gcc cac gtc gcc cgc gcc gtc ccc aag cgc ctg cac gag ttc gcc      385
Ala Ala His Val Ala Arg Ala Val Pro Lys Arg Leu His Glu Phe Ala
         35                  40                  45 acc gtc cgg gtg tgc gcc cgc gcc gcc ctc ggc cgg ctg ggc ctc ccg      433
Thr Val Arg Val Cys Ala Arg Ala Ala Leu Gly Arg Leu Gly Leu Pro
     50                  55                  60 ccc ggt ccg ctg ctg ccc ggc cga cgg ggc gcg ccg agc tgg ccg gac      481
Pro Gly Pro Leu Leu Pro Gly Arg Arg Gly Ala Pro Ser Trp Pro Asp
 65                  70                  75 ggg gtg gtg ggg agc atg acg cac tgt cag ggc ttc cgg ggc gcc gcg      529
Gly Val Val Gly Ser Met Thr His Cys Gln Gly Phe Arg Gly Ala Ala
 80                  85                  90                  95 gtc gcc cgg gcc gcc gac gcc gcg tcg ctc ggg ata gac gcc gag ccg      577
Val Ala Arg Ala Ala Asp Ala Ala Ser Leu Gly Ile Asp Ala Glu Pro
             100                 105                 110 aac ggg ccg ctc ccg gac ggc gtc ctc gcc atg gtc tcg ctg ccg tcc      625
Asn Gly Pro Leu Pro Asp Gly Val Leu Ala Met Val Ser Leu Pro Ser
         115                 120                 125 gag cgc gag tgg ctc gcc gga ctg gcg gcc cgc cgg ccg gac gtg cac      673
Glu Arg Glu Trp Leu Ala Gly Leu Ala Ala Arg Arg Pro Asp Val His
     130                 135                 140 tgg gac cgg ctg ctg ttc agc gcc aag gag agc gtc ttc aag gcg tgg      721
Trp Asp Arg Leu Leu Phe Ser Ala Lys Glu Ser Val Phe Lys Ala Trp
 145                 150                 155 tac ccg ctg acc ggc ctg gag ctg gac ttc gac gag gcc gag ctg gcc      769
Tyr Pro Leu Thr Gly Leu Glu Leu Asp Phe Asp Glu Ala Glu Leu Ala
 160                 165                 170                 175 gtc gat ccg gac gcc ggg acg ttc acg gcc cgg ctg ctg gtg ccg gga      817
Val Asp Pro Asp Ala Gly Thr Phe Thr Ala Arg Leu Leu Val Pro Gly
             180                 185                 190 ccg gtg gtc ggc ggc cgt cgg ctg gac ggg ttc gag ggg cgc tgg gcg      865
Pro Val Val Gly Gly Arg Arg Leu Asp Gly Phe Glu Gly Arg Trp Ala
         195                 200                 205 gcg ggc gag ggc ctc gtc gtc acg gcc atc gcc gtc gcg gcg ccg gcc      913
Ala Gly Glu Gly Leu Val Val Thr Ala Ile Ala Val Ala Ala Pro Ala
     210                 215                 220
```

```
ggt acc gcg gag gaa tcg gcg gaa ggg gcc ggg aag gaa gcg act gcg    961
Gly Thr Ala Glu Glu Ser Ala Glu Gly Ala Gly Lys Glu Ala Thr Ala
    225                 230                 235 gac gac cgg acc gcc gtc ccg taaaccgccc cgaacaccgg cgtggcgccc      1012
Asp Asp Arg Thr Ala Val Pro
240                 245 gccgaccgtg tcggggcgc cacgaacggg cgccggcccg gcgggccctc cgccgtgcgg   1072
agcggaggcc cggcgcggac gcgcccggtg tcgtcggata cgtgcgtcag tcggcgacgc   1132
agacgttgcc gttggtcgag ttgagcagcc cgacgatgtc gatggtgttg ccgcagaggt   1192
tgatggggat gtggacgggg atctggatga cgttgcccga gacgacgccc ggggagccga   1252
cggccgcccc cttggcgttc gagtcggcga gggcggtgcc ggagacgccg gcgagcgccg   1312
tgcccacggt ggcggtgagg gccgctgcct tggcgattcg tgacatgggg tgacaccttc   1372
gttcggtctg acagggtcga gctcacggcc tctgacggcc gggagcccgg atcaacgccc   1432
gatcaccccg aagtttcga atcgtgcggc ggacgggtga ccgcggccg aacggcctcg    1492 ccgggccccc ggaaggtgcc atgacgtccg tgcgccatct gtacagcccg gtcccgcgcc   1552
gcgtacaagg gacggacgga cggccggtgg acggacgacc ggcggggagg ggaggccatg   1612
agccggatcg cgatcgtcgg ggcgggtcag gccggactgc atctggcgct ggggctgctg   1672
ggggcgggga gcggctcttc ccgtcacgag gtgctgctcg tgtccgacgg gacgccggac   1732
gagatccgcg ccgggcgggt gcggtcgac                                    1761

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:
      Illustrative motif
<221> NAME/KEY: MOD_RES
<222> LOCATION: (3)..(5)
<223> OTHER INFORMATION: Variable amino acid

<400> SEQUENCE: 4

His His Xaa Xaa Xaa Asp Gly
  1               5

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
atgagccacg ccatcgga                                                  18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
tcaggcgcgt tcgggggc                                                  18
```

```
<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 7
gtgaacaccg acctgccc                                                        18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 8
tcatggggtg tctccctc                                                        18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 9
atgagcgccc cgcggggc                                                        18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 10
tcaccggtcc cgctcccc                                                        18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 11
atgagcgccg acccgtcc                                                        18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 12
tcatgagcgg gccgccgt                                                        18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Primer
```

```
<400> SEQUENCE: 13
atgaccaccc ccatgacc                                              18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 14
tcatggggta ctcctgat                                              18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 15
atgaccacga ccccgcgg                                              18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 16
tcaggtgccg gacacgcg                                              18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 17
gtgaccgccc ccggcaca                                              18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 18
tcatcggtgg ctcctcgt                                              18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 19
gtgaaccggc acggcccc                                              18
```

-continued

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 20
tcacgcgctc acctcgtc                                                18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 21
gtgacgagcg cccggccc                                                18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 22
tcacggggcc tccgtgcg                                                18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 23
atgctgcacg gcgccgcg                                                18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 24
tcactccggt ccacctcc                                                18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 25
gtgaggcccg tgtgcggc                                                18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Primer

```
<400> SEQUENCE: 26
tcagccaccg ttgccgcc                                              18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 27
gtgaaggacc tcggccgg                                              18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 28
tcactccccc ggtgccgg                                              18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 29
gtgacatgga ccgtggtg                                              18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 30
tcaggcatcg gccctccc                                              18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 31
atgcgcgggc atgacgac                                              18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 32
tcacggtgtc tctccctc                                              18
```

```
<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 33
atgagccggc cggccggc                                                   18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 34
tcatgctcgg tcatcgcc                                                   18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 35
gtgaccacgc cccgcatc                                                   18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 36
tcattcggga cgcgggca                                                   18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 37
atgagccatg ccgacgcg                                                   18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 38
tcacagcacc acctcttc                                                   18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Primer
```

```
<400> SEQUENCE: 39
atgaccccgg ccgccgac                                                18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 40
tcatcgtccg ccgcctttt                                                18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 41
atgcctcggt gtgcccga                                                 18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 42
tcattcggcg gcacctcc                                                 18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 43
gtgggtttcc gtcgagcg                                                 18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 44
ttacaccctc cgtttctc                                                 18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 45
atggcacagg acctgaac                                                 18
```

```
<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 46
tcaacgccac cggatctt                                                   18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 47
gtgagctccc tcgccgtc                                                   18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 48
tcatcgtcgg gcactcgg                                                   18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 49
gtgccggttc cgctgtat                                                   18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 50
tcaccgggca ctgacctc                                                   18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 51
gtgaccgaga accttccg                                                   18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Primer
```

```
<400> SEQUENCE: 52
tcagaccttc ttgaccac                                                18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 53
atggcctcag acgctttg                                                18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 54
tcattgagac tcctcctc                                                18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 55
atgatgaagt caagccgc                                                18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 56
tcagtggctt acaaggag                                                18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 57
atgactgacc tgccgttg                                                18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 58
tcacaccagc agcgaggt                                                18
```

-continued

```
<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 59
atggatttcc ccctcacc                                                   18

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 60
tcatgcccct acctcggc                                                   18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 61
atgaccgcgc gcgtcgac                                                   18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 62
tcactcctcg gcttcggc                                                   18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 63
gtgtccaaga acgcggcg                                                   18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 64
tcatcggctc gcctcgtg                                                   18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Primer
```

```
<400> SEQUENCE: 65
atgaccctca ccctgcgg                                                   18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 66
tcactcgggc actccttc                                                   18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 67
gtgaccggtt ccgtaacg                                                   18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 68
tcatgagtcc gccgaggt                                                   18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 69
atgacagagg tccgaggt                                                   18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 70
cccggcaacc gccctccc                                                   18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 71
gtgatcgccg ccctcctg                                                   18
```

```
<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 72
ttacgggacg gcggtccg                                                  18

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (19)
<223> OTHER INFORMATION: a, t, c or g
<221> NAME/KEY: modified_base
<222> LOCATION: (22)
<223> OTHER INFORMATION: a, t, c or g

<400> SEQUENCE: 73
cggcatggtc ggctcchtnc ancaytg                                        27

<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (20)
<223> OTHER INFORMATION: a, t, c or g
<221> NAME/KEY: modified_base
<222> LOCATION: (26)
<223> OTHER INFORMATION: a, t, c or g

<400> SEQUENCE: 74
tgcagcagaa caggaggckn ycccankg                                       28

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (18)
<223> OTHER INFORMATION: a, t, c or g

<400> SEQUENCE: 75
tgggtcagcg ggtaccanrc yttrwa                                         26

<210> SEQ ID NO 76
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 76
aacccatggc tgcttccctg acccgcctgg cc                                  32
```

```
<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 77
cctagatcta cgggcaggtg gggcggt                                        27

<210> SEQ ID NO 78
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 78
gggaattcca tatgatcctc acgtccttcc ac                                  32

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 79
ggcaagcttg ggtgagggtc cgttcggt                                       28

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence:
      Illustrative motif
<221> NAME/KEY: MOD_RES
<222> LOCATION: (4)
<223> OTHER INFORMATION: Variable amino acid

<400> SEQUENCE: 80

Leu Gly Gly Xaa Ser
  1               5

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence:
      Illustrative motif
<221> NAME/KEY: MOD_RES
<222> LOCATION: (4)
<223> OTHER INFORMATION: Variable amino acid

<400> SEQUENCE: 81

Leu Gly Gly Xaa Ser
  1               5

<210> SEQ ID NO 82
<211> LENGTH: 39
<212> TYPE: DNA
<213> ORGANISM: Artificial Sequence
<220> FEATURE:
<223> OTHER INFORMATION: Description of Artificial Sequence: Primer
```

```
<400> SEQUENCE: 82
ccgcccatgg gtgctccgcg tggcgagcgg acccggcgc                              39

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 83
tgccccctcg ccctggcctc tagatcc                                          27

<210> SEQ ID NO 84
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 84
ggaattccat atgggcacca ccgtcgccgc g                                     31

<210> SEQ ID NO 85
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 85
cgcgaggtgc gggccagggt tcgaacgg                                         28

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: "THC"
      motif
<221> NAME/KEY: MOD_RES
<222> LOCATION: (2)
<223> OTHER INFORMATION: Variable amino acid
<221> NAME/KEY: MOD_RES
<222> LOCATION: (5)
<223> OTHER INFORMATION: Variable amino acid
<221> NAME/KEY: MOD_RES
<222> LOCATION: (7)..(8)
<223> OTHER INFORMATION: Variable amino acid
<221> NAME/KEY: MOD_RES
<222> LOCATION: (11)
<223> OTHER INFORMATION: Met or Leu
<221> NAME/KEY: MOD_RES
<222> LOCATION: (15)
<223> OTHER INFORMATION: Variable amino acid

<400> SEQUENCE: 86

Pro Xaa Trp Pro Xaa Gly Xaa Xaa Gly Ser Xaa Thr His Cys Xaa Gly
  1               5                  10                  15

Tyr

<210> SEQ ID NO 87
<211> LENGTH: 4
<212> TYPE: PRT
<213> ORGANISM: Artificial Sequence
```

```
<220> FEATURE:
<223> OTHER INFORMATION: Description of Artificial Sequence:
      (V/I)G(V/I)D motif
<221> NAME/KEY: MOD_RES
<222> LOCATION: (1)
<223> OTHER INFORMATION: Val or Ile
<221> NAME/KEY: MOD_RES
<222> LOCATION: (3)
<223> OTHER INFORMATION: Val or Ile

<400> SEQUENCE: 87

Xaa Gly Xaa Asp
  1

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (20)
<223> OTHER INFORMATION: A, C, T or G
<221> NAME/KEY: modified_base
<222> LOCATION: (26)
<223> OTHER INFORMATION: A, C, T or G

<400> SEQUENCE: 88
tgcagcagaa caggaggckn ycccankg                                      28

<210> SEQ ID NO 89
<211> LENGTH: 26
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (18)
<223> OTHER INFORMATION: A, T, C or G

<400> SEQUENCE: 89
tgggtcagcg ggtaccanrc yttrwa                                        26

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (19)
<223> OTHER INFORMATION: A, T, C or G
<221> NAME/KEY: modified_base
<222> LOCATION: (22)
<223> OTHER INFORMATION: A, T, C or G

<400> SEQUENCE: 90
cggcatggtc ggctcchtna cncaytg                                       27

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence:
      Illustrative motif
<221> NAME/KEY: MOD_RES
<222> LOCATION: (1)
<223> OTHER INFORMATION: Phe or Trp
```

```
<221> NAME/KEY: MOD_RES
<222> LOCATION: (2)
<223> OTHER INFORMATION: Ser, Cys or Thr
<221> NAME/KEY: MOD_RES
<222> LOCATION: (3)
<223> OTHER INFORMATION: Variable amino acid
<221> NAME/KEY: MOD_RES
<222> LOCATION: (6)
<223> OTHER INFORMATION: Ala or Ser

<400> SEQUENCE: 91

Xaa Xaa Xaa Lys Glu Xaa His His Lys
 1               5

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: NAD/FAD
      binding motif
<221> NAME/KEY: MOD_RES
<222> LOCATION: (2)
<223> OTHER INFORMATION: Variable amino acid
<221> NAME/KEY: MOD_RES
<222> LOCATION: (4)..(5)
<223> OTHER INFORMATION: Variable amino acid
<221> NAME/KEY: MOD_RES
<222> LOCATION: (7)..(9)
<223> OTHER INFORMATION: Variable amino acid
<221> NAME/KEY: MOD_RES
<222> LOCATION: (11)..(16)
<223> OTHER INFORMATION: Variable amino acid

<400> SEQUENCE: 92

Gly Xaa Gly Xaa Xaa Gly Xaa Xaa Xaa Gly Xaa Xaa Xaa Xaa Xaa Xaa
 1               5                  10                  15
Gly

<210> SEQ ID NO 93
<211> LENGTH: 113
<212> TYPE: PRT
<213> ORGANISM: Streptomyces verticillus
<220> FEATURE:
<223> OTHER INFORMATION: ORF30

<400> SEQUENCE: 93

Met Pro Val Pro Leu Tyr Gln Ala Lys Ala Glu Phe Phe Arg Met Leu
 1               5                  10                  15

Gly His Pro Val Arg Ile Arg Val Leu Glu Leu Leu Gln Asp Gly Pro
            20                  25                  30

Met Pro Val Arg Asp Leu Leu Ala Ala Ile Glu Ile Glu Pro Ser Ala
        35                  40                  45

Leu Ser Gln Gln Leu Ala Val Leu Arg Arg Ser Gly Ile Val Thr Ser
    50                  55                  60

Thr Arg Thr Gly Ser Thr Val Val Tyr Glu Leu Ala Gly Gly Asp Val
65                  70                  75                  80

Ala Glu Leu Met Ser Ala Ala Arg Arg Ile Leu Thr Glu Met Leu Asn
                85                  90                  95

Gly Gln His Glu Leu Leu Glu Glu Leu Arg Glu Ala Glu Val Ser Ala
            100                 105                 110

Arg
```

<210> SEQ ID NO 94
<211> LENGTH: 582
<212> TYPE: PRT
<213> ORGANISM: Streptomyces verticillus
<220> FEATURE:
<223> OTHER INFORMATION: ORF29

<400> SEQUENCE: 94

```
Met Ser Ser Leu Ala Val Arg Val Gly Ala Arg Val Arg Ser Val Leu
 1               5                  10                  15

Pro Thr Arg Ala Asp Leu Ala Gly Met Gly Arg Ser Pro Arg Arg Asp
                20                  25                  30

Leu Leu Ala Gly Leu Thr Val Ala Ile Val Ala Leu Pro Leu Ala Leu
            35                  40                  45

Gly Phe Gly Val Ser Ser Gly Leu Gly Ala Glu Ala Gly Leu Ala Thr
        50                  55                  60

Ala Val Val Ala Gly Ala Leu Ala Ala Val Phe Gly Gly Ser Asn Leu
65                  70                  75                  80

Gln Val Ser Gly Pro Thr Gly Ala Met Thr Val Val Leu Val Pro Ile
                85                  90                  95

Val Ala Arg Tyr Gly Pro Gly Val Leu Thr Val Gly Leu Leu Ala
            100                 105                 110

Gly Leu Met Leu Ile Ala Leu Ala Leu Ala Arg Ala Gly Arg Tyr Met
        115                 120                 125

Gln Tyr Val Pro Ala Pro Val Val Glu Gly Phe Thr Leu Gly Ile Ala
    130                 135                 140

Cys Val Ile Gly Leu Gln Gln Val Pro Asn Ala Leu Gly Val Ala Lys
145                 150                 155                 160

Pro Glu Gly Asp Lys Val Leu Val Val Thr Trp Arg Ala Val Glu Thr
                165                 170                 175

Phe Ala Gly Ala Pro Asn Trp Thr Ala Ala Gly Leu Ala Ala Ala Val
            180                 185                 190

Ala Ala Val Met Leu Thr Gly Ala Arg Trp Arg Pro Val Val Pro Phe
        195                 200                 205

Ser Leu Leu Ala Val Thr Gly Ala Thr Val Val Ala Gln Leu Cys His
    210                 215                 220

Leu Asp Ala Ala Arg Pro Ile Gly Asp Leu Pro Ala Gly Leu Pro Ala
225                 230                 235                 240

Pro Ser Leu Ala Phe Leu Asp Leu Gly Ala Leu Gly Ser Leu Leu Ala
                245                 250                 255

Pro Ala Val Ala Val Ala Ala Leu Ala Ala Leu Glu Ser Leu Leu Ser
            260                 265                 270

Ala Ser Val Ala Asp Gly Met Thr Val Gly Gln Lys His Asp Pro Asp
        275                 280                 285

Lys Glu Leu Phe Gly Gln Gly Leu Ala Asn Leu Ala Ala Pro Leu Phe
    290                 295                 300

Gly Gly Val Pro Ala Thr Gly Ala Ile Ala Arg Thr Ala Val Asn Val
305                 310                 315                 320

Arg Thr Gly Ala Ser Ser Arg Leu Ala Ala Leu Thr His Ala Ala Ile
                325                 330                 335

Leu Ala Val Ile Val Phe Ala Ala Ala Pro Leu Val Ser Arg Ile Pro
            340                 345                 350

Leu Ala Ala Leu Ala Gly Val Leu Ile Ala Thr Ala Ile Arg Met Val
        355                 360                 365
```

```
Glu Val Gly Ser Leu Arg Ala Met Ala Arg Ala Thr Arg Ser Asp Gly
    370                 375                 380

Leu Val Leu Ile Leu Thr Ala Val Ala Thr Val Ala Leu Asp Leu Val
385                 390                 395                 400

Tyr Ala Val Ile Ile Gly Leu Val Ala Gly Ala Leu Ala Leu Arg
                405                 410                 415

Ala Val Ala Lys Gln Val Arg Leu Asp Gln Val Ser Leu Lys Glu Asp
            420                 425                 430

Leu Thr Gly Asp His Ser Ala Glu Glu His Ala Leu Leu Ala Glu His
            435                 440                 445

Ile Val Ala Tyr Arg Ile Asp Gly Pro Leu Phe Phe Ala Ala Ala His
            450                 455                 460

Arg Phe Leu Leu Glu Leu Ser Asp Val Ala Asp Val Arg Val Val Ile
465                 470                 475                 480

Leu Arg Met Ser Arg Val Thr Thr Met Asp Ala Thr Gly Ala Leu Val
                485                 490                 495

Leu Lys Asp Ala Val Thr Lys Leu Asn Arg Arg Gly Ile Thr Val Leu
            500                 505                 510

Ala Ser Gly Val Arg Pro Gly Gln Arg Val Leu Asp Ser Val Gly
            515                 520                 525

Ala Leu Gly Leu Leu Arg Ala Ala Thr Gly Asp Asp Tyr Thr Gly Thr
530                 535                 540

Pro Glu Ala Ile Ala Ala Arg Ser His Leu His Gly Ala Gly Val
545                 550                 555                 560

Leu Ala Pro Ala Cys Pro Gly Pro Pro Pro Val Pro Pro Pro Cys
                565                 570                 575

Ala Pro Ser Ala Arg Arg
            580

<210> SEQ ID NO 95
<211> LENGTH: 239
<212> TYPE: PRT
<213> ORGANISM: Streptomyces verticillus
<220> FEATURE:
<223> OTHER INFORMATION: ORF28

<400> SEQUENCE: 95

Met Ala Gln Asp Leu Asn Asp Trp Ile Glu Asp Glu Val Val Pro Tyr
  1               5                  10                  15

Glu Glu Lys Pro Leu Glu Trp Ile Ser Gln Tyr His Phe Phe Arg Asp
                 20                  25                  30

Pro Ala Arg Ala Ala Tyr Val Asp His Thr Tyr Phe Phe Ser Pro Ala
             35                  40                  45

Asp Gly Ala Ile Val Tyr Gln Lys Val Val Asp Pro Gln Glu Ser Ile
         50                  55                  60

Ile Asp Ile Lys Gly Lys Pro Tyr Ser Leu Ala Ala Leu Arg Asp
 65                  70                  75                  80

Glu Ser Phe Gly His Arg Cys Leu Val Ile Gly Ile Phe Met Thr Phe
                 85                  90                  95

Phe Asp Val His Ile Asn Arg Met Pro Tyr Gly Gly Arg Leu Ser Phe
            100                 105                 110

Ala Leu Lys Glu Pro Ile Gly Thr Phe Asn Leu Pro Met Leu Ala Met
        115                 120                 125

Glu Gln Asp Leu Leu Glu Arg Leu Arg Val Asn Pro Ala His Ala Arg
    130                 135                 140
```

```
Tyr Leu His Leu Asn Glu Arg Met Val Asn Arg Val Asp Ala Pro Arg
145                 150                 155                 160

Leu Arg Gly Pro Tyr Trp Met Leu Gln Ile Ala Asp Tyr Asp Val Asp
                165                 170                 175

Ser Ile Thr Pro Phe Cys Arg Arg Gln Gly Met Phe Arg Ser Gln Gly
            180                 185                 190

Arg Arg Phe Ser Gln Ile Arg Tyr Gly Ser Gln Val Asp Leu Val Ile
        195                 200                 205

Pro Met Ala Ala Asp Arg Glu Tyr Val Pro Val Glu Ala Val Gly Arg
    210                 215                 220

His Val Lys Ala Gly Leu Asp Pro Leu Val Lys Ile Arg Trp Arg
225                 230                 235

<210> SEQ ID NO 96
<211> LENGTH: 688
<212> TYPE: PRT
<213> ORGANISM: Streptomyces verticillus
<220> FEATURE:
<223> OTHER INFORMATION: ORF27

<400> SEQUENCE: 96

Met Gly Phe Arg Arg Ala Gln Arg Ala Gly Gly Pro Gly Ala Gly Arg
1               5                   10                  15

Arg Glu Ser Ala Arg Phe Arg Pro Asp Gly Pro Ser Ala Pro Arg Asp
            20                  25                  30

Arg Pro Leu Pro Leu Ser Ala Gly Gln Leu Phe Glu Trp Val Phe Asp
        35                  40                  45

Lys Leu Val Asp Gly Asp Leu Ser His Gln Pro Thr Ile Val Arg Leu
    50                  55                  60

Arg Gly Pro Leu Asn Thr Ala Ala Leu Arg Met Ala Tyr Ala Arg Leu
65                  70                  75                  80

Val Arg Arg His Glu Cys Leu Arg Thr Arg Phe Pro Val Ile Asp Gly
                85                  90                  95

Glu Pro Val Gln Val Ile Glu Gly Ile Gly Lys Ala Ala Gly Gly Pro
            100                 105                 110

Leu Pro Leu Ile Asp Leu Arg His Leu Pro Glu Ala Leu Arg Ala Arg
        115                 120                 125

Glu Ile Ala Arg Ile Arg Glu Glu Thr Leu Ser Thr Pro Val Pro Phe
    130                 135                 140

Asp Lys Arg Pro Pro Val Arg Val Ala Leu Ile Arg Ala Ala Pro Glu
145                 150                 155                 160

Glu His Leu Phe Leu Val Gly Ile Pro His Ile Thr Ala Asp Leu Trp
                165                 170                 175

Ser Ala Thr Leu Leu Asn Asp Glu Leu Met Ala His Tyr Arg Ala Gly
            180                 185                 190

Ala Glu Gly Thr Pro Ser Arg Ala Pro Thr Pro Val Ala Gln Tyr Ala
        195                 200                 205

Asp Phe Ala Gln Trp Gln Arg Ala Trp Trp Asn Arg Asp Arg Thr Glu
    210                 215                 220

Arg Glu Ala Gly Arg Trp Arg Ala Arg Leu Asp Gly Leu Ser Ala Val
225                 230                 235                 240

Glu Leu Pro Leu Asp Arg Pro Arg Pro Ala Gly Arg Arg Asp Cys
                245                 250                 255

Phe Leu Ile Gly Asp Thr Phe Asp Ala Glu Leu Ser Asp Arg Leu Arg
            260                 265                 270
```

```
Ala Leu Ala Arg Thr Ala Asp Val Thr Leu Tyr Val Leu Leu Ala
        275                 280                 285

Ala Phe His Trp Leu Val Gly Arg Met Ser Gly Ala Gly Arg Leu Val
        290                 295                 300

Thr Thr Ser Leu Val Ala Ala Arg His Gly Ser Ala Val Gln Gly Met
305                 310                 315                 320

Thr Gly Pro Phe Ser Asp Tyr Leu Ala Leu Val Gly Asp Leu Ser Gly
                325                 330                 335

Asp Pro Asp Phe Leu Glu Ser Leu Arg Arg Val Arg Asp Glu Cys Leu
            340                 345                 350

Thr Ala His Asp His Gln Arg Leu Pro Phe Ser Gln Val Leu Glu Val
        355                 360                 365

Met Asp Pro Gly Arg Glu Leu His Pro His Pro Leu Glu Gln Leu Gly
370                 375                 380

Phe Asn Leu His Asn Ile Pro Pro Ala Val Met Asp Phe Ser Gly Asp
385                 390                 395                 400

Val Val Val Ser Ala Val Asn Pro Glu Gly Asp Asp Gly Glu Ser Gly
                405                 410                 415

Asp Gly Glu Tyr Val Pro Trp Thr Ala Asp Leu Thr Phe Asp Val Tyr
            420                 425                 430

Asp Tyr Gly Thr Gly His Met Pro Phe Asp Val Ile Leu Asp Arg Arg
        435                 440                 445

Leu Ala Asp Pro Ala Thr Ala Arg Glu Trp Ala Gly His Tyr Arg Ser
450                 455                 460

Val Leu Arg Ala Val Ala Asp Pro Gly Val Arg Leu Ser Ala Leu
465                 470                 475                 480

Gly Thr Leu Leu Ser Leu Pro Arg Pro Ser Ala Thr Ser Phe Gly
                485                 490                 495

Gly Arg Glu Ile Asp Val Arg Arg Val Glu Arg Glu Leu Ala Gly Arg
            500                 505                 510

Asp Gly Ile Thr Ala Ala Leu Val Ala Val Ala Pro Arg Arg Leu Ala
        515                 520                 525

Thr Gly Leu Arg Val Arg Glu Leu Val Ala Tyr Cys Ala Val Glu Gly
530                 535                 540

Thr Pro Arg Pro Asn Ala Ala His Asp Ile Arg Gly Arg Leu Arg Glu
545                 550                 555                 560

Arg Leu Pro Asp Gly Trp Val Pro Thr Val Phe Val Glu Arg Pro Pro
                565                 570                 575

Glu Glu Ile Arg Lys Ala Leu Ala Ala Arg Ala Ala Gly Gly Glu Arg
            580                 585                 590

Ala Glu Pro Leu Pro Pro Glu Asp Cys Val Pro Leu Pro Glu Glu
        595                 600                 605

Gly Arg Pro Pro Ser Asp Pro Ser Glu Arg Arg Leu Ala Ala Leu Trp
610                 615                 620

Ala Glu Ile Leu Gly Ala Pro Lys Ser Val Thr Glu Pro Phe Phe
625                 630                 635                 640

Arg Val Gly Val Thr Asp Lys Asp Ala Leu Arg Phe Leu Ala Arg Val
                645                 650                 655

Ala Glu Asp Phe Gly Val Thr Val Pro Phe Ala Asp Phe Leu Ser Ala
            660                 665                 670

Pro Asn Leu Arg Met Val Lys Asp Asn Leu Ala Glu Lys Arg Arg Val
        675                 680                 685
```

```
<210> SEQ ID NO 97
<211> LENGTH: 2162
<212> TYPE: PRT
<213> ORGANISM: Streptomyces verticillus
<220> FEATURE:
<223> OTHER INFORMATION: ORF26

<400> SEQUENCE: 97
```

| | | | | | | | | | | | | | | | |
|---|---|---|---|---|---|---|---|---|---|---|---|---|---|---|---|
|Met|Pro|Arg|Cys|Ala|Arg|Gly|Ala|Leu|Ser|Thr|Ala|Val|His|Thr|Thr|
|1| | | |5| | | | |10| | | | |15| |
|Arg|Gln|Gly|Ser|Trp|Asn|Val|Met|Glu|Thr|Ala|Asn|Ser|Gly|Tyr|Arg|
| | | | |20| | | | |25| | | | |30| |
|Val|Ser|Pro|Gln|Gln|Arg|His|Leu|Trp|Ala|Met|Leu|Thr|Arg|Gly|Arg|
| | | |35| | | | |40| | | | |45| | |
|Asp|Gly|Gly|Arg|Arg|Ala|Phe|Thr|Gln|Ser|Ala|Val|Val|Val|Asp|Arg|
| |50| | | | |55| | | | |60| | | | |
|Ser|Leu|Asp|Ala|Ala|Arg|Leu|Arg|Ala|Ala|Leu|Ala|Ser|Val|Val|Ala|
|65| | | | |70| | | | |75| | | | |80|
|Ala|His|Glu|Pro|Leu|Arg|Thr|Thr|Phe|Thr|Gly|Leu|Ala|Gly|Arg|Thr|
| | | | |85| | | | |90| | | | |95| |
|Ala|Pro|Val|Gln|Val|Val|His|Asp|Pro|Asp|Glu|Gln|Pro|Leu|Ser|Val|
| | | |100| | | | |105| | | | |110| | |
|Val|Asp|Leu|Pro|Pro|Ser|Cys|Ala|Asp|Gly|Ser|Gly|Pro|Glu|Leu|Asp|
| |115| | | | |120| | | | |125| | | | |
|Glu|Leu|Arg|Leu|Arg|Glu|Arg|Ala|Ala|Leu|Asp|Pro|Arg|Gly|Gly|Pro|
|130| | | | |135| | | | |140| | | | | |
|Val|Phe|Arg|Ala|Ala|Leu|Ala|Arg|Ala|Gly|Glu|Asp|Arg|Ala|Val|Leu|
|145| | | | |150| | | | |155| | | | |160|
|Val|Leu|Thr|Ala|His|Ala|Leu|Val|Ala|Asp|Arg|Leu|Ser|Leu|Arg|Leu|
| | | | |165| | | | |170| | | | |175| |
|Leu|Ala|Gly|Gln|Ile|Leu|Ala|Ala|Tyr|Ser|Gly|Glu|Thr|Val|Ser|Pro|
| | | |180| | | | |185| | | | |190| | |
|Asp|Gly|Pro|Pro|Leu|Gln|Tyr|Ala|Asp|Phe|Ala|Ala|Trp|His|His|
| |195| | | | |200| | | | |205| | | | |
|Asp|Leu|Leu|Thr|Ala|Glu|Asp|Ala|Ala|Pro|Asp|Arg|Ala|His|Trp|Ala|
|210| | | | |215| | | | |220| | | | | |
|Ala|His|Thr|Ala|Thr|Ala|Gly|Thr|Gly|Pro|Leu|Pro|Gly|Val|Val|Arg|
|225| | | | |230| | | | |235| | | | |240|
|Pro|Gly|Ala|Ala|Pro|Gly|Pro|Trp|Arg|Ala|Arg|Glu|Trp|Glu|Leu|Pro|
| | | | |245| | | | |250| | | | |255| |
|Ala|Glu|Leu|Val|Ala|Gly|Ile|Asp|Gly|Val|Ala|Gly|Lys|Leu|Ser|Thr|
| | | |260| | | | |265| | | | |270| | |
|Asp|Pro|Ala|Thr|Val|Leu|His|Ala|Ala|Phe|Arg|Ile|Ala|Val|Trp|Arg|
| |275| | | | |280| | | | |285| | | | |
|Leu|Ala|Gly|Glu|Arg|Asn|Leu|Pro|Val|Ala|Leu|Thr|Arg|Asp|Gly|Arg|
| |290| | | | |295| | | | |300| | | | |
|Ser|His|Pro|Glu|Leu|Arg|Thr|Ala|Ile|Gly|Ala|Phe|Glu|Arg|Glu|Leu|
|305| | | | |310| | | | |315| | | | |320|
|Pro|Leu|Val|His|Glu|Ile|Arg|His|Glu|Thr|Ala|Phe|Ala|Glu|Tyr|Ala|
| | | | |325| | | | |330| | | | |335| |
|Arg|Ala|Leu|Asp|Ala|Leu|Val|Ala|Glu|Gly|Glu|Glu|Leu|Leu|Asp|His|
| | | |340| | | | |345| | | | |350| | |
|Cys|Asp|Pro|Glu|Leu|Leu|Gly|Ser|Leu|Asp|Gly|Thr|Ala|Glu|Gly|Pro|
| |355| | | | |360| | | | |365| | | | |

-continued

```
Cys Phe Thr Phe Thr His His Gln Ala Glu Thr Pro Val Arg Arg Ala
370                 375                 380

Gly Ile Thr Phe Thr Thr Val His Gln Asp Ser Gly Thr Pro Ile Pro
385                 390                 395                 400

Val Arg Leu Thr Ala Arg Arg Asp Gly Ala Arg Leu Arg Met Glu Leu
                405                 410                 415

Gly Tyr Asp Glu Gly Arg Ile Asp Glu Thr Phe Pro Glu Asn Ala Ala
            420                 425                 430

Ala Cys Leu Thr Arg Ile Leu Glu Gly Val Val Ser Ala Pro Glu Gly
                435                 440                 445

Pro Val Gly Asp Ile Arg Met Leu Ser Asp Glu Thr Ala Arg Leu Leu
        450                 455                 460

Arg Glu Ala Gly Leu Gly Pro Arg Val Glu Leu Pro Gly Lys Ala Val
465                 470                 475                 480

His Glu Leu Phe Ala Glu Gln Ala Ala Arg Thr Pro Gly Ala Val Ala
                485                 490                 495

Val Ser Ala Gly Glu Asp Ala Leu Thr Tyr Ala Glu Leu Asp Glu Arg
                500                 505                 510

Ser Asn Arg Leu Ala His His Leu Thr Gly Leu Gly Val Thr Pro Gly
            515                 520                 525

Arg His Val Val Ser Val Gly Arg Ser Ala Glu Leu Leu Val Gly
        530                 535                 540

Leu Leu Gly Val Leu Lys Ala Gly Ala Phe Val Pro Val Asp Val
545                 550                 555                 560

Gly Phe Pro Arg Lys Arg Leu Glu Phe Val Leu Arg Glu Thr Ala Ala
                565                 570                 575

Pro Val Leu Leu Cys Thr Ala Asp Val Arg Asp Arg Ile Gly Thr Arg
            580                 585                 590

Thr Leu Asp Asp Ala Gly Val Thr Pro Val Ala Leu Asp Ala Asp Arg
        595                 600                 605

Arg Arg Ile Ala Ala His Pro Ala Gly Pro Thr Gly Ile Ala Thr Thr
    610                 615                 620

Pro Asp Ala Pro Ala Tyr Val Val Tyr Thr Ser Gly Thr Thr Gly Lys
625                 630                 635                 640

Pro Asn Gly Val Arg Val Pro His Arg Gly Leu Thr Asn Tyr Leu Thr
                645                 650                 655

Trp Cys Thr Gly Ala Tyr Gly Leu Asp Gly Thr Gly Thr Leu Val
            660                 665                 670

His Thr Ser Ile Ser Phe Asp Leu Thr Leu Thr Thr Leu Phe Gly Pro
            675                 680                 685

Leu Leu Ala Gly Gly Gln Val Val Met Leu Ser Glu Thr Ala Gly Val
    690                 695                 700

Thr Gly Leu Ile Ala Ala Leu Arg Ser Arg Arg Asp Leu Thr Leu Val
705                 710                 715                 720

Lys Leu Thr Pro Thr His Leu Asp Val Val Asn Gln Leu Leu Thr Pro
                725                 730                 735

Asp Glu Leu Arg Gly Ala Val Arg Thr Leu Val Val Gly Gly Glu Ala
            740                 745                 750

Val Arg Ala Glu Ser Leu Glu Pro Phe Arg Ala Ser Gly Thr Arg Val
                755                 760                 765

Val Asn Glu Tyr Gly Pro Ser Glu Thr Val Val Gly Ser Val Ala His
770                 775                 780
```

-continued

```
Val Val Asp Ala Ala Thr Pro Arg Thr Gly Pro Val Pro Ile Gly Arg
785                 790                 795                 800

Pro Ile Ala Asn Thr Thr Val His Leu Leu Asp Gln Arg Arg Pro
            805                 810                 815

Val Pro Asp Gly Val Val Gly Glu Leu Trp Ile Gly Gly Ala Gly Val
820                 825                 830

Ala Asp Gly Tyr Leu Gly Arg Pro Glu Leu Thr Gly Glu Arg Phe Leu
        835                 840                 845

Pro Ser Asp Tyr Pro Pro Asp Gly Gly Arg Val Tyr Arg Thr Gly Asp
    850                 855                 860

Leu Ala Arg Arg Arg Ala Asp Gly Thr Leu Glu Tyr Leu Gly Arg Thr
865                 870                 875                 880

Asp Ala Gln Val Lys Ile Arg Gly Val Arg Val Glu Pro Ala Glu Thr
                885                 890                 895

Glu Ala Val Leu Ala Ser His Pro Gly Val Gly Gln Ala Val Val Val
            900                 905                 910

Ala Arg Leu Asp Glu Asp Pro Gly Arg Ser Ser Pro Leu Ala Gly Glu
        915                 920                 925

Leu Thr Leu Thr Gly Tyr Val Val Pro Ala Arg Gly Ala Gln Ala Pro
    930                 935                 940

Pro His Glu Glu Leu Ile Ala Tyr Cys Arg Glu Arg Leu Pro Glu His
945                 950                 955                 960

Phe Val Pro Ala Val Leu Val Thr Leu Asp Ala Leu Pro Val Thr Gly
                965                 970                 975

His Gly Lys Ile Asp Arg Gly Ala Leu Pro Lys Pro His Ala Arg Ala
            980                 985                 990

Arg Asp Gly Ala Ala Tyr Val Ala Pro Arg Thr Ala Thr Glu Glu Ile
        995                 1000                1005

Leu Ala Ala Thr Val Ala Lys Val Leu Gly Val Glu Arg Val Gly Ile
    1010                1015                1020

Asp Asp Asn Tyr Phe Val Leu Gly Gly Asp Ser Ile Arg Ser Val Met
1025                1030                1035                1040

Val Ala Ser Arg Ala Gln Ala Arg Gly Val Glu Val Thr Val Ala Asp
                1045                1050                1055

Leu His Arg His Pro Thr Val Arg Ala Cys Ala Ala His Leu Asp Ala
            1060                1065                1070

Arg Glu Asp Leu Pro Arg Thr Pro Val Thr Glu Pro Phe Ala Leu Ile
        1075                1080                1085

Ser Ala Glu Asp Arg Ala Leu Val Pro Asp Asp Val Glu Asp Ala Phe
    1090                1095                1100

Pro Leu Asn Leu Leu Gln Glu Gly Met Ile Phe His Arg Asp Phe Ala
1105                1110                1115                1120

Ala Lys Ser Ala Val Tyr His Ala Ile Ala Ser Val Arg Leu Arg Ala
                1125                1130                1135

Pro Phe Asp Leu Ala Val Leu Arg Met Val Val Arg Gln Leu Val Glu
            1140                1145                1150

Arg His Pro Met Leu Arg Thr Ser Phe Asp Met Ser Arg Phe Ser Arg
        1155                1160                1165

Pro Leu Gln Leu Val His Arg Glu Phe Ala Asp Pro Leu His Tyr Glu
    1170                1175                1180

Asp Leu Arg Gly Arg Ser Ala Glu Glu Gln Asp Ala Arg Val Glu Glu
1185                1190                1195                1200
```

-continued

```
Trp Ile Glu Arg Glu Lys Glu Arg Gly Phe Glu Leu His Glu Phe Pro
            1205                1210                1215
Leu Ile Arg Phe Met Ala Gln Arg Leu Glu Asp Asp Val Phe Gln Phe
            1220                1225                1230
Thr Tyr Gly Phe His His Glu Ile Val Asp Gly Trp Ser Glu Ala Leu
            1235                1240                1245
Met Ile Thr Glu Leu Phe Ser His Tyr Phe Ser Val Ile Tyr Asp Glu
            1250                1255                1260
Pro Ile Ala Ile Lys Pro Pro Thr Ala Gly Met Arg Asp Ala Val Ala
1265                1270                1275                1280
Leu Glu Leu Glu Ala Leu Ala Asp Arg Arg Asn Tyr Glu Phe Trp Asp
            1285                1290                1295
Ser Tyr Leu Ala Asp Ala Thr Leu Met Arg Leu Pro Arg Pro Gly Thr
            1300                1305                1310
Gly Pro Arg Ala Asp Lys Gly Asp Arg Asp Ile Thr Arg Ile Ala Val
            1315                1320                1325
Pro Val Pro Thr Glu Leu Ser Asp Gly Leu Lys Arg Val Ala Ala Thr
            1330                1335                1340
His Ala Val Pro Leu Lys Thr Val Leu Ala Ala His Met Val Val
1345                1350                1355                1360
Met Ser Leu Tyr Gly Gly His Glu Asp Thr Leu Thr Tyr Thr Val Thr
            1365                1370                1375
Asn Gly Arg Pro Glu Thr Ala Asp Gly Ser Thr Ala Ile Gly Leu Phe
            1380                1385                1390
Val Asn Ser Leu Ala Leu Arg Val Arg Met Thr Gly Gly Thr Trp Ala
            1395                1400                1405
Asp Leu Ile Thr Ala Thr Leu Glu Ser Glu Arg Ala Ser Met Pro Tyr
            1410                1415                1420
Arg Arg Leu Pro Met Ala Glu Leu Lys Arg His Gln Gly Asn Glu Pro
1425                1430                1435                1440
Leu Ala Glu Thr Leu Phe Phe Phe Thr Asn Tyr His Val Phe His Val
            1445                1450                1455
Leu Asp Arg Trp Ile Asp Arg Gly Val Gly His Val Ala Asn Glu Leu
            1460                1465                1470
Tyr Gly Glu Ser Thr Phe Pro Phe Cys Gly Ile Phe Arg Leu Asn Arg
            1475                1480                1485
Glu Thr Gly Glu Leu Glu Val Arg Ile Glu Tyr Asp Ser Leu Gln Phe
            1490                1495                1500
Ser Asp Ala Leu Met Glu Ser Val Arg Asp Ser Tyr Ala Arg Val Leu
1505                1510                1515                1520
Ala Ala Leu Val Ala Asp Pro Asp Gly Arg Tyr Asp Arg His Glu Phe
            1525                1530                1535
Arg Ser Asp Arg Asp Arg Ala Ala Leu Ala Val Leu Thr Arg Gly Pro
            1540                1545                1550
Glu Ala Pro Ala Ala Asp Arg Cys Leu His Asp Leu Val Ala Asp Arg
            1555                1560                1565
Ala Ala Asp Arg Pro Asp Ala Pro Ala Val Gln Leu Asp Thr Asp Val
            1570                1575                1580
Leu Ser Tyr Gly Glu Leu Asp Arg Arg Ala Asn Arg Leu Ala His His
1585                1590                1595                1600
Leu Arg Ser Leu Gly Ile Gly Pro Glu Ser Val Val Gly Val Leu Ala
            1605                1610                1615
```

-continued

Glu Arg Ser Leu Ala Gln Ile Ile Gly Leu Leu Ala Val Leu Lys Ala
    1620                1625                1630

Gly Ala Ala Tyr Val Pro Leu Asp Pro Ala Gln Pro Asp Glu Arg Leu
        1635                1640                1645

Ala Ala Val Ile Ala Gly Ser Gly Ala Ala Val Leu His Arg Pro
1650                1655                1660

Gly Leu Glu Gly Arg Leu Pro Ala Gly Val Arg Ala Leu Pro Thr Asp
1665                1670                1675                1680

Ala Ala Asp Gly Ser Thr Ala Thr His Asp Pro Gly Pro Thr Ala Thr
            1685                1690                1695

Pro Arg Asn Ala Ala Tyr Val Met Tyr Thr Ser Gly Ser Thr Gly Glu
        1700                1705                1710

Pro Lys Gly Ile Val Val Glu His Arg Asn Val Val Ala Ser Leu Ala
    1715                1720                1725

Ala Arg Gly Ala His Tyr Ala Ala Gly Pro Gly Arg Phe Leu Leu Leu
    1730                1735                1740

Ser Ser Phe Ala Phe Asp Ser Ser Val Ala Gly Ile Phe Trp Thr Leu
1745                1750                1755                1760

Thr Gln Gly Gly Thr Leu Val Leu Pro Gly Glu Gly Gln Gln Leu Asp
        1765                1770                1775

Pro Ala Ala Leu Val Glu Thr Ile Ala Arg Gln Arg Pro Thr His Thr
        1780                1785                1790

Leu Ala Ile Pro Ser Leu Leu Ala Pro Val Leu Asp Gln Ala Ala Pro
        1795                1800                1805

Gly Asp Leu Ala Ser Leu Arg Thr Val Ile Ala Ala Gly Glu Ser Cys
    1810                1815                1820

Pro Ala Glu Leu Ala Ala Ala Cys Arg Asp Leu Leu Pro Gly Ser Thr
1825                1830                1835                1840

Phe His Asn Glu Tyr Gly Pro Thr Glu Thr Thr Val Trp Ser Thr Val
            1845                1850                1855

Trp Ser Gln Glu Asn Glu His Asp Gly Pro His Leu Pro Ile Gly Arg
        1860                1865                1870

Pro Val Ala Gly Thr Trp Val His Pro Arg Asp His Arg Gly Arg Thr
        1875                1880                1885

Val Pro Leu Gly Val Ala Gly Glu Leu Ser Ile Gly Gly Ala Gly Val
    1890                1895                1900

Ala Arg Gly Tyr Leu Gly Arg Pro Arg Asp Thr Ala Ala Ala Phe Arg
1905                1910                1915                1920

Pro Asp Pro Glu Ala Thr Ala Pro Gly Gly Arg Ala Tyr Ala Thr Gly
            1925                1930                1935

Asp Leu Gly Arg Tyr Leu Pro Asp Gly Asn Leu Glu Phe Leu Gly Arg
        1940                1945                1950

Ala Asp His Gln Val Lys Ile Arg Gly Phe Arg Val Glu Leu Gly Glu
        1955                1960                1965

Ile Glu Ala Val Leu Asp Thr His Pro Glu Leu Gln Arg Thr Ile Val
    1970                1975                1980

Met Ala Arg Gly Asp His Pro Gly Asp Gln Val Leu Val Ala Tyr Val
1985                1990                1995                2000

Leu Pro Ala Pro Gly Arg Arg Pro Glu Pro Ala Asp Ile Gln Gly Tyr
            2005                2010                2015

Val Arg Asp Arg Leu Pro Arg Tyr Met Val Pro Thr Ala Val Ile Val
        2020                2025                2030

-continued

```
Leu Asp Ala Val Pro Leu Thr Ala Ala Gly Lys Val Asp Arg Ala Ser
    2035                2040                2045

Leu Pro Ala Pro Ser His Ala Gln Leu Thr Arg Asp Gln Glu Tyr Val
2050                2055                2060

Glu Pro Gly Thr Asp Thr Glu Arg Ala Leu Ala Ala Ile Trp Ala Asp
2065                2070                2075                2080

Val Leu Lys Leu Asp Arg Ile Gly Ala Gly Asp Arg Phe Phe Asp Val
            2085                2090                2095

Gly Gly Glu Ser Leu Arg Ala Met Gln Ala Thr Ala Ala Ala Asn Lys
        2100                2105                2110

Met Phe Arg Thr Arg Val Ser Val Arg Arg Leu Phe Glu Ala Pro Ser
    2115                2120                2125

Leu Arg Glu Phe Ala His Glu Ile Asp Lys Ala Arg Leu Ala Gly Gly
2130                2135                2140

Gly Thr Gly Leu Thr Gly Pro Ala Ala Ala Pro Ala Thr Gly Gly Ala
2145                2150                2155                2160

Ala Glu
```

<210> SEQ ID NO 98
<211> LENGTH: 1066
<212> TYPE: PRT
<213> ORGANISM: Streptomyces verticillus
<220> FEATURE:
<223> OTHER INFORMATION: ORF25

<400> SEQUENCE: 98

```
Met Thr Pro Ala Ala Asp Thr Thr His Pro Leu Ser Pro Ala Gln Arg
1               5                   10                  15

Ser Met Trp Phe Leu His Arg Leu Ala Pro Glu Val Pro Ala Tyr Asn
            20                  25                  30

Ile Cys Thr Ala Ile Glu Leu Thr Gly Thr Pro Arg Pro Ala Ala Leu
        35                  40                  45

Arg Asp Val Val Arg Arg Leu Gly Arg Arg His Glu Ala Leu Arg Thr
    50                  55                  60

Val Phe Pro Ser Val Gly Glu Thr Pro Arg Gln Arg Val Thr Asp Arg
65                  70                  75                  80

Ala Ala Pro Leu Arg Thr Val Asp Leu Thr His Leu Thr Pro Ala Ala
            85                  90                  95

Ala Glu Ala Glu Thr Ala Arg Thr Leu Arg Cys Ala Ala Ala Arg Pro
        100                 105                 110

Phe Arg Leu Asp Thr Gly Pro Leu Ala Glu Trp Thr Leu Leu Arg Arg
    115                 120                 125

Ala Pro Gly His Ala Leu Leu Val Leu Ser Val His His Ile Val Phe
130                 135                 140

Asp Gly Gly Ser Leu His Val Val Cys Arg Glu Leu Glu Glu Ala Tyr
145                 150                 155                 160

Gly Ala Ala Leu Ala Gly Arg Pro Asp Pro Leu Gly Thr Pro Ala Pro
            165                 170                 175

Gly Tyr Gly Arg Gln Cys Arg Thr Arg Ala Ala Glu Gln Asp Glu Ala
        180                 185                 190

Gly Arg Glu Phe Trp Arg Arg Glu Leu Ser Gly Ala Pro Pro Arg Thr
    195                 200                 205

Thr Val Phe Arg Gly Thr Gly Arg Pro Ala Gly Pro Pro Ala Arg Ala
210                 215                 220
```

-continued

```
Thr Val His Tyr Gly Thr Asp Asp Pro Ala Pro Thr Ala Asp Phe Cys
225                 230                 235                 240

Arg Glu His Ala Val Thr Gly Tyr Val Leu Leu Ala Ala Leu Ala
            245                 250                 255

Cys Leu Val Ala Arg Tyr Thr Gly Arg Thr Asp Val Val Ile Gly Ser
            260                 265                 270

Pro Val Gly Leu Arg Glu Asp Pro Glu Gly Leu Ala Thr Val Gly Pro
            275                 280                 285

Met Leu Asn Leu Leu Pro Leu Arg Leu Arg Leu His Gly Asp Pro Gly
    290                 295                 300

Phe Gly Glu Val Leu Ala Arg Thr Arg Glu Thr Leu Leu Gly Ala Leu
305                 310                 315                 320

Glu His Arg Thr Thr Pro Phe Glu Asp Ile Val Asp Ala Val Gly Ala
                325                 330                 335

Asp Arg Asp Pro Asp Val Ser Pro Leu Phe Gln Ile Leu Phe Ala His
                340                 345                 350

Glu Arg Pro Pro Ala Pro Pro Ala Leu Pro Gly Val Arg Ala Arg Val
            355                 360                 365

Val Pro Val Pro Ala Pro Ala Lys Tyr Glu Leu Ala Val Thr Ala
370                 375                 380

Thr Glu Thr Pro Asp Gly Leu Arg Leu Ile Val Glu Ala Glu His Gly
385                 390                 395                 400

His Gly Glu Pro Ala Glu Leu Ala Ala Phe Ala Arg His Phe Gly Val
            405                 410                 415

Leu Leu Ala Ala Gly Val Arg Ala Pro Asp Thr Pro Leu Ser Arg Leu
            420                 425                 430

Pro Leu Leu Thr Asp Glu Glu Arg Arg Leu Thr Asp Thr Thr Ala
    435                 440                 445

Pro Arg Thr Ala Pro Glu Ala Pro Tyr Arg Pro Leu His Arg Leu Val
    450                 455                 460

Glu Glu Ser Ala Ala Arg Arg Pro Asp Ala Leu Ala Val Val Gly Gly
465                 470                 475                 480

Thr Arg His Leu Ser Tyr Arg Glu Leu Asn Cys Arg Ala Asn Arg Arg
                485                 490                 495

Ala Ala Trp Leu Arg Arg Ala Gly Ile Gly Thr Glu Asp Val Val Gly
            500                 505                 510

Val Arg Leu Glu Arg Gly Pro Glu Leu Leu Val Ser Leu Leu Ala Val
            515                 520                 525

Leu Lys Ala Gly Ala Ala Tyr Leu Pro Val Asp Pro Ala Leu Pro Ala
530                 535                 540

Glu Arg Val Arg Leu Met Leu Asp Asp Ala Arg Ala Ala Leu Leu Leu
545                 550                 555                 560

Thr Glu Thr Ala Leu Gly Thr Pro Ala Pro Ala Gly Thr Pro Val
                565                 570                 575

His His Val Asp Gly Pro Pro Pro Thr Arg Pro Gly Asp Asp Ala
            580                 585                 590

Asp His Thr Gly Pro Asp Leu Pro Thr Ser Leu Ala Tyr Leu Leu Tyr
            595                 600                 605

Thr Ser Gly Ser Thr Gly Arg Pro Lys Ala Val Ala Leu Gln His Asp
610                 615                 620

Ser Ala Ala Ala Phe Leu Arg Trp Ala Gly Arg Ala Phe Asp Gly Gly
625                 630                 635                 640
```

-continued

```
Glu Leu Ala Ala Val Leu Ala Thr Thr Ser Ala Gly Phe Asp Leu Ser
            645                 650                 655

Val Phe Glu Leu Phe Ala Pro Leu Ala His Gly Gly Thr Val Val Leu
        660                 665                 670

Ala Asp Ser Ala Leu His Val Pro Ala Leu Pro Trp Ala Pro Ala Ala
        675                 680                 685

Thr Leu Leu Asn Thr Val Pro Ser Ala Ala Ala Leu Leu Asp Ala
        690                 695                 700

Asp Gly Leu Pro Asp Gly Leu Thr Ala Val Asn Leu Ala Gly Glu Pro
705                 710                 715                 720

Leu Thr Ala Glu Leu Val Ala Arg Leu His Ala Arg Leu Pro Lys Ala
            725                 730                 735

Ala Val Arg Asn Leu Tyr Gly Pro Ser Glu Ala Thr Thr Tyr Ala Thr
            740                 745                 750

Ala Ala Leu Val Pro Ala Gly Gly Thr Glu Ala Pro Ala Ile Gly Arg
        755                 760                 765

Ala Leu Gly Ala Ala Arg Val Trp Thr Ala Asp Asp Arg Gln Arg Pro
        770                 775                 780

Leu Pro Gly Ala Val Val Gly Glu Leu Leu Ile Gly Gly Thr Ala Pro
785                 790                 795                 800

Ala Arg Gly Tyr Leu Gly Arg Pro Gly Pro Thr Ala Asp Ala Phe Arg
            805                 810                 815

Pro Asp Pro Thr Gly Pro Pro Gly Ser Arg Leu Tyr Arg Thr Gly Asp
            820                 825                 830

Leu Ala Val Arg Arg Pro Asp Gly Arg Phe Val Phe Leu Gly Arg Lys
        835                 840                 845

Asp Glu Gln Ile Lys Leu Arg Gly Val Arg Ile Glu Pro Gly Glu Val
        850                 855                 860

Glu Ala Ala Leu Arg Gln Cys Ala Pro Val Ala Ala Ala Val Val
865                 870                 875                 880

Leu Ala Gly Thr Thr Ala Glu Asn His Arg Leu Val Gly Phe Val Thr
            885                 890                 895

Pro Ser Pro Gly Ala Arg Val Asp Pro Glu Arg Thr Leu Ala Ala Leu
        900                 905                 910

Arg Ser Arg Leu Pro Ala Ala Leu Val Pro Ala Ala Leu Val Val Cys
        915                 920                 925

Asp Ala Leu Pro Leu Thr Ala Asn Gly Lys Thr Asp Arg Ala Ala Leu
        930                 935                 940

Ala Arg Arg Ala Arg Gly His Arg Pro Asp His Gly Ala Tyr Ala Pro
945                 950                 955                 960

Pro Arg Thr Arg Val Glu Lys Ala Val Ala Ala Ile Trp Arg Glu Val
            965                 970                 975

Leu Gly Thr Glu Arg Val Gly Ile His Gln Gly Phe Phe Asp Ala Gly
            980                 985                 990

Gly Thr Ser Leu Ser Leu Leu Arg Leu His His Arg Leu Val Ala Ser
        995                 1000                 1005

Val His Pro Gly Leu Arg Leu Ala Asp Val Phe Arg Leu Pro Thr Val
    1010                 1015                 1020

Ala Ala Leu Ala Ala Phe Val Asp Gly Gln Glu Asp Ala Arg Glu Thr
1025                 1030                 1035                 1040
```

```
Ala Val Gly Asp Ala Ala Leu Arg Ala Gly Arg Arg Ala Ala Val
            1045                1050                1055

Ala Ala Arg Arg Arg Lys Gly Gly Arg
        1060                1065

<210> SEQ ID NO 99
<211> LENGTH: 1841
<212> TYPE: PRT
<213> ORGANISM: Streptomyces verticillus
<220> FEATURE:
<223> OTHER INFORMATION: ORF24

<400> SEQUENCE: 99

Met Ser His Ala Asp Ala Gly Asp Gly Leu Asp Ala Ala Asp Thr Thr
  1               5                  10                  15

Asp Ala Ala Asp Gly Ile Ala Val Ile Ser Leu Gly Gly Arg Phe Pro
             20                  25                  30

Gly Ala Asp Arg Val Asp Arg Leu Trp Thr Asn Leu Leu Asp Arg Glu
         35                  40                  45

Asp Ala Ile Ser His Phe Thr Ala Asp Glu Arg Leu Ala Arg Gly Arg
     50                  55                  60

Asp Pro Glu Leu Val Arg His Pro Arg Phe Val Gly Ala Glu Gly Val
 65                  70                  75                  80

Leu Gly Asp Val Ser Leu Phe Asp Ala Glu Phe Phe Gly Cys Ser Pro
                 85                  90                  95

Arg Glu Ala Glu Val Met Asp Pro Gln His Arg Leu Cys Leu Glu Glu
            100                 105                 110

Ala Trp His Val Phe Asp Thr Ala Gly Tyr Asp Pro Ala Ala Thr Gly
        115                 120                 125

Thr Ala Val Gly Val Phe Leu Ser Ala Ser Leu Ser Ser Tyr Leu Ile
    130                 135                 140

Arg Asn Val Leu Pro Gly Gly Ala Ala Gln Arg Leu Leu Gly Gly Phe
145                 150                 155                 160

Pro Leu Leu Ile His Asn Asp Lys Asp Phe Leu Ala Thr Thr Val Ser
                165                 170                 175

His Lys Leu Gly Leu Thr Gly Pro Ser Tyr Ala Val Gly Ser Ala Cys
            180                 185                 190

Ser Ser Ser Leu Val Ala Val His Leu Ala Cys Gln Ser Leu Leu Thr
        195                 200                 205

Glu Glu Cys Asp Met Ala Leu Ala Gly Gly Val Ser Leu Gln Val Pro
    210                 215                 220

Gln Gly Gln Gly Tyr Val His Ala Asp Gly Ile Tyr Ser Pro Asp
225                 230                 235                 240

Gly Arg Cys Ala Pro Phe Asp Ala Gly Ala Gly Thr Val Gly Gly
                245                 250                 255

Ser Gly Val Gly Leu Val Leu Leu Lys Arg Leu Ala Asp Ala Val Arg
            260                 265                 270

Asp Gly Asp Arg Val His Ala Val Ile Leu Gly Ser Ala Val Asn Asn
        275                 280                 285

Asp Gly Ala Asp Lys Val Gly Tyr Thr Ala Pro Gly Val Thr Gly Gln
    290                 295                 300

Ser Ala Val Val Ala Glu Ala Leu Ala Val Ala Gly Ile Ser Ala Ala
305                 310                 315                 320

Thr Val Gly Val Leu Glu Ala His Gly Thr Gly Thr Arg Leu Gly Asp
                325                 330                 335
```

```
Pro Val Glu Val Ala Ala Leu Thr Arg Ala Phe Arg Ala His Thr Asp
                340                 345                 350

Arg Ser Gly Phe Cys Ala Leu Gly Ser Val Lys Ala Asn Val Gly His
            355                 360                 365

Leu Asp Ala Ala Ala Gly Val Thr Gly Leu Ile Lys Ala Val Leu Ala
        370                 375                 380

Val Arg Glu Gly Val Ile Pro Gly Thr Pro His Tyr Arg Ser Pro Asn
385                 390                 395                 400

Pro Ala Ile Asp Phe Ala Thr Thr Pro Phe Tyr Val Thr Ala Asp Thr
                405                 410                 415

Leu Ala Trp Pro Glu Ala Asp His Pro Arg Arg Ala Gly Val Ser Ser
                420                 425                 430

Phe Gly Ile Gly Gly Thr Asn Ala His Val Ile Leu Glu Gln Ala Pro
            435                 440                 445

Pro Ala Ala Pro Arg Ala Asp Arg Thr Ala Gly Val Pro Met Pro Leu
        450                 455                 460

Val Val Ser Ala Arg Thr Arg Glu Ala Leu Ala Glu Ala Val Arg Asp
465                 470                 475                 480

Leu Ala Ala Trp Ser Ala Pro Glu Pro Gly Thr Arg Leu Ala Asp Leu
                485                 490                 495

Ala Ala Thr Leu Ala Gly Arg Arg Ala Phe Pro Tyr Arg Ala Ala Val
            500                 505                 510

Val Cys His Asp Leu Pro Glu Ala Ala Arg Leu Leu Gly Gly Ala Arg
        515                 520                 525

Gly Glu Thr Ala Leu Pro Gly Arg Glu Ala Val Phe Leu Phe Pro Gly
530                 535                 540

Gln Gly Thr Leu Pro Pro Asp Thr Gly Arg Gly Leu Tyr Ala Asp Val
545                 550                 555                 560

Pro Ala Phe Arg Ala His Phe Asp Ala Cys Ala Glu Gly Phe Ala Pro
                565                 570                 575

Leu Gly Thr Asp Leu His Ala Ala Leu Gly Ala Pro Ala Asp Asp Thr
                580                 585                 590

Arg Ala Ala Gln Pro Ala Leu Phe Ala Val Glu Tyr Ala Leu Ala Arg
            595                 600                 605

Thr Leu Met Asp Trp Gly Val Arg Pro Ala Ala Met Leu Gly His Ser
        610                 615                 620

Leu Gly Glu Tyr Val Ala Ala Thr Leu Ala Gly Val Leu Ser Leu Pro
625                 630                 635                 640

Asp Ala Leu Thr Leu Val Arg Ala Arg Ala Glu Ala Gln His Thr Met
                645                 650                 655

Pro Pro Gly Arg Met Leu Ala Val Pro Leu Thr Pro Asp Asp Leu Arg
            660                 665                 670

Pro Leu Leu Pro Pro Glu Val Glu Phe Ser Ala Phe Asn Ala Pro Gly
        675                 680                 685

Arg Cys Val Val Gly Gly Pro Pro Glu Pro Val Ala Glu Leu Arg Ala
690                 695                 700

Arg Leu Ala Arg Arg Gly Val Pro Ala Ala Glu Leu Ala Thr Ala His
705                 710                 715                 720

Ala Phe His Ser Ala Ala Val Glu Pro Leu Leu Asp Gly Phe Arg Gly
                725                 730                 735

Val Leu Glu Gly Val Arg Leu Arg Pro Pro Arg Leu Arg Tyr Val Ser
            740                 745                 750
```

-continued

```
Ser Leu Thr Gly Asp Trp Ala Asp Ala Val Thr Thr Pro Ala Tyr
        755                 760                 765

Trp Leu Ala His Leu Arg Arg Pro Val Arg Phe Ala Asp Gly Leu Arg
        770                 775                 780

Arg Cys Leu Asp Leu Gly Pro Val Ala Leu Val Glu Thr Gly Pro Arg
785                 790                 795                 800

Ala Gly Leu Thr Gly Leu Ala Arg Arg Ala Ala Gly Pro Gly Glu Pro
                805                 810                 815

Pro Tyr Thr Val Arg Cys Leu Ala Ala Pro Asp Glu Ala Ala Ser Leu
                820                 825                 830

Thr His Ala Val Ala Val Leu Trp Arg Ser Gly Cys Ala Val Asp Trp
            835                 840                 845

Thr Ala Phe His Arg Pro Gly Arg Pro Arg Thr Thr Val Pro Gly
850                 855                 860

Tyr Pro Phe Gln Arg Val Arg His Trp Ile Asp Ala Pro Asp Glu Ser
865                 870                 875                 880

Glu Pro Thr Asp Leu Ala Thr Ala Leu Arg Ala Glu Leu Arg Thr Asp
                885                 890                 895

Gly Asp Pro Pro Leu Ala Val Asp Gln Arg Pro Gly Leu Arg Thr Gly
                900                 905                 910

Leu Asn Arg Leu Cys Ala Ala Leu Ala Arg Asp Tyr Leu Ala Thr Gly
            915                 920                 925

Val Glu Ala Ser Gly Val Leu Pro Gly Phe His Arg Phe Leu Asp Tyr
    930                 935                 940

Leu Arg Thr Leu Ala Ala Ser Ala Pro Ala Ala Asp Asp Ala Gly Thr
945                 950                 955                 960

Ile Ala Ala Glu Ile Thr Ala Ala His Pro Ser Phe Ser Gly Leu Val
                965                 970                 975

Asp Leu Leu Arg His Cys Ala Gln Gly Tyr Pro Arg Ala Leu Ser Thr
                980                 985                 990

Pro Gly Ala Ala Leu Asp Val Leu Tyr Pro Ala Gly Ser Gly Asp Leu
            995                 1000                1005

Leu Arg Arg Thr Leu Gly Glu Gly Thr Ala Asp His Arg Ala Thr Gly
    1010                1015                1020

Arg Leu Thr Arg Leu Ala Gly Ser Leu Leu Asp Arg Leu Ala Ala Asp
1025                1030                1035                1040

Arg Glu Pro Gly Arg Pro Leu Arg Val Leu Glu Ala Gly Ala Gly Ala
                1045                1050                1055

Gly Ser Leu Thr Gln Ala Leu Val Thr Arg Ala Pro Gly Arg Leu Asp
            1060                1065                1070

Tyr His Ala Thr Asp Ile Ser Arg His Phe Val Thr Ala Leu Gly Arg
    1075                1080                1085

Glu Ala Ala Arg Arg Gly Leu Asp Phe Val Arg Ala Arg Val Leu Asp
    1090                1095                1100

Ile Ala Arg Asp Pro Gly Glu Gln Gly Phe Ala Gly Glu Arg Phe Asp
1105                1110                1115                1120

Val Val Cys Gly Leu Asp Val Val His Ala Thr Pro Asp Leu Arg Thr
                1125                1130                1135

Thr Leu Gly His Leu Arg Ser Leu Met Ala Pro Asp Gly Thr Leu Ala
            1140                1145                1150

Leu Ile Glu Thr Thr Ala Asp Asp Pro Trp Leu Thr Met Ile Trp Gly
    1155                1160                1165
```

-continued

```
Leu Thr Asp Gly Trp Trp His His Thr Asp Arg Arg Thr His Gly Pro
    1170                1175                1180
Leu Leu Asp Ala Ala Gly Trp Arg Ala Leu Leu Ala Gly Glu Asp Phe
1185                1190                1195                1200
Ala Thr Ala Asp Val Ile Val Pro Pro Asp Gly Pro Gln Asp Ala Ala
        1205                1210                1215
Leu Leu Leu Ala Arg Gln Thr Pro Arg Pro Ala Ala Ala Ala Pro Ser
        1220                1225                1230
Val Gly Lys Arg Asp Val Gly Thr Trp Cys Tyr Ala Arg Gly Trp Arg
        1235                1240                1245
His Ala Ala Pro Ala Asp Pro Ala Pro Leu Thr Gly Gly Cys Leu Leu
        1250                1255                1260
Leu Gly Asp Gly Asp Thr Ala Lys Ala Val Ala Ser Arg Leu Glu Ala
1265                1270                1275                1280
Leu Gly Val Pro Val Thr Thr Val Gly Gly Gly Arg Pro Pro Gly Pro
        1285                1290                1295
Glu Arg Tyr Arg Glu Leu Val Gly Pro Ala Thr Arg Leu Ala Val Asp
        1300                1305                1310
Leu Trp Pro Leu Arg Asp Ala Ser His Arg Gly Arg Ala Ala Gly Ala
        1315                1320                1325
Ala Gly Val Arg Thr Ala Gln Asp Ala Ala Leu His Asn Leu Leu His
        1330                1335                1340
Leu Ala Arg Ala Phe Gly Ala Leu Glu Glu Arg His Pro Ala Arg Val
1345                1350                1355                1360
Val Thr Val Thr Thr Gly Ala His Asp Val Leu Gly Asp Asp Leu Ala
                1365                1370                1375
His Pro Glu His Ala Thr Val Pro Ala Ala Ala Lys Val Ile Pro Arg
        1380                1385                1390
Glu Tyr Pro Trp Ile Ala Cys Thr Ala Leu Asp Val Glu Pro Gly Leu
        1395                1400                1405
Asp Ala Glu Arg Leu Ala Asp Leu Ile Val Arg Glu Leu Gly Ala Ala
        1410                1415                1420
Arg Glu Thr Thr Val Thr Ala Cys Arg Gly Arg Arg Arg Phe Thr Pro
1425                1430                1435                1440
Cys Pro Val Arg Gln Pro Leu Pro Ala Ala Pro Glu Arg Pro Ala Val
                1445                1450                1455
Arg Pro Gly Gly Val Tyr Leu Val Cys Gly Gly Leu Gly Gly Ile Gly
            1460                1465                1470
Leu His Leu Ala Glu Tyr Leu Gly Arg Ala Arg Thr Thr Val Val Leu
        1475                1480                1485
Thr His Arg Arg Pro Phe Pro Ala Pro Gly Ala Trp Asp Gly Leu Pro
    1490                1495                1500
Ala Gly His Pro Glu Ala Ala Val Val Arg Arg Leu Arg Ser Leu Ala
1505                1510                1515                1520
Ala Thr Gly Ala Thr Val Val Arg Arg Ala Asp Leu Thr Asp His
                1525                1530                1535
Asp Ala Met Arg Ala Leu Ala Asp Glu Val Glu Gln Ala His Gly Pro
            1540                1545                1550
Val Arg Gly Val Val His Ala Ala Gly Val Pro Asp Thr Ala Gly Met
        1555                1560                1565
Ile Gln Arg Arg Asp Arg Ala Gly Thr Asp Ala Ala Leu Ala Ala Lys
    1570                1575                1580
```

```
Leu Thr Gly Thr Leu Val Leu Asp Glu Val Phe Ala His Arg Asp Leu
1585                1590                1595                1600

Asp Phe Leu Val Leu Cys Ser Ser Ile Gly Thr Val Leu His Lys Leu
                1605                1610                1615

Lys Phe Gly Glu Val Gly Tyr Val Ala Gly Asn Glu Phe Leu Asp Ala
            1620                1625                1630

Tyr Ala Ala His Arg Ala Ala Arg Arg Pro Gly Arg Thr Leu Ser Ile
        1635                1640                1645

Ala Trp Thr Asp Trp Arg Glu Ser Gly Met Trp Ala Ala Ala Gln Arg
    1650                1655                1660

Arg Leu Thr Glu Arg Tyr Gly Thr Gly Ala Asp Leu Pro Val Pro Pro
1665                1670                1675                1680

Gly Gly Asp Leu Leu Gly Ala Ile Ser Pro Glu Glu Gly Val Asp Val
                1685                1690                1695

Phe Ala Arg Leu Leu Ala Ala Asp Thr Gly Pro Asn Val Ile Val Ser
            1700                1705                1710

Ala Gln Asp Leu Asp Glu Leu Leu Ala Arg His Ala Ala Tyr Thr Thr
        1715                1720                1725

Asp Asp His Leu Ala Ala Leu Gly Asp Leu Arg Ile Ala Ala Ala Arg
    1730                1735                1740

Asp Arg Ser Ala Pro Ala Ala Pro Tyr Ala Ala Pro His Thr Pro Ala
1745                1750                1755                1760

Gln Arg Arg Ile Ala Gly Trp Tyr Arg Asp Leu Leu Gly Val Glu His
                1765                1770                1775

Val Gly Leu Asp Asp Asp Phe Phe Ala Leu Gly Gly Asp Ser Leu Leu
            1780                1785                1790

Ala Leu Arg Leu Leu Ser Gln Leu Arg Asp Ala Tyr Gly Val Glu Ile
        1795                1800                1805

Ser Val Ala Arg Met Phe Asp Glu Pro Thr Val Ala Ala Leu Ala Ala
    1810                1815                1820

Ala Thr Gly Pro Pro Pro Glu Glu Thr Pro Gly Gln Glu Glu Val Val
1825                1830                1835                1840

Leu

<210> SEQ ID NO 100
<211> LENGTH: 1218
<212> TYPE: PRT
<213> ORGANISM: Streptomyces verticillus
<220> FEATURE:
<223> OTHER INFORMATION: ORF23

<400> SEQUENCE: 100

Met Thr Thr Pro Arg Ile Thr Asp Leu Leu Thr Glu Leu Arg Gly Arg
1               5                   10                  15

Gln Val Thr Leu Thr Ala Asp Gly Asp Arg Leu His Cys Arg Ala Pro
            20                  25                  30

Arg Gly Ala Leu Thr Asp Glu Leu Leu Ala Thr Ile Arg Ala Arg Arg
        35                  40                  45

Asp Glu Leu Leu Ala His Leu Arg Ala Asp Arg Ile Pro Arg His
    50                  55                  60

Asp Gly Pro Ala Pro Leu Ser Phe Ala Gln Glu Arg Leu Trp Leu Leu
65                  70                  75                  80

His Gln Phe His Pro His Asp Ser Ala Tyr Asn Ile Pro Leu His Ile
                85                  90                  95
```

```
Ala Leu Arg Gly Pro Leu Asn Pro Ala Ala Leu Arg Ala Ala Leu Ala
            100                 105                 110
Glu Val Val Arg Arg His Asp Val Leu Arg Thr Arg Tyr Ala Ile Ser
            115                 120                 125
Arg Gly Leu Pro Arg Pro Val Val Glu Pro Ala His Thr Pro Pro Leu
        130                 135                 140
Pro Leu Thr Asp Leu Thr Gly Leu Pro Ala His His Arg Asp Ala Glu
145                 150                 155                 160
Leu Ala Arg Leu Ala Ala Gln Glu Ala Arg Arg Pro Phe Asp Leu Ala
                165                 170                 175
Gln Gly Pro Val Leu Arg Ala Arg Leu Leu Arg Thr Ala Pro Glu Glu
            180                 185                 190
His Arg Leu Leu Leu Thr Arg His His Ile Ala Ser Asp Gly Trp Ser
            195                 200                 205
Leu Asp Ile Leu Leu Arg Glu Leu Gly Thr Phe Tyr Arg Ala Gly Arg
        210                 215                 220
Asp Gly Thr Pro Ala Gly Leu Asp Ala Leu Pro Leu Arg Tyr Ala Asp
225                 230                 235                 240
Phe Ala Ala Tyr Gln Arg Glu Gln Ala Glu Arg Pro Glu Thr Ala Glu
                245                 250                 255
Arg Ser Thr Arg Trp Ala Arg His Leu Arg Gly Ala Pro Ala Thr Leu
            260                 265                 270
Asp Val Leu Gly Pro Pro Ala Glu Pro Ser His Ala Pro Ala Gly
        275                 280                 285
Thr Val Arg Thr Asp Leu Pro Ala Ala Leu Val Thr Gly Leu Arg Gln
290                 295                 300
Leu Gly Gly Arg Ala Arg Thr Thr Leu Phe Pro Leu Leu Ser Ala
305                 310                 315                 320
Phe Gly Leu Ala Leu Ala Gly Pro Pro Gly Pro Tyr Asp Val Met Val
                325                 330                 335
Gly Ile Pro Val Ala Gly Arg Pro Arg Thr Glu Leu Glu Pro Leu Ile
            340                 345                 350
Gly Cys Phe Ala Thr Ile Ala Pro Met Arg Leu Thr Ser Asp Gly Thr
            355                 360                 365
Glu Pro Leu Thr Arg Leu Ala Ala Arg Ala Gln Gln His Val Gln Asp
        370                 375                 380
Ala Leu Asp Gly Pro Asp Val Pro Phe Glu Arg Leu Val His Ala Leu
385                 390                 395                 400
Arg Pro Glu Arg Asp Leu Ala Glu Asn Pro Leu Phe Ser Ala Ser Phe
                405                 410                 415
Ala Phe Gln Asn Thr Pro Arg Thr Ala Val Arg Leu Pro Gly Leu Asp
            420                 425                 430
Ala Glu Val Leu Pro Ser Pro Val Ala Pro Lys Phe Pro Leu Ala
            435                 440                 445
Leu Thr Ala Thr Ala Arg Ala Asp Gly Gly Met Gly Leu Glu Leu Glu
        450                 455                 460
Phe Asp Arg Asp Arg Ile Ala Glu Pro Val Ala Arg Gly Ile Leu Thr
465                 470                 475                 480
Ser Phe His Ala Ala Leu Ala Arg Ala Val Ala Asp Pro Glu Ala Pro
                485                 490                 495
Ala Ala Pro Val Pro Ala Ala Ala Val Asp Arg Arg Pro Gly Arg Glu
            500                 505                 510
```

```
Gly His Glu Cys Leu His Glu Pro Val Ala Arg Ala Ala Ala Arg His
        515                 520                 525

Pro Asp Ala Val Ala Val Ser Cys Gly Gly Thr Gln Leu Ser Tyr Gly
    530                 535                 540

Ala Leu Asp Thr Arg Ala Glu Arg Leu Ala Ala Val Leu Arg Ala His
545                 550                 555                 560

Gly Ala Gly Pro Glu Arg Leu Val Ala Leu Cys Leu Pro Thr Gly Pro
                565                 570                 575

Glu Trp Val Val Gly Ala Leu Ala Ile Leu Lys Ser Gly Ala Ala Tyr
                580                 585                 590

Leu Pro Leu Asp Pro Gly Asp Pro Ala Glu Arg Arg Ala Ser Val Ala
            595                 600                 605

Ala Asp Ala Gly Ala Thr Leu Ile Val Ser Asp Thr Ala Leu Pro Pro
610                 615                 620

Leu His Arg Val Asp Val Thr Ala Thr Leu Pro Asp Gly Ala Pro Glu
625                 630                 635                 640

Pro Thr Ala Arg Ala Val Leu Pro Gly Asn Leu Ala Tyr Ala Val Tyr
                645                 650                 655

Thr Ser Gly Ser Thr Gly Gly Pro Lys Gly Val Leu Val Thr His Ala
                660                 665                 670

Asn Val Thr Gly Leu Leu Ala Ala Cys Arg Glu Ala Leu Pro Ala Leu
        675                 680                 685

Asp Ala Pro Arg Thr Trp Ser Ala Thr His Ser Pro Ala Phe Asp Phe
690                 695                 700

Ser Val Trp Glu Val Trp Gly Pro Leu Thr Ala Gly Gly Arg Leu Val
705                 710                 715                 720

Leu Val Pro Pro Asp Val Ala Arg Ala Pro Asp Glu Leu Trp Asp Thr
                725                 730                 735

Leu Arg Asp Glu Gln Val Glu Val Leu Ser Gln Thr Pro Ser Ala Phe
            740                 745                 750

His His Leu Leu Pro Thr Ala Val Arg Arg Ala Ala Gln Ala Thr Ala
        755                 760                 765

Leu Glu Leu Val Val Leu Gly Gly Glu Ala Cys Glu Pro Ala Arg Leu
770                 775                 780

Thr Pro Trp Trp Asp Ala Leu Gly Asp Arg Arg Pro Ala Val Val Asn
785                 790                 795                 800

Met Tyr Gly Ile Thr Glu Asn Thr Ile His Val Thr Val Arg Arg Met
                805                 810                 815

Thr Ala Ala Asp Arg Ser Gly Ser Pro Val Gly Arg Pro Leu Pro Gly
                820                 825                 830

Gln Arg Ala Asp Leu Leu Asp Pro His Gly Arg Pro Val Ala Pro Gly
            835                 840                 845

Gly Arg Gly Glu Leu Phe Val Gly Gly Val Gly Leu Ala Arg Gly Tyr
    850                 855                 860

Leu Gly Arg Pro Gly Leu Thr Ala Arg Ser Phe Leu Pro Asp Asp Thr
865                 870                 875                 880

Pro Gly Trp Pro Gly Ala Arg Tyr Arg Ser Gly Asp Leu Ala Arg
                885                 890                 895

Leu Leu Pro Asp Gly Gly Leu Asp Tyr Ala Gly Arg Ser Asp Ala Gln
                900                 905                 910

Val Lys Val Arg Gly Tyr Arg Val Glu Pro Ala Glu Thr Glu Ala Ala
        915                 920                 925
```

-continued

Ala Leu Thr His Pro Ala Val Arg His Cys Val Val Pro Arg Gly
         930                 935                 940

Asp Gly Asp Arg Arg His Leu Ala Ala Tyr Val Val Ala Asp Thr Arg
945                 950                 955                 960

Ala Cys Asp Gly Pro Gly Leu Arg Thr His Leu Ala Glu Arg Leu Pro
                965                 970                 975

Arg His Leu Val Pro Ala Ser Val Val Phe Leu Lys Arg Ile Pro Leu
            980                 985                 990

Thr Arg Asn Gly Lys Leu Asp Val Ala Ala Leu Pro Asp Pro Ala Ala
        995                 1000                1005

His Arg Ala Pro Ala Arg Glu Arg Pro Arg Thr Ala Thr Glu Arg Thr
    1010                1015                1020

Leu Thr Arg Leu Leu Ala Ala Leu Leu Lys Ala Pro Pro Glu Thr Ile
1025                1030                1035                1040

Gly Thr His Asp Asn Leu Phe Asp Leu Gly Gly Asp Ser Leu Thr Val
                1045                1050                1055

Thr Gln Phe His Ser Arg Val Val Glu Glu Phe Ala Val Asp Leu Pro
            1060                1065                1070

Val Arg Arg Val Tyr Gln Ala Leu Asp Ile Ala Thr Leu Ala Val Thr
        1075                1080                1085

Val Asp Asp Phe Arg Arg Arg Ala Glu Arg Thr Ala Val Leu Arg Ala
    1090                1095                1100

Leu Ala Ala Ala Glu Ala Met Glu Pro Gly Gly Thr Ala Gly Glu Ser
1105                1110                1115                1120

Gly Gly Asn Pro Glu Glu Ser Ala Ala Thr Ala Arg Gly Pro Ala Val
                1125                1130                1135

Ala Ala Asn Glu Pro Gly Ala Ala Ala Arg Glu Ser Gly Ala Ala Pro
            1140                1145                1150

Val Glu Pro Ala Val Ala Val Gln Glu Ser Ala Ala Thr Lys Gly Glu
        1155                1160                1165

Pro Gly Thr Ala Ala Asn Glu Leu Gly Ala Glu Ala Arg Glu Pro Gly
    1170                1175                1180

Thr Ala Ala Gln Glu Pro Gly Thr Asp Pro Arg Pro Ala Ala Thr
1185                1190                1195                1200

Pro Gln Asp Pro Arg Thr Thr Pro Gln Glu Gly Gln Pro Cys Pro Arg
                1205                1210                1215

Pro Glu

<210> SEQ ID NO 101
<211> LENGTH: 2675
<212> TYPE: PRT
<213> ORGANISM: Streptomyces verticillus
<220> FEATURE:
<223> OTHER INFORMATION: ORF22

<400> SEQUENCE: 101

Met Ser Arg Pro Ala Gly Ile Val Asp Ile Ala Arg Arg His Ala Glu
1               5                   10                  15

Arg Thr Pro Ala Arg Pro Ala Tyr Ala Phe Leu Pro Asp Gly Glu Thr
            20                  25                  30

Glu Ser Val Arg Phe Ser Phe Ala Asp Ile Asp Arg Arg Ala Arg Ala
        35                  40                  45

Val Ala Ala Val Leu Gln Asp Arg Gly Leu Ala Gly Glu Arg Val Leu
    50                  55                  60

-continued

```
Val Ala Tyr Pro Ser Gly Pro Glu Tyr Val Gln Ala Phe Leu Gly Cys
 65              70                  75                  80

Leu Tyr Ala Gly Val Ala Val Pro Cys Asp Glu Pro Arg Ser Gly
             85                  90                  95

Pro Ser Ala Glu Arg Leu Ala Gly Ile Arg Ala Asp Ala Arg Pro Ala
            100                 105                 110

Leu Ala Leu Thr Ala Gly Ala Pro Glu Ala Gly Leu Ala Gly Leu Ala
            115                 120                 125

Thr Leu Asp Val Ala Gly Val Pro Asp Ser Ala Ala Gly Ala Trp Thr
            130                 135                 140

Asp Pro Val Ala Gly Pro Asp Ala Leu Ala Phe Leu Gln Tyr Thr Ser
145                 150                 155                 160

Gly Ser Thr Arg Arg Pro Arg Gly Val Met Val Gly His Gly Asn Leu
                165                 170                 175

Leu Ala Asn Glu Arg Cys Ile Ala Ala Ala Cys Gly His Asp Arg Asp
            180                 185                 190

Ser Thr Phe Val Gly Trp Ala Pro Phe Phe His Asp Met Gly Leu Val
            195                 200                 205

Ala Asn Leu Leu Gln Pro Leu Tyr Leu Gly Ser Leu Ser Val Leu Met
            210                 215                 220

Pro Pro Met Ala Phe Leu Gln Arg Pro Ala Arg Trp Leu Arg Ala Val
225                 230                 235                 240

Ser Arg Tyr Arg Ala His Thr Ser Gly Gly Pro Asn Phe Ala Tyr Asp
                245                 250                 255

Leu Cys Val Asp Arg Val Gly Glu Asp Glu Arg Ala Gly Leu Asp Leu
            260                 265                 270

Ser Gly Trp Lys Val Ala Tyr Asn Gly Ala Glu Pro Val Arg Ala Asp
            275                 280                 285

Thr Leu Arg Arg Phe Thr Asp Arg Phe Ala Pro His Gly Phe Thr Pro
            290                 295                 300

Gly Ala His Phe Pro Thr Tyr Gly Leu Ala Glu Ala Thr Leu Leu Val
305                 310                 315                 320

Ala Thr Gly Pro Lys Gly Val Pro Pro Arg Thr Leu Thr Ala Asp Arg
                325                 330                 335

Ala Ala Leu Arg Ala Gly Arg Leu Arg Pro Ala Gly Pro Gly Glu Ala
            340                 345                 350

Gly Leu Glu Leu Val Gly Asn Gly Thr Ala Gly Leu Asp Thr Thr Leu
            355                 360                 365

Arg Ile Val Asp Pro Ala Thr Ala Arg Glu Cys Pro Pro Gly Glu Val
            370                 375                 380

Gly Glu Val Trp Val Arg Gly Pro Gly Val Ala Arg Gly Tyr Phe Gly
385                 390                 395                 400

Arg Pro Arg Glu Ser Ala Pro Leu Leu Ala Ala Arg Leu Pro Gly Gly
                405                 410                 415

Glu Gly Pro Tyr Leu Arg Thr Gly Asp Leu Gly Ala Leu His Asp Gly
            420                 425                 430

Glu Leu Phe Leu Thr Gly Arg His Lys Asp Leu Ile Val Ile Arg Gly
            435                 440                 445

Gln Asn His His Pro His Asp Leu Glu Arg Thr Ala Glu Gln Ala His
            450                 455                 460

Pro Ala Leu Arg Pro Thr Cys Ala Ala Ala Phe Ala Val Pro Gly Asp
465                 470                 475                 480
```

-continued

```
Gly Ala Glu Arg Leu Val Leu Val Cys Glu Leu Thr Ser Tyr Arg Ala
                485                 490                 495

Val Asp Pro Ala Ala Val Ala Glu Ala Val Arg Ala Ala Leu Ala Ala
            500                 505                 510

Arg His Gly Val Ala Pro His Thr Leu Val Val Leu Arg Arg Gly Gly
        515                 520                 525

Ile Pro Lys Thr Thr Ser Gly Lys Val Arg Arg Gly His Cys Arg Thr
    530                 535                 540

Ala Tyr Leu Asp Gly Thr Leu Pro Val His Thr Ala Val Arg Leu Pro
545                 550                 555                 560

Ala Gly Glu Glu Gly Thr Glu Ala Leu Pro Leu Thr Thr Asp Pro Gly
                565                 570                 575

Arg Leu Ala Thr Ala Leu Arg Asp Leu Ala Ala His Ala Gly Leu
            580                 585                 590

Ala Gly Pro Leu Pro Gly Thr Asp Glu Pro Val Ser Ala Leu Gly Leu
        595                 600                 605

Asp Ser Leu Ala Ser Leu Arg Leu His His His Val Gln Ser Ala Tyr
    610                 615                 620

Gly Val Thr Leu Pro Val Thr Ala Leu Leu Gly Asp Thr Thr Tyr Arg
625                 630                 635                 640

Arg Leu Ala Glu Leu Thr Leu Ala Ala Pro Arg Pro Ala Arg Ala Pro
                645                 650                 655

Glu Gly Gln Val Thr Gly Val Trp Arg Pro Leu Thr His Gly Gln Arg
            660                 665                 670

Ala Leu Trp Tyr Glu Gln Ala Leu Ala Pro His Ala Ala Ala Tyr His
        675                 680                 685

Leu Val Arg Ala Leu Ala Leu Arg Gly Pro Val Asp Glu Glu Ala Leu
    690                 695                 700

Ala Glu Ala Val Arg Arg Val Val Arg His Pro Ala Leu Arg Thr
705                 710                 715                 720

Arg Phe Ala Leu Arg Asp Gly Glu Pro Ala Arg Arg Thr Glu Pro Tyr
                725                 730                 735

Gly Pro Glu Leu Asp Val Arg Asp Ala Thr Gly Leu Pro Ala Asp Arg
            740                 745                 750

Leu Arg Glu His Leu Ala Ala Ala Gly Asp Arg Pro Phe Asp Leu Ala
        755                 760                 765

Ala Gly Asp Arg Pro Val Arg Leu Thr Leu Tyr Arg Thr Asp Gly Gly
    770                 775                 780

His Ile Leu Leu Leu Val Ala His His Leu Val Ala Asp Phe Trp Ser
785                 790                 795                 800

Leu Val Val Leu Leu Gly Asp Leu Ala Arg Ala His Ala Gly Glu Asp
                805                 810                 815

Leu Pro Pro Ala Pro Glu Gly Asp Pro Gly Asp Glu Ala Thr Asp Ala
            820                 825                 830

Asp Arg Thr Tyr Trp Arg His Arg Leu Ala Asp Ala Pro Pro Ala Leu
        835                 840                 845

Asp Leu Pro Thr Asp Leu Pro His Pro Ala Glu Arg Gly Phe Ala Gly
    850                 855                 860

Ala Thr His Ala Phe Arg Leu Pro Pro Asp Leu Thr Ala Arg Leu Thr
865                 870                 875                 880

Ala Leu Ser Arg Glu Arg His Cys Thr Leu Phe Thr Thr Leu Leu Ala
                885                 890                 895
```

```
Ala His Gln Leu Leu His Arg Leu Thr Gly Gln Asp Asp Leu Val
            900                 905                 910

Val Gly Thr Leu Leu Ala Arg Arg Asp Thr Ala Glu Ala Ala Gly Ala
            915                 920                 925

Val Gly Tyr Leu Val Asn Pro Leu Pro Leu Arg Ser Val Arg Glu Pro
            930                 935                 940

Gly Glu Thr Phe Thr Glu Leu Leu Arg Arg Thr Arg Arg Thr Val Leu
945                 950                 955                 960

Asp Ala Val Ala His Gly Arg His Pro Phe Gly Pro Leu Val Ser Arg
                965                 970                 975

Leu Ala Pro Ala Arg Thr Pro Gly Arg Ala Pro Leu Leu Gln Ser Leu
            980                 985                 990

Phe Val Leu Gln Arg Glu Tyr Gly Asp Glu Ala Asp Gly Tyr Arg Ala
            995                 1000                1005

Leu Ala Leu Gly Val Gly Gly Arg Leu Arg Val Gly Gly Leu Asp Leu
    1010                1015                1020

Glu Ala Leu Ala Leu Pro Arg Arg Trp Ser Gln Leu Asp Leu Ser Leu
1025                1030                1035                1040

Ser Met Ala Arg Leu Gly Asp Gly Leu Thr Gly Val Trp Glu Tyr Arg
            1045                1050                1055

Thr Asp Leu Phe Thr Glu Ala Thr Val Ala Glu Leu Ser Glu Ala Phe
            1060                1065                1070

Val His Leu Leu Arg Ala Ala Val Glu Asp Pro Gly Ala Pro Val Glu
            1075                1080                1085

Thr Leu Pro Leu Thr Gly Gly Arg Glu Thr Gly Pro Arg Arg Gly Pro
            1090                1095                1100

Ser Ala Ala Arg Pro Ala Leu Pro Leu His Arg Leu Val Ala Ala Ala
1105                1110                1115                1120

Ala Arg Arg Asp Pro Ala Arg Thr Ala Val Val Ala Leu Ala Pro Asp
            1125                1130                1135

Gly Thr Ala His His Ile Ser His Gly Ala Leu His Arg Ala Ala Thr
            1140                1145                1150

Thr Leu Ala Ala Arg Leu Arg Arg Glu Gly Ala Gly Pro Glu Arg Pro
        1155                1160                1165

Val Ala Val Leu Val Glu Arg Gly Pro Trp Leu Pro Val Ala Tyr Leu
    1170                1175                1180

Gly Ile Leu His Ala Gly Ala Thr Val Leu Pro Leu Asp Pro Glu Asp
1185                1190                1195                1200

Pro Pro His Arg Leu Ala Arg Thr Ile Ala Asn Ser Gly Ala Arg Leu
            1205                1210                1215

Leu Leu Thr Glu Thr Gly Thr Ala Ser Arg Ala Ala Glu Ala Ala Gly
            1220                1225                1230

Pro Gly Val Arg Ala Leu Thr Val Arg Glu Gly Ala Thr Gly Gly Glu
            1235                1240                1245

Arg Phe Ser Ala Asp Val His Pro Glu Gln Ser Ala Tyr Leu Leu Tyr
    1250                1255                1260

Thr Ser Gly Ser Thr Gly Asp Pro Lys Gly Val Leu Val Pro His Arg
1265                1270                1275                1280

Ala Ile Val Asn Arg Leu Leu Trp Met Gln Glu Thr Tyr Arg Leu Arg
            1285                1290                1295

Pro Gly Glu Arg Val Leu His Lys Thr Pro Val Thr Phe Asp Val Ser
            1300                1305                1310
```

-continued

```
Met Trp Glu Leu Leu Trp Pro Leu Thr Ala Gly Ala Thr Val Val Met
    1315                1320                1325

Ala Arg Pro Gly Thr His Arg Asp Pro Ala Arg Leu Val Arg Arg Ile
        1330                1335                1340

Ala Arg Glu Ala Val Thr Thr Val His Phe Val Pro Ser Met Leu Thr
1345                1350                1355                1360

Pro Phe Leu Thr Glu Leu Ala Arg Gly Thr Thr Arg Leu Pro Ala Leu
            1365                1370                1375

Arg Arg Val Val Cys Ser Gly Glu Glu Leu Pro Ala Ala Ala Val Asn
        1380                1385                1390

Arg Ala Ala Gly Leu Leu Asp Ala Arg Leu Tyr Asn Leu Tyr Gly Pro
            1395                1400                1405

Thr Glu Ala Ala Val Asp Val Thr Ala Trp Pro Cys Arg Pro Pro Glu
    1410                1415                1420

Pro Gly Pro Val Pro Ile Gly Leu Pro Ile Ala Asn Thr Thr Thr Glu
1425                1430                1435                1440

Val Leu Asp Gly Arg Leu Arg Pro Leu Pro Arg Pro Val Pro Gly Glu
            1445                1450                1455

Leu Tyr Leu Gly Gly Ala Cys Leu Ala His Gly Tyr His His Asp Pro
            1460                1465                1470

Ala Leu Thr Ala Ala Arg Phe Leu Pro Ala Pro Gly Gly Gly Arg Arg
    1475                1480                1485

Tyr Arg Thr Gly Asp Leu Val Arg Gln Arg Ala Asp Gly Ala Leu Val
    1490                1495                1500

Phe Arg Gly Arg Thr Asp Asp Gln Val Lys Ile Gly Gly Ile Arg Val
1505                1510                1515                1520

Glu Pro Gly Glu Val Ala Glu Ala Leu Arg Ala Leu Pro Gly Val Ala
            1525                1530                1535

Asp Ala Ala Val Val Pro His Asp Gly Arg Leu Ala Ala Tyr Ala Val
            1540                1545                1550

Ala Asp Pro Val Gly Pro Ala Pro Ala Asp Ala Leu Arg Asp Ala
        1555                1560                1565

Leu Arg Arg Arg Leu Pro Gly His Leu Val Pro Ala Ala Leu Thr Leu
    1570                1575                1580

Leu Asp Arg Leu Pro Leu Thr Pro Ala Gly Lys Leu Asp Arg Arg Ala
1585                1590                1595                1600

Leu Pro His Pro Ser Ala Pro Pro Asp Gly Gly Arg Pro Pro Thr
            1605                1610                1615

Thr Gly Thr Glu Arg Leu Val Ala Arg Val Trp Ala Glu Arg Leu Gly
        1620                1625                1630

Arg Glu Val Val Gly Val Asp Arg Asp Phe Phe Ser Leu Gly Gly Asp
            1635                1640                1645

Ser Val Arg Ala Leu Gly Val Thr Ala Ala Leu Arg Ala Ala Gly Leu
    1650                1655                1660

Pro Val Thr Val Thr Asp Leu Leu Arg Leu Pro Thr Val Ala Ala Leu
1665                1670                1675                1680

Ala Arg His Ala Asp Glu Arg Ala Asp Arg Arg Pro Ala Arg Gln Glu
            1685                1690                1695

Thr Pro Pro Gly Pro Phe Ala Leu Cys Pro Glu Ala Ala Gly Val Pro
            1700                1705                1710

Gly Leu Glu Asp Ala Tyr Pro Met Ser Met Ala Gln Arg Ala Val Leu
    1715                1720                1725
```

-continued

Phe His Arg Asp His Asn Pro Gly Tyr Glu Val Tyr Val Thr Ser Val
    1730                1735                1740

Ala Val Ser Thr Pro Leu Asp Arg Thr Arg Leu Ala Ala Ala Val Asp
1745                1750                1755                1760

Arg Leu Leu Asp Arg His Ala Tyr Leu Arg Ser Ser Phe Asp Leu Val
        1765                1770                1775

Ser His Pro Glu Pro Thr Gln Leu Val Trp Thr His Leu Pro Thr Pro
        1780                1785                1790

Leu Glu Val Val Glu Ser Ser Asp Pro Ala Gly Phe Asp Ala Trp Leu
        1795                1800                1805

His Ala Glu Arg Lys Arg Pro Leu Asp Val Gly Thr Gly Pro Leu Ala
    1810                1815                1820

Arg Phe Thr Ala His Asp Ala Gly Ala Ala Gly Phe Arg Leu Thr Val
1825                1830                1835                1840

Ser Ser Phe Ala Leu Asp Gly Trp Cys Val Ala Thr Val Leu Thr Glu
        1845                1850                1855

Leu Leu Arg Asp Tyr Trp Ser Ala Leu Arg Gly Ala Pro Leu Ser Leu
        1860                1865                1870

Pro Ala Pro Ala Ala Ser Tyr Arg Glu Phe Val Ala Leu Glu Arg Ala
    1875                1880                1885

Ala Gln His Asp Pro Ala His Arg Glu Phe Trp Arg Thr Glu Leu Ala
    1890                1895                1900

Gly Ala Arg Pro His Pro Leu Pro Arg Arg Pro Val Pro Pro Pro Gly
1905                1910                1915                1920

Pro Asp Gly Ile Arg Gln His Arg His Val Val Pro Val Glu Asp Thr
        1925                1930                1935

Val Ala Lys Gly Leu Ser Ala Leu Ala Gly Glu Leu Gly Val Gly Leu
        1940                1945                1950

Lys His Val Leu Leu Gly Val His Leu Arg Val Val Arg Ala Leu Ser
    1955                1960                1965

Gly Asp Pro Asp Val Ile Thr Ala Val Glu Thr His Gly Arg Leu Glu
    1970                1975                1980

Arg His Asp Gly Asp Arg Val Leu Gly Val Phe Asn Asn Ile Leu Pro
1985                1990                1995                2000

Leu Arg Gln Arg Val Asp Gly Gly Ser Trp Ala Asp Leu Ala Arg Ala
        2005                2010                2015

Ala His Ala Ala Glu Ala Arg Thr Gly Glu Tyr Arg Arg Tyr Pro Leu
        2020                2025                2030

Ala Gln Ala Gln Arg Asp His Gly Ala Ala Gly Leu Phe Asp Thr Leu
    2035                2040                2045

Phe Val Phe Thr His Phe His Leu Tyr Arg Ala Leu Ala Asp Leu Asp
    2050                2055                2060

Gly Met Ala Val Ser Asp Leu Arg Ala Pro Asp Gln Thr Tyr Val Pro
2065                2070                2075                2080

Leu Thr Ala His Phe Asn Val Asp Ala Thr Asp Gly Gly Leu Arg
        2085                2090                2095

Leu Leu Leu Glu Ser Asp Pro Arg Glu Phe Pro Asp Glu Gln Val Ala
        2100                2105                2110

Glu Phe Ala Ala Tyr Tyr Arg Arg Ala Leu Arg Ala Ala Asp Ala
    2115                2120                2125

Pro His Arg Pro Tyr Arg Asp Thr Pro Leu Thr Asp Arg Pro Ala Gly
    2130                2135                2140

```
Pro Ala Pro His Arg Ala Glu Arg Ser Val His Ala Leu Phe Ala Ala
2145                2150                2155                2160

Pro Ala Arg Asn His Pro Asp Arg Ile Ala Leu Asp Gly Glu Asp Gly
            2165                2170                2175

Pro Val Ser His Gly Ala Leu Ala Arg Arg Ala Ala Arg Leu Ala Gly
            2180                2185                2190

Thr Leu Arg Ala Ala Gly Ala Gly Pro Asp Thr Val Val Gly Ile Trp
        2195                2200                2205

Ala Pro Arg Arg Ala Asp Ala Val Val Ala Leu Leu Ala Ala Leu His
    2210                2215                2220

Ala Gly Ala Ala Tyr Leu Pro Leu Asp Pro Val His Pro Pro Arg Arg
2225                2230                2235                2240

Gln Arg Gln Val Leu Thr Glu Ala Gly Ala Arg Leu Leu Val Leu Pro
            2245                2250                2255

Ala Gly Leu Asp Thr Pro Leu Arg Ala Cys Gly Leu Pro Val Val Ala
            2260                2265                2270

Pro Asp Asp Leu Gly Ala Pro Ile Ala Pro Val Ser Val His Pro Glu
        2275                2280                2285

Gln Leu Ala Ala Val Met Ala Thr Ser Gly Ser Thr Gly Thr Pro Lys
    2290                2295                2300

Thr Ile Gly Val Pro Gln Arg Ala Leu Ala Gly Tyr Leu Arg Trp Ala
2305                2310                2315                2320

Ile Gly His Tyr Arg Leu Asp Glu Glu Thr Val Ser Pro Val His Ser
            2325                2330                2335

Ser Leu Gly Phe Asp Leu Thr Val Thr Ala Leu Leu Ala Pro Leu Ala
            2340                2345                2350

Ala Gly Gly Gln Ala Arg Leu Thr Asp Ser Gly Asp Pro Gly Ala Leu
        2355                2360                2365

Gly Ala Ala Leu Ala Ala Gly His His Thr Leu Leu Lys Ile Thr Pro
    2370                2375                2380

Ala His Leu Ala Ala Leu Ala His Gln Leu Gly Ala Pro Thr Ala Leu
2385                2390                2395                2400

Arg Thr Val Val Ala Gly Gly Glu Pro Leu His Ala Gly His Val Arg
            2405                2410                2415

Ala Leu Arg Ala Phe Ala Pro Gly Ala Arg Leu Val Asn Glu Tyr Gly
            2420                2425                2430

Pro Thr Glu Thr Thr Val Gly Cys Cys Ala His Asp Val Ala Pro Asp
        2435                2440                2445

Pro Gly Glu Ala Pro Ile Pro Val Gly Thr Pro Ile Ala Gly Leu Ser
    2450                2455                2460

Ala Cys Val Val Asp Asp Ala Leu Pro Ala Pro Pro Gly Val Arg Gly
2465                2470                2475                2480

Glu Leu Tyr Ile Gly Gly Thr Gly Val Thr Arg Gly Tyr Leu Gly Arg
            2485                2490                2495

Pro Ala Thr Ala Ala Ala Tyr Val Pro Asp Pro Ala Ala Pro Gly
            2500                2505                2510

Ala Arg Arg Tyr Arg Thr Gly Asp Leu Ala Arg Arg Leu Pro Asp Gly
        2515                2520                2525

Thr Leu Leu Leu Ala Gly Arg Ala Asp Arg Gln Val Lys Ile Arg Gly
    2530                2535                2540

His Arg Val Glu Pro Gly Glu Val Glu Gln Val Leu Gly Gly His Pro
2545                2550                2555                2560
```

```
Gly Val Arg Glu Ala Val Val Ala His Pro Ala Pro Gly Gly Gly
            2565                2570                2575

Arg Arg Leu Val Ala Tyr Trp Val Pro Ala Glu Pro Ala Arg Pro Pro
        2580                2585                2590

Ser Ala Asp Ala Leu Thr Ala Leu Ala Asp Arg Leu Pro Pro Tyr
        2595                2600                2605

Ala Val Pro Ala Glu Leu Val Arg Leu Pro Ala Leu Pro Thr Thr Pro
    2610                2615                2620

Asn Gly Lys Val Asp His Thr Arg Leu Pro Ala Ala Gly Arg Asp Arg
2625                2630                2635                2640

Arg Leu Ala Glu Leu Leu Asp Arg Ile Glu Ala Leu Ser Asp Ala Glu
            2645                2650                2655

Ala Ala Ser Ala Leu Arg Asp Ser Arg Pro Ala Pro Gly Ser Gly Asp
            2660                2665                2670

Asp Arg Ala
    2675

<210> SEQ ID NO 102
<211> LENGTH: 645
<212> TYPE: PRT
<213> ORGANISM: Streptomyces verticillus
<220> FEATURE:
<223> OTHER INFORMATION: ORF21

<400> SEQUENCE: 102

Met Arg Gly His Asp Asp Arg Val Gly Arg Leu Ser Ala Asp Trp Ser
  1               5                  10                  15

Val Pro Pro Thr Arg Leu Pro Ala Gly Asp Pro Ala Gly Ser Val Gly
                 20                  25                  30

Pro Gly Gly Gly Pro Pro Val Pro His Glu Glu Val Thr Met Ser Glu
             35                  40                  45

Tyr Asp Asp Arg Leu Ala Arg Leu Ser Asp Asn Gln Arg Ala Leu Leu
         50                  55                  60

Asp Arg Trp Leu Ala Glu Asp Pro Ala Gly Ala Gly Pro Leu Arg
 65                  70                  75                  80

Pro Asp Gly Arg Pro Arg Thr Glu Ala Glu Arg Ile Leu Ala Gly
                 85                  90                  95

Val Trp Glu Glu Val Leu Glu Thr Gly Gly Ile Gly Ala Asp Asp Asp
            100                 105                 110

Tyr Phe Ala Leu Gly Gly Asp Ser Val His Ala Ile Val Ile Val Ala
        115                 120                 125

Lys Ala Arg Gln Ala Gly Leu Ala Leu Thr Ala His Asp Leu Phe Glu
130                 135                 140

Ala Arg Thr Leu Ala Ala Val Ala Arg Arg Ala Ala Pro Ala Gly Pro
145                 150                 155                 160

Ala Glu Pro Val Pro Asp Ala Gly Gly Ala Val Arg Tyr Pro Leu
                165                 170                 175

Thr Pro Met Gln Gln Gly Met Leu Tyr His Ser Ala Gly Ser Thr
            180                 185                 190

Pro Gly Ala Tyr Val Val Gln Val Cys Cys Arg Leu Thr Gly Asp Leu
        195                 200                 205

Asp Val Ala Ala Phe Arg Thr Ala Trp Gln Ala Val Leu Ser Ala Asn
    210                 215                 220

Pro Ala Leu Ala Val Ser Phe His Trp Ser Asp Gly Ser Pro Pro Glu
225                 230                 235                 240
```

```
Gln Val Val Asp Pro Asp Ala Arg Val Thr Val Asp Thr Ala Asp Trp
                    245                 250                 255

Arg Asp Arg Thr Pro Ala Glu Arg Asp Asp Ala Phe Ala Arg Phe Leu
                260                 265                 270

Asp Thr Asp Arg Ala Ala Gly Phe Asp Leu Ala Arg Ala Pro Leu Met
            275                 280                 285

Arg Leu Thr Leu Phe Arg Glu Gly Glu His Ala Tyr Arg Cys Val Trp
        290                 295                 300

Thr His His His Leu Val Leu Asp Gly Trp Ser Gln Gln Leu Val Leu
305                     310                 315                 320

Arg Asp Val Leu Asp Cys Tyr Met Arg Leu Arg Ala Gly Arg Gly Ala
                325                 330                 335

Glu Pro Pro Ala Arg Pro Ser Phe Thr Gly His Leu Arg Arg Leu Glu
            340                 345                 350

Arg Gln Asp Gly Ile Asp Glu Glu Phe Trp Arg Asp His Leu Gly Gly
        355                 360                 365

Leu Pro Ala Pro Ser Arg Val Ala Gly Pro Gly Cys Arg Asp Gly Arg
    370                 375                 380

Val Val Ala Val Arg Arg Ala Glu His Arg His Arg Val Ser Ala Ala
385                 390                 395                 400

Thr Gly Arg Glu Leu Thr Gly Phe Cys Arg Arg His Gly Leu Thr Pro
                405                 410                 415

Ala Ala Val Leu His Gly Gly Trp Ala Val Leu Leu Ser Leu His Cys
            420                 425                 430

Gly Gln Asp Asp Val Val Phe Gly Thr Thr Leu Ser Gly Arg Pro Glu
        435                 440                 445

Asp Leu Pro Gly Val Thr Glu Cys Val Gly Leu Phe Ile Asn Thr Leu
    450                 455                 460

Pro Leu Arg Val Arg Cys Gly Glu Asp Thr Asp Val Val Asp Trp Leu
465                 470                 475                 480

His Gly Val Gln Ser Asp Leu Ala Ala Leu Trp Asp His Ala His Val
                485                 490                 495

Pro Leu Ser Arg Val Glu Arg Gly Leu Gly Leu Gly Arg Gly Gly Gly
            500                 505                 510

Leu Phe Asp Ser Ile Met Val Val Glu Asn Phe Pro Ala Ala Val Ala
        515                 520                 525

Asp Gly His Glu Ala Gly Gly Leu Arg Val Thr Glu Pro Arg Ala Leu
    530                 535                 540

Val Asp Glu Gly Tyr Pro Leu Val Leu Glu Ala Thr Thr Gly Asp Arg
545                 550                 555                 560

Pro Val Leu His Ala Arg Tyr Asp Pro His Arg Leu Ala Gly Gly Arg
                565                 570                 575

Val Gln Ala Leu Leu Ala Ala Phe Asp Asp Tyr Leu Arg Ala Val Thr
            580                 585                 590

Ala Asp Pro Ala Arg Pro Leu Pro Asp Leu Arg Ala Val Leu Ala Arg
        595                 600                 605

Asp His Ala Arg Arg Asp Gly Ala Ala Arg Gly Arg Arg Ala Ala
    610                 615                 620

Asp Arg Thr Arg Leu Thr Leu Ala Arg Arg Pro Ala Thr Thr Thr
625                 630                 635                 640

Glu Gly Glu Thr Pro
                645
```

<210> SEQ ID NO 103
<211> LENGTH: 325
<212> TYPE: PRT
<213> ORGANISM: Streptomyces verticillus
<220> FEATURE:
<223> OTHER INFORMATION: ORF20

<400> SEQUENCE: 103

```
Met Thr Trp Thr Val Val Thr Gly Ala Gly Gly Phe Ile Gly Ser His
  1               5                  10                  15

Leu Val Arg Arg Leu Val Arg Asp Gly His Arg Val Arg Gly Val Asp
                 20                  25                  30

Leu Val Pro Pro Arg Tyr Gly Pro Gly Glu Ala Gln Glu Phe Val Ile
             35                  40                  45

Ala Asp Leu Arg Asp Ala Ala Gln Ala Ala Arg Ala Val Ala Gly Ala
         50                  55                  60

Asp Ser Val Phe Ala Leu Ala Ala Asn Met Gly Ile Gly Trp Thr
 65                  70                  75                  80

His Thr Ala Pro Ala Glu Ile Leu His Asp Asn Leu Leu Ile Ser Thr
                 85                  90                  95

His Thr Ile Glu Ala Cys Arg Ala Ala Gly Val Arg Thr Thr Val Tyr
            100                 105                 110

Thr Ser Ser Ala Cys Val Tyr Pro Ala Ser Leu Gln Arg Glu Pro Asp
        115                 120                 125

Ala Ala Pro Leu Ala Glu Asp Pro Val Phe Pro Ala Glu Pro Asp Met
130                 135                 140

Glu Tyr Gly Trp Glu Lys Leu Thr Thr Glu Ile Leu Cys Gly Ala Tyr
145                 150                 155                 160

Arg Arg Ser His Gly Met Asp Ile Lys Thr Ala Arg Leu His Ala Ile
                165                 170                 175

Tyr Gly Pro Leu Gly Thr Tyr Thr Gly Pro Arg Ala Lys Ser Leu Ser
            180                 185                 190

Met Leu Cys Asp Lys Val Ala Arg Ile Pro Gly Asp Glu Gly Glu Ile
        195                 200                 205

Glu Val Trp Gly Asp Gly Thr Gln Thr Arg Ser Tyr Cys Tyr Val Asp
210                 215                 220

Asp Cys Val Glu Gly Leu Ile Arg Leu Ala Arg Ser Asp Val Ala Glu
225                 230                 235                 240

Pro Val Asn Ile Gly Ser Glu Glu Arg Val Asp Ile Ala Ser Leu Val
                245                 250                 255

Glu Arg Ile Ala Gly Val Ala Gly Lys Lys Val Arg Cys Ala Phe Ala
            260                 265                 270

Pro Asp Arg Pro Val Gly Pro Arg Gly Arg Val Ser Asp Asn Thr Arg
        275                 280                 285

Cys Arg Glu Leu Leu Gly Trp Ala Pro Glu Thr Ser Leu Ala Ala Gly
290                 295                 300

Leu Glu Arg Thr Tyr Pro Trp Ile Glu Arg Gln Val Leu Ala Glu Ala
305                 310                 315                 320

Gly Arg Ala Asp Ala
                325
```

<210> SEQ ID NO 104
<211> LENGTH: 494
<212> TYPE: PRT
<213> ORGANISM: Streptomyces verticillus
<220> FEATURE:
<223> OTHER INFORMATION: ORF19

<400> SEQUENCE: 104

```
Met Lys Asp Leu Gly Arg Leu Leu Gly His Ala Ala Arg Phe Arg
 1               5                  10                  15

Gly Arg Glu Leu Gln Asp Val Ala Thr Arg Ala Leu Arg Ala Ser Gly
                20                  25                  30

Gly Glu Asn Ala Trp Val Val Ser Val Asn Thr Ser Leu Arg Ala
            35                  40                  45

Arg Gln Ala Val Asp His Ala Leu Arg Leu Ala Pro Arg Arg Gly Leu
        50                  55                  60

Ser Arg Leu Arg Tyr Pro Phe Ser Ala His His Thr Ala Thr Pro
 65              70                  75                  80

Pro Arg Thr Leu Ser Leu Leu Cys Pro Thr Arg Glu Arg Val Gly Asn
                85                  90                  95

Val Glu Arg Phe Leu Asp Ser Val Ala Arg Thr Ala Ala Pro Gly
            100                 105                 110

Arg Ile Glu Ala Leu Phe Tyr Val Asp Asp Asp Pro Gln Leu Pro
            115                 120                 125

Ala Tyr His Glu Leu Phe Glu His Ala Arg Trp Arg Tyr Gly Arg Ile
        130                 135                 140

Gly Arg Cys Ala Leu His Val Gly Ala Pro Val Gly Val Pro His Ala
145                 150                 155                 160

Trp Asn His Leu Ala Arg Asn Ala Ala Gly Asp Val Leu Met Met Ala
                165                 170                 175

Asn Asp Asp Gln Leu Tyr Ile Asp Tyr Gly Trp Asp Thr Ala Leu Asp
            180                 185                 190

Ala Arg Val Thr Glu Leu Ser Ala Leu His Pro Asp Gly Val Leu Cys
        195                 200                 205

Leu Tyr Phe Asp Asp Gly Gln Tyr Pro Glu Gly Gly Cys Asp Phe Pro
210                 215                 220

Met Val Thr Arg Pro Trp Tyr Gly Thr Leu Gly Tyr Phe Thr Pro Thr
225                 230                 235                 240

Ile Phe Gln Gln Trp Glu Val Glu Lys Trp Val Phe Asp Ile Ala Asp
                245                 250                 255

Arg Leu His Arg Leu Tyr Pro Val Pro Gly Val Leu Val Glu His Arg
            260                 265                 270

His Tyr Gln Asp Tyr Lys Ala Pro Phe Asp Ala Thr Tyr Gln Arg His
        275                 280                 285

Arg Met Thr Arg Glu Lys Ser Phe Ala Asp His Ala Leu Phe Leu Arg
        290                 295                 300

Thr Glu Pro Asp Arg Glu Ala Glu Thr Asp Arg Leu Arg Ala Val Ile
305                 310                 315                 320

Ala Arg Ala Gly Asn Thr Pro Asp Ala Asp His Ala Asp His Ala Val
                325                 330                 335

His Asp Ala Glu Thr Phe Trp Phe Thr Gly Leu Leu Arg Glu Ser His
            340                 345                 350

Ala Lys Leu Leu Ala Glu Leu Asp Asp Ala Pro Gly Pro Ala Ala Gly
        355                 360                 365

Ala Val Leu Phe Ala Asp Gly Ser Trp Thr Gly Val Ala Tyr Arg Thr
        370                 375                 380

His Pro Leu Ala Thr Ala Leu Leu Ala Ser Ile Pro Glu Ala Thr Leu
385                 390                 395                 400

Asp Ser Gly Arg Ala Asp Leu Leu Val Val Pro Pro Gly Ala Ser His
                405                 410                 415
```

```
His His Pro Asp Gly Thr Val Asp Ser Ala Phe Gly Ser Asp Ala Gly
            420                 425                 430

Leu Arg Val Leu Phe Gly Leu Arg Val Pro Asp Ala Ala Gln Leu Arg
        435                 440                 445

Val Gly Asp Gly Pro Val Pro Trp Gly Asn Gly Gln Cys Leu Ile His
450                 455                 460

Asp Thr Ala Ala Pro Ser Thr Leu Arg Asn Asp Gly Thr Glu Ser Leu
465                 470                 475                 480

Ala Ala Leu Thr Phe Val Val Pro Arg Pro Ala Pro Gly Glu
                485                 490

<210> SEQ ID NO 105
<211> LENGTH: 638
<212> TYPE: PRT
<213> ORGANISM: Streptomyces verticillus
<220> FEATURE:
<223> OTHER INFORMATION: ORF18

<400> SEQUENCE: 105

Met Arg Pro Val Cys Gly Ile Val Ala Ile Arg Ser Ala Asp Gly Gly
1               5                   10                  15

Leu Asp Gly Gly Glu Leu Thr Ala Pro Met Ala Asp Leu Arg Pro Arg
            20                  25                  30

Gly Pro Asp Gly Glu Gly Thr Trp Val Ser Pro Thr Gly Arg Ala Ala
        35                  40                  45

Leu Gly His Thr Arg Leu Ala Val Ile Ala Pro Asp Ala Gly Arg Gln
    50                  55                  60

Pro Val Ala Gly Pro Asp Gly Thr Val Arg Leu Val Val Asn Gly Glu
65                  70                  75                  80

Phe Tyr Gly Tyr Arg Glu Ile Arg Ala Glu Leu Arg Ala Ala Gly Cys
                85                  90                  95

Arg Phe Arg Thr Gly Ser Asp Ser Glu Ile Ala Leu His Leu Tyr Leu
            100                 105                 110

Arg Asp Gly Arg Arg Ala Leu Glu Arg Leu Arg Gly Glu Phe Ala Phe
        115                 120                 125

Val Leu Trp Asp Glu Arg Arg Ala Thr Leu Phe Ala Ala Arg Asp Arg
130                 135                 140

Phe Gly Val Lys Pro Leu Tyr Tyr Thr Glu Arg Asp Gly Arg Leu Tyr
145                 150                 155                 160

Val Ala Ser Thr Val Arg Ala Leu Leu Ser Cys Gly Ala Pro Ala Arg
                165                 170                 175

Trp Asp Thr Ala Ala Phe Ala Ala His Leu Gln Leu Gly Leu Pro Pro
            180                 185                 190

Asp Arg Thr Leu Phe Ala Gly Ile Arg Gln Leu Pro Pro Gly Cys His
        195                 200                 205

Leu Ile Ala Asp Ala His Gly Thr Arg Val Thr Pro Tyr Trp Asp Leu
    210                 215                 220

Asp Tyr Pro Pro Ala Gly Glu Leu Ala Arg Gly Ser Leu Asp Asp
225                 230                 235                 240

His Leu Asp Ala Val Arg Glu Arg Thr Asp Glu Ala Val Arg Leu Arg
                245                 250                 255

Thr Val Ala Asp Val Pro Leu Ala Cys His Leu Ser Gly Gly Leu Asp
            260                 265                 270

Ser Ser Ala Val Ala Ala Ser Ala Ala Arg His Thr Arg Leu Thr Ala
        275                 280                 285
```

```
Phe Thr Val Arg Phe Asp Asp Pro Ala Phe Asp Glu Ser Ala Val Ala
    290                 295                 300

Arg Arg Thr Ala Ala His Leu Ala Ile Asp His Arg Glu Val Ala Ser
305                 310                 315                 320

Glu Arg Ala His Phe Ala Asp His Leu Arg Asp Val Val Arg Ala Gly
                325                 330                 335

Glu Met Val Gln Glu Asn Ser His Gly Ile Ala Arg Tyr Leu His Ser
            340                 345                 350

Ala His Ile Lys Lys Ala Gly Phe Thr Ala Val Leu Ala Gly Glu Gly
        355                 360                 365

Gly Asp Glu Leu Phe Leu Gly Tyr Pro Gln Phe Arg Lys Asp Leu Thr
    370                 375                 380

Leu Ser Leu Ser Ala Asp Ala Arg Asp Lys Ala Asp Arg Gly Tyr Ala
385                 390                 395                 400

Arg Leu Val Ala Ala Gly Leu Leu Pro Pro Tyr Leu Arg Thr Leu Leu
                405                 410                 415

Gly Thr Leu Gly Phe Leu Pro Ser Trp Ile Val Asp Arg His Leu Ala
            420                 425                 430

Val Thr Gln Pro Val Ala Ala Leu Leu Arg Pro Asp Phe Ala Ala Glu
        435                 440                 445

Leu Ala Arg Ala Asp Ala Ala Pro Leu Leu Ala Ala Gly Ala Gly
450                 455                 460

Leu Leu Ala Gly Arg Ala Pro Ala His Gln Ala Thr Tyr Leu Phe Ala
465                 470                 475                 480

Lys Thr Trp Leu Pro Gly Tyr Leu Leu Ala Ala Glu Arg Leu Asp Ala
                485                 490                 495

Ala Gln Ala Val Glu Val Arg Leu Pro Leu Phe Asp His His Leu Phe
            500                 505                 510

Asp Leu Val Arg His Thr Pro Pro Ala Trp Tyr Asp Lys Asp Gly Thr
        515                 520                 525

Gly Lys Tyr Pro Leu Arg Ala Ala Met Arg His Arg Leu Pro Arg Glu
    530                 535                 540

Val Thr Glu Gly Arg Lys Gln Gly Phe Leu Ala Pro Pro Met Ala Asp
545                 550                 555                 560

Asp Asp Thr Leu Leu Asp Ala Leu Arg Glu Arg Leu Ala Gly Pro Gly
                565                 570                 575

Ala Gly Asp Asp Pro Phe Phe Asp Pro His Ala Val Arg Ala Leu Leu
            580                 585                 590

Asp Arg Leu Ala Ala Ala Pro Pro Gly Gln Arg Ser Gly Gly Glu Lys
        595                 600                 605

Leu Leu Gln Leu Val Ala Ser Thr Ala Glu Leu Ala Asp Glu Phe Gly
    610                 615                 620

Leu Thr Thr Ala Pro Ser Gly Gln Lys Gly Gly Asn Gly Gly
625                 630                 635
```

<210> SEQ ID NO 106
<211> LENGTH: 2626
<212> TYPE: PRT
<213> ORGANISM: Streptomyces verticillus
<220> FEATURE:
<223> OTHER INFORMATION: ORF17

<400> SEQUENCE: 106

```
Met Leu His Gly Ala Ala His Pro Arg Pro Gly Ile Pro Arg Arg Gly
  1               5                  10                  15
```

```
Ala Thr Ala Ala Pro Ala Ser Tyr Gly Gln Glu Arg Leu Trp Leu Leu
            20                  25                  30

Thr Gly Leu Leu Pro Thr Ala Tyr Asn Tyr Ala Thr Ala Leu Arg Leu
            35                  40                  45

Arg Gly Asp Leu Ser Val Pro Ala Leu Arg Gly Ala Leu Arg Gly Ile
 50                  55                  60

Val Arg Arg His Glu Val Leu Arg Thr Thr Phe Arg Leu Asp Gly Asp
 65                  70                  75                  80

Asp Leu Ile Gln Val Val His Pro Thr Ala Asp Val Pro Val Arg Leu
                 85                  90                  95

Ala Asp Leu Thr Gly Arg Ser Ala Asp Thr Gly Arg Leu Met Arg Glu
            100                 105                 110

Glu Ala Arg Arg Pro Phe Asp Leu Glu His Gly Pro Leu Leu Arg Leu
            115                 120                 125

Thr Leu Phe Arg Leu Gly Pro Arg Asp His Leu Ala Leu Leu Ala Val
130                 135                 140

His His Ala Val Thr Asp Gly Trp Ser Asn Gly Val Leu Val Thr Glu
145                 150                 155                 160

Leu Ala Thr Gly Tyr Arg Glu Leu Arg Ala Gly Arg Pro Asp Arg Arg
                165                 170                 175

Pro Ala Pro Pro Val Gln Tyr Gly Asp Tyr Ala His Trp Gln Arg Glu
            180                 185                 190

Arg Leu Thr Gly Pro Glu Leu Arg Ala Leu Glu Asp Tyr Trp Arg Thr
            195                 200                 205

Ala Val Arg Asp Leu Pro Arg Thr Asp Leu Pro Thr Asp Arg Pro Arg
210                 215                 220

Pro Ala Ala Arg Arg Gly Glu Gly Ala Asn His Ala Leu Leu Leu Ser
225                 230                 235                 240

Pro Glu Leu Thr Gly Arg Leu Ala Asp Leu Arg Arg Glu Gly Gly
            245                 250                 255

Ser Leu Phe Met Leu Val Leu Ser Ala Leu Leu Val Val Leu Arg Gly
                260                 265                 270

Thr Gly Gly Arg Asp Arg Leu Ala Val Gly Thr Leu Val Ala Gly Arg
            275                 280                 285

Thr Arg Pro Glu Leu Glu Pro Leu Ile Gly Tyr Phe Val Asn Val Leu
290                 295                 300

Leu Leu Pro Phe Glu Thr Gly Gly Arg Thr Ser Phe Ala Glu Leu Trp
305                 310                 315                 320

Arg Arg Val Arg Gly Arg Leu Val Glu Ala Tyr Ala His Gln Glu Leu
                325                 330                 335

Pro Leu Glu Lys Ala Leu Glu Leu Leu Arg Ala Asp Gly Thr Ala Pro
            340                 345                 350

Ala Asp Pro Pro Val Gly Val Val Cys Val Ala Gln Gln Pro Ala Pro
            355                 360                 365

Ala Ile Thr Leu Pro Gly Leu Asp Ala Ser Val Glu Asp Val Asp Leu
370                 375                 380

Gly Thr Ala Gln Phe Asp Leu Val Val Glu Val Arg Glu Arg Pro Glu
385                 390                 395                 400

Gly Val Gln Ile Ala Phe Gln Tyr Asp Arg Asp Leu Phe Asp Ala Ala
                405                 410                 415

Thr Val Arg Leu Leu Ala Asp His Val His Ala Val Leu Asp Gln Ala
            420                 425                 430
```

```
Ala Ala Asp Pro Thr Leu Pro Cys Ala Glu Leu Pro Ala Pro Pro Ala
        435                 440                 445

Pro Ala Ala Pro Ala Arg Thr Ala Gly Ala Thr Thr Leu His Ala Leu
    450                 455                 460

Phe Glu Ser Arg Ala Ala Lys Ser Pro Asp Ala Val Ala Leu Val Asp
465                 470                 475                 480

Gly Gly His Arg Val Thr Tyr Arg Thr Leu Asn Thr Arg Ala Asn Arg
                485                 490                 495

Leu Ala Arg His Leu Arg Ala Val Gly Val Arg Thr Glu Asp Arg Val
                500                 505                 510

Ala Leu Arg Leu Pro Arg Gly Thr Asp Ala Val Thr Ala Thr Leu Ala
            515                 520                 525

Ala Leu Lys Ala Gly Ala Ala Tyr Val Pro Leu Asp Pro Ala Leu Pro
        530                 535                 540

Glu Glu Arg Leu Thr Arg Val Leu Ala Asp Ala Arg Pro Ala Val Val
545                 550                 555                 560

Leu Thr Pro Ala Tyr Leu His Asp Arg Ser Ala Glu Ile Thr Ala His
                565                 570                 575

Ala Gly His Asp Leu Asn Leu Pro Val His Pro Asp Asn Leu Ala Tyr
            580                 585                 590

Leu Leu His Thr Ser Gly Ser Thr Gly Thr Pro Lys Gly Val Leu Gly
        595                 600                 605

Thr His Arg Gly Ala Val Asn Arg Val Asp Trp Met Ser Thr Ala Tyr
    610                 615                 620

Pro Phe Arg Thr Gly Asp Val Ala Val Ala Arg Thr Ala Pro Gly Phe
625                 630                 635                 640

Val Asp Ala Val Trp Glu Leu Phe Gly Pro Leu Ala Ala Gly Val Pro
                645                 650                 655

Leu Val Leu Leu Pro Thr Asp Glu Ala Arg Asp Pro Ala Leu Leu Thr
            660                 665                 670

Ala Ala Leu Glu Arg His Arg Val Ser Arg Met Val Thr Val Pro Ser
        675                 680                 685

Leu Leu Thr Met Leu Leu Asp Glu Ser Ala Arg Ala Thr Asp Leu Gly
    690                 695                 700

Thr Arg Leu Ala Cys Leu Arg Thr Trp Ile Thr Ser Gly Glu Pro Leu
705                 710                 715                 720

Pro Pro Ala Leu Ala Arg Arg Phe His Asp Arg Leu Pro Gly Arg Thr
                725                 730                 735

Leu Leu Asn Leu Tyr Gly Ser Ser Glu Thr Ala Ala Asp Ala Thr Ala
            740                 745                 750

Ala Arg Ile Asp Pro Ala Pro Gly Thr Ala Leu Pro Glu Arg Ser Pro
        755                 760                 765

Ile Gly Thr Pro Ile Thr Gly Val Ser Ala Leu Val Arg Gly Pro Asp
    770                 775                 780

Leu Arg Pro Leu Pro Ala Leu Met Pro Gly Glu Leu Tyr Ala Gly Gly
785                 790                 795                 800

Ala Cys Val Ala Arg Gly Tyr His Ala Arg Pro Ala Glu Thr Ala Ala
                805                 810                 815

Ala Phe Pro Pro Asp Pro Asp Gly Gly Pro Gly Ala Arg Met Phe Arg
            820                 825                 830

Thr Gly Asp Arg Ala Arg Leu Arg Ala Asp Gly Arg Leu Glu Leu Leu
        835                 840                 845
```

-continued

```
Gly Arg Val Asp Arg Gln Val Gln Ile Arg Gly Gln Arg Ala Glu Pro
        850                 855                 860
Gly Glu Val Glu His Ala Leu Leu Ala His Pro Ala Val Arg Ala Ala
865                 870                 875                 880
Ala Val Thr Ala Asn Pro Asp Ala Thr Gly Leu Trp Ala Tyr Val Arg
                885                 890                 895
Leu Ala Pro Gly Pro Phe Ala Ala Gly Ser Pro Gln Thr Glu Leu Thr
            900                 905                 910
Ala Phe Leu Arg Arg Thr Leu Pro Ala His Leu Val Pro Thr Ala Val
            915                 920                 925
Thr Val Leu Asp Glu Leu Pro Val Thr Ala His Gly Lys Thr Asp His
        930                 935                 940
Ala Arg Leu Pro Ala Pro Asp Pro Arg Ala Gly Arg Pro Ala Pro Thr
945                 950                 955                 960
Ala Pro Arg Thr Pro Thr Glu Arg Thr Val Ala Asp Val Phe Ala Gly
                965                 970                 975
Val Leu Gly Leu Glu Gly Pro Val Gly Ala His Asp Asp Phe Phe Leu
            980                 985                 990
Leu Gly Gly His Ser Leu Leu Ala Ala Arg Ser Arg Gly Gly Thr Pro
        995                 1000                1005
Arg Pro Pro Arg Arg Pro Asp Arg Ala Glu Arg Arg Leu Arg Gly Pro
    1010                1015                1020
His Arg Arg Arg Ser Val Ala Ala Arg Thr Asp Ala Ala Arg Pro Gly
1025                1030                1035                1040
Thr Gly Pro Glu His Thr Pro Phe Val Thr Asp Pro Gly Ala Arg His
                1045                1050                1055
Glu Pro Phe Pro Leu Thr Asp Val Gln Arg Ala Tyr Tyr Val Gly Arg
            1060                1065                1070
Glu Gly Gly Phe Ala Leu Gly Gly Val Ser Thr His Ala Tyr Leu Glu
        1075                1080                1085
Ile Glu Ala Pro Arg Ile Asp Val Ala Arg Phe Thr Gly Ala Leu Arg
    1090                1095                1100
Gly Val Ile Ala Arg His Pro Met Leu Arg Ala Val Ile Arg Pro Asp
1105                1110                1115                1120
Gly Leu Gln Gln Val Leu Thr Asp Val Pro Pro Tyr Asp Val Ala Val
                1125                1130                1135
His Asp Leu Arg Asp Leu Asp Glu Pro Ala Arg Gln Arg Arg Arg Ala
            1140                1145                1150
Ala Leu Arg Glu Glu Met Ser His Gln Val Val Pro Ala Asp Leu Trp
        1155                1160                1165
Pro Leu Phe Asp Val Arg Val Ser Leu Gly Pro Thr Asp Ala Leu Val
    1170                1175                1180
His Val Gly Val Asp Ala Leu Ile Cys Asp Ala His Ser Phe Gly Leu
1185                1190                1195                1200
Val Leu Ala Glu Leu Ala Ala Arg Tyr Ala Asp Pro Ala Arg Arg Phe
                1205                1210                1215
Pro Pro Leu Thr Ala Asp Phe Arg Asp His Val Leu His Gln Glu Ala
            1220                1225                1230
Leu Arg Gly Thr Ala Glu Tyr Ala Ala Ala Glu Arg Tyr Trp Arg Glu
        1235                1240                1245
Arg Leu Pro Glu Leu Pro Pro Gly Pro Glu Leu Pro Leu Ala Val Ala
    1250                1255                1260
```

-continued

```
Pro Glu Thr Leu Gly Thr Pro Arg Phe Thr Arg Arg Ser Gly Arg Leu
1265                1270                1275                1280

Asp Ala Ala Ser Trp Thr Ala Val Lys Asp Arg Ala Arg Arg Ala Gly
            1285                1290                1295

Leu Ser Pro Ser Gly Val Leu Leu Ala Ala Phe Ala Glu Val Ile Thr
        1300                1305                1310

Ala Trp Ser Gly Arg Pro Arg Tyr Ser Leu Met Leu Thr Val Phe Asp
    1315                1320                1325

Arg Pro Pro Leu His Pro Asp Leu Gly Arg Ile Val Gly Asp Phe Thr
    1330                1335                1340

Ser Leu Ser Leu Leu Glu Val Asp His Ser Arg Pro Gly Asp Phe Thr
1345                1350                1355                1360

Asp Arg Ala Arg Ala Leu Gln Arg Arg Leu Trp Gln Asp Leu Asp His
            1365                1370                1375

Leu Ala Val Gly Gly Val Thr Val Thr Arg Glu Arg Ala Leu Arg His
        1380                1385                1390

Asp Ala Arg Pro Gly Leu Leu Thr Pro Val Val Phe Thr Ser Asp Leu
    1395                1400                1405

Pro Val Gly Glu Thr Ala Ala Glu Asp Ala Asp Gly Glu Gly Trp
    1410                1415                1420

Ala Leu Gly Glu Pro Val Tyr Gly Val Ser Gln Thr Pro Gln Val His
1425                1430                1435                1440

Leu Asp His Gln Val Ala Glu Asp Arg Gly Glu Leu Val Phe Asn Trp
            1445                1450                1455

Asp Ala Val Glu Asp Leu Phe Ala Pro Gly Ala Leu Asp Ala Met Phe
        1460                1465                1470

Ala Ala Tyr Thr Ala Ser Leu Thr Arg Leu Ala Arg Ser Pro Glu Ala
    1475                1480                1485

Trp Arg Arg Pro Gly Thr Pro Pro Leu Pro Thr Ala Gln Ala Ala Val
    1490                1495                1500

Arg Arg Arg Thr Ala Ala Thr Glu Ala Pro Leu Pro Ala Arg Leu Leu
1505                1510                1515                1520

His Glu Ala Val Gly Asp Ala Ala Arg Arg His Ala Asp Leu Thr Ala
            1525                1530                1535

Leu Val Asp Gly Asp Thr Arg Met Thr Tyr Arg Arg Leu Thr Glu His
        1540                1545                1550

Ala Arg Arg Val Gly Arg Thr Leu Arg Arg Leu Gly Ala Arg Pro Gly
    1555                1560                1565

Arg Leu Val Pro Val Val Ala Arg Lys Gly Trp Arg Gln Ala Val Ala
    1570                1575                1580

Ala Leu Gly Val Leu Glu Ser Gly Ala Ala Tyr Leu Pro Leu Asp Pro
1585                1590                1595                1600

Glu Leu Pro Ala Glu Arg Leu Val His Leu Val Arg Arg Ala Glu Ala
            1605                1610                1615

Ala Leu Leu Leu Thr Glu Arg Ala Leu Leu Asp Thr Leu Ala Val Pro
        1620                1625                1630

Val Gly Val Thr Val Leu Ala Val Asp Asp Ala Ala Leu Asp Ala
    1635                1640                1645

Asp Gly Gly Pro Leu Gln Ser Val Gln Asn Leu Thr Asp Leu Ala Tyr
    1650                1655                1660

Thr Ile Phe Thr Ser Gly Ser Thr Gly Glu Pro Lys Gly Val Met Ile
1665                1670                1675                1680
```

```
Asp His Leu Gly Ala Ala Asn Thr Leu Glu Cys Val Asn Arg Arg Phe
            1685                1690                1695

Gly Thr Gly Pro Gly Asp Ala Val Leu Ala Val Ser Ser Pro Ser Phe
        1700                1705                1710

Asp Leu Ala Val Tyr Asp Leu Phe Gly Val Leu Ala Ala Gly Gly Thr
        1715                1720                1725

Val Val Val Pro Ala His Asp Arg Arg Arg Asp Pro Gly His Trp Ala
    1730                1735                1740

Glu Leu Ile Arg Arg Glu Arg Val Thr Leu Trp Asn Ser Val Pro Ala
1745                1750                1755                1760

Leu Gly Thr Leu Leu Thr Glu Tyr Ala Glu Ala Leu Ala Pro Asp Ala
            1765                1770                1775

Leu Arg Thr Leu Arg Ala Val Leu Leu Ser Gly Asp Trp Ile Pro Leu
        1780                1785                1790

Gly Leu Pro Asp Arg Ile Arg Ala Leu Ser Ala Pro Gly Ala Thr Val
        1795                1800                1805

Met Ser Leu Gly Gly Ala Thr Glu Ala Ser Ile Trp Ser Val Trp Tyr
    1810                1815                1820

Glu Ile Gly Lys Val His Glu Ala Trp Ser Ser Ile Pro Tyr Gly Thr
1825                1830                1835                1840

Pro Met Ala Asn Gln Arg Leu Glu Val Leu Asp Glu Gln Leu Arg Pro
            1845                1850                1855

Arg Pro Asp Trp Val Pro Gly Glu Leu Tyr Ile Gly Gly Thr Gly Val
        1860                1865                1870

Ala Lys Gly Tyr Trp Arg Asp Pro Glu Gln Thr Ser Leu Arg Phe Pro
        1875                1880                1885

Val His Pro Gly Ser Gly Gln Arg Leu Tyr Arg Thr Gly Asp Phe Ala
    1890                1895                1900

Arg His Leu Pro Asp Gly Thr Leu Glu Phe Leu Gly Arg Gln Asp Asp
1905                1910                1915                1920

Gln Val Lys Ile Gly Gly Phe Arg Val Glu Leu Gly Glu Val Glu Ala
            1925                1930                1935

Ala Leu Gly Arg Leu Pro Asp Val Ala Ala Gly Ala Val Ile Ala Thr
        1940                1945                1950

Gly Asp Pro Arg Gly Asp Arg Arg Leu Val Gly Phe Ala Val Pro Ala
        1955                1960                1965

Arg Glu Gly Gly Phe Asp Ala Ala Gly Leu Arg Arg Gln Leu Ala Arg
        1970                1975                1980

Arg Leu Pro Ala Tyr Met Val Pro Thr Thr Leu Leu Pro Leu Asp Arg
1985                1990                1995                2000

Leu Pro Leu Thr Ala Asn Gly Lys Val Asp Arg Ala Ala Leu Gln Arg
            2005                2010                2015

Leu Val Pro Gly Arg Ala Pro Ala Pro Ala Glu Pro Ala Thr Ala Pro
        2020                2025                2030

Pro Ala Arg Ser Arg Ala Val Pro Val Pro Gly Trp Leu Ala Asp Leu
        2035                2040                2045

Trp Cys Glu Leu Leu Asp Val Pro Glu Ala Asp Pro Asp Ala Asn Phe
    2050                2055                2060

Phe Ala Leu Gly Gly Thr Ser Arg Val Ala Ile Thr Leu Val Thr Arg
2065                2070                2075                2080

Ile Glu Ala Arg Leu Ala Val Arg Val Pro Leu Ala Arg Leu Phe Asp
            2085                2090                2095
```

```
Ala Arg Thr Leu Gly Gly Leu Ala Glu Thr Ile Ala Glu Leu Ser Ala
        2100                2105                2110

Ala Ala Glu Glu Glu Pro Ala Pro Ala Glu Pro Val Tyr Ala Pro Asp
        2115                2120                2125

Pro Ala Thr Arg His Glu Pro Phe Pro Leu Thr Asp Ile Gln Arg Ala
        2130                2135                2140

Tyr Trp Leu Gly Arg His Arg Ser Leu Ser Leu Gly Gly Val Ala Thr
2145                2150                2155                2160

His Thr Tyr Leu Glu Leu Asp Val Glu Asp Leu Asp Pro Gly Arg Leu
        2165                2170                2175

Gln Thr Ala Leu Arg Arg Leu Ile Asp Arg His Asp Ala Leu Arg Leu
        2180                2185                2190

Val Val Leu Pro Asp Gly Arg Gln Gln Ile Leu Gly Asp Val Pro Pro
        2195                2200                2205

Tyr Leu Leu Ala His Thr Asp Leu Arg Gly Arg Ala Asp Ala Glu Ala
        2210                2215                2220

Glu Leu Ala Arg Val Arg Glu His Met Ser His Glu Val Arg Asp Ala
2225                2230                2235                2240

Ser Arg Trp Pro Leu Phe Asp Val Arg Thr His Arg Leu Asp Asp Val
        2245                2250                2255

Arg Thr Arg Leu His Leu Ser Leu Asp Leu Leu Ile Ala Asp Ala His
        2260                2265                2270

Ser Val His Val Leu Thr Gly Asp Leu Leu Thr Phe Tyr Ala Asp Pro
        2275                2280                2285

Asp Ala Ala Leu Pro Pro Leu Gly Cys Ser Phe Arg Asp Tyr Val Leu
        2290                2295                2300

Ala Val Arg Ala His Ala Glu Gly Glu Pro Arg Arg Arg Ala Leu Asp
2305                2310                2315                2320

His Trp Arg Ala Arg Leu Ala Asp Leu Pro Gly Pro Pro Gly Leu Pro
        2325                2330                2335

Leu Arg Cys Arg Pro Glu Glu Leu Thr Ala Pro Arg Phe Ala Arg Leu
        2340                2345                2350

Thr Thr Gly Leu Gly Pro Asp Ala Trp Ala Arg Leu Arg Arg Ala Ala
        2355                2360                2365

Ala Ala Ala Glu Leu Thr Pro Ala Ala Leu Ile Cys Ala Ala Phe Cys
        2370                2375                2380

Asp Val Leu Ala Gln Trp Ser Asp Thr Pro Arg Phe Thr Leu Asn Leu
2385                2390                2395                2400

Thr Thr Phe His Arg Pro Ala Leu Leu Pro Gly Val Asp Asp Leu Val
        2405                2410                2415

Gly Asp Phe Thr Thr Thr Leu Leu Gly Val Asp Gly Glu Gly Asp
        2420                2425                2430

Thr Phe Arg Asp Arg Ala Arg Arg Leu Gln Asp Arg Ile Trp Glu Asp
        2435                2440                2445

Leu Glu His Arg Val Val Ser Gly Val Glu Val Leu Arg Met Leu Arg
        2450                2455                2460

Arg Glu Arg Gly Thr His Asp Ala Val Arg Met Pro Val Val Phe Thr
2465                2470                2475                2480

Ser Thr Leu Arg Ala Ala Gly Pro Ala Pro Arg Thr Ala Pro Pro Ala
        2485                2490                2495

Trp Arg Val Arg Pro Gly Tyr Ala Ile Ser Gln Thr Pro Gln Val Leu
        2500                2505                2510
```

-continued

```
Leu Asp His Gln Val Ser Glu Ser Asp Gly Arg Leu Val Cys Thr Trp
    2515                2520                2525

Asp Tyr Val Ala Asp Ala Tyr Pro Pro Gly Leu Ile Glu Ala Met Phe
    2530                2535                2540

Gly Ala Phe Glu Ala Leu Leu Ala Ser Leu Ala Gly His Asp Asp Asp
2545                2550                2555                2560

Ala Gly His Asp Asp Ala Gly His Asp Gly Pro Gly His Asp
            2565                2570                2575

Asp Gly Pro Gly His Asp Asp Gly Pro Gly His Asp Asp Gly Pro Gly
            2580                2585                2590

His Asp Gly Pro Gly Arg Asp Asp Ser Ala Asp His Gly His Ser
            2595                2600                2605

Ala Thr His Asp Asp Ser Ala Ala Arg Asn Asp Arg Glu Gly Gly Gly
    2610                2615                2620

Pro Glu
2625

<210> SEQ ID NO 107
<211> LENGTH: 935
<212> TYPE: PRT
<213> ORGANISM: Streptomyces verticillus
<220> FEATURE:
<223> OTHER INFORMATION: ORF16

<400> SEQUENCE: 107

Met Thr Ser Ala Arg Pro Thr Pro Thr Leu Leu Pro Ala Asp Gln Arg
  1               5                  10                  15

Glu Leu Leu Arg Met Met Asn Asp Arg Thr Ala Pro Val Pro Ala His
             20                  25                  30

Thr Leu Thr Ala Gln Leu Ala Asp Ala Ala Arg Thr His Asp Arg Ala
         35                  40                  45

Leu Ala Leu Val Ala Pro Gly Leu Thr Leu Ser His Ala Glu Leu Asp
     50                  55                  60

Ala Arg Ala Ala Ala Val Ala Ala Arg Leu Thr Ala Ala Gly Val Ile
 65                  70                  75                  80

Pro Gly Asp Arg Val Ala Leu Ala Val Glu Tyr Gly Trp Glu Gln Val
                 85                  90                  95

Val Gly Ala Leu Ala Ala Leu Arg Ala Gly Ala Val Cys Leu Pro Val
            100                 105                 110

Ala Pro Gly Leu Pro Arg Pro Ala Arg Trp Gln His Ala Thr Arg Ala
        115                 120                 125

Gly Ala Thr Ala Val Leu Thr Gln Ser Trp Leu Thr Gln Arg Ile Asp
    130                 135                 140

Trp Pro Gln Glu Leu Pro Val Leu Ser Val Asp Glu Pro Gly Pro Pro
145                 150                 155                 160

Val Pro Pro Thr Thr Ala Pro Ala Asp Gly Arg Ser Ala Thr Asp Ala
                165                 170                 175

Ala Tyr Arg Leu Asp Ala Pro Val Ser His Arg Ala Ile Thr Thr Ala
            180                 185                 190

Ala Leu Glu Ile Asp Arg Ala Phe Arg Val Gly Pro Gly Asp Arg Leu
        195                 200                 205

Leu Ala Leu Ala Pro Ala Asp Ser Pro Leu Ala Leu Tyr Glu Leu Phe
    210                 215                 220

Gly Pro Leu Leu Ala Gly Ala Ala Leu Val Leu Thr Arg Asp Ile Asp
225                 230                 235                 240
```

-continued

```
Leu Arg Asp Pro Gly Ala Leu His Glu Ala Leu Arg Thr His Gly Val
            245                 250                 255
Thr Leu Trp His Ser Pro Ala Leu Leu Gly Leu Leu Leu Asp His
        260                 265                 270
Leu Ala Asp Arg Gly Gly Lys Leu Pro Glu Ser Leu Arg Leu Val Leu
        275                 280                 285
Leu Gly Gly Glu Arg Leu Asp Pro Ala Leu Val Arg Val Arg Glu
    290                 295                 300
Ser Ala Pro His Gln Pro Ala Val Ala His Leu Ser Ser Ala Thr Pro
305                 310                 315                 320
Ser Gly Pro Trp Thr Thr Cys Leu Glu Thr Gly Asp Leu Ala Pro Glu
                325                 330                 335
Trp Arg Ser Val Pro Val Gly Ala Pro Leu Pro Asn Gln Arg Ala His
            340                 345                 350
Ile Leu Ser Glu Thr Leu Arg Pro Cys Pro Val Trp Val Thr Gly Arg
        355                 360                 365
Leu His Tyr Gly Gly Val Ala Ala Glu Pro Pro Thr Gly Glu Glu His
    370                 375                 380
Ala Pro Ala Thr Val Pro His Pro Glu Thr Gly Glu Pro Leu Leu Arg
385                 390                 395                 400
Thr Gly Leu Phe Ala Arg Leu Leu Pro Glu Gly Leu Ile Asp Val Val
                405                 410                 415
Gly Asp Glu Thr Ala Arg Ile Ser Val Arg Asp Arg Pro Leu Asn Leu
            420                 425                 430
Gln Asp Thr Glu Thr Ala Leu Ala Ala His Glu Asp Val His Ser Ala
        435                 440                 445
Val Val Val Pro Val Gly Arg Gly Asp Glu Ser Leu Ala Arg Val Arg
    450                 455                 460
Leu His Pro Gly Ala Thr Ala Gly Pro Asp Glu Leu Leu Ala His Leu
465                 470                 475                 480
Arg Arg Lys Val Ser Pro Tyr Leu Leu Pro Gly His Ile Glu Val Gly
                485                 490                 495
Gly Pro Leu Pro Leu Thr Arg Asp Gly Arg Val Asp Arg Ala Arg Val
            500                 505                 510
Thr Ala Glu Ala Pro Ala Pro Ala Ala Val Pro Ala Ala Ala Pro Ala
        515                 520                 525
Ala Ser Ala Pro Ala Arg Asp Glu Ala Glu Leu Leu Ala Gln Val Ala
    530                 535                 540
Arg Val Thr Cys Arg Val Leu Gly Ile Gly Ala Val Glu Pro Asp Met
545                 550                 555                 560
Asn Leu Leu Asp Ala Gly Ala Thr Ser Val Glu Leu Val Arg Leu Ala
                565                 570                 575
Thr Ala Leu Glu Glu Glu Leu Gly Leu Asp Thr Asp Ile Glu Glu Leu
            580                 585                 590
Leu Ala Phe Pro Ser Val Ala Val Ile Val Gly Arg His Leu Gly Arg
        595                 600                 605
Arg Thr Ala Pro Pro Ala Arg Asp Pro Leu Pro Ala Ser Val Ala
    610                 615                 620
Phe Ala Pro Gly Ser Val Leu Pro Ala Pro Ala Pro Gly Pro Val
625                 630                 635                 640
Pro Pro Ala Ser Val Pro Pro Ala Pro Ala Ser Val Pro Pro Ala Ser
                645                 650                 655
```

-continued

Glu Ser Ser Pro Leu Ala Pro Ala Pro Gly Pro Val Pro Pro Thr
            660                 665                 670

Pro Val Pro Pro Ala Ser Val Pro Ala Ser Gly Ala Ala Pro His
        675                 680                 685

Val Pro Pro Ala Pro Ala Pro Ile Pro Ala Pro Ser Val Pro Pro
    690                 695                 700

Ala Pro Arg Pro Gln Pro Pro Leu Leu Thr Gly Ile Gly Ala Arg Gln
705                 710                 715                 720

Ala Phe Lys Asp Ala His His Gly Ile Arg His Glu Phe Asp Ala Thr
                725                 730                 735

Asp Gly Val Ala Leu Ser Gly Pro Asp His His Leu Thr Ala Arg
            740                 745                 750

Arg Ser His His Arg Phe Asp Pro Gly Pro Val Thr Leu Pro Asp Leu
        755                 760                 765

Ala Ala Leu Leu Gly Ala Leu Arg Arg Val Arg Gly Pro Gly Gly Glu
    770                 775                 780

Pro Lys Tyr Ala Tyr Pro Ser Ala Gly Ser Ser Tyr Pro Val Gln Thr
785                 790                 795                 800

Tyr Leu Leu Val His Pro Gly Lys Val Thr Gly Leu Pro Gly Gly Ser
                805                 810                 815

His Tyr Val His Pro Ala Arg Asn Arg Leu Val Ser Ile Asp Pro Thr
            820                 825                 830

Ala Thr Leu Pro Ala Asp Ala His Ala Glu Ile Asn Arg Ala Ala Tyr
        835                 840                 845

Gly Glu Ala Ala Phe Ser Leu Tyr Leu Ile Ala Ala Ile Asp Ala Ile
    850                 855                 860

Thr Pro Leu Tyr Gly Asp Leu Ser Trp Asp Phe Thr Val Phe Glu Ala
865                 870                 875                 880

Gly Ala Met Thr Gln Leu Leu Met Arg Thr Ala Val Gly Thr Gly Ile
                885                 890                 895

Gly Leu Cys Pro Val Gly Thr Met Asp Pro Ala Pro Leu Arg Arg Ala
            900                 905                 910

Phe Ala Leu Thr Asp Arg His Arg Phe Val His Ala Leu Leu Gly Gly
        915                 920                 925

Arg Pro Arg Thr Glu Ala Pro
    930                 935

<210> SEQ ID NO 108
<211> LENGTH: 339
<212> TYPE: PRT
<213> ORGANISM: Streptomyces verticillus
<220> FEATURE:
<223> OTHER INFORMATION: ORF15

<400> SEQUENCE: 108

Met Asn Arg His Gly Pro Leu Ala Gly Arg Arg Gln Ser Val Asp Thr
1               5                   10                  15

Arg Ser Ala Ala Trp Val Ala Pro Thr Gly Thr Pro Gly Leu Pro Leu
            20                  25                  30

Glu Val Ala Ala Thr Arg Asp Gly Val Asp Pro Ala Glu Trp Ala Arg
        35                  40                  45

Thr His Leu Asp Thr Val Thr Gly Trp Leu His Arg His Gly Ala Val
    50                  55                  60

Leu Phe Arg Gly Phe Gly Val Gly Leu Asp Gly Phe Gly Asp Val Val
65              70                  75                  80

-continued

```
His Ala Leu Ala Gly Ser Pro Glu Ala Tyr Val Arg Ser Ser Pro
                 85                  90                  95

Arg Thr Ala Leu Gly His His Leu Tyr Thr Ala Thr Asp His Pro Ala
                100                 105                 110

Asp Gln Pro Ile Pro Pro His Asn Glu Asn Ser Tyr Gln Leu Arg Phe
                115                 120                 125

Pro Gly Arg Leu Val Phe Gly Cys Leu Thr Pro Ala Arg Thr Gly Gly
            130                 135                 140

Ala Thr Pro Leu Ala Asp Thr Arg Arg Val Leu Gly Arg Leu Asp Pro
145                 150                 155                 160

Ala Leu Val Ala Ala Phe Ala Arg Arg Gly Val Leu Tyr Gln Arg Asn
                165                 170                 175

Tyr Gly Asp Gly Ile Gly Met Ser Trp Gln Asp Ala Phe Gln Thr Arg
                180                 185                 190

Asp Lys Ala Ala Val Thr Ala Tyr Cys Ala Ala Arg Arg Val Asp Val
                195                 200                 205

Glu Trp Lys Pro Asp Gly Gly Leu Arg Thr Thr Gln Val Arg Pro Ala
            210                 215                 220

Leu Ala Val His Pro Ala Thr Gly Glu Arg Val Trp Phe Asn His Ala
225                 230                 235                 240

Ala Phe Phe His Val Ser Ala Arg Pro Ala Leu Arg Asp Ala Leu
                245                 250                 255

Leu Ala Gln Phe Asp Glu Arg Asp Leu Pro Ser His Ser Cys Tyr Gly
                260                 265                 270

Asp Gly Arg Pro Ile Glu Pro Ala Val Met Glu Leu His His Ala
            275                 280                 285

Tyr Ala Ala Glu Leu Val Ala Pro Ala Trp Arg Ala Gly Asp Val Leu
            290                 295                 300

Leu Val Asp Asn Leu Leu Thr Ala His Gly Arg Glu Pro Phe Thr Gly
305                 310                 315                 320

Glu Arg Arg Val Val Val Gly Met Ala Gln Pro Leu Asp Trp Asp Glu
                325                 330                 335

Val Ser Ala

<210> SEQ ID NO 109
<211> LENGTH: 462
<212> TYPE: PRT
<213> ORGANISM: Streptomyces verticillus
<220> FEATURE:
<223> OTHER INFORMATION: ORF14

<400> SEQUENCE: 109

Met Thr Ala Pro Gly Thr Pro Leu Pro Ala Thr Phe Val Gln Arg Gly
  1               5                  10                  15

Leu Trp Pro Ser Thr Arg His Ala Arg Pro Ala Glu Val Thr His Val
                 20                  25                  30

Arg Ala Leu Arg Leu Thr Gly Asp Thr Asp Thr Ala Arg Leu Thr Glu
             35                  40                  45

Ala Val Arg Arg Val Thr Ala Ala Leu Pro Ala Leu Thr Ala Glu Leu
         50                  55                  60

Ser Gly Asp Glu Glu Pro Arg Leu Thr Leu Arg Pro Asp Ala Pro Glu
65                  70                  75                  80

Val Thr Pro Val Asp Leu Arg Gly Ala Pro Ser Ala Gly Arg Asp Ala
                 85                  90                  95
```

-continued

Val Cys Val Ala Leu Leu Arg Ala Asp Arg Asp His Pro Arg Ala Gly
            100                 105                 110

Arg His Arg Ala Arg Phe His Leu Val Arg Leu His Asp Asp Glu Thr
        115                 120                 125

Val Leu Ala Leu Thr Ala His Thr Leu Leu Asp Thr Pro Ser Leu
130                 135                 140

Tyr Ala Val Leu Gly Ala Val Cys Gln Ala Tyr Ala Gly Arg Phe Arg
145                 150                 155                 160

Pro Glu His Tyr Arg Asp Ala Thr Thr Leu Pro Asp Ala Pro His Ala
                165                 170                 175

Pro Leu Ser Gly Arg Ala Arg Ala Ser Arg Arg Trp Trp His Arg
            180                 185                 190

Arg Leu Ala Ala Leu Pro Gly Pro Ala Pro Ala Pro Ala Gly Pro Pro
        195                 200                 205

Arg Asp Arg Val Thr Glu Thr His Arg Leu Arg Ile Pro Ala Ala Arg
    210                 215                 220

Trp Lys Ala Leu Thr Ala Leu Thr Ala Leu Gly Gly Pro Leu Gly Gly
225                 230                 235                 240

Asn Gly Ser Leu Ala Val Met Ala Leu Ala Ala Trp Cys Leu Arg Ala
                245                 250                 255

Pro Asp His Arg Gly Pro Ala Arg Phe Thr Thr Val Val Asp Leu Arg
            260                 265                 270

Asp His Leu Gly Leu Gly Pro Ala Val Gly Pro Phe Thr Asp Arg Leu
        275                 280                 285

Val Phe Gly Ala Asp Leu Gly Glu Ala Pro Arg Pro Ser Phe Arg Asp
290                 295                 300

Val Thr Leu Arg Ala Gln Ser Gly Phe Leu Asp Ala Val Val His Tyr
305                 310                 315                 320

Leu Pro Tyr Gly Asp Val Val Glu Leu Gly Arg Glu Leu Gly Arg Val
                325                 330                 335

Thr Ala Pro Arg Thr Ala Ala His Trp Asp Val Ala Leu Asn Phe Cys
            340                 345                 350

Arg Asn Pro Pro Thr Ser Ala Ala Thr Arg Gly Glu Arg Thr Leu Ala
        355                 360                 365

Glu Arg Gly Leu Ser Ile Glu Leu Phe Arg Glu Ala Asp Leu Leu Gly
    370                 375                 380

Ala Ala Gly Thr Gly Pro Ala His Arg Trp Asp Gly Thr Val Leu Ala
385                 390                 395                 400

Leu Ser Leu Gly Glu Leu Gly Asp Asp Thr Val Leu Val Leu Asp Ala
                405                 410                 415

Asp Arg Asp His Pro His His Gly Thr Ala Asp Arg Leu Leu His Arg
            420                 425                 430

Met Asp Glu Ala Leu Leu Ala Ala Val Ala Asp Pro Asp Ala Pro Leu
        435                 440                 445

Pro Pro Leu Pro Ala Pro Ala His Thr Thr Arg Ser His Arg
    450                 455                 460

<210> SEQ ID NO 110
<211> LENGTH: 187
<212> TYPE: PRT
<213> ORGANISM: Streptomyces verticillus
<220> FEATURE:
<223> OTHER INFORMATION: ORF13

-continued

```
<400> SEQUENCE: 110

Met Thr Thr Thr Pro Arg Thr Ala Ala Glu Pro Thr Tyr His Val Val
1               5                   10                  15

Val Asn Asp Glu Glu Gln Tyr Ser Ile Trp Leu Ala Glu Gln Glu Ile
            20                  25                  30

Pro Ala Gly Trp Arg Ala Thr Gly Thr Ser Gly Thr Gln Glu Glu Cys
        35                  40                  45

Leu Arg His Ile Asp Glu Val Trp Thr Asp Met Arg Pro Arg Ser Leu
    50                  55                  60

Arg Glu Ala Met Ala Ala Glu His Ala Glu Pro Ala Pro Ala Pro
65                  70                  75                  80

Ala Pro Ala Glu Glu Glu Pro Ser Leu Val Asp Arg Leu Cys Ala Gly
                85                  90                  95

Asp Gln Pro Val Glu Ser Val Leu Arg Pro Glu Arg Thr Ala Ala Ala
            100                 105                 110

Leu Arg Glu Ala Val Asp Arg Gly Tyr Val Phe Val Arg Phe Ala Ala
        115                 120                 125

Thr Arg Gly Gly Thr Glu Leu Gly Val Ala Val Asp Pro Ala Ala Thr
    130                 135                 140

Thr Met Asp Gly Thr Glu Leu Arg Leu Thr Gly Thr Leu Thr Leu Asp
145                 150                 155                 160

Phe Glu Pro Val Arg Cys His Ala Arg Val Asp Val Thr Thr Phe Thr
                165                 170                 175

Gly Glu Gly Arg Leu Glu Arg Val Ser Gly Thr
            180                 185

<210> SEQ ID NO 111
<211> LENGTH: 390
<212> TYPE: PRT
<213> ORGANISM: Streptomyces verticillus
<220> FEATURE:
<223> OTHER INFORMATION: ORF12

<400> SEQUENCE: 111

Met Thr Thr Pro Met Thr Thr Pro Thr Thr Thr Arg Thr Thr Thr Arg
1               5                   10                  15

Thr Ala Val Phe Ala His Leu Arg Ala Pro Gly Leu Gly Asp Leu Leu
            20                  25                  30

Gln Arg Asn Ile Gly Leu Ala Leu Val Arg Arg Ala Arg Pro Ala Thr
        35                  40                  45

Ala Val Thr Leu Val Val Gly Glu Asp Leu Ala Ala Arg Phe Gly Pro
    50                  55                  60

Ala Leu Thr Arg His Thr Tyr Ala Thr Asp Val Leu Pro Cys Pro Gln
65                  70                  75                  80

Arg Gly Glu Ala Asp Pro Arg Trp Pro Ala Phe Leu Arg Thr Leu Ala
                85                  90                  95

Asp Arg Arg Phe Ala Leu Ala Val Val Asp Pro Asp Ser Gln Gly Leu
            100                 105                 110

His Ala Gly His Ala Arg Ala Ala Gly Val Pro Glu Arg Ile Gly Leu
        115                 120                 125

Pro Gln Asp Arg Pro Gly Asp Glu His Ile Thr His Pro Ile Arg Leu
    130                 135                 140

Pro Arg Pro Leu Trp Gly Thr Pro Asp Leu Tyr Glu Tyr Ala Thr Ala
145                 150                 155                 160
```

-continued

```
Leu Ala Ala Ala Leu Gly Leu Pro Ala Pro Arg Pro Gly Asp Val
                165                 170                 175

Leu Pro Glu Leu Pro Arg Thr Arg Gly Val Arg Pro Pro Thr Ala Gly
            180                 185                 190

Leu Pro Arg Pro Leu Val Ala Val His Pro Gly Gly Ala Pro His Trp
        195                 200                 205

Asn Arg Arg Trp Pro Leu Glu His Tyr Ala Arg Leu Cys Ala Arg Leu
    210                 215                 220

Ala Ala Glu Leu Ser Ala Ser Leu Cys Leu Gly Asp Glu Ala Glu
225                 230                 235                 240

Arg Pro Glu Leu Glu Leu Arg His Ala Val Leu Thr Arg Ser Pro
                245                 250                 255

Arg Ala Val Val His Leu Glu Ala Gly Ala Asp Leu Asp Arg Thr Ala
            260                 265                 270

Asn Val Leu Ala Asp Ala Asp Leu Leu Val Gly Asn Asp Ser Ser Leu
        275                 280                 285

Ala His Val Ala Ala Ala Val Arg Thr Pro Ser Val Leu Tyr Gly
    290                 295                 300

Pro Thr Gly Thr Glu Tyr Leu Trp Thr Arg Ile Tyr Pro Tyr His Arg
305                 310                 315                 320

Gly Val Ser Leu Arg Trp Pro Cys Gln Arg Leu Arg His Ala Ala Gly
                325                 330                 335

Glu Leu Ala Gly Arg Arg Cys Ala His Gly Cys Val Leu Pro Tyr Gln
            340                 345                 350

Gly Pro Ala Gly Pro Tyr Pro Arg Cys Leu Ala Asp Leu Pro Val Asp
        355                 360                 365

Arg Val Trp Pro Ala Val Thr Ala Arg Trp Ala Ser Pro His Pro Val
    370                 375                 380

Thr Ile Arg Ser Thr Pro
385                 390

<210> SEQ ID NO 112
<211> LENGTH: 545
<212> TYPE: PRT
<213> ORGANISM: Streptomyces verticillus
<220> FEATURE:
<223> OTHER INFORMATION: ORF11

<400> SEQUENCE: 112

Met Ser Ala Asp Pro Ser Arg Val Arg Thr Ile Leu Ser Val Asn Phe
1               5                   10                  15

Asn His Asp Gly Ser Gly Val Leu Leu Arg Glu Gly Arg Ile Ala Gly
            20                  25                  30

Tyr Val Thr Thr Glu Arg Arg Ser Arg Leu Lys Lys His Pro Gly Leu
        35                  40                  45

Arg Glu Glu Asp Leu Asp Glu Leu Leu Asp Gln Ala Gly Ala Asp Leu
    50                  55                  60

Ser Asp Ile Asp His Val Met Leu Cys Asn Leu His Thr Met Asp Thr
65                  70                  75                  80

Pro Asp Ile Pro Arg Leu His Gly Ser Asp Leu Lys Glu Thr Trp Leu
                85                  90                  95

Ala Phe Trp Val Asn Gln Arg Asn Asp Glu Val Ser Leu Arg Gly Arg
            100                 105                 110

Arg Ile Pro Cys Thr Val Asn Pro Asp His His Leu Ile His Ala Ala
        115                 120                 125
```

```
Thr Ala Tyr Tyr Thr Ser Gly Tyr Asp Ser Ala Met Ala Val Ala Ile
130                 135                 140

Asp Pro Thr Gly Cys Arg Ala Phe Ala Gly Lys Gly Ser Arg Leu Tyr
145                 150                 155                 160

Pro Leu Arg Arg Asp Leu Asp Ala Trp Phe Asn Ala Asn Ile Gly Tyr
                165                 170                 175

Cys Tyr Val Ala Asp Leu Met Phe Gly Ser Ser Ile Val Gly Ala Gly
            180                 185                 190

Lys Val Met Gly Leu Ala Pro Tyr Gly Arg Pro Ala Asp Gly Ala Gly
        195                 200                 205

Pro Asp Glu Glu Pro Glu Thr Val Arg Asp Phe Ala Ala Leu Val
210                 215                 220

Ala Leu Ala Asp Arg His Pro Arg Leu Val Asp Val Asp Gly Arg Lys
225                 230                 235                 240

Leu Asn Ala Thr Leu Ala His Tyr Ile Gln Leu Gly Leu Glu Arg Gln
                245                 250                 255

Leu Thr Ala Val Phe Ala Glu Leu Ala Pro Leu Cys Ala Arg Asn Gly
            260                 265                 270

Ile Ala Pro Asp Ile Cys Leu Ser Gly Gly Thr Ala Leu Asn Ala Ile
        275                 280                 285

Ala Thr Gln Leu Ala Phe Glu Ser Thr Gly Phe Glu Arg Met His Leu
290                 295                 300

His Pro Ala Cys Gly Asp Asp Gly Thr Ala Ile Gly Ala Ala Leu Trp
305                 310                 315                 320

His Trp His His Val Leu Gly His Pro Arg Leu His His Thr Asn Ala
                325                 330                 335

Asp Leu Met Tyr Ser Val Arg Glu Tyr Pro Glu His Thr Val Arg Arg
            340                 345                 350

Ala Val Arg Asp His Ala Ala Asp Leu Val Val Glu Glu Thr Gly Asp
        355                 360                 365

Tyr Val Ala Arg Ala Ala Glu Leu Val Ala Gly Gly Ala Val Ile Gly
370                 375                 380

Trp Tyr Asp Gly Ala Gly Glu Val Gly Pro Arg Ala Leu Gly His Arg
385                 390                 395                 400

Ser Ile Val Ala Asp Pro Arg Asp Pro Ala Met Arg Asp Arg Leu Asn
                405                 410                 415

Ser Gln Val Lys Phe Arg Glu His Phe Arg Pro Phe Ala Pro Ser Val
            420                 425                 430

Leu Lys Glu His Ala Ala Glu Trp Phe Gly Leu Ser Asp Ser Pro Phe
        435                 440                 445

Met Leu Arg Ala Thr Pro Val Leu Lys Pro Gly Val Pro Ala Ile Thr
        450                 455                 460

His Val Asp Gly Thr Ser Arg Ile Gln Ser Val Thr Arg Gln Asp Thr
465                 470                 475                 480

Pro Ala Phe His Asp Leu Ile His Ala Phe Lys Asp Arg Thr Gly Ile
                485                 490                 495

Pro Met Val Leu Asn Thr Ser Leu Asn Thr Lys Gly Glu Pro Ile Ala
            500                 505                 510

Glu Thr Pro Glu Asp Ala Leu Arg Thr Leu Leu Gly Ser Arg Leu Asp
        515                 520                 525
```

```
His Leu Val Leu Pro Gly Leu Ile Val Ser Gly Arg Thr Ala Ala Arg
    530                 535                 540

Ser
545

<210> SEQ ID NO 113
<211> LENGTH: 90
<212> TYPE: PRT
<213> ORGANISM: Streptomyces verticillus
<220> FEATURE:
<223> OTHER INFORMATION: ORF10

<400> SEQUENCE: 113

Met Ser Ala Pro Arg Gly Glu Arg Thr Arg Arg Ala Leu Glu Arg
  1               5                  10                  15

Asp Ile Ala Ala Ile Trp Ala Glu Thr Leu Gly Arg Asp Ser Val Gly
                 20                  25                  30

Pro His Glu Asp Phe Ala Ala Leu Gly Gly Asn Ser Ile His Ala Ile
             35                  40                  45

Lys Ile Thr Asn Arg Val Glu Glu Leu Val Asp Ala Glu Leu Ser Ile
         50                  55                  60

Arg Val Leu Leu Glu Thr Arg Thr Val Ala Gly Met Thr Asp His Val
 65                  70                  75                  80

His Ala Thr Leu Thr Gly Glu Arg Asp Arg
                 85                  90

<210> SEQ ID NO 114
<211> LENGTH: 498
<212> TYPE: PRT
<213> ORGANISM: Streptomyces verticillus
<220> FEATURE:
<223> OTHER INFORMATION: ORF9

<400> SEQUENCE: 114

Met Asn Thr Asp Leu Pro Arg Leu Leu Asp Arg Ile Ala Gly Leu Arg
  1               5                  10                  15

Val Leu Val Ile Gly Asp Val Ile Leu Asp Thr Tyr Val Trp Gly Ala
                 20                  25                  30

Thr Ser Gly Leu Cys Arg Glu Ser Pro Val Pro Ala Val Thr Leu Thr
             35                  40                  45

Ser Val Ala His Gln Cys Gly Gly Ala Ala Asn Val Ala Val Asn Leu
         50                  55                  60

Arg Ala Leu Gly Ala Glu Pro Val Leu Ser Ala Thr Gly Asp Asp
 65                  70                  75                  80

Arg Ala Gly Arg Arg Leu Arg Glu Ala Leu Arg Ala Arg Asp Val Asp
                 85                  90                  95

Thr Gly Gly Leu Phe Val Gln Pro Gly Arg Thr Thr Val Thr Lys Arg
            100                 105                 110

Arg Val Met Ala Asp Gly Gln Met Leu Leu Arg Leu Asp Glu Gly Gly
        115                 120                 125

Glu His Pro Leu Pro Val Ala Thr Asp Thr Gly Ser Arg Leu Leu Glu
    130                 135                 140

Arg Ala Ala Gly Leu Leu Pro Ala Val Asp Ala Val Ile Val Ser Asp
145                 150                 155                 160

Tyr Gly Tyr Gly Val Trp Glu Pro Asp Thr Val Ala Arg Leu Ala Ala
                165                 170                 175

His Arg Glu Leu Gly Pro Ser Thr Leu Val Val Asp Ser Arg Arg Pro
            180                 185                 190
```

```
Ala Arg Phe Thr Ala Leu Arg Ala Ser Ala Val Lys Pro Asn His Ala
        195                 200                 205

Glu Ala Leu Arg Leu Leu Asp Ala Gly Glu Pro Pro Gly Pro Ala
    210                 215                 220

Arg Ala Asp Trp Ala Ala Ala Leu Gly Asp Arg Leu Leu Arg Leu Thr
225                 230                 235                 240

Gly Ala Glu Arg Val Ala Leu Thr Leu Asp Ala Asp Gly Ser Leu Leu
                245                 250                 255

Phe Glu Arg Asp Arg Pro Pro Val Arg Thr Phe Ala Arg Gly Ser Arg
                260                 265                 270

Ala Pro Val Thr Ala Ala Val Gly Ala Gly Asp Ala Phe Thr Ala Ala
            275                 280                 285

Leu Thr Leu Ala Leu Ala Ala Gly Ala Asp Ser Ala Val Ala Ala Glu
        290                 295                 300

Leu Ala Ser Ala Ala Ala Gly Thr Ala Val Ala Thr Pro Gly Thr Ser
305                 310                 315                 320

Thr Trp His Ala Asp Glu Leu Arg Arg Leu Leu Gly Thr Gly Leu Lys
                325                 330                 335

Val Cys Arg Thr Gly Thr Leu Pro Ala Arg Leu Leu Asp Pro Ala Ala
            340                 345                 350

Arg Asp Arg Arg Val Val Phe Thr Asn Gly Cys Phe Asp Leu Leu His
            355                 360                 365

Gly Gly His Val Ser Cys Leu Ser Arg Ala Lys Glu Leu Gly Asp Leu
        370                 375                 380

Leu Val Val Gly Val Asn Ser Asp Ala Ser Val Arg Arg Leu Lys Gly
385                 390                 395                 400

Pro Arg Arg Pro Val Ile Pro Leu Ala Glu Arg Met Arg Val Leu Ala
                405                 410                 415

Ala Leu Ser Cys Val Asp Leu Val Val Pro Phe Asp Asp Asp Ser Pro
            420                 425                 430

Ala Ala Leu Ile Glu Ala Leu Arg Pro Glu Val Tyr Ala Lys Gly Gly
        435                 440                 445

Asp Tyr Thr Leu Ala Thr Leu Pro Glu Ala Pro Leu Val Gln Arg Leu
    450                 455                 460

Gly Gly Val Val His Leu Leu Pro Ser Val Ala Asp Thr Ser Thr Thr
465                 470                 475                 480

Asp Ile Ile Arg Arg Ile His Ala Leu Ser Arg Thr Gly Glu Gly Asp
                485                 490                 495

Thr Pro

<210> SEQ ID NO 115
<211> LENGTH: 424
<212> TYPE: PRT
<213> ORGANISM: Streptomyces verticillus
<220> FEATURE:
<223> OTHER INFORMATION: ORF8

<400> SEQUENCE: 115

Met Ser His Ala Ile Gly Pro Ser Arg Leu Ile Pro Ala Ile Arg Glu
  1               5                  10                  15

Ala Leu Gly Asp Glu Lys Asp Pro Arg Leu Ala Leu Tyr Val His Val
                20                  25                  30

Pro Phe Cys Ser Ser Lys Cys His Phe Cys Asp Trp Val Thr Asp Ile
            35                  40                  45
```

```
Pro Val Ala Arg Leu Arg Gly Asp Ser Arg Glu Arg Ser Pro Tyr Val
     50                  55                  60

Thr Ala Leu Cys Asp Gln Ile Arg Phe Tyr Gly Pro Gln Leu Thr Arg
 65                  70                  75                  80

Leu Gly Tyr Arg Pro Glu Val Met Tyr Trp Gly Gly Thr Pro Thr
             85                  90                  95

Arg Leu Thr Gly Asp Glu Met Thr Ala Val His Gln Ala Leu Asp Asp
                100                 105                 110

Ala Phe Asp Leu Thr Gly Leu Arg Gln Trp Ser Val Glu Ser Thr Pro
            115                 120                 125

Asn Asp Leu Asp Pro Ala Thr Leu Asp Thr Leu Arg Gly Leu Gly Val
    130                 135                 140

Thr Arg Val Ser Val Gly Val Gln Ser Leu Asn Pro Tyr Gln Leu Arg
145                 150                 155                 160

Lys Ala Gly Arg Ala His Ser Arg Glu Gln Ala Leu Ala Ala Val Pro
                165                 170                 175

Leu Leu Arg Arg Ala Gly Ile Asp Glu Phe Asn Val Asp Leu Ile Ala
            180                 185                 190

Gly Phe Pro Gly Glu Ala Val Glu Ser Phe Glu Thr Leu Arg Thr
            195                 200                 205

Val Leu Ala Leu Asp Pro Pro His Val Ser Val Tyr Pro Tyr Arg Ala
210                 215                 220

Thr Pro Lys Thr Val Met Ala Met Gln Leu Asp Arg Glu Phe Val Glu
225                 230                 235                 240

Ala Arg Asn Arg Asp Gly Met Ile Asp Ala Tyr Glu Arg Ala Met Ala
                245                 250                 255

Ala Leu Gly Ala Ala Gly Tyr His Glu Tyr Cys His Gly Tyr Trp Val
            260                 265                 270

Arg Asp Ala Arg His Glu Asp Gln Asp Gly Asn Tyr Lys Tyr Asp Leu
            275                 280                 285

Ala Gly Asp Lys Ile Gly Phe Gly Ser Gly Ala Glu Ser Ile Ile Gly
    290                 295                 300

His His Leu Leu Trp Asn Glu Asn Ser Ala Tyr Ala Arg Tyr Leu Leu
305                 310                 315                 320

Ala Pro Arg Glu Phe Ser Ala Ala His Arg Phe Thr Thr Ala Glu Pro
                325                 330                 335

Asp Arg Leu Thr Ala Pro Val Gly Gly Ala Leu Met Thr Arg Glu Gly
            340                 345                 350

Val Val Phe Ala Arg Phe Arg Leu Thr Gly Leu Asp Phe Ala Asp
            355                 360                 365

Val Arg Ala Thr Pro Tyr Phe Arg Gln Trp Phe Glu Leu Leu Glu Arg
    370                 375                 380

Cys Gly Gly Arg Phe Val Glu Thr Pro Tyr Ser Leu Arg Leu Glu Pro
385                 390                 395                 400

Ser Thr Ile His Arg Ala Tyr Ile Thr His Leu Ala Tyr Thr Met Ala
                405                 410                 415

His Gly Leu Ala Pro Glu Arg Ala
            420

<210> SEQ ID NO 116
<211> LENGTH: 117
<212> TYPE: PRT
<213> ORGANISM: Streptomyces verticillus
<220> FEATURE:
<223> OTHER INFORMATION: ORF31
```

```
<400> SEQUENCE: 116

Met Thr Glu Asn Leu Pro Ser Cys Pro Glu Cys Ser Ser Ala Tyr Thr
 1               5                  10                  15

Tyr Glu Met Gly Ala Leu Leu Val Cys Pro Glu Cys Gly His Glu Trp
            20                  25                  30

Pro Pro Ala Thr Ala Glu Ser Ala Asp Asn Pro Glu Asp Gly Ala Ile
        35                  40                  45

Arg Asp Ala Val Gly Asn Val Leu Ala Asp Gly Asp Thr Val Thr Val
    50                  55                  60

Val Lys Ser Leu Lys Val Lys Gly His Pro Thr Gly Ile Lys Ala Gly
 65                  70                  75                  80

Thr Lys Val Arg Asn Ile Arg Leu Val Glu Gly Val Ala Gly His Asp
                85                  90                  95

Ile Asp Cys Lys Ile Asp Gly Phe Gly Ala Met Gln Leu Lys Ser Ser
            100                 105                 110

Val Val Lys Lys Val
            115

<210> SEQ ID NO 117
<211> LENGTH: 2841
<212> TYPE: PRT
<213> ORGANISM: Streptomyces verticillus
<220> FEATURE:
<223> OTHER INFORMATION: ORF32

<400> SEQUENCE: 117

Met Ala Ser Asp Ala Leu Ser Ala His Leu Glu Val Ser Asp Cys Arg
 1               5                  10                  15

Gln Arg Gly Gly Ile Thr Val Thr Asn Asp Gly Ser Glu Leu Ala Gly
            20                  25                  30

Gln Asn Val Ala Ala Val Arg Phe Glu Arg Tyr Ser Ala Ile Ala Pro
        35                  40                  45

Glu Arg Thr Ala Ile Leu His Lys Gly Ala Ala Thr Gly Tyr Asp Glu
    50                  55                  60

Leu Asn Arg Arg Ala Glu Leu Thr Ala Thr Arg Leu Ala Asp Ala Gly
 65                  70                  75                  80

Ala Gly Pro Ser Thr Leu Val Ala Val Ala Leu Pro Arg Asp Pro Asp
                85                  90                  95

Leu Val Ala Thr Leu Cys Ala Leu Leu Lys Leu Gly Ala Ala Cys Leu
            100                 105                 110

Pro Leu Asp Pro Gly Ile Pro Ala Gly Arg Leu Arg Glu Ile Met Ala
            115                 120                 125

Asp Ala Ser Pro Asp Val Leu Val Thr Thr Arg Ala Val Ala Pro Ala
    130                 135                 140

Phe Thr Gly Asp Gly Pro Val Leu Phe Leu Asp Asp Ala Pro Pro Thr
145                 150                 155                 160

Cys Ser Ala Val Leu Pro Arg His Ser Ala Gly Thr Ala Ser Glu Ile
                165                 170                 175

Ala Tyr Val Leu Tyr Pro Thr Thr Pro Asp Glu Lys Ser Glu Asn Ser
            180                 185                 190

Val Val Ser Tyr Arg Asp Met Ala Arg Tyr Leu Asp Asp Pro Thr Ala
            195                 200                 205

Gly Ile Pro Ala Arg Ala Glu Ile Leu Arg Leu Val Ala Pro Leu Leu
    210                 215                 220
```

-continued

```
Ser Gly Gly Arg Leu Val Leu Asp Ala Asp Glu Thr Arg Pro Arg Pro
225                 230                 235                 240

Val Thr Arg Glu Ala Pro Arg Asp Met Val Glu Asp Val Val Ala Gln
            245                 250                 255

Val Trp Cys Ala Val Leu Gly Val Asp Arg Val Gly Val Arg Asp Arg
            260                 265                 270

Phe Phe Asp Leu Gly Gly Lys Ser Leu Ala Ala Val Gln Val Val Ala
            275                 280                 285

Arg Leu Arg Lys Leu Leu Gly Val Glu Leu Pro Leu Arg Ala Leu Phe
            290                 295                 300

Asp Ala Pro Thr Val Glu Glu Leu Ala Ala Arg Val Arg Ala Glu Gln
305                 310                 315                 320

Ala Gly Gly Gln Gly Val Arg Glu Ala Ala Leu Glu Pro Val Gly
                    325                 330                 335

Arg Ser Glu Pro Leu Pro Leu Ser Phe Ala Gln Gln Arg Leu Trp Phe
                340                 345                 350

Leu Asp Arg Leu Met Pro Asp Arg Ala Phe Tyr Thr Met Cys Asp Ala
            355                 360                 365

Phe Arg Val Arg Gly Gly Ile Asp Leu Gly Ala Leu Arg Arg Ala Leu
            370                 375                 380

Arg Met Leu Val Gly Arg His Glu Thr Leu Arg Thr Ala Phe Val Glu
385                 390                 395                 400

Arg Asp Gly Val Pro Tyr Gln Leu Val Gly Pro Ala Asp Gly Pro Gly
                    405                 410                 415

Ala Arg Arg Val Ala Ala Pro Thr Arg Val Asp Leu Ser Leu Leu Glu
                420                 425                 430

Pro Ala Glu Arg Glu Glu Ala Val Arg Asn Leu Val Ala Ala Glu Ala
            435                 440                 445

Arg Thr Pro Phe Arg Pro Ala Asp Gly Ala Leu Leu Arg Val Val Val
450                 455                 460

Ala Arg Leu Ala Asp Asp His Val Leu Val Ser Thr His His
465                 470                 475                 480

Ile Val Ser Asp Ala Trp Ser Val Gly Val Leu Val Asp Glu Leu Gly
                    485                 490                 495

Arg Leu Tyr Arg Glu Cys Val Thr Gly Asp Pro Ala Ala Leu Pro Pro
                500                 505                 510

Pro Ala Val Gln Tyr Ala Asp Phe Ala Val Trp Gln Arg Ala Trp Met
            515                 520                 525

Ala Gly Pro Val Gln Glu Glu His Leu Ala Tyr Trp Lys Arg Ala Leu
530                 535                 540

Asp Gly Ala Pro Ser Val Leu Arg Leu Pro Met Asp His Pro Arg Pro
545                 550                 555                 560

Ala Val Gln Ser Glu Arg Gly Glu Thr Val Gly Phe Ala Leu Pro Asp
                565                 570                 575

Ala Leu Val Ala Ala Leu Glu Lys Leu Gly Arg Glu Gln Gly Ala Thr
            580                 585                 590

Leu Phe Met Thr Leu Leu Gly Ala Phe Gln Val Leu Leu Ala Arg His
            595                 600                 605

Ala Gly Gln Glu Asp Ile Val Val Gly Val Pro Ala Ala Gly Arg Thr
            610                 615                 620

Arg Thr Glu Thr Glu Pro Leu Val Gly Phe Phe Val Asn Thr Leu Pro
625                 630                 635                 640
```

-continued

```
Leu Arg Ala Ile Cys Ala Pro Gly Leu Ser Phe Arg Asp Leu Leu Asp
                645                 650                 655
Gln Val Arg Glu Ala Ala Leu Gly Ala Phe Ala His Gln Asp Leu Pro
            660                 665                 670
Phe Glu Ala Leu Val Glu Ala Leu Ala Pro Glu Arg Asp Leu Gly His
        675                 680                 685
Asn Pro Leu Val Gln Val Thr Phe Gln Leu Leu Gly Thr Pro Ala Ala
    690                 695                 700
Arg Pro Asp Leu Ile Gly Thr Glu Val Glu Arg Tyr Pro Val Gln Glu
705                 710                 715                 720
Ala Val Ser Gln Phe Asp Leu Ser Leu Asp Ile Lys Arg Ala Asp Asp
                725                 730                 735
Gly Ser Tyr Arg Gly Ile Leu Asn Tyr Cys Pro Asp Leu Phe Asp Arg
            740                 745                 750
Arg Arg Met Glu Val Leu Val Gly His Tyr Leu Thr Leu Leu Gly Ala
        755                 760                 765
Ala Ala Ala Asp Pro Gly Arg Pro Ile Gly Glu Leu Pro Leu Ser Asp
    770                 775                 780
Gly Ala Glu Arg Leu Arg Leu Leu Asp Gly Phe Gly Lys Arg Asp Ala
785                 790                 795                 800
Ala Tyr Ala Gly Pro Gly Ser Val Pro Glu Arg Phe Ala Glu Val Ala
                805                 810                 815
Arg Thr Ala Pro Asp Ala Arg Ala Val Thr Cys Gly Ala Thr Thr Leu
            820                 825                 830
Thr Phe Ala Glu Leu Asn Asp Arg Val Glu Arg Leu Ala Gln Ala Leu
        835                 840                 845
Leu Gly Ala Gly Val Thr Arg Glu Thr Pro Val Ala Val Arg Leu Pro
    850                 855                 860
Arg Ser Thr Asp Ser Val Val Ala Leu Leu Ala Val Met Arg Ala Gly
865                 870                 875                 880
Gly Val Tyr Val Pro Leu Asp Pro Asp Trp Pro Ala Asp Arg Thr Ala
                885                 890                 895
Tyr Ile Leu Asp Asp Thr Ala Ala Ser Val Val Ile Thr Arg Asp Leu
            900                 905                 910
Pro Ala Leu Pro Gly Arg Leu His Val Asp Pro Arg Arg Pro Ala Ala
        915                 920                 925
Asp Gly Leu Val Pro Ala Pro Arg Ile Asp Pro Asp Gln Ala Ala Tyr
    930                 935                 940
Val Ile Tyr Thr Ser Gly Ser Thr Gly Ala Pro Lys Gly Val Val Val
945                 950                 955                 960
Arg His Arg Ser Leu Asn His Leu Thr Ser Ala Leu Gln Ala Thr Phe
                965                 970                 975
Leu Gly His Asp Pro Tyr Leu Ala Gly Ala Asp Gly Val Pro Pro Gly
            980                 985                 990
Asp Ala Lys Leu Arg Thr Thr Leu Thr Ala Pro Phe Thr Phe Asp Ala
        995                 1000                1005
Ser Met Glu Gln Leu Ser Trp Met Leu Ala Gly His Glu Leu Phe Ile
    1010                1015                1020
Val Pro Glu Asp Val Arg Arg Asp Pro Ser Ala Leu Val Arg Phe Val
1025                1030                1035                1040
Arg Glu His Arg Ile Asp Val Ile Asp Thr Thr Ser Ser Gln Leu Glu
                1045                1050                1055
```

```
Leu Leu Val Ser His Gly Leu Leu Asp Gly Glu Trp Ala Pro Ser Met
        1060                1065                1070

Val Met Val Gly Gly Glu Ala Val Ser Pro Ser Leu Trp Arg Thr Leu
        1075                1080                1085

Arg Asp Gln Arg Arg Thr Arg Cys Phe Asn Leu Tyr Gly Pro Thr Glu
        1090                1095                1100

Ala Thr Val Asp Ala Thr Cys His Asp Leu Ser Asp Pro Ala Asp Val
1105                1110                1115                1120

Pro Val Ile Gly Thr Pro Leu Pro His Thr His Val Arg Val Leu Asp
                1125                1130                1135

Asp Arg Leu Arg Pro Val Pro Val Gly Val Ala Gly Glu Ile Tyr Leu
        1140                1145                1150

Gly Gly Thr Gly Leu Ala Arg Gly Tyr Leu Asn Arg Pro Ala Leu Thr
        1155                1160                1165

Ala Arg Arg Phe Val Ala Asp Pro Tyr Pro Asp Thr Pro Gly Ser Arg
1170                1175                1180

Leu Tyr Arg Thr Gly Asp Arg Ala Arg Trp Arg Pro Asp Gly Thr Leu
1185                1190                1195                1200

Glu Tyr Leu Gly Arg Thr Asp Asp Gln Ile Lys Ile Arg Gly Phe Arg
        1205                1210                1215

Val Glu Pro Gly Glu Ile Glu Ala Val Leu Thr His His Pro Ala Val
        1220                1225                1230

Lys Glu Ala Ala Val Val Asp Asp Ala His Ala Arg Leu Val Ala Tyr
        1235                1240                1245

Val Thr Leu Ala Glu Gly Gly Gly Ala Gly Pro Thr Asp Val Arg Arg
        1250                1255                1260

Phe Ala Gln Gly Arg Leu Pro Ala His Met Val Pro Ser Ala Val Val
1265                1270                1275                1280

Val Leu Glu Ala Leu Pro Leu Thr Ser Asn Gly Lys Leu Asp Arg Ala
        1285                1290                1295

Arg Leu Pro Ala Pro Ala Ala Gly Arg Pro Glu Leu Asp Val Arg Phe
        1300                1305                1310

Val Ala Pro Arg Asp Met Val Glu Glu Val Val Ala Gln Val Trp Cys
        1315                1320                1325

Ala Val Leu Gly Val Asp Arg Val Gly Val His Asp Asp Phe Phe Glu
        1330                1335                1340

Leu Gly Gly His Ser Leu Leu Val Gln Val Met Thr Arg Ile Arg
1345                1350                1355                1360

Lys Leu Leu Gly Val Glu Val Pro Leu Arg Glu Leu Phe Asp Ala Ala
        1365                1370                1375

Thr Val Glu Glu Leu Ala Ala Arg Val Arg Ala Ala Arg Thr Glu Gly
        1380                1385                1390

Leu Gly Arg Gly Ala Ala Pro Pro Leu Gly Pro Val Asp Arg Ser Gly
        1395                1400                1405

Pro Leu Pro Leu Ser Phe Ala Gln Gln Arg Leu Trp Tyr Leu Asp Gln
        1410                1415                1420

Leu Ala Pro Asp Ser Val Ser Tyr Asn Met Cys Asp Ala Tyr Arg Val
1425                1430                1435                1440

Arg Gly Pro Leu Asp Leu Asp Ala Leu Arg Arg Ala Leu Arg Thr Leu
                1445                1450                1455

Val Glu Arg His Glu Thr Leu Arg Thr Ala Phe Val Glu Arg Asp Gly
        1460                1465                1470
```

-continued

```
Val Pro His Gln Val Val Ser Ala Pro Asp Ala Pro Ala Arg Arg
    1475                1480                1485

Ala Ala Glu Val Val Arg Ile Glu Ala Ala Gly Arg Thr Asp Glu Ala
    1490                1495                1500

Val Arg Asp Leu Val Ala Ala Glu Ala Arg Thr Pro Phe Arg Pro Ala
1505                1510                1515                1520

Asp Gly Ala Leu Met Arg Val Ala Val Ala Arg Leu Ala Asp Asp Asp
                1525                1530                1535

His Val Leu Val Val Thr Thr His His Ile Val Ser Asp Gly Trp Ser
        1540                1545                1550

Val Asp Ile Leu Val Asp Glu Leu Gly Arg Leu Tyr Arg Glu His Val
    1555                1560                1565

Thr Gly Asp Pro Ala Gly Leu Pro Pro Leu Asp Val Gln Tyr Ala Asp
    1570                1575                1580

Phe Ala Val Trp Gln Arg Ser Trp Met Thr Gly Pro Val Arg Glu Glu
1585                1590                1595                1600

His Leu Ala Tyr Trp Lys Arg Ala Leu Asp Gly Ala Pro Ser Val Leu
                1605                1610                1615

Arg Leu Pro Ala Asp His Pro Arg Pro Ala Val Gln Ser Gln Arg Gly
            1620                1625                1630

Glu Thr Val Glu Phe Pro Leu Pro Ala Pro Leu Val Ala Arg Leu Glu
        1635                1640                1645

Ala Leu Cys Arg Glu Gln Gly Val Thr Leu Phe Met Ala Leu Phe Gly
    1650                1655                1660

Ala Phe Gln Val Leu Leu Ala Arg Tyr Ser Gly Gln Asp Asp Val Val
1665                1670                1675                1680

Val Gly Val Pro Thr Ala Asn Arg Thr Arg Ala Glu Thr Glu Pro Leu
                1685                1690                1695

Val Gly Phe Phe Val Asn Thr Leu Pro Val Arg Val Ala Cys Ser Pro
            1700                1705                1710

Glu Leu Ser Phe Arg Ala Leu Leu Asp Arg Val Arg Glu Ala Ala Leu
        1715                1720                1725

Gly Ala Phe Ala His Gln Asp Leu Pro Phe Glu Ala Leu Val Glu Ala
    1730                1735                1740

Leu Ala Pro Glu Arg Asp Leu Gly His His Pro Leu Val Gln Val Thr
1745                1750                1755                1760

Phe Gln Leu Leu Asp Ala Pro Asp Glu Arg Leu Val Leu His Gly Thr
                1765                1770                1775

Asp Cys Val Ser Leu Gly Phe Gly Gly Val Thr Ser Arg Phe Asp Leu
            1780                1785                1790

Ser Leu Asp Val Val Ser Gly Arg Arg Gly Lys Arg Cys Val Leu Thr
        1795                1800                1805

Tyr Cys Pro Asp Leu Phe Asp Arg Pro Arg Met Glu Val Leu Ala Gly
    1810                1815                1820

His Tyr Leu Thr Leu Leu Gly Ala Ala Asp Asp Pro Gly Leu Arg
1825                1830                1835                1840

Val Gly Asp Leu Pro Leu Ser Asp Asp Val Glu Arg Leu Arg Leu Leu
                1845                1850                1855

Gly Gly Ser Arg Pro Arg Tyr Leu Pro Ala Pro Gly Ala Glu Thr Val
            1860                1865                1870

Pro Asp Ala Phe Ala Ala Gln Val Arg Ala Thr Pro Asp Ala Pro Ala
        1875                1880                1885
```

-continued

```
Leu Val His Gly Asp Ser Thr Leu Thr Phe Ala Glu Leu Asp Thr Arg
    1890                1895                1900

Val Thr Ala Leu Ala Val Arg Leu Arg Arg Cys Gly Val Ala Ala Glu
1905                1910                1915                1920

Thr Pro Val Ala Val Cys Leu Pro Arg Ser Ala Asp Ala Val Val Ala
                1925                1930                1935

Leu Leu Ala Val Leu Arg Ala Gly Gly Val Tyr Val Pro Val Asp Pro
            1940                1945                1950

Glu Trp Pro Ser Gly Arg Val Ala His Val Leu Asp Glu Thr Ala Ala
        1955                1960                1965

Pro Val Val Ile Thr Arg Asp Leu Pro Ala Asp Pro Gly Arg Val His
    1970                1975                1980

Leu Asp Pro Arg Gln Ala Pro Ala Asp Arg Asp Pro Leu Pro Arg
1985                1990                1995                2000

Leu His Arg Asp Gln Ala Ala Tyr Ile Ile Phe Thr Ser Gly Ser Thr
                2005                2010                2015

Gly Ala Pro Lys Gly Val Val Arg His Gly Ser Leu Tyr His Leu
            2020                2025                2030

Leu Gly His Val Arg Arg Met Ala Glu Gly Gly Pro Arg Arg Asn Val
        2035                2040                2045

Ala His Thr Thr Ala Met Thr Phe Asp Pro Ser Leu Glu Gln Phe Leu
    2050                2055                2060

Trp Leu Val Ala Gly His Thr Leu His Val Ala Pro Glu Glu Val Arg
2065                2070                2075                2080

Arg Asp Pro Glu Ala Leu Val Ala Leu Val Arg Arg Ala Ala Ile Asp
                2085                2090                2095

Val Leu Asn Val Thr Pro Ser His Leu Thr Leu Leu Ile Glu Ala Gly
            2100                2105                2110

Leu Leu Glu Gly Asp Arg Val Pro Gly Thr Val Leu Val Gly Gly Glu
        2115                2120                2125

Ala Val Pro Ala Ala Leu Trp Arg Thr Leu Arg Glu Arg Thr Gly Ala
    2130                2135                2140

Thr Arg Phe Phe Asn Leu Tyr Gly Pro Thr Glu Ala Thr Val Asp Ala
2145                2150                2155                2160

Thr Cys His Asp Leu Ser Asp Pro Ala Asp Val Pro Val Ile Gly Thr
                2165                2170                2175

Pro Leu Pro His Thr His Val Arg Val Leu Asp Asp Arg Leu Arg Pro
            2180                2185                2190

Val Pro Val Gly Val Ala Gly Glu Ile Tyr Leu Gly Gly Thr Gly Leu
        2195                2200                2205

Ala Arg Gly Tyr Leu Asn Arg Pro Ala Leu Thr Ala Gln Arg Phe Val
    2210                2215                2220

Ala Asp Pro Tyr Pro Asp Thr Pro Gly Ser Arg Leu Tyr Arg Thr Gly
2225                2230                2235                2240

Asp Arg Ala Arg Trp Arg Pro Asp Gly Thr Leu Glu Tyr Leu Gly Arg
                2245                2250                2255

Thr Asp Asp Gln Ile Lys Ile Arg Gly Phe Arg Val Glu Pro Gly Glu
            2260                2265                2270

Ile Glu Ala Val Leu Thr His His Pro Ala Val Lys Glu Ala Ala Val
        2275                2280                2285

Thr Val Ala Thr Asp Asp Gly Ala Ala Arg Leu Val Ala Leu Val Val
    2290                2295                2300
```

```
Pro Ala Pro Arg Ala Pro His Gly Asp Ser Ala Asp Gly Ala Pro Asp
2305                2310                2315                2320

Ala Gln Val Glu Glu Trp Asn Ala Val Phe Glu Ala Thr His Thr Asp
            2325                2330                2335

Ala Ala Asp Gly Glu Leu Thr Phe Asn Ile Lys Gly Trp Asn Asp Ser
        2340                2345                2350

Leu Thr Gly Ala Pro Ile Pro Ala Glu His Met Arg Glu Trp Val Asp
    2355                2360                2365

Thr Thr Val Ala Arg Leu Leu Glu Arg Pro Ala Glu Arg Val Leu Glu
2370                2375                2380

Ile Gly Ser Gly Thr Gly Leu Leu Met Trp Arg Leu Leu Pro His Val
2385                2390                2395                2400

Thr Glu Tyr Thr Gly Thr Asp Phe Ser Arg Pro Ala Val Asp Trp Leu
            2405                2410                2415

Arg Asp Gly Leu Arg Arg Arg Pro Ala His Arg Val Arg Leu Leu His
        2420                2425                2430

Arg Glu Ala Thr Asp Phe Thr Gly Val Arg Ala Ala Ser Thr Asp Leu
    2435                2440                2445

Val Val Val Asn Ser Val Val Gln Tyr Phe Pro Asp Arg Ala Tyr Leu
2450                2455                2460

Asp Thr Val Leu Ala Arg Ala Leu Asp Ala Thr Ala Asp Arg Gly Arg
2465                2470                2475                2480

Val Phe Val Gly Asp Val Arg Asn Leu Ala Leu Ala Pro Gln Phe Tyr
            2485                2490                2495

Ala Arg Gln Ala Leu Ala His Ala Gly Pro Gly Ala Ala Ala Arg Asp
        2500                2505                2510

Val Ala Arg Ala Ala Gly Glu Phe Ala Ala Met Asp Gly Glu Leu Leu
    2515                2520                2525

Val Ser Pro Ala Tyr Phe Ala Ala Leu Ala Ala Arg Ser Pro Arg Val
2530                2535                2540

Thr Gly Val Glu Ile Leu Pro Arg Arg Gly Arg His Arg Asn Glu Met
2545                2550                2555                2560

Ser Leu Tyr Arg Tyr Asp Val Val Leu His Val Gly Gly Asp Arg Pro
            2565                2570                2575

Ala Ala Pro Glu Ala Glu Val Leu Thr Trp Gly Asp Gln Val His Asp
        2580                2585                2590

Leu Ala Ser Leu Ser Ala Arg Leu Gly Arg Gly Gly Pro Asp Ala Leu
    2595                2600                2605

Leu Val Arg Gly Val Ala Asn Asp Arg Leu Thr Arg Asp Asn Glu Leu
2610                2615                2620

Leu Asp Ala Pro Ala Arg Thr Thr Ala Val Glu Pro Glu Asp Leu Trp
2625                2630                2635                2640

Gly Leu Ala Asp Ser Thr Pro Tyr Arg Val Ser Val Ser Trp Ala Ala
            2645                2650                2655

Ala Asp Pro Arg Gly Ala Met Asp Val Leu Leu Val Arg Arg Asp Ala
        2660                2665                2670

His Asp Asp Gly Pro Leu Leu Val Pro His Pro Val Pro Glu Pro Ser
    2675                2680                2685

Ala Pro Leu Thr Asn Thr Pro Thr Arg His Pro Ser Ala Arg Gln Gly
2690                2695                2700

Gly Ser Ala Ala Asp Gly Leu Arg Ser Trp Leu Ala Glu Arg Leu Pro
2705                2710                2715                2720
```

```
Ala His Leu Leu Pro Ala Arg Ile Thr Glu Val Asp Ala Leu Pro Arg
        2725                2730                2735

Thr Gly Thr Gly Lys Leu Asp Arg Gly Ala Leu Gly Gly Leu Val Thr
        2740                2745                2750

Ala Gly Arg Gly Arg Ala Gly Asp Arg Pro Ala Thr Ala Pro Arg
        2755                2760                2765

Thr Gly Leu Glu Arg Thr Leu Ala Asp Ala Trp Ala Arg Val Leu Gly
    2770                2775                2780

Leu Pro Glu Val Gly Val His Glu Asn Phe Phe Ala Leu Gly Gly Asp
2785                2790                2795                2800

Ser Leu Leu Ala Val Arg Ala Val Ala Arg Cys Arg Arg Ala Gly Val
        2805                2810                2815

Arg Leu Thr Val Arg Gln Leu Leu Ser Glu Gln Thr Val Ala Ala Leu
        2820                2825                2830

Ala Ala Ala Leu Glu Glu Glu Ser Gln
        2835                2840

<210> SEQ ID NO 118
<211> LENGTH: 451
<212> TYPE: PRT
<213> ORGANISM: Streptomyces verticillus
<220> FEATURE:
<223> OTHER INFORMATION: ORF33

<400> SEQUENCE: 118

Met Met Lys Ser Ser Arg Leu Arg Asp Arg Gln Leu Gly Gly Glu Asp
1               5                   10                  15

Pro Val Val Ala Gln Glu Ser Pro Gln Asp Ala Gly Pro Thr Pro Cys
            20                  25                  30

Gln Gly Asp Asp Gly Leu Asn Val Phe Ala Ala Leu Ala Ala Leu Leu
        35                  40                  45

Glu Val Glu Val Pro Val Arg Pro Leu Pro His His Ala Gly Leu Gly
    50                  55                  60

Arg His Val Glu His Ser Ser Gln Ala Ala Val Ala Leu Gly Pro
65                  70                  75                  80

Met Gln Val Ala Ser Ala Thr Thr Gly Val Ala Gly Asp Gly His Gln
            85                  90                  95

Ala Gly Arg Arg Gly Gln Val Thr Gly Val Gly Val Gly Arg Glu Val
        100                 105                 110

Ala Gly Gly Asp Asp Glu Leu Gly Ala Glu Asp Arg Pro His Ala Arg
    115                 120                 125

Gln Arg Leu Asp Asp Leu Gly Leu Trp Met Ala Ala Glu Arg Leu Ala
130                 135                 140

Asp Leu Leu Val Asn Pro Leu Gln Thr Val Val Gln Gly Gln Asp Leu
145                 150                 155                 160

Arg Gly Gln Val Ser His Asp Leu Gly Gly Asp Val Leu Pro Gly Gln
            165                 170                 175

Arg Gly Leu Leu Ser Leu Gly Ser Leu Gln Arg Arg Gly Asp Gly
        180                 185                 190

Val Gly Thr Ala His Ala Ser Val Gly Gln Pro Gly Arg Gln Pro Gly
    195                 200                 205

Pro Ala Ala Ala Glu Ser Cys Arg Gly Leu Val Arg Gln Gln
        210                 215                 220

Asp Gln Arg Ala Leu Leu Arg Ala Val Val Glu Gly Pro Phe Gln Arg
225                 230                 235                 240
```

Gly Glu Asp Ala Gly Gln Arg Val Ala Glu Thr Val Asp His Pro Asp
                245                 250                 255

Pro Val Gly His Glu Val Gly Thr Val Gly Gly Gln Gln Arg Glu Val
            260                 265                 270

Gly Gly Gln Leu Gly Gly His Val Asp Arg Arg Glu Val Pro Ser Val
        275                 280                 285

Ala Gly Gly Phe Gly Asp Asp Val Gly Val Ala Gly Val Gly Leu Arg
    290                 295                 300

Leu Ala Pro Val Ser Ala Gly His Ala Val Asp Arg Ala Ala Gly His
305                 310                 315                 320

Val Asp Gly Leu Leu Ala Val Gly Arg Glu Gln Gly Gln Gln Gln Arg
                325                 330                 335

Gly Gly Arg Ala Gly Asp Val His Cys Pro Val Asp Leu Val Gly Gln
            340                 345                 350

Val Glu Asp Leu Thr His Gly Gly Gln Asp Arg Arg Leu Ile Val Ala
        355                 360                 365

Asp Leu Leu Arg Pro Gln Arg His Thr Gly Leu Val Asp His Arg Arg
    370                 375                 380

Pro Val Met Pro Leu Ala Arg Val Asp Pro Gly Pro Asp Pro Gly Pro
385                 390                 395                 400

Ser Leu Ala His Ser Pro Leu Leu Thr Pro Asn Ser Ile Pro Ser Thr
                405                 410                 415

Arg Gly Thr Pro Arg Cys His Leu Arg Lys Lys Arg Pro Lys Arg Thr
            420                 425                 430

Ser Gln Ser Ala Ala Arg Ala Pro Arg Arg Thr Gly Arg Pro Leu Leu
        435                 440                 445

Val Ser His
    450

<210> SEQ ID NO 119
<211> LENGTH: 337
<212> TYPE: PRT
<213> ORGANISM: Streptomyces verticillus
<220> FEATURE:
<223> OTHER INFORMATION: ORF34

<400> SEQUENCE: 119

Met Thr Asp Leu Pro Leu Arg Thr Val Ala Leu Thr Gly Glu Glu Ser
  1               5                  10                  15

Ala Glu Val Asp Asp Leu Leu Arg Thr Leu Ala Asp Val Pro Val Asp
                 20                  25                  30

Ser Thr Val Gly Leu Leu His Arg Thr Arg Leu Ala Ala Gln Glu Leu
             35                  40                  45

Pro Leu Arg Ile Arg Ala Glu Leu Thr Gly Met Arg Leu Tyr Asp Ser
         50                  55                  60

Pro Arg Ala Leu Val Val Thr Gly Phe Gly Val Asp Asp Glu Arg Ile
     65                  70                  75                  80

Gly Pro Thr Pro Ala Ala Arg Pro Ala Pro Asp Pro Glu Arg Thr Arg
                 85                  90                  95

Asp Leu Glu Leu Leu Leu Leu His Ala Ala Leu Leu Gly Glu Ala
            100                 105                 110

Phe Gly Trp Ala Thr Gln Gln Asn Gly Arg Leu Val His Asp Val Leu
        115                 120                 125

Pro Val Pro Gly Glu Glu Thr Ala Gln Met Gly Ser Ser Ser Glu Thr
    130                 135                 140

-continued

```
Glu Leu Leu Trp His Thr Glu Asp Ala Phe His Pro Leu Arg Cys Asp
145                 150                 155                 160

Tyr Val Gly Leu Leu Cys Leu Arg Asn His Gln Arg Ala Ala Thr Thr
                165                 170                 175

Val Gly Trp Pro Asp Leu Ser Arg Leu Thr Thr Glu Asp Arg Ala Val
            180                 185                 190

Leu Leu Glu Pro Arg Tyr Leu Ile Arg Pro Asp Thr Ser His Thr Pro
        195                 200                 205

Ala Gln Asn Ala Thr Gly Thr Arg Ser Ala Glu Arg Phe Ala Ala Ile
    210                 215                 220

Ala Glu Met Asp Asp Ala Pro Glu Arg Val Ala Val Leu Phe Gly Asp
225                 230                 235                 240

Pro Glu Asp Pro Tyr Leu Arg Ile Asp Pro Ala Tyr Met Ser Pro Ala
                245                 250                 255

Pro Gly Asp Ala Ala Ala Arg Arg Ala Tyr Asp Thr Val Thr Ala Leu
            260                 265                 270

Ile Glu Asp Glu Leu Arg His Val Val Leu Asp Ala Gly Ser Leu Leu
        275                 280                 285

Leu Val Asp Asn Tyr Gln Ala Val His Gly Arg Lys Pro Phe Ala Ala
    290                 295                 300

Ala Tyr Asp Gly Arg Asp Arg Trp Leu Lys Arg Val Asn Ile Thr Arg
305                 310                 315                 320

Asp Leu Arg Arg Ser Arg Ser Ala Arg Arg Ser Ala Thr Ser Leu Leu
                325                 330                 335

Val
```

<210> SEQ ID NO 120
<211> LENGTH: 250
<212> TYPE: PRT
<213> ORGANISM: Streptomyces verticillus
<220> FEATURE:
<223> OTHER INFORMATION: ORF35

<400> SEQUENCE: 120

```
Met Asp Phe Pro Leu Thr Arg Val Asn Pro Trp Phe Ser Gly Gly Cys
1               5                   10                  15

Asp Gly Arg Pro Arg Val Arg Leu Cys Ala Leu Pro Tyr Ala Gly Gly
            20                  25                  30

Thr Ala Ala Val Phe Lys Asp Trp Pro Ala Ala Leu Pro Pro Gly Val
        35                  40                  45

Glu Leu Leu Thr Ala His Leu Pro Gly Arg Gly Asp Arg Phe Thr Glu
    50                  55                  60

Pro Pro Pro Ala Thr Leu Glu Glu Thr Ala Glu Arg Leu Cys Glu Ala
65                  70                  75                  80

Leu Pro Pro Ser Asp Leu Pro Thr Val Val Leu Gly His Ser Met Gly
                85                  90                  95

Ala Leu Leu Gly Tyr Glu Val Ala Ala Arg Leu Ala Ala Arg Gly Arg
            100                 105                 110

Ala Pro Asn Leu Leu Ile Ala Ala Cys Arg Pro Pro His Val Pro
        115                 120                 125

Pro Asp Ala Ser Gly Pro Val Thr Glu Ala Glu Leu Ala Ala Thr Leu
    130                 135                 140

Arg Ala Glu Arg Pro Trp Asp Thr Ala Leu Arg Asp Glu Glu Leu Met
145                 150                 155                 160
```

-continued

```
Glu Ala Val Leu Pro Ala Leu Val Ala Asp Ile Thr Ala Gly Asp Arg
                165                 170                 175

Tyr His Arg Pro Arg Pro Arg Pro Leu Asp Leu Pro Leu Lys Val Tyr
            180                 185                 190

Ile Gly Ala Asp Asp Gly Thr Asp Trp Arg Thr Thr Leu Gly Trp
        195                 200                 205

Arg Ala Cys Thr Ala Arg Asp Cys Glu Val Val Leu Pro Gly Gly
    210                 215                 220

His Tyr Phe Leu Glu Thr Asp Arg Ala Ala Val Leu Thr Arg Val Ala
225                 230                 235                 240

Thr Asp Leu Ala Glu Ala Glu Val Gly Ala
                245                 250
```

<210> SEQ ID NO 121
<211> LENGTH: 427
<212> TYPE: PRT
<213> ORGANISM: Streptomyces verticillus
<220> FEATURE:
<223> OTHER INFORMATION: ORF36

<400> SEQUENCE: 121

```
Met Thr Ala Arg Val Asp Ala Thr Pro Thr Tyr Leu Ala Val Leu Ala
 1               5                  10                  15

Val Arg Glu Ala Arg Ala Pro Leu Leu Gly Ser Cys Leu Ala Arg Met
             20                  25                  30

Ser Phe Ala Val Leu Pro Leu Ala Leu Leu Ser Val Arg Asp Ala
         35                  40                  45

Thr Gly Ser Phe Ala Val Ala Gly Leu Thr Ser Gly Ala Leu Ser Ala
     50                  55                  60

Thr Leu Thr Leu Phe Ala Pro Ala Arg Ala Arg Leu Ile Asp Arg Arg
 65                  70                  75                  80

Gly Ser Arg Ser Gly Leu Val Arg Leu Thr Val Pro Tyr Leu Leu Gly
                 85                  90                  95

Leu Ala Val Leu Ile Thr Leu Ala Glu Ala Glu Ala Pro Thr Ala Ala
                100                 105                 110

Leu Leu Val Ala Ala Val Ala Gly Val Phe Ala Pro Pro Leu Gly
            115                 120                 125

Pro Thr Met Arg Val Leu Trp Ala Arg Ile Leu His Gly Arg Gln Pro
    130                 135                 140

Leu Leu His Thr Ala Tyr Ala Leu Asp Ser Val Thr Glu Glu Val Val
145                 150                 155                 160

Phe Thr Val Gly Pro Leu Leu Ala Gly Gly Leu Ile Ala Val Ala Ala
                165                 170                 175

Pro Leu Ala Ser Met Ile Thr Val Met Val Leu Ile Ala Ala Gly Thr
            180                 185                 190

Ala Cys Phe Val Leu Ser Ala Ala Thr Ala Ala Pro Ala Ser Gly
        195                 200                 205

Glu Ala Asp Glu Asp Arg Pro His Gly Arg Pro Met Ala Leu Pro Gly
    210                 215                 220

Met Arg Thr Ile Val Leu Ser Phe Gly Val Gly Leu Val Val Gly
225                 230                 235                 240

Val Leu Gln Val Val Leu Pro Phe Ile Ala Asp His Ala Gly Ser Pro
                245                 250                 255

Gly Ala Gly Gly Ile Leu Leu Ser Met Leu Ser Ala Gly Ser Ala Val
            260                 265                 270
```

-continued

```
Gly Gly Leu Ala Tyr Gly Arg Ile Ala Trp Arg Ser Thr Pro Val Arg
            275                 280                 285

Arg Phe Val Val Leu Val Thr Gly Phe Thr Leu Ala Val Leu Pro Leu
        290                 295                 300

Cys Leu Thr Ala Ser Pro Val Pro Ala Gly Ala Phe Ala Leu Leu Val
305                 310                 315                 320

Gly Leu Cys Leu Ala Pro Leu Phe Thr Thr Ala Tyr Leu Leu Val Asn
                325                 330                 335

Asp Leu Val Thr Ala Ser Gly Thr Ala Pro Thr Glu Ala Asn Thr Trp
            340                 345                 350

Val Ser Thr Ala Asn Asn Gly Phe Ala Ala Gly Ser Ala Ala Ala
        355                 360                 365

Gly Val Leu Leu Asp Ser Arg Gly Pro Thr Val Thr Val Thr Ala Ala
    370                 375                 380

Phe Ala Val Ala Ala Thr Ala Val Met Thr Val Leu Arg Arg Arg
385                 390                 395                 400

Thr Leu Leu Leu Gly Ala Gly His Pro Glu Pro Ala Ala Ala Thr Pro
                405                 410                 415

Ala Asp Arg Thr Ala Pro Ala Glu Ala Glu Glu
            420                 425

<210> SEQ ID NO 122
<211> LENGTH: 272
<212> TYPE: PRT
<213> ORGANISM: Streptomyces verticillus
<220> FEATURE:
<223> OTHER INFORMATION: ORF37

<400> SEQUENCE: 122

Met Ser Lys Asn Ala Ala His Trp Ser Arg Ile Arg Thr Gly Asp Ala
1               5                   10                  15

Pro Gly Val Val Leu Ala Val Asp Phe Tyr Gly Thr Gly Arg Gln Glu
            20                  25                  30

Ala Thr Phe Arg His Leu Cys Asp Leu Leu Thr Asp Pro Val Glu Val
        35                  40                  45

Trp His Ala Val Pro Pro Ala Pro Asp Gly Asp Trp Ser Thr Ala Thr
    50                  55                  60

Gly Ala Gly His Leu Arg Trp Trp Thr Glu Gly Leu Asp Thr Val Leu
65                  70                  75                  80

Ala Gly Arg Pro Val Arg Ala Leu Val Gly Tyr Cys Ala Gly Gly Val
                85                  90                  95

Phe Ala Ser Ala Leu Ala Asp Ala Leu Val Glu Arg Glu Gly His Arg
            100                 105                 110

Pro Arg Val Val Leu Phe Asn Pro Ser Ala Pro Gly Val Ala Thr Leu
        115                 120                 125

Thr Arg Asp Phe Arg Gly Leu Ile Ala Gly Met Asp Leu Leu Thr Asp
    130                 135                 140

Gly Glu Arg Ala Ala Leu Leu Ala Glu Thr Thr Ala Ile Arg Arg Ala
145                 150                 155                 160

His Ala Pro Asp Ala Leu Val Pro Val Ala Glu Arg Tyr Ala Ala Leu
                165                 170                 175

Tyr Arg Glu Gly Cys Asp Leu Leu Cys Glu Arg Leu Gly Val Asp Ala
            180                 185                 190

Ser Phe Gly Ala Glu Leu Ala Ala Val Leu His Ser Tyr Leu Ala Tyr
        195                 200                 205
```

```
Leu Thr Ala Ala Leu Asp Val Pro Pro Thr Pro Leu Trp Arg Gly Ala
    210                 215                 220

Val Ser Leu Thr Ser Arg Glu His Gln Gly Thr Asp Phe Thr Asp Val
225                 230                 235                 240

Glu His Gly Phe Asp Val Ala Arg Ala Glu Leu Leu Ser Ser Pro Gln
                245                 250                 255

Val Val Ala Ala Leu Thr Ala Leu Leu Arg Glu His Glu Ala Ser Arg
                260                 265                 270
```

<210> SEQ ID NO 123
<211> LENGTH: 578
<212> TYPE: PRT
<213> ORGANISM: Streptomyces verticillus
<220> FEATURE:
<223> OTHER INFORMATION: ORF38

<400> SEQUENCE: 123

```
Met Thr Leu Thr Leu Arg Asp Ala Phe Leu Asp Gln Ala Ala Arg Thr
1               5                   10                  15

Pro Asp Ala His Ala Val Val His Gly Asp Thr Val Trp Thr Tyr Arg
                20                  25                  30

Glu Leu Glu Leu Arg Ala Gly Arg Met Ala Arg Thr Leu Ala Ala Arg
            35                  40                  45

Gly Ala Gly Pro Gly Thr Leu Val Ala Val Arg Leu Pro Arg Gly Pro
    50                  55                  60

Glu Pro Val Ala Ala Leu Leu Ala Val Val Leu Thr Gly Ala Gly Tyr
65                  70                  75                  80

Val Pro Leu Ala Asp Asp Pro Pro Asp Arg Cys Arg His Ile Leu
                85                  90                  95

Asp Asp Cys Ala Ala Ala Leu Leu Ala Glu His Pro Ser Arg Asp
                100                 105                 110

Gly Arg Thr Leu Thr Pro Asp Glu Ala Leu Ala Pro Ala Arg Pro Phe
            115                 120                 125

Asp Ala Ala Pro Val Arg Ala Gly Asp Pro Ala Tyr Val Ile Tyr Thr
    130                 135                 140

Ser Gly Ser Ser Gly Arg Pro Lys Gly Val Leu Val Glu Gln Gly Ala
145                 150                 155                 160

Leu Gly Ala Tyr Leu Ala Gln Ala Arg Ala Arg Tyr Asp Gly Leu Ser
                165                 170                 175

Gly Arg Thr Val Leu His Ser Ser Leu Ser Phe Asp Met Ala Val Thr
            180                 185                 190

Ser Leu Trp Gly Pro Leu Val Ser Gly Gly Ala Ile His Val Leu Asp
    195                 200                 205

Leu Lys Ala Ile Ala Ser Gly Thr Gln Pro Pro Ala Ala Ser Ala
    210                 215                 220

Arg Pro Ser Phe Leu Lys Val Thr Pro Ser His Leu Pro Leu Leu Gly
225                 230                 235                 240

Leu Leu Pro Asp Ser Cys Leu Pro Thr Gly Gln Leu Val Ile Gly Gly
                245                 250                 255

Glu Ala Leu Thr Gly Ser Ala Leu Gly Pro Trp Arg Ala Ala His Pro
            260                 265                 270

Asp Val Thr Val Val Asn Glu Tyr Gly Pro Thr Glu Ala Thr Val Gly
    275                 280                 285

Cys Cys Ala Tyr Thr Val Arg Pro Gly Asp Ala Val Asp Pro Gly Ala
    290                 295                 300
```

-continued

```
Val Pro Ile Gly Arg Pro Phe Ala Gly Thr Arg Leu Tyr Val Leu Asp
305                 310                 315                 320

Ala Asp Gly Glu Pro Val Ala Val Gly Gly Val Gly Glu Leu His Ile
            325                 330                 335

Ala Gly Asp Gln Leu Ala Arg Gly Tyr Leu Gly Arg Pro Arg Leu Thr
        340                 345                 350

Glu Glu Arg Phe Val Pro Asp Pro Phe Ala Ala Asp Gly Ser Arg Met
    355                 360                 365

Tyr Arg Thr Gly Asp Leu Val Arg Glu Arg Pro Asp Gly Asp Leu Glu
370                 375                 380

Tyr Leu Gly Arg Ala Asp Gly Gln Val Lys Val Ser Gly Tyr Arg Ile
385                 390                 395                 400

Glu Pro Gly Glu Ile Glu Ala Val Leu Arg Gly His Ala Gly Val Arg
                405                 410                 415

Asp Cys Ala Val Val Ala Val Gly Glu Ala Asp Ala Arg Arg Leu Val
            420                 425                 430

Ala Tyr Val Val Pro Asp Pro Asp Ser Pro Pro Gly Thr Ala Ala Pro
        435                 440                 445

Ala Arg His Ala Ala Glu Ala Leu Pro Pro Tyr Met Val Pro Ala Thr
    450                 455                 460

Phe Val Thr Val Pro Glu Leu Pro Leu Thr Pro Asn Gly Lys Leu Asp
465                 470                 475                 480

Arg Asp Ala Leu Pro Gly Pro Pro Ala Gly Asp Ala Gly Pro Gly Asp
                485                 490                 495

Arg Thr Pro Ala Glu Thr Leu Leu Cys Glu Leu Leu Ala Arg Ala Leu
            500                 505                 510

Gly Ile Pro Glu Ile Asp Ala Asp Ala Asp Phe Leu Thr Ser Gly Gly
        515                 520                 525

Thr Ser Ile Thr Ala Leu Lys Leu Val Ala Gly Ala Arg Arg Val Gly
    530                 535                 540

Ile Arg Leu Glu Leu Thr Thr Val Leu Arg Glu Arg Thr Val Arg Arg
545                 550                 555                 560

Ile Leu Ala Ala Gln Pro Asp Ala Ala Ser Pro Leu Ala Glu Gly Val
                565                 570                 575

Pro Glu
```

<210> SEQ ID NO 124
<211> LENGTH: 328
<212> TYPE: PRT
<213> ORGANISM: Streptomyces verticillus
<220> FEATURE:
<223> OTHER INFORMATION: ORF39

<400> SEQUENCE: 124

```
Met Thr Gly Ser Val Thr Leu Thr Pro Leu Gly Gly Ile Ile Pro Arg
1               5                   10                  15

Pro Arg Gly Glu Gly Leu Thr Thr Gly Ala Glu Tyr Asp Leu Gly Pro
            20                  25                  30

Leu Gly Asp Ala Gly Pro Asp Trp Val Arg Ala His Gly Pro Arg Leu
        35                  40                  45

Arg Glu Arg Leu Ala Thr Asp Gly Leu Ile Leu Leu His Gly Leu Pro
    50                  55                  60

Thr Asp Gly Asp Gly Val Asp Gly Phe His Asp Val Val Gly Ser Val
65                  70                  75                  80
```

```
Gly Gly Asp Pro Leu Pro Tyr Thr Glu Arg Ser Thr Pro Arg Ser Val
                85                  90                  95

Val Lys Gly Asn Ile Tyr Thr Ser Thr Glu Tyr Pro Ala Asp Gln Pro
            100                 105                 110

Ile Pro Met His Asn Glu Asn Ser Tyr Ala Ala His Trp Pro Ser Thr
        115                 120                 125

Leu Tyr Phe Phe Cys His Thr Ala Pro Asp Thr Gly Gly Ala Thr Pro
130                 135                 140

Ile Ala Asp Gly Arg Ala Val Leu Asp Leu Ile Pro Ala Glu Val Arg
145                 150                 155                 160

Arg Arg Phe Ser Gln Gly Val Val Tyr Thr Arg Thr Phe Arg Ala Asp
                165                 170                 175

Met Gly Leu Ser Trp Gln Glu Ala Phe Gln Thr Glu Asp Arg Gly Asp
            180                 185                 190

Val Glu Arg His Cys Arg Ala His Gly Gln Glu Phe Ser Trp Asp Gly
        195                 200                 205

Asp Val Leu Arg Thr Arg His His Arg Pro Ala Thr Ala Val Asp Pro
210                 215                 220

Gly Thr Gly Ala Glu Val Trp Phe Asn Gln Ala His Leu Phe His Pro
225                 230                 235                 240

Ser Ser Leu Asp Pro Asp Leu Arg Gln Val Leu Leu Glu Thr Tyr Gly
                245                 250                 255

Glu Asn Gly Leu Pro Arg Asp Ala Leu Phe Ala Asp Gly Thr Pro Ile
            260                 265                 270

Pro Asp Ala Asp Leu Ala Thr Val Arg Ala Ala Tyr Thr Arg Ala Ala
        275                 280                 285

Leu Ala Leu Pro Trp Arg Glu Gly Asp Ile Met Leu Val Asp Asn Leu
290                 295                 300

Arg Met Ala His Gly Arg Glu Pro Phe Thr Gly Glu Arg Arg Val Leu
305                 310                 315                 320

Val Ala Met Thr Ser Ala Asp Ser
                325

<210> SEQ ID NO 125
<211> LENGTH: 337
<212> TYPE: PRT
<213> ORGANISM: Streptomyces verticillus
<220> FEATURE:
<223> OTHER INFORMATION: ORF40

<400> SEQUENCE: 125

Met Thr Glu Val Arg Gly Glu Leu Ile Arg Ala Leu Pro Gly Val Leu
  1               5                  10                  15

Glu Ala Arg Ala Ala Arg Ala Gly His Thr Thr Ala Phe Leu Asp Ala
                20                  25                  30

Arg Arg Cys Val Thr Tyr Arg Glu Leu Glu Ala Arg Thr Arg Arg Leu
            35                  40                  45

Ala Gly Ser Pro Gly Ala Val Gly Gly Ala Gln Gly Gln Thr Gly Trp
        50                  55                  60

Arg Ser Ser Met Gly Asn Arg Gly Asp Gly Gly Phe Pro Pro
65                  70                  75                  80

Arg Cys Cys Gly Pro Glu Arg Gly Cys Ser Ile Pro Gly Pro Arg
                85                  90                  95

Thr Arg Ser Ser Arg Thr Ser Ser Thr Thr Val Glu Arg Trp Arg Trp
            100                 105                 110
```

-continued

```
Ser Pro Arg Arg Arg Cys Cys Arg Gly Ser Arg Asp Arg Ala Tyr
        115                 120                 125
Gly Ser Trp Trp Gly Val Arg Thr Pro Ser Arg Arg Glu Arg Leu Pro
    130                 135                 140
Ala Ser Thr Pro Ser Ser Gly Ser Arg Arg Ile Arg Gly Ala Arg
145                 150                 155                 160
His Gly Thr Thr Ser Ala Ser Thr Ser Arg Pro Gly Ser Ser Thr Arg
                    165                 170                 175
Arg Gly Pro Arg Ala Gly Ala Arg Ala Trp Ser Ala Ala Ser Ala Pro
            180                 185                 190
Arg Cys Gly Pro Trp Arg Arg Thr Cys Arg Arg Gly Val Trp Gly
        195                 200                 205
Arg Arg Thr Gly Cys Cys Gly Arg Cys Pro Cys Ser Thr Pro Thr Arg
    210                 215                 220
Thr Arg Cys Ala Cys Ser Gly Trp Trp Pro Trp Ala Arg Ala Arg Thr
225                 230                 235                 240
Ser Ser Thr Gly Ala Arg Ala Ser Ser Gly Arg Leu Arg Asn Ser Gly
                245                 250                 255
Ala Ala Ser Trp Pro Val Tyr Pro Pro Thr Ala Cys Ser Arg Ala
            260                 265                 270
Pro Ser Ala Thr Pro Pro Gly His Arg Pro Ala Cys Asp Cys Ala Ser
        275                 280                 285
Pro Gly Ala Ala Pro Cys Pro Pro Gly Leu Arg Ala Asp Val Glu Glu
    290                 295                 300
Leu Leu Gly Val Pro Leu Leu Asp Gly Tyr Gly Ser Thr Glu Thr Cys
305                 310                 315                 320
Gly Lys Ile Thr Val Glu Arg Leu Gly Gly Ser Arg Glu Gly Gly Cys
                325                 330                 335
Arg
```

<210> SEQ ID NO 126
<211> LENGTH: 246
<212> TYPE: PRT
<213> ORGANISM: Streptomyces verticillus
<220> FEATURE:
<223> OTHER INFORMATION: ORF41

<400> SEQUENCE: 126

```
Met Ile Ala Ala Leu Leu Pro Ser Trp Ala Val Thr Glu His Ala Phe
1               5                   10                  15
Thr Asp Ala Pro Asp Asp Pro Val Ser Leu Leu Phe Pro Glu Glu Ala
                20                  25                  30
Ala His Val Ala Arg Ala Val Pro Lys Arg Leu His Glu Phe Ala Thr
            35                  40                  45
Val Arg Val Cys Ala Arg Ala Ala Leu Gly Arg Leu Gly Leu Pro Pro
        50                  55                  60
Gly Pro Leu Leu Pro Gly Arg Arg Gly Ala Pro Ser Trp Pro Asp Gly
65                  70                  75                  80
Val Val Gly Ser Met Thr His Cys Gln Gly Phe Arg Gly Ala Ala Val
                85                  90                  95
Ala Arg Ala Ala Asp Ala Ala Ser Leu Gly Ile Asp Ala Glu Pro Asn
            100                 105                 110
Gly Pro Leu Pro Asp Gly Val Leu Ala Met Val Ser Leu Pro Ser Glu
        115                 120                 125
```

```
Arg Glu Trp Leu Ala Gly Leu Ala Ala Arg Arg Pro Asp Val His Trp
    130                 135                 140

Asp Arg Leu Leu Phe Ser Ala Lys Glu Ser Val Phe Lys Ala Trp Tyr
145                 150                 155                 160

Pro Leu Thr Gly Leu Glu Leu Asp Phe Asp Glu Ala Glu Leu Ala Val
                165                 170                 175

Asp Pro Asp Ala Gly Thr Phe Thr Ala Arg Leu Leu Val Pro Gly Pro
            180                 185                 190

Val Val Gly Arg Arg Leu Asp Gly Phe Glu Gly Arg Trp Ala Ala
        195                 200                 205

Gly Glu Gly Leu Val Val Thr Ala Ile Ala Val Ala Ala Pro Ala Gly
    210                 215                 220

Thr Ala Glu Glu Ser Ala Glu Gly Ala Gly Lys Glu Ala Thr Ala Asp
225                 230                 235                 240

Asp Arg Thr Ala Val Pro
                245

<210> SEQ ID NO 127
<211> LENGTH: 291
<212> TYPE: DNA
<213> ORGANISM: Streptomyces verticillus
<220> FEATURE:
<221> NAME/KEY: CDS
<222> LOCATION: (19)..(288)

<400> SEQUENCE: 127
ccggacggcg gcccgctc atg agc gcc ccg cgg ggc gag cgg acc cgg cgc         51
                    Met Ser Ala Pro Arg Gly Glu Arg Thr Arg Arg
                      1               5                  10 cgc gcg ctc gaa cgc gac atc gcc gcg atc tgg gcc gag acc ctc ggc         99
Arg Ala Leu Glu Arg Asp Ile Ala Ala Ile Trp Ala Glu Thr Leu Gly
             15                  20                  25 agg gac agc gtc ggc ccg cac gag gac ttc gcc gcg ctg ggc ggc aac        147
Arg Asp Ser Val Gly Pro His Glu Asp Phe Ala Ala Leu Gly Gly Asn
         30                  35                  40 tcc atc cac gcc atc aag atc acc aac cgg gtg gag gaa ctc gtc gac        195
Ser Ile His Ala Ile Lys Ile Thr Asn Arg Val Glu Glu Leu Val Asp
     45                  50                  55 gcc gag ctg tcc atc cgc gtc ctg ctc gag acg cgc acc gtg gcc ggc        243
Ala Glu Leu Ser Ile Arg Val Leu Leu Glu Thr Arg Thr Val Ala Gly
 60                  65                  70                  75 atg acg gac cac gtc cac gcc acg ctc acg ggg gag cgg gac cgg tga        291
Met Thr Asp His Val His Ala Thr Leu Thr Gly Glu Arg Asp Arg
                 80                  85                  90

<210> SEQ ID NO 128
<211> LENGTH: 90
<212> TYPE: PRT
<213> ORGANISM: Streptomyces verticillus

<400> SEQUENCE: 128

Met Ser Ala Pro Arg Gly Glu Arg Thr Arg Arg Ala Leu Glu Arg
  1               5                  10                  15

Asp Ile Ala Ala Ile Trp Ala Glu Thr Leu Gly Arg Asp Ser Val Gly
                 20                  25                  30

Pro His Glu Asp Phe Ala Ala Leu Gly Gly Asn Ser Ile His Ala Ile
             35                  40                  45

Lys Ile Thr Asn Arg Val Glu Glu Leu Val Asp Ala Glu Leu Ser Ile
         50                  55                  60
```

```
Arg Val Leu Leu Glu Thr Arg Thr Val Ala Gly Met Thr Asp His Val
 65                  70                  75                  80

His Ala Thr Leu Thr Gly Glu Arg Asp Arg
                 85                  90
```

<210> SEQ ID NO 129
<211> LENGTH: 90
<212> TYPE: PRT
<213> ORGANISM: Unknown Organism
<220> FEATURE:
<223> OTHER INFORMATION: Description of Unknown Organism: Grs-2

<400> SEQUENCE: 129

```
Ile Ser Ile Gly Thr Glu Tyr Val Ala Pro Arg Thr Met Leu Glu Gly
 1               5                  10                  15

Lys Leu Glu Glu Ile Trp Lys Asp Val Leu Gly Leu Gln Arg Val Gly
             20                  25                  30

Ile His Asp Asp Phe Phe Thr Ile Gly Gly His Ser Leu Lys Ala Met
         35                  40                  45

Ala Val Ile Ser Gln Val His Lys Glu Cys Gln Thr Glu Val Pro Leu
     50                  55                  60

Arg Val Leu Phe Glu Thr Pro Thr Ile Gln Gly Leu Ala Lys Tyr Ile
 65                  70                  75                  80

Glu Glu Thr Asp Thr Glu Gln Tyr Met Ala
                 85                  90
```

<210> SEQ ID NO 130
<211> LENGTH: 89
<212> TYPE: PRT
<213> ORGANISM: Unknown Organism
<220> FEATURE:
<223> OTHER INFORMATION: Description of Unknown Organism: Srfa-3

<400> SEQUENCE: 130

```
Asp Gln Leu Ala Glu Glu Trp Ile Gly Pro Arg Asn Glu Met Glu Glu
 1               5                  10                  15

Thr Ile Ala Gln Ile Trp Ser Glu Val Leu Gly Arg Lys Gln Ile Gly
             20                  25                  30

Ile His Asp Asp Phe Phe Ala Leu Gly Gly His Ser Leu Lys Ala Met
         35                  40                  45

Thr Ala Val Pro His Gln Gln Glu Leu Gly Ile Asp Leu Pro Val Lys
     50                  55                  60

Leu Leu Phe Glu Ala Pro Thr Ile Ala Gly Ile Ser Ala Tyr Leu Lys
 65                  70                  75                  80

Asn Gly Gly Ser Asp Gly Leu Gln Asp
                 85
```

<210> SEQ ID NO 131
<211> LENGTH: 90
<212> TYPE: PRT
<213> ORGANISM: Unknown Organism
<220> FEATURE:
<223> OTHER INFORMATION: Description of Unknown Organism: Vir-S

<400> SEQUENCE: 131

```
Gly Arg Ser Val Glu Gly Arg Gly Val Pro Arg Thr Pro Gln Gln Glu
 1               5                  10                  15

Ile Leu Ala Ser Leu Phe Ala Glu Val Leu Gly Leu Ser Lys Val Gly
             20                  25                  30
```

```
Ile His Glu Asp Phe Phe Asp Leu Gly Gly His Ser Leu Leu Ala Thr
         35                  40                  45

Arg Leu Thr Ser Arg Ile Arg Thr Val Leu Gly Ala Glu Ile Ala Val
     50                  55                  60

Arg Asp Leu Phe Glu Ala Pro Thr Val Glu Ala Leu Ala Glu Thr Leu
 65                  70                  75                  80

Glu Glu Ala Arg Glu Val Arg Pro Ala Leu
                 85                  90

<210> SEQ ID NO 132
<211> LENGTH: 90
<212> TYPE: PRT
<213> ORGANISM: Unknown Organism
<220> FEATURE:
<223> OTHER INFORMATION: Description of Unknown Organism: Saf-B

<400> SEQUENCE: 132

Leu Asp Pro Gly Gln Asp Tyr Leu Ala Pro Arg Asn Glu Leu Glu Ala
 1               5                  10                  15

Arg Ile Ala Ala Ile Trp Glu Gly Leu Leu Arg Arg Glu Arg Val Gly
             20                  25                  30

Val His Asp Ser Phe Phe Asp Leu Gly Gly Asn Ser Leu Leu Ala Thr
         35                  40                  45

Arg Leu Ala Thr Arg Leu Ala Ala Thr Leu Gln Val Gln Ala Gly Val
     50                  55                  60

Arg Thr Val Phe Glu His Arg Thr Val Ala Ala Gln Ala Ala His Phe
 65                  70                  75                  80

Thr Gln Ala Thr Lys Thr His Gln Ala His
                 85                  90

<210> SEQ ID NO 133
<211> LENGTH: 89
<212> TYPE: PRT
<213> ORGANISM: Unknown Organism
<220> FEATURE:
<223> OTHER INFORMATION: Description of Unknown Organism: BlmI

<400> SEQUENCE: 133

Met Ser Ala Pro Arg Gly Glu Arg Thr Arg Arg Ala Leu Glu Arg
 1               5                  10                  15

Asp Ile Ala Ala Ile Trp Ala Glu Thr Leu Gly Arg Asp Ser Val Gly
             20                  25                  30

Pro His Glu Asp Phe Ala Ala Leu Gly Gly Asn Ser Ile His Ala Ile
         35                  40                  45

Lys Ile Thr Asn Arg Val Glu Glu Leu Val Asp Ala Glu Leu Ser Ile
     50                  55                  60

Arg Val Leu Leu Glu Thr Arg Thr Val Ala Gly Met Thr Asp His Val
 65                  70                  75                  80

Ala Thr Leu Thr Gly Glu Arg Asp Arg
                 85
```